United States Patent
Lange et al.

(10) Patent No.: US 9,051,280 B2
(45) Date of Patent: Jun. 9, 2015

(54) TETRALINE AND INDANE DERIVATIVES, PHARMACEUTICAL COMPOSITIONS CONTAINING THEM, AND THEIR USE IN THERAPY

(75) Inventors: Udo Lange, Ludwigshafen (DE);
Wilhelm Amberg, Ludwigshafen (DE);
Michael Ochse, Ludwigshafen (DE);
Berthold Behl, Ludwigshafen (DE);
Frauke Pohlki, Ludwigshafen (DE);
Charles W. Hutchins, Green Oaks, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 2 days.

(21) Appl. No.: 13/546,434

(22) Filed: Jul. 11, 2012

(65) Prior Publication Data
US 2012/0295881 A1 Nov. 22, 2012

Related U.S. Application Data

(63) Continuation-in-part of application No. 13/207,160, filed on Aug. 10, 2011, now Pat. No. 8,883,839.

(60) Provisional application No. 61/373,654, filed on Aug. 13, 2010.

(51) Int. Cl.
| | |
|---|---|
| A61K 31/135 | (2006.01) |
| C07D 231/00 | (2006.01) |
| C07D 233/00 | (2006.01) |
| C07C 211/16 | (2006.01) |
| A61K 31/131 | (2006.01) |
| C07D 233/84 | (2006.01) |
| C07C 311/05 | (2006.01) |
| C07C 311/10 | (2006.01) |
| C07C 311/14 | (2006.01) |
| C07D 403/12 | (2006.01) |
| C07D 205/04 | (2006.01) |

(52) U.S. Cl.
CPC ............ *C07D 233/84* (2013.01); *C07C 311/05* (2013.01); *C07C 311/10* (2013.01); *C07C 311/14* (2013.01); *C07C 2101/02* (2013.01); *C07C 2101/04* (2013.01); *C07C 2102/08* (2013.01); *C07C 2102/10* (2013.01); *C07D 403/12* (2013.01); *C07D 205/04* (2013.01)

(58) Field of Classification Search
USPC ................. 564/308; 514/647, 403; 548/356.1
See application file for complete search history.

(56) References Cited

U.S. PATENT DOCUMENTS

| | | | |
|---|---|---|---|
| 4,927,838 A | 5/1990 | Guthrie et al. | |
| 5,506,246 A | 4/1996 | Junge et al. | |
| 5,519,034 A | 5/1996 | Kozlik et al. | |
| 5,545,755 A | 8/1996 | Lin et al. | |
| 6,057,357 A * | 5/2000 | Horwell et al. ............... 514/422 |
| 6,331,636 B1 | 12/2001 | Romero et al. | |
| 6,426,364 B1 | 7/2002 | Egle et al. | |
| 7,189,850 B2 | 3/2007 | Ceccarelli et al. | |
| 7,427,612 B2 | 9/2008 | Alberati-giani et al. | |
| 7,462,617 B2 | 12/2008 | Alberati-giani et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 8,420,670 B2 | 4/2013 | Amberg et al. | |
| 8,642,587 B2 | 2/2014 | Lange et al. | |
| 8,653,100 B2 | 2/2014 | Amberg et al. | |
| 2002/0169197 A1 | 11/2002 | Egle et al. | |
| 2003/0083359 A1 | 5/2003 | Lee et al. | |

(Continued)

FOREIGN PATENT DOCUMENTS

| | | |
|---|---|---|
| DE | 10315570 | 10/2004 |
| EP | 0091241 | 10/1983 |

(Continued)

OTHER PUBLICATIONS

Copending U.S. Appl. No. 13/207,030, commonly assigned.*
Copending U.S. Appl. No. 13/207,030, commonly assigned, filed Aug. 10, 2011.*
Harsing, L.G. et al., "Glycine transporter Type-1 and its inhibitors," Curr. Med. Chem. (2006) 13:1017-1044.
Hashimoto, K., "Glycine transporter inhibitors as therapeutic agents for schizophrenia," Recent Patents on CNS Drug Discovery (2006) 1:43-53.
International Search Report for Application No. PCT/EP2010/051903, mailed May 26, 2010.
Javitt, D.C., "Glutamate as a therapeutic target in psychiatric disorders," Mol. Psychiatry (2004) 9:984-997.

(Continued)

*Primary Examiner* — Kamal Saeed
*Assistant Examiner* — Janet L Coppins
(74) *Attorney, Agent, or Firm* — Lisa V. Mueller; Michael Best & Friedrich LLP

(57) ABSTRACT

The present invention relates to tetraline and indane derivatives of the formula (I)

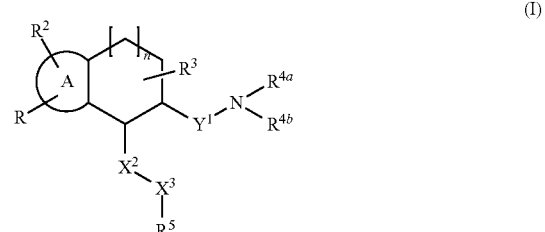

or a physiologically tolerated salt thereof.
The invention relates to pharmaceutical compositions comprising such tetraline and indane derivatives, and the use of such tetraline and indane derivatives for therapeutic purposes. The tetraline and indane derivatives are GlyT1 inhibitors.

20 Claims, No Drawings

(56) References Cited

U.S. PATENT DOCUMENTS

| | | |
|---|---|---|
| 2004/0026364 A1 | 2/2004 | Kihara |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0074105 A1 | 4/2006 | Ware et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0021408 A1 | 1/2007 | Molino et al. |
| 2007/0155753 A1 | 7/2007 | Ye et al. |
| 2007/0214087 A1 | 9/2007 | Kawaguchi et al. |
| 2008/0070941 A1 | 3/2008 | Dargazanli et al. |
| 2008/0119486 A1 | 5/2008 | Jolidon et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0273739 A1 | 10/2010 | Amberg et al. |
| 2012/0040947 A1 | 2/2012 | Pohlki et al. |
| 2012/0040948 A1 | 2/2012 | Pohlki et al. |
| 2012/0077796 A1 | 3/2012 | Pohlki et al. |
| 2012/0088790 A1 | 4/2012 | Pohlki et al. |
| 2012/0316153 A1 | 12/2012 | Amberg et al. |
| 2013/0035323 A1 | 2/2013 | Amberg et al. |
| 2013/0131132 A1 | 5/2013 | Amberg et al. |
| 2013/0184238 A1 | 7/2013 | Amberg et al. |
| 2013/0203749 A1 | 8/2013 | Amberg et al. |
| 2013/0210880 A1 | 8/2013 | Amberg et al. |

FOREIGN PATENT DOCUMENTS

| | | |
|---|---|---|
| EP | 0258755 | 3/1988 |
| EP | 0303961 | 2/1989 |
| EP | 0420064 | 4/1991 |
| EP | 1199306 | 4/2002 |
| EP | 1254662 | 11/2002 |
| EP | 1284257 | 2/2003 |
| EP | 2246331 | 11/2010 |
| WO | 81/03491 | 12/1981 |
| WO | WO 90/15047 | 12/1990 |
| WO | WO 92/06967 | 4/1992 |
| WO | WO 92/19234 | 11/1992 |
| WO | WO 92/22533 | 12/1992 |
| WO | WO 93/13073 | 7/1993 |
| WO | WO 95/07271 | 3/1995 |
| WO | WO 97/10223 | 3/1997 |
| WO | WO 97/45115 | 12/1997 |
| WO | WO 98/04521 | 2/1998 |
| WO | WO 98/56757 | 12/1998 |
| WO | WO 00/07978 | 2/2000 |
| WO | WO 00/20376 | 4/2000 |
| WO | WO 01/09120 | 2/2001 |
| WO | 02/076979 | 10/2002 |
| WO | WO 03/031435 | 4/2003 |
| WO | WO 03/045924 | 6/2003 |
| WO | WO 03/053942 | 7/2003 |
| WO | WO 03/055478 | 7/2003 |
| WO | WO 03/076420 | 9/2003 |
| WO | WO 03/087086 | 10/2003 |
| WO | WO 03/089411 | 10/2003 |
| WO | WO 03/097586 | 11/2003 |
| WO | WO 2004/007468 | 1/2004 |
| WO | WO 2004/013100 | 2/2004 |
| WO | WO 2004/013101 | 2/2004 |
| WO | WO 2004/022528 | 3/2004 |
| WO | WO 2004/071445 | 8/2004 |
| WO | WO 2004/072034 | 8/2004 |
| WO | WO 2004/080968 | 9/2004 |
| WO | WO 2004/096761 | 11/2004 |
| WO | WO 2004/110149 | 12/2004 |
| WO | WO 2004/112787 | 12/2004 |
| WO | WO 2004/113280 | 12/2004 |
| WO | WO 2004/113301 | 12/2004 |
| WO | WO 2005/014563 | 2/2005 |
| WO | WO 2005/023260 | 3/2005 |
| WO | WO 2005/037781 | 4/2005 |
| WO | WO 2005/037782 | 4/2005 |
| WO | WO 2005/037783 | 4/2005 |
| WO | WO 2005/037785 | 4/2005 |
| WO | WO 2005/037792 | 4/2005 |
| WO | WO 2005/023261 | 5/2005 |
| WO | WO 2005/040166 | 5/2005 |
| WO | WO 2005/046601 | 5/2005 |
| WO | WO 2005/049023 | 6/2005 |
| WO | WO 2005/058317 | 6/2005 |
| WO | WO 2005/058882 | 6/2005 |
| WO | WO 2005/058885 | 6/2005 |
| WO | WO 2005/099353 | 10/2005 |
| WO | WO 2005/123681 | 12/2005 |
| WO | WO 2006/008754 | 1/2006 |
| WO | WO 2006/034235 | 3/2006 |
| WO | WO 2006/063709 | 6/2006 |
| WO | WO 2006/082001 | 8/2006 |
| WO | WO 2006/102760 | 10/2006 |
| WO | WO 2006/121767 | 11/2006 |
| WO | WO 2007/143823 | 12/2007 |
| WO | WO 2008/038053 | 4/2008 |
| WO | WO 2008/148755 | 12/2008 |
| WO | WO 2009/024611 | 2/2009 |
| WO | WO 2009/121872 | 10/2009 |
| WO | WO 2010/020548 | 2/2010 |
| WO | WO 2010/025856 | 3/2010 |
| WO | WO 2010/029180 | 8/2010 |
| WO | WO 2010/092181 | 8/2010 |
| WO | WO 2010/138901 | 12/2010 |
| WO | WO 2012/020130 | 2/2012 |
| WO | WO 2012/020131 | 2/2012 |
| WO | WO 2012/020133 | 2/2012 |
| WO | WO 2012/152915 | 11/2012 |

OTHER PUBLICATIONS

Lindsley, C.W. et al., "Design, synthesis, and in vivo efficacy of glycine transporter-1 (GlyT1) inhibitors derived from a series of [4-phenyl-1-(propylsulfonyl)piperidin-4-yl]methyl benzamides," Chem. Med. Chem. (2006) 1(8):807-811.

Lindsley, C.W. et al., "Progress in the preparation and testing of glycine transporter type-1 (glyT1) inhibitors," Curr. Top. Med. Chem. (2006) 6:1883-1896.

Lindsley, C.W. et al., "Progress towards validating the NMDA receptor hypofunction hypothesis of schizophrenia," Cur. Top. Med. Chem. (2006) 6:771-785.

Lowe, J. et al., "A novel-nonsubstrate-based series of glycine type 1 transporter inhibitors derived from high-throughput screening," Bioorg. Med. Chem. Lett. (2007) 17(6):1675-1678.

Nunez, E. et al., "Differential effects of the tricyclic antidepressant amoxapine on glycine uptake mediated by the recombinant GLYT1 and CLYT2 glycine transporters," Br. J. Pharm. (2000) 129(1):200-206.

Written Opinion for Application No. PCT/EP2010/051903, mailed Aug. 16, 2011.

Zhao, Z. et al., "Synthesis and SAR of GlyT1 inhibitors derived from a series of N-((4-(morpholine-4-carbonyl)-1-(propylsulfonyl) piperidin-4-yl) methyl) benzamindes," Bioorg. Med. Chem. Lett. (2006) 16(23):5968-5972.

United States Patent Office Notice of Allowance for U.S. Appl. No. 12/706,326 dated Jun. 11, 2013 (10 pages).

United States Patent Office Notice of Allowance for U.S. Appl. No. 12/706,326 dated Feb. 21, 2013 (9 pages).

United States Patent Office Action for U.S. Appl. No. 12/706,326 dated Sep. 21, 2012 (7 pages).

U.S. Appl. No. 14/031,265, filed Sep. 19, 2013, Amberg et al.

(56) References Cited

OTHER PUBLICATIONS

Kamitani, T. et al., "Studies on the syntheses of heterocyclic compounds. Part DLXXVII. Synthesis of 2,3,4,5-tetrahydro-1H-benzazepine derivatives by phenolic cyclisation," J. Chem. Soc. Perkin Trans. (1974) 22:2602-2604.
Registry No. 1025812-32-1; entered in STN Jun. 5, 2008, "4-morpholineacetamide, N-[2[[1-[2,4-dihydroxy-5-(1-methylethyl)benzoyl]-2,3-dihydro-1H-isoindol-5-y]]oxy]ethyl]".
United States Patent Office Action for U.S. Appl. No. 14/317,104 dated Nov. 5, 2014 (11 pages).
United States Patent Office Action for U.S. Appl. No. 14/282,712 dated Oct. 3, 2014 (12 pages).
United States Patent Office Action for U.S. Appl. No. 13/468,682 dated Sep. 10, 2014 (12 pages).
United States Patent Office Action for U.S. Appl. No. 13/764,454 dated Sep. 30, 2014 (11 pages).
United States Patent Office Notice of Allowance for U.S. Appl. No. 13/792,105 dated Oct. 2, 2014 (10 pages).
United States Patent Office Notice of Allowance for U.S. Appl. No. 13/206,750 dated Nov. 7, 2014 (8 pages).
United States Patent Office Notice of Allowance for U.S. Appl. No. 13/206,937 dated May 15, 2014 (9 pages).
United States Patent Office Action for U.S. Appl. No. 13/792,105 dated Apr. 16, 2014 (6 pages).
United States Patent Office Action for U.S. Appl. No. 13/789,967 dated Apr. 1, 2014 (11 pages).
United States Patent Office Action for U.S. Appl. No. 14/031,265 dated Apr. 15, 2014 (14 pages).
United States Patent Office Notice of Allowance for U.S. Appl. No. 13/680,488 dated Apr. 28, 2014 (13 pages).
United States Patent Office Notice of Allowance for U.S. Appl. No. 13/207,030 dated May 13, 2015 (9 pages).
United States Patent Office Notice of Allowance for U.S. Appl. No. 13/207,160 dated Jun. 6, 2014 (9 pages).
United States Patent Office Notice of Allowance for U.S. Appl. No. 13/566,051 dated May 29, 2014 (8 pages).
United States Patent Office Corrected Notice of Allowance for U.S. Appl. No. 13/680,488 dated Jun. 12, 2014 (7 pages).
Ashby, E.C. et al., "Single electron transfer in reactions of alkyl halides with lithium thiolates," J. Org. Chem. (1985) 50(25):5184-5193.
Barbasiewicz, M. et al., "Intermolecular reactions of chlorohydrine anions: acctalization of carbonyl compounds under basic conditions," Org. Lett. (2006) 8(17):3745-3748.
Belliotti, T.R. et al., "Structure-activity relationships of pregabalin and analogues that target the alpha(2)-delta protein," J. Med. Chem. (2005) 48(7):2294-2307.
Bermejo, A. et al., "Syntheses and antitumor targeting G1 phase of the cell cycle of benzoyldihydroisoquinolines and related 1-substituted isoquinolines," J. Med. Chem. (2002) 45:5058-5068.
Beylot, M. et al., "In vivo studies of intrahepatic metabolic pathways," Diabetes Metabolism (1997) 23(3):251-257.
Bishop, D.C., "Analgetics based on the azetidine ring," Azetidine Analgetics (1968) 11:466-470.
Blagojevic, N. et al., "Role of heavy water in boron neutron capture therapy," Topics in Dosimetry and Treatment Planning for Neutron Capture Thearpy (1994) 125-134.
Blake, M.I. et al., "Studies with deuterated drugs," J. Pharm. Sci. (1975) 64(3):367-391.
Boulay, D. et al., "Characterization of SSR 103800, a selective inhibitor of the glycine transporter-I in models predictive of therapeutic activity in schizophrenia," Pharmacology, Biochemistry and Behavior (2008) 91:47-58.
Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.
Burn, D., "Alkylation with the vilsmeier reagent," Chem. and Industry (1973) 870-873.

Burns, N.Z. et al., "Total synthesis of haouamine A: the indeno-tetrahydropyridine core," Tetrahedron (2009) 65(33):6600-6610.
Butte, N.F. et al., "Measurement of milk intake: tracer-to-infant deuterium dilution method," Br. J. Nutrition (1991) 65:3-14.
Cheng, Y. et al., "Relationship between the inhibition constant (KI) and the concentration of inhibitor which causes 50 percent inhibition (I.sub.50) of an enzymatic reaction," Biochem. Pharmacol. (1973) 22:3099-3108.
Cheung, F.K. et al., "The use of a [4+2] cycloadditional reaction for the preparation of a series of 'tethered' Ru(II)-diamine and aminoalcohol complexes," Org. & Biomol. Chem. (2007) 5(7):1093-1103.
Chrzanowska, M. et al., "Asymmetric synthesis of isoquinoline alkaloids," Chem. Rev. (2004) 104(7):3341-3370.
Clayden et al., Tetra. Lett. (2003) 44(15):3059-3062.
Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.
Colandrea, V.J. et al., "Synthesis and regioselective alkylation of 1.6- and 1.7-naphthyridines," Tetra. Lett. (2000) 41:8053-8057.
Coward, W.A. et al., "New method for measuring milk intakes in breast-fed babies," The Lancet (1979) 13-14.
Czajka, D.M. et al., "Effect of deuterium oxide on the reproductive potential of mice," Annals of the New York Academy of Sciences (1960) 84:770-779.
Czajka, D.M. et al., "Physiological effects of deuterium on dogs," Am. J. Physiology (1961) 201(2):357-362.
Denkewalter, R.G. et al., Progress of Pharmaceutical Research, Drug Research (1966) 10:223-226.
Di, L. et al., "Optimization of a higher throughput microsomal stability screening assay for profiling drug discovery candidates," J. Biomol. Screening (2003) 8(4):453-462.
Dohi, T. et al., "Glycine transporter inhibitors as a novel drug discovery strategy for neuropathic pain," Pharma. & Therapeutics (2009) 123(1):54-79.
Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.
Erhunmwunse, M.O. et al., "A novel rearrangement reaction of beta-diaxo-alpha-ketoacetals," Tetra. Lett. (2009) 50:3568-3570.
Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.
Fiedler, H.B., "Lexikon der hilfsstoffe fur pharmazie, Kosmetik und angrenzende Gebiete," (1996) 4th Edition, Table of Contents.
Foster, A.B. et al., "Deuterium isotope effects in the metabolism of drugs and xenobiotics: implications for drug design," Advances in Drug Research (1985) 14:2-36.
Fraser et al., Canadian Journal of Chemistry (1971) 49(5):800-802.
Grant & Hackh's Chemical Dictionary, 5th Edition (1987), p. 148.
Green, G.M. et al., "Polystyrene-supported benzenesulfonyl azide: a diazo transfer reagent that is both efficient and safe," J. Org. Chem. (2001) 66(7):2509-2511.
Greene, T.W. et al., in Protective Groups in Organic Synthesis, 2nd Edition, John Wiley & Sons, Inc., (1991) Table of Contents.
Greene, T.W. et al., in Protective Groups in Organic Synthesis, 3rd Edition, John Wiley & Sons, Inc., (1999) Preface, Table of Contents and Abbreviations.
Guillonneau, C. et al., "Synthesis of 9-O-substituted derivatives of 9-hydroxy-5, 6-dimethyl-6H-pyrido[4,3-b]carbazole-1-carboxylic acid (2-(dimethylamino)ethyl)amide and their 10- and 11-methyl analogues with improved antitumor activity," J. Med. Chem. (1999) 42(12):2191-2203.
Gupta, A. et al., "Simple and efficient synthesis of steroidal hybrids of estrogen and vitamin D3," Synthetic Comm. (2009) 39:61-69.
Hashimoto, K. "Glycerine transport inhibitors for the treatment of schizophrenia," The Open Medicinal Chemistry Journal (2010) 4:10-19.
Hashimoto, K. et al., "Phencyclidine-induced cognitive deficits in mice are improved by subsequent subchronic administration of the

(56) References Cited

OTHER PUBLICATIONS glycine transporter-1 inhibitor NFPS and D-serine," Eurp. Neuropsychopharmacology (2008) 18:414-421.
Hillier, M.C. et al., "A one-pot preparation of 1,3-disubstituted azetidines," J. Org. Chem. (2006) 71(20):7885-7887.
Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.
Jellimann, C. et al., "Synthesis of phenalene and acenaphthene derivatives as new conformationally restricted ligands for melatonin receptors," J. Med. Chem. (2000) 43(22):4051-4062.
Jensen, B.L. et al., "Total synthesis of 4,5,7a,8-tetrahydro-1,2-dimethoxyphenanthro[10,1-bc]-azepin-6(7H)-one: a photochemical approach," J. Heterocyclic Chem. (1986) 23:343-347.
Jetter, M.C. et al., "Heteroaryl beta-tetralin ureas as novel antagonists of human TRPV1," Bioorg. Med. Chem. Lett. (2007) 17(22):6160-6163.
Jutz, C. et al., "The Vilsmeier-Haackarnold acylations. C—C bond-forming reactions of chloromethyleniminium ions," Adv. Org. Chem. (1976) 9(1):225-342.
Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(I I):2381-2384.
Kato, S. et al., "Synthesis of deuterated mosapride citrate," J. Labelled Compounds and Radiopharmaceuticals (1995) 36(10):927-932.
King, F.D., editor "Bioisosteres, conformational restriction and pro-drugs—case history: an example of a conformational restriction approach," Medical Chemistry: Principles and Practice (1994), Chapter 14, 206-209.
Kinney, G.G. et al., "The glycerine transporter type I inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neurosci. (2003) 23(20):7586-7591.
Kocienski, P.J., Protective Groups, Georg Thieme Verlag Stuttgart, Germany, Table of Contents (1994).
Kreher, R.P., Hetarene II, Georg Thieme Verlag Stuttgart, Germany (1991) 583-726.
Kuhakarn, C. et al., "Synthesis of alkylated indolizidine alkaloids via pummcrcr mediated cyclization: synthesis of indolizidine 167B, 5-butylindolizidine and monomorine I," Tetrahedron (2008) 64(8):1663-1670.
Kushner et al., "Pharmacological uses and perspectives of heavy water and deuterated compounds," Canadian J. Physiol. Pharmacol. (1999) 77(2):79-88.
Lizondo, J. et al., "Linezolid: oxazolindinone antibacterial," Drugs of the Future (1996) 21(11):1116-1123.
MacLennan, A.H. et al., "Neonatal body water turnover: a putative index of perinatal morbidity," Amer. J. Obstetrics & Gynecology (1981) 139(8):948-952.
Mai, K. et al., "A fast n-substituted alpha-aminonitrile synthesis," Synthetic Commun. (1985) 15(2):157-163.
Mallesham, B. et al., "Highly efficient cul-catalyzed coupline of aryl bromides with oxazolidinones using Buchwald's protocol: a short route to linezolid and toloxatone," Org. Lett. (2003) 5(7):963-965.
McOmie, J.F.W., ed., Protective Groups in Organic Chemistry, Plenum Press (1973) Table of Contents.
Meek, J.S. et al., "Diels-Alder reactions of 9-substituted anthracenes.1 II. 9-cyanoanthracene," J. Amer. Chem. Soc. (1956) 78(20):5413-5416.
Memetzidis, G. et al., "Synthesis of aromatic chloroberbines," Heterocycles (1990) 31(2):341-351.
Mezler, M. et al., "Inhibitors of GlyT1 affect glycine transport via discrete binding sites," Mol. Pharmacol. (2008) 74(6):1705-1715.
Munson, P.J. et al., "Ligand: a versatile computerized approach for characterization of ligand-binding systems," Anal. Biochem. (1980) 107(1):220-239.
Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.
Obach, R.S., "The prediction of human clearance from hepatic microsomal metabolism data," Curr. Opin. Drug Disc. & Development (2001) 4(1):36-44.
Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.
Papageorgiou, C. et al., "163 synthesis of hydroxy-and methoxy-substituted octahydrobenzo[g]isoquinolines as potential ligands for serotonin receptors," Helvetica Chimica Acta (1989) 72:1463-1470.
Pinard, E. et al., "Selective gly T1 inhibitors: discovery of [4-(3-fluoro-5-trifluaremethylpyridin-2-yl)piperazin-1-yl]-]-[5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.
Pitts, M.R. et al., "Indium metal as a reducing agent in organic synthesis," J. Chem Soc. Perkin Transactions (2001) 1:955-977.
Pons, G. et al., "Stable isotopes labeling of drugs in pediatric clinical pharmacology," Pediatrics (1999) 104(3-2):633-639.
Prout, F.S. et al., "3-Benzyl-3-Methylpentanoic acid," Organic Syntheses, Coll. (1963) 4:93; (1955) 35:6.
Quirante, J. et al., "Synthesis of diazatricyclic core of magangamines from Cis-perhydroisoquinolines," J. Org. Chem. (2008) 73(7):768-771.
Ranu et al., "Indium (III) chloride-promoted rearrangement of epoxides: a selective synthesis of substituted benzylic aldehydes and ketones," J. Org. Chem. (1998) 8212-8216.
Reddy, K.S. et al., "Synthesis of a 9-fluorenone derived beta-amino alcohol ligand depicting high catalytic activity and pronounced non-linear stereochemical effects," Synthesis (2000) 1:165-176.
Reddy, M.P. et al., "Applications of the Vilsmeier reaction. 13. Vilsmeier approach to polycyclic aromatic hydrocarbons," J. Org. Chem. (1981) 46:5371-5373.
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCI3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tavares, F.X. et al., "Potent, selective, and orally efficacious antagonists of melanin-concentrating hormone receptor 1," J. Med. Chem. (2006) 49(24):7095-7107.
Thompson, H.W. et al., "Stereochemical control of reductions. 9. Haptophilicity studies with 1,1-disubstituted 2-methyleneacenaphthenes," J. Org. Chem. (2002) 67(9):2813-2825.
Thomson, J.F., "Physiological effects of D20 in mammals," Annals of the N.Y. Academy of Sci. (1960) 84:736-744.
Ting, P.C. et al., "The synthesis of substituted bipiperidine amide compounds as CCR3 antagonists," Bioorg. Med. Chem. Lett. (2005) 15(5):1375-1378.
Tsai, G. et al., "Gene knockout of glycine transporter 1: characterization of the behavioral phenotype," PNAS (2004) 101(22):8485-8490.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.

(56) References Cited

OTHER PUBLICATIONS

White, J.D. et al., "Catalyzed asymmetric diels-alder reaction of benzoquinone. Total synthesis of (−)-ibogamine," Org. Lett. (2000) 2(15):2373-2376.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Jul. 19, 2012 (7 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United States Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).
United States Patent Office Notice of Allowance for U.S. Appl. No. 13/206,937 dated Feb. 21, 2014 (9 pages).
United States Patent Office Action for U.S. Appl. No. 13/206,937 dated Aug. 28, 2013 (6 pages).
United States Patent Office Action for U.S. Appl. No. 13/206,750 dated Feb. 19, 2014 (6 pages).
United States Patent Office Notice of Allowance for U.S. Appl. No. 13/207,030 dated Mar. 11, 2014 (9 pages).
United States Patent Office Notice of Allowance for U.S. Appl. No. 13/207,160 dated Mar. 17, 2014 (9 pages).
United States Patent Office Action for U.S. Appl. No. 13/566,051 dated Sep. 16, 2013 (15 pages).
United States Patent Office Action for U.S. Appl. No. 13/680,488 dated Dec. 5, 2013 (17 pages).
United States Patent Office Action for U.S. Appl. No. 13/680,488 dated Jun. 21, 2013 (43 pages).
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
Written Opinion for Application No. PCT/EP2008/061007 dated Aug. 10, 2009 (7 pages).
Written Opinion for Application No. PCT/EP2009/053800 dated Nov. 20, 2009 (7 pages).
Written Opinion for Application No. PCT/EP2012/058760 dated Aug. 27, 2012 (4 pages).
United States Patent Office Notice of Allowance for U.S. Appl. No. 14/031,265 dated Jan. 27, 2015 (11 pages).

\* cited by examiner

TETRALINE AND INDANE DERIVATIVES, PHARMACEUTICAL COMPOSITIONS CONTAINING THEM, AND THEIR USE IN THERAPY

CROSS-REFERENCE TO RELATED APPLICATIONS

This is a continuation-in-part of U.S. patent application Ser. No. 13/207,160, filed on Aug. 10, 2011, which claims priority to U.S. Provisional Patent Application No. 61/373,654, filed on Aug. 13, 2010, the contents of all of which are herein fully incorporated by reference.

BACKGROUND OF THE INVENTION

The present invention relates to tetraline and indane derivatives, pharmaceutical compositions comprising such tetraline and indane derivatives, and the use of such tetraline and indane derivatives for therapeutic purposes. The tetraline and indane derivatives are GlyT1 inhibitors.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

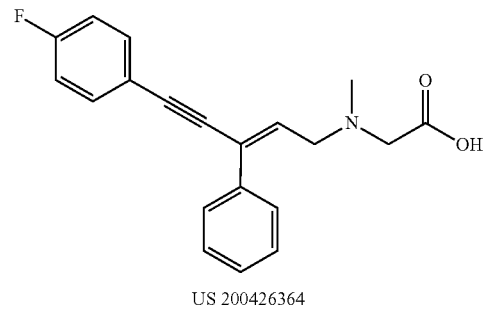

US 200426364

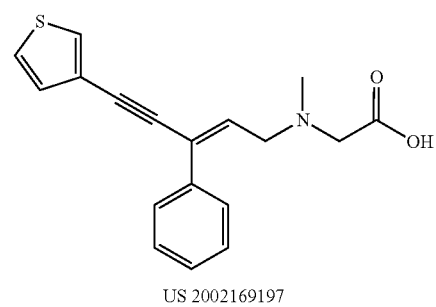

US 2002169197

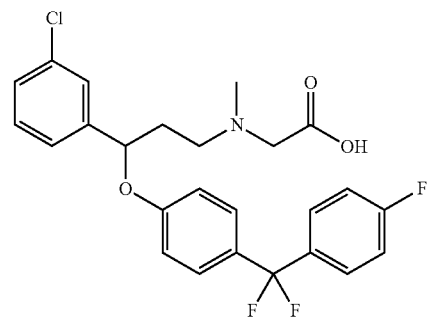

EP 1 284 257

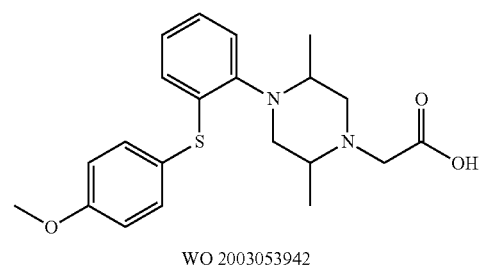

WO 2003053942

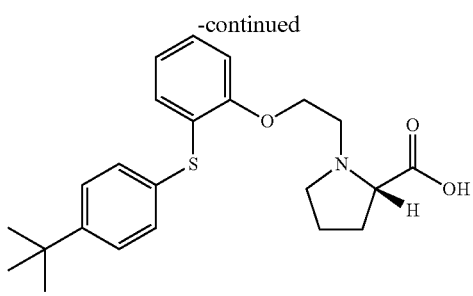
WO 2004096761
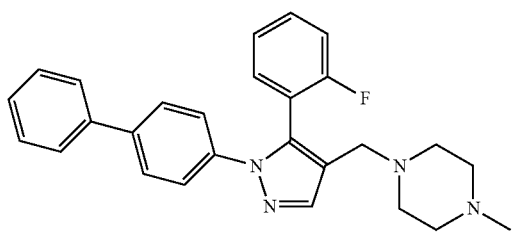
WO 2003031435
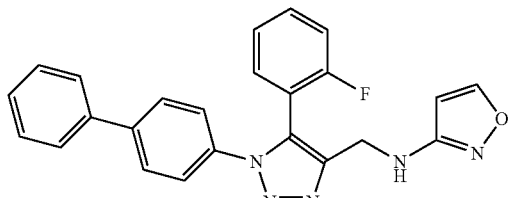
DE 10315570
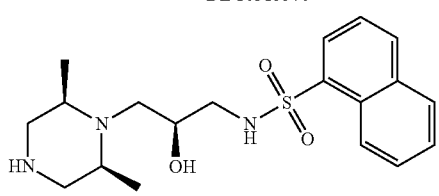
WO 2003055478
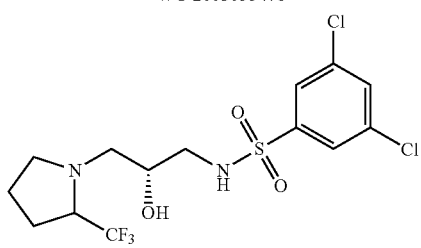
WO 2004113280
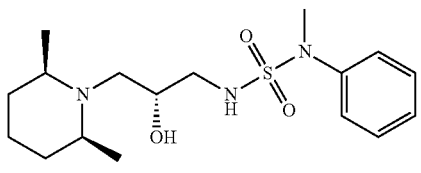
WO 2004112787
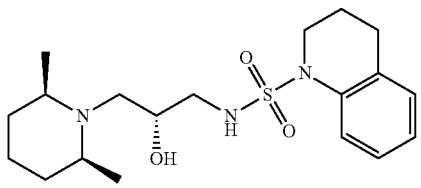
WO 2004113301
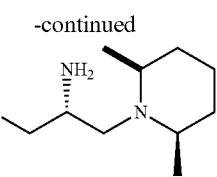
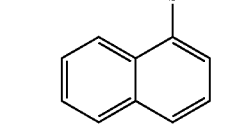
WO 02005049023
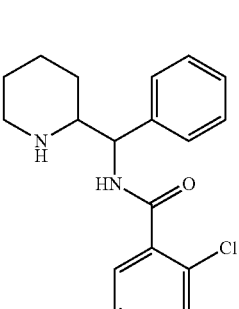
WO 2003089411
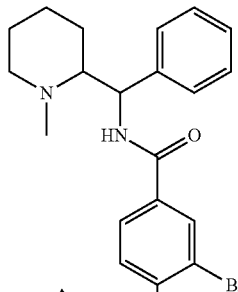
WO 2004013100
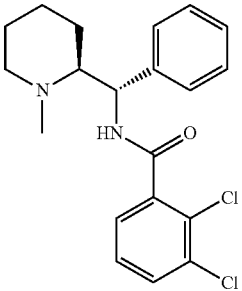
WO 2004013101
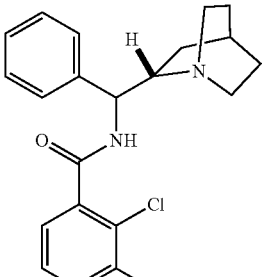
WO 2005037783
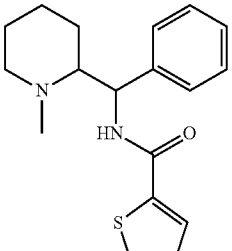
WO 2005037792
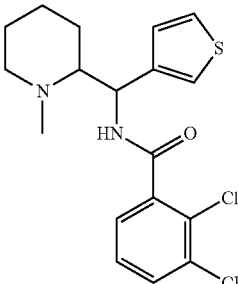
WO 2005037781
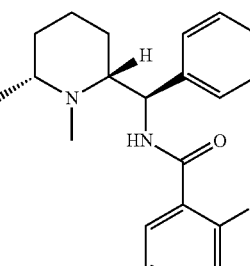
WO 2005037781
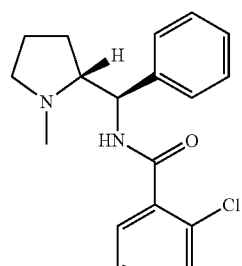
WO 2005037785

5
-continued
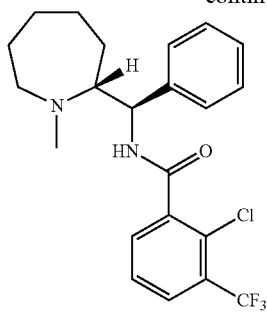
WO 2005037785
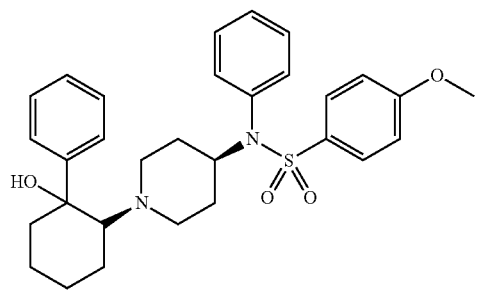
WO 2004072034
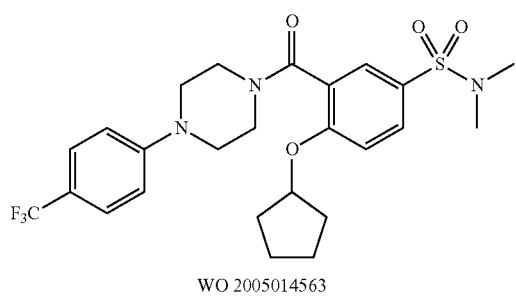
WO 2005014563
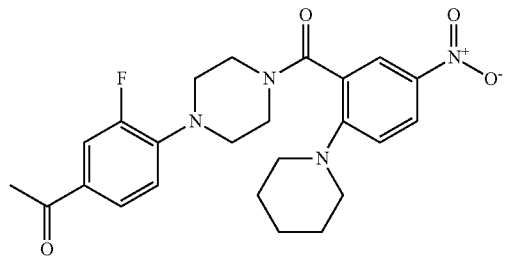
WO 2005023260
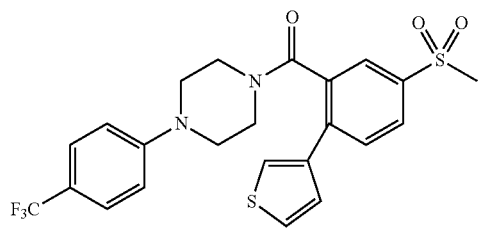
WO 2005023261
6
-continued
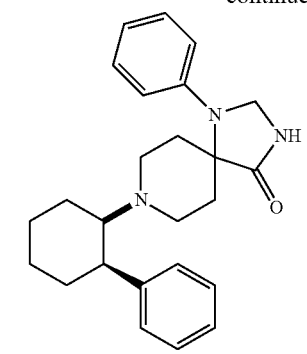
WO 2005040166
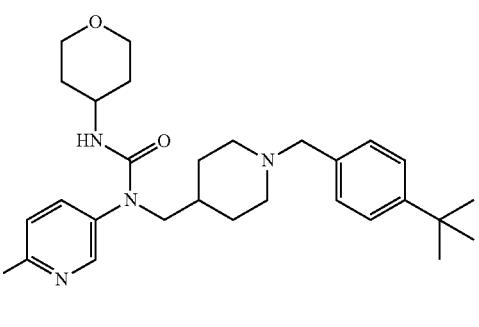
WO 2005058882
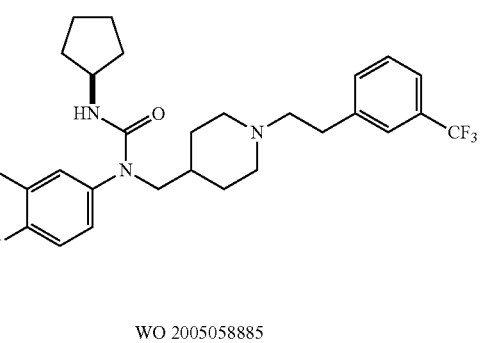
WO 2005058885
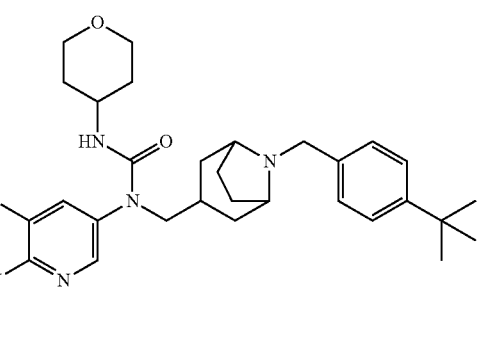
WO 2005058317

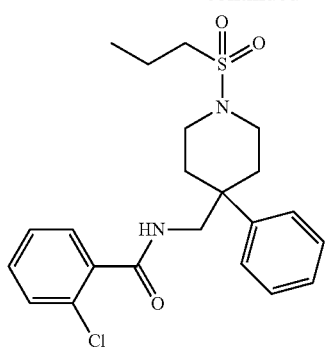

WO 2005046601

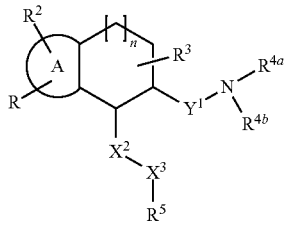

WO 2003087086

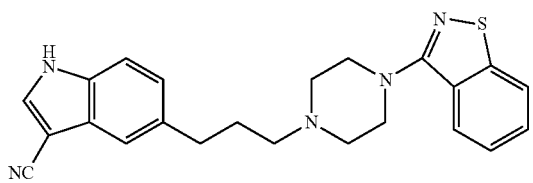

WO 2003076420

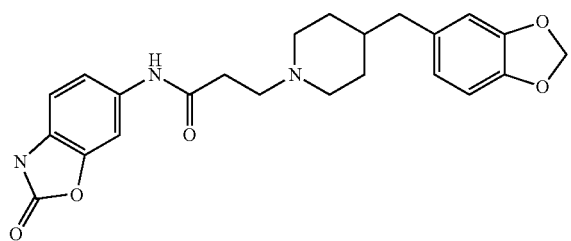

WO 2004022528

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to tetraline and indane derivatives of the formula (I)

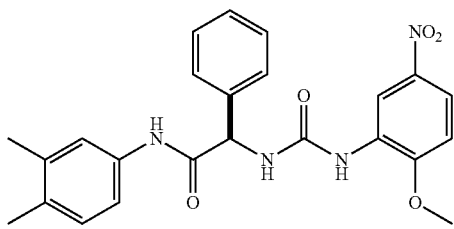

(I)

wherein

A is a 5- or 6-membered ring;

R is $R^1$—W-$A^1$-Q-Y-$A^2$-$X^1$—;

$R^1$ is hydrogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl) aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl) sulfonylamino, arylsulfonylamino or optionally substituted heterocyclyl;

W is —$NR^8$— or a bond;

$A^1$ is optionally substituted alkylene or a bond;

Q is —$S(O)_2$— or —C(O)—;

Y is —$NR^9$— or a bond;

$A^2$ is optionally substituted alkylene, alkylene-CO—, —CO-alkylene, alkylene-O-alkylene, alkylene-$NR^{10}$-alkylene, optionally substituted alkenylene, optionally substituted alkynylene, optionally substituted arylene, optionally substituted heteroarylene or a bond;

$X^1$ is —O—, —$NR^{11}$—, —S—, optionally substituted alkylene, optionally substituted alkenylen, optionally substituted alkynylene;

$R^2$ is hydrogen, halogen, alkyl, halogenated alkyl, hydroxyalkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals $R^2$ together with the ring atoms of A to which they are bound form a 5- or 6-membered ring;

$R^3$ is hydrogen, halogen, alkyl or alkoxy, or two radicals $R^3$ together with the carbon atom to which they are attached form a carbonyl group;

$Y^1$ is optionally substituted alkylene;

$R^{4a}$ is hydrogen, alkyl, cycloalkylalkyl, halogenated alkyl, hydroxyalkyl, alkoxyalkyl, aminoalkyl, $CH_2CN$, aralkyl, cycloalkyl, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl; or $R^{4a}$ is optionally substituted alkylene that is bound to a carbon atom in $Y^1$;

$R^{4b}$ is hydrogen, alkyl, halogenated alkyl, hydroxyalkyl, alkoxyalkyl, aminoalkyl, $CH_2CN$, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl; or $R^{4a}$, $R^{4b}$ together are optionally substituted alkylene, wherein one —CH$_2$— of alkylene may be replaced by an oxygen atom or —NR$^{16}$;

$X^2$ is —O—, —NR$^6$—, —S—, >CR$^{12a}$R$^{12b}$ or a bond;

$X^3$ is —O—, —NR$^7$—, —S—, >CR$^{13a}$R$^{13b}$ or a bond;

$R^5$ is optionally substituted aryl, optionally substituted cycloalkyl or optionally substituted heterocyclyl;

n is 0, 1 or 2;

$R^6$ is hydrogen or alkyl;

$R^7$ is hydrogen or alkyl;

$R^8$ is hydrogen or alkyl;

$R^9$ is hydrogen, alkyl, cycloalkyl, aminoalkyl, optionally substituted arylalkyl or heterocyclyl; or $R^9$, $R^1$ together are alkylene; or $R^9$ is alkylene that is bound to a carbon atom in $A^2$ and $A^2$ is alkylene or to a carbon atom in $X^1$ and $X^1$ is alkylene;

$R^{10}$ is hydrogen, alkyl or alkylsulfonyl;

$R^{11}$ is hydrogen or alkyl, or $R^9$, $R^{11}$ together are alkylene, $R^{12a}$ is hydrogen, optionally substituted alkyl, alkylaminoalkyl, dialkylaminoalkyl, heterocyclylalkyl, optionally substituted aryl or hydroxy;

$R^{12b}$ is hydrogen or alkyl, or $R^{12a}$, $R^{12b}$ together are carbonyl or optionally substituted alkylene, wherein one —CH$_2$— of alkylene may be replaced by an oxygen atom or —NR$^{14}$—;

$R^{13a}$ is hydrogen, optionally substituted alkyl, alkylaminoalkyl, dialkylaminoalkyl, heterocyclylalkyl, optionally substituted aryl or hydroxy;

$R^{13b}$ is hydrogen or alkyl, or $R^{13a}$, $R^{13b}$ together are carbonyl or optionally substituted alkylene, wherein one —CH$_2$— of alkylene may be replaced by an oxygen atom or —NR$^{15}$—;

$R^{14}$ is hydrogen or alkyl;

$R^{15}$ is hydrogen or alkyl; and $R^{16}$ is hydrogen or alkyl, or a physiologically tolerated salt thereof.

According to a second aspect, the present invention relates to tetraline and indane derivatives of the formula (I) or a physiologically tolerated salt thereof, wherein the $Y^1$ is a bond, $R^{4a}$ is cycloalkyl and A, $R^1$, W, $A^1$, Q, Y, $A^2$, $R^2$, $R^3$, $R^{4b}$, $X^2$, $X^3$, $R^5$, n are as defined herein, provided that the tetraline and indane derivative is not propane-1-sulfonic acid (8-benzyl-7-cyclopropylamino-5,6,7,8-tetrahydro-naphthalen-2-ylmethyl)-amide or a physiologically tolerated salt thereof such as the hydrochloride.

Thus, the present invention relates to tetraline and indane derivatives having the formula (Ia)

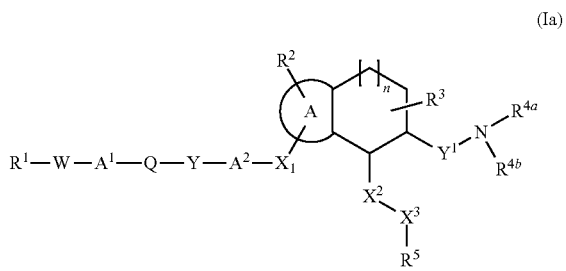

(Ia)

wherein A, $R^1$, W, $A^1$, Q, Y, $A^2$, $X^1$, $R^2$, $R^3$, $Y^1$, $R^{4a}$, $R^{4b}$, $X^2$, $X^3$, $R^5$, n are as defined herein.

Further, the present invention relates to tetraline and indane derivatives of formula (I) wherein R is —CN, i.e. tetraline and indane derivatives having the formula (Ib)

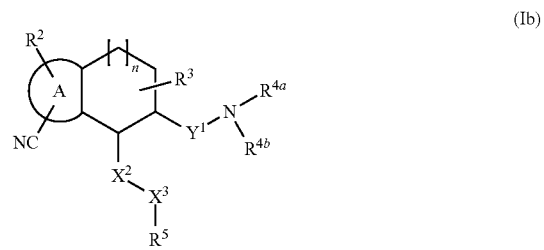

(Ib)

wherein A, $R^2$, $R^3$, $Y^1$, $R^{4a}$, $R^{4b}$, $X^2$, $X^3$, $R^5$, n are as defined herein.

Thus, the term tetraline and indane derivative is used herein to denote in particular tetralines (n=1) and fused cyclohexanes (n=1) wherein the benzene ring is replaced by a 5- or 6-membered heterocyclic ring as well as homologous bicyclic compounds wherein n is 0 or 2.

Said compounds of formula (I), i.e., the tetraline and indane derivatives of formula (I) and their physiologically tolerated salts, are glycine transporter inhibitors and thus useful as pharmaceuticals.

The present invention thus further relates to the compounds of formula (I) for use in therapy.

The present invention also relates to pharmaceutical compositions which comprise a carrier and a compound of formula (I).

In particular, said compounds, i.e., the tetraline and indane derivatives and their physiologically tolerated salts, are inhibitors of the glycine transporter GlyT1.

The present invention thus further relates to the compounds of formula (I) for use in inhibiting the glycine transporter.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention further relates to the compounds of formula (I) for use in treating pain.

The present invention also relates to the use of the compounds of formula (I) in the manufacture of a medicament for treating a neurologic or psychiatric disorder and corresponding methods of treating said disorders. The present invention also relates to the use of the compounds of formula (I) in the manufacture of a medicament for treating pain and corresponding methods of treating pain.

The present invention further relates to tetraline and indane derivatives of formula (II)

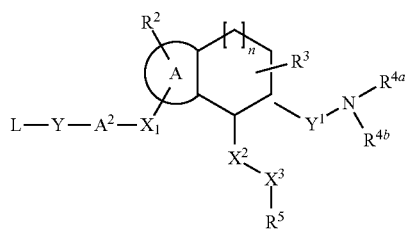

(II)

wherein L is an amino-protecting group, Y is $NR^9$, and $A^2$, $X^1$, $R^2$, $R^3$, $Y^1$, $R^{4a}$, $R^{4b}$, $X^2$, $X^3$, $R^5$, n and $R^9$ are defined as above.

The tetraline and indane derivatives of formula (II) are useful as intermediates in the preparation of GlyT1 inhibitors, in particular those of formula (I).

DETAILED DESCRIPTION OF THE INVENTION

Provided that the tetraline and indane derivatives of the formula (I) or (II) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) or (II) and/or of their salts.

According to one embodiment, an enantiomer of the compounds of the present invention has the following formula:

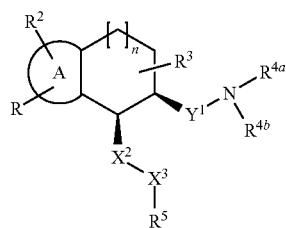

wherein A, R, $R^2$, $R^3$, $Y^1$, $R^{4a}$, $R^{4b}$, $X^2$, $X^3$, $R^5$, n are as defined herein.

According to another embodiment, an enantiomer of the compounds of the present invention has the following formula:

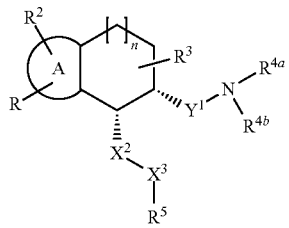

wherein A, R, $R^2$, $R^3$, $Y^1$, $R^{4a}$, $R^{4b}$, $X^2$, $X^3$, $R^5$, n are as defined herein.

According to one embodiment, an enantiomer of the compounds of the present invention has the following formula:

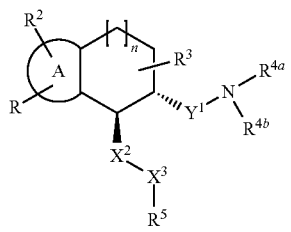

wherein A, R, $R^2$, $R^3$, $Y^1$, $R^{4a}$, $R^{4b}$, $X^2$, $X^3$, $R^5$, n are as defined herein.

According to another embodiment, an enantiomer of the compounds of the present invention has the following formula:

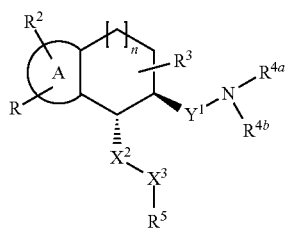

wherein A, R, $R^2$, $R^3$, $Y^1$, $R^{4a}$, $R^{4b}$, $X^2$, $X^3$, $R^5$, n are as defined herein.

The physiologically tolerated salts of the tetraline and indane derivatives of the formula (I) or (II) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. The physiologically tolerated salts of the tetraline and indane derivatives also include salts of a physiologically tolerated anion with tetraline and indane derivatives wherein one or more than one nitrogen atom is quaternized, e.g. with an alkyl residue (e.g. methyl or ethyl).

The present invention moreover relates to compounds of formula (I) or (II) as defined herein, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, such compounds contain more of the respective isotope than this naturally occurs and thus is anyway present in the compounds (I) or (II).

Stable isotopes (e.g., deuterium, $^{13}C$, $^{18}N$, $^{18}O$) are nonradioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic Press, London, 1985; Kato et al., J. Labelled Comp. Radiopharmaceut., 36(10):927-932 (1995); Kushner et al., Can. J. Physiol. Pharmacol., 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7:13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003);

PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$-$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1C_4$-alkoxy-$C_1$-$C_4$ alkyl, amino-$C_1$-$C_4$-alkyl, $C_1$-$C_4$-alkenyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, $NH_2$, NH—$C_1$-$C_6$-alkyl, N—($C_1$-$C_6$-alkyl)$_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2$NH—$C_6$-$C_{12}$-aryl, CONH—$C_3$-$C_{12}$-heterocyclyl, $SO_2$NH—$C_3$-$C_{12}$-heterocyclyl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl, oxo (=O) being a further substituent, wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, iso-butylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, iso-propylsulfonylaminomethyl, n-butylsulfonylaminomethyl, 2-butylsulfonylaminomethyl, iso-butylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is $>C=O$.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene. A further example is propylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, iso-butoxy(2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, iso-propylcarbonylaminomethoxy, n-butylcarbonylaminomethoxy, 2-butylcarbonylaminomethoxy, iso-butylcarbonylaminomethoxy, tert-butylcarbonyl-aminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonyl-amino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, iso-butoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(iso-butoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy(2-propen-1-yloxy), 1-propen-1-yloxy, 2-propen-2-yloxy, methallyloxy (2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is $NH_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido(methylcarbonylamino), propionamido, n-butyramido, 2-methylpropionamido(isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino(2-propen-1-ylamino), 1-propen-1-ylamino, 2-propen-2-ylamino, methallylamino(2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, iso-propylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene.

With respect to the compounds' capability of inhibiting glycine transporter 1, the variables A, R, $R^1$, W, $A^1$, Q, Y, $A^2$, $X^1$, $R^2$, $R^3$, $Y^1$, $R^{4a}$, $R^{4b}$, $X^2$, $X^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, n preferably have the following meanings which, when taken alone or in combination, represent particular embodiments of the compounds of the formula (I), (II) or any other formula disclosed herein.

In said formula (I) or (II), there may be one or more than one substituent R, $R^2$ and/or $R^3$. More particularly, there may be up to 3 substituents $R^2$, and up to 6 substituents $R^3$. Preferably there is one substituent R and 1, 2 or 3 substituents $R^2$. Formula (I) may thus be depicted as follows:

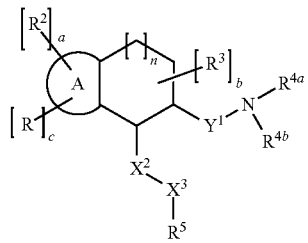

wherein a is 1, 2 or 3, b is 1, 2, 3, 4, 5 or 6 and c is 1. If there is more than one radical $R^2$, these may be the same or different radicals. If there is more than one radical $R^3$, these may be the same or different radicals.

A is a 5- or 6-membered ring which includes two carbon atoms from the cyclopentane, cyclohexane or cycloheptane moiety to which A is fused. A may be a homocyclic or heterocyclic ring. The ring may be saturated, unsaturated non-aromatic or aromatic. According to a particular embodiment, A is a benzene ring. As a heterocyclic ring, A may include 1, 2 or 3 heteroatoms as ring member atoms, which are selected, independently of each other from N, S and O. Preferred heterocyclic rings comprise 1 nitrogen atom as ring member atom and optionally 1 or 2 further heteroatoms as ring members, which are selected, independently of each other from O, S and N. Likewise preferred heterocyclic rings comprise 1 heteroatom as ring member atom, which is selected from O, S and N, and optionally 1 or 2 further nitrogen atoms as ring member atoms. According to a particular embodiment, A is a heterocyclic ring selected from the group consisting of the following 5- or 6-membered heterocyclic rings:

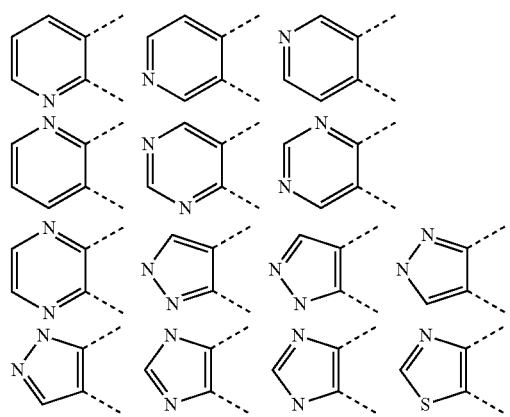

-continued

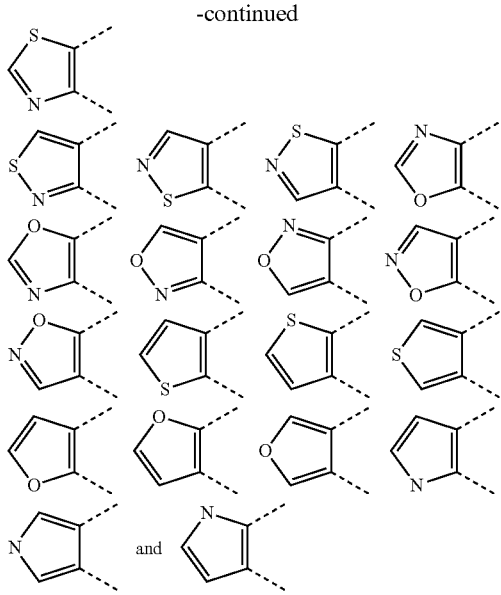

In said formulae, hydrogen atoms are not depicted. This is meant to illustrate that the free valency of a carbon or nitrogen atom may be either bound to a hydrogen atom, to R or to $R^2$. Accordingly, R and $R^2$ may be C- or N-bound at any position of ring A.

The skilled person will appreciate that some of the rings depicted above may be represented with a different structure, e.g. with hydrogen atoms having other positions than those shown above, for instance as given in the following structures:

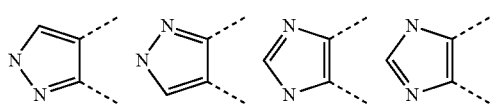

Preferably, A is a heterocyclic ring selected from the group consisting of the following 5- or 6-membered heterocyclic rings:

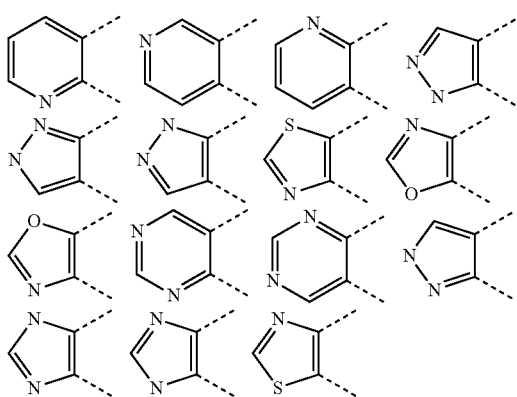

According to a further particular embodiment, A is a heterocyclic ring selected from the group consisting of the following 5- or 6-membered heterocyclic rings:

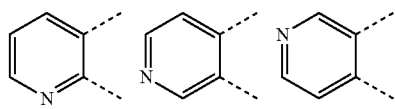

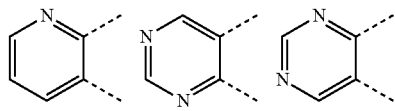

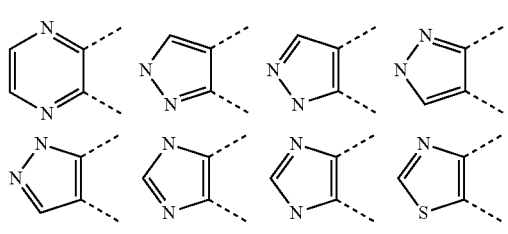

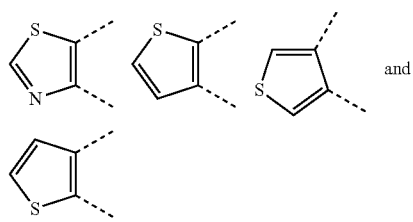

According to a preferred embodiment, A is a heterocyclic ring selected from the group consisting of the following 5- or 6-membered heterocyclic rings:

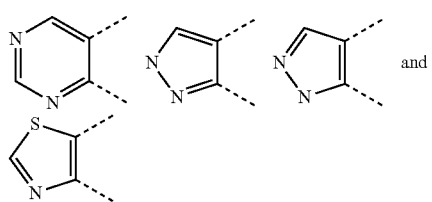

If ring A is a 5-membered heterocyclic ring it is preferred that R is bound to $G^1$ or $G^2$, in particular $G^2$:

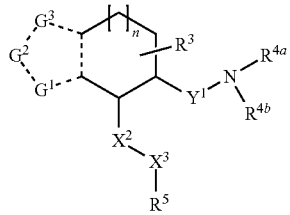

In said formula, $G^1$, $G^2$ and $G^3$ independently are —CH=, —CH$_2$—, —N=, —NH—, S or O, at least one of $G^1$, $G^2$ and $G^3$ is —CH= or —CH$_2$—, the dotted line represents a single or a double bond and $R^3$, $Y^1$, $R^{4a}$, $R^{4b}$, $X^2$, $X^3$, $R^5$, n are as defined herein.

If ring A is 6-membered heterocyclic ring it is preferred that R is bound to $G^1$ or $G^2$, in particular $G^2$:

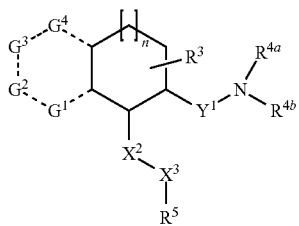

In said formula, $G^1$, $G^2$, $G^3$ and $G^4$ independently are —CH=, —CH$_2$—, —N=, —NH—, S or O, at least one of $G^1$, $G^2$, $G^3$ and $G^4$ is —CH= or —CH$_2$—, the dotted line represents a single or a double bond and $R^3$, $Y^1$, $R^{4a}$, $R^{4b}$, $X^2$, $X^3$, $R^5$, n are as defined herein.

Heterocyclic compounds having the following partial structures are preferred:

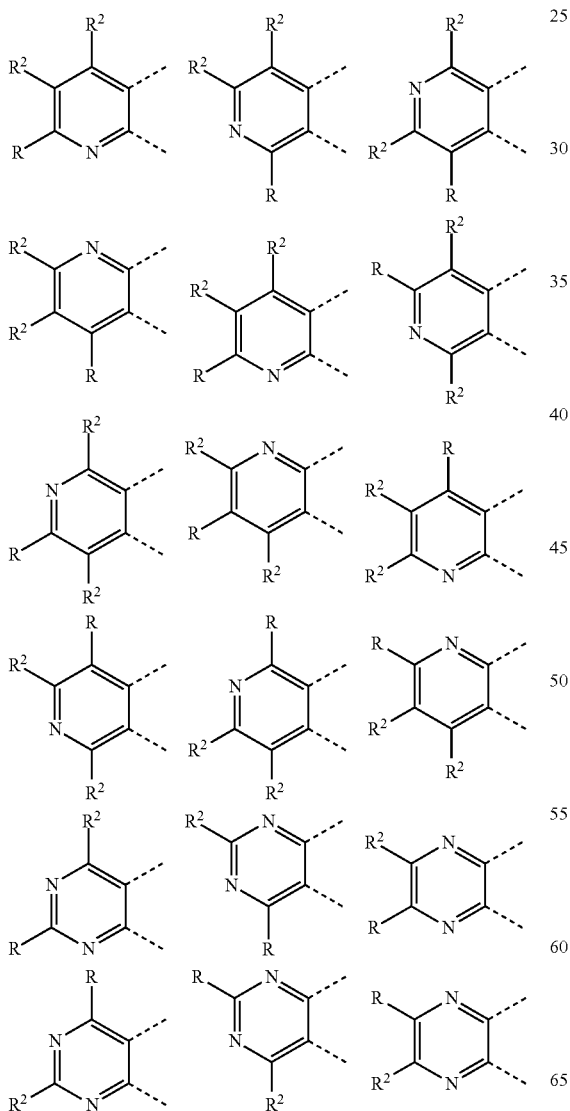

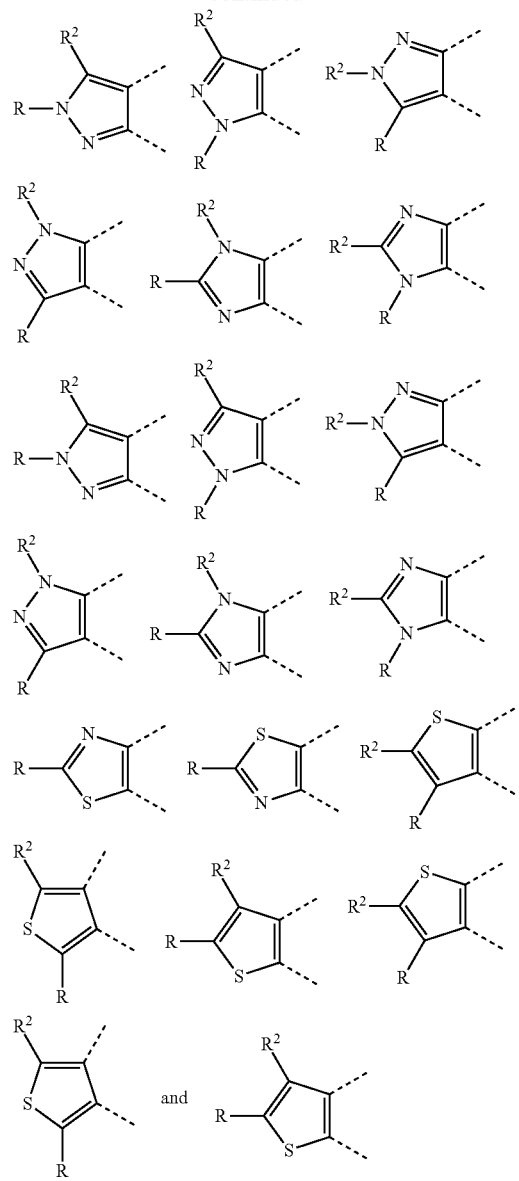

Heterocyclic compounds having the following partial structures are particularly preferred:

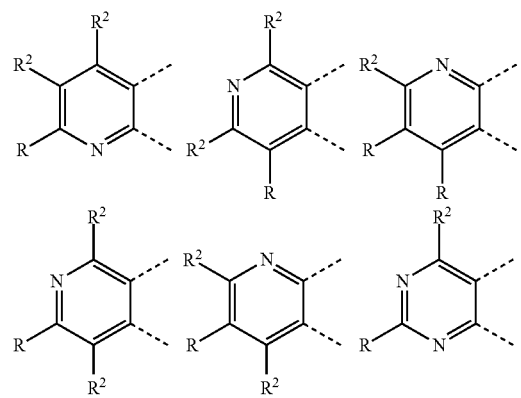

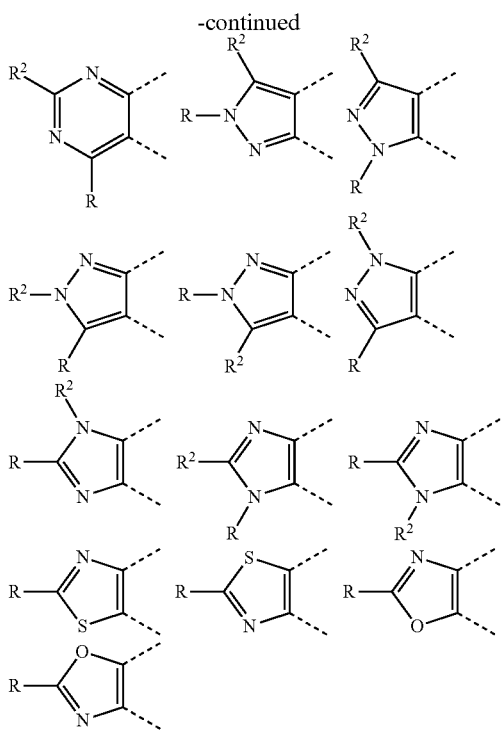

In said formulae, R and $R^2$ are as defined herein. If there is more than one radical $R^2$, these may be the same or different radicals.

According to a particular embodiment, the partial structures depicted above are fused with a cyclohexane moiety (i.e., n is 1). The same applies to the preferred and particular embodiments disclosed for ring A.

According to one embodiment, R is cyano.

Preferably, R is $R^1$—W-$A^1$-Q-Y-$A^2$-$X^1$— and A, $R^1$, W, $A^1$, Q, Y, $A^2$, $X^1$, $R^2$, $R^3$, $Y^1$, $R^{4a}$, $R^{4b}$, $X^2$, $X^3$, $R^5$, n are as defined herein.

$R^1$ is hydrogen, $C_1$-$C_6$-alkyl (e.g. methyl, ethyl, n-propyl, isopropyl, n-butyl, sec-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), hydroxy-$C_1$-$C_4$-alkyl, $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl (e.g. cyclopropyl or cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl (e.g. prop-1,2-en-1-yl), $C_2$-$C_6$-alkynyl, optionally substituted $C_6$-$C_{12}$-aryl (e.g. phenyl, 2-methylphenyl), hydroxy, $C_1$-$C_6$-alkoxy (e.g. tert-butyloxy), halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino (e.g. dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl, 3-pyrrolidinyl, 1-methyl-pyrrol-3-yl, 2-pyridyl, 1-methyl-1,2-diazol-3-yl, 1-methyl-3-trifluoromethyl-1,2-diazol-4-yl, 1,2-dimethyl-1,3-diazol-4-yl, 5-methylisoxazol-3-yl or 1-methyl-1,2,4-triazol-3-yl).

Preferably, $R^1$ is $C_1$-$C_6$-alkyl (e.g. methyl, ethyl, n-propyl, isopropyl, sec-butyl, n-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl).

In particular, $R^1$ is $C_1$-$C_6$-alkyl (e.g. n-propyl), $C_3$-$C_{12}$-cycloalkyl-$C_1$-$C_4$-alkyl (e.g. cyclopropylmethyl), $C_3$-$C_{12}$-cycloalkyl (e.g. cyclobutyl), or optionally substituted $C_3$-$C_{12}$-heterocyclyl (e.g. 3-pyridyl, 1-methyl-1,2-diazol-4-yl, 1-methyl-1,3-diazol-4-yl, 3-oxetanyl, 1-methyl-pyrrol-3-yl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, piperidinyl, piperazinyl or morpholinyl, pyrrolyl, isoxazolyl and triazolyl being further examples of such $C_3$-$C_{12}$-heterocyclyl, substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl). The same applies to substituted $C_3$-$C_{12}$-heteroaryl in substituted $C_3$-$C_{12}$-heteroaryl-$C_1$-$C_4$-alkyl.

According to one embodiment, W is —$NR^8$— and Y is a bond. According to an alternative embodiment, W is a bond and Y is —$NR^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —$S(O)_2$—. According to an alternative embodiment, Q is —$C(O)$—.

According to a particular embodiment, —W-$A^1$-Q-Y— is —W-$A^1$—$S(O)_2$—$NR^9$—, —$NR^8$—$S(O)_2$—, -$A^1$-$S(O)_2$— or —$S(O)_2$—. According to a further particular embodiment, —W-$A^1$-Q-Y— is —W-$A^1$—CO—$NR^9$— or —$NR^8$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —$NR^8$—.

$A^2$ is optionally substituted $C_1$-$C_4$-alkylene (e.g. 1,2-ethylene or 1,3-propylene), $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond. Additionally, $A^2$ may be optionally substituted $C_2$-$C_4$-alkenylene or optionally substituted $C_2$-$C_4$-alkynylene. Preferably, $A^2$ is optionally substituted $C_1$-$C_4$-alkylene (e.g. 1,2-ethylene or 1,3-propylene). More preferably, $A^2$ is $C_1$-$C_4$-alkylene (e.g. 1,2-ethylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, $X^1$ is preferably optionally substituted $C_1$-$C_4$-alkylene. Alternatively, if $A^2$ is a bond, $X^1$ is in particular optionally substituted $C_2$-$C_4$-alkenylene or optionally substituted $C_2$-$C_4$-alkynylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g, morpholino or piperidinyl).

$X^1$ is —O—, —$NR^{11}$—, —S— or optionally substituted $C_1$-$C_4$-alkylene (e.g. —$CH_2$—, 1,2-ethylene and 1,3-propylene). In connection with $X^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Additionally, $X^1$ may be optionally substituted $C_2$-$C_4$-alkenylen or optionally substituted $C_2$-$C_4$-alkynylene (e.g. propynylene). In connection with $X^1$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano. Preferably, $X^1$ is —O—, —$NR^{11}$, —S—. More preferably, $X^1$ is —O—. Alternatively, it is preferred if $X^1$ is optionally substituted $C_1$-$C_4$-alkylene (e.g. —$CH_2$— or 1,2-ethylene).

According to a particular embodiment, $A^2$ is a bond and $X^1$ is optionally substituted $C_1$-$C_4$-alkylene, optionally substituted $C_2$-$C_4$-alkenylene or optionally substituted $C_2$-$C_4$-alkynylene.

According to a particular embodiment, $R^1$—W-$A^1$-Q-Y-$A^2$-$X^1$— is $R^1$—$S(O)_2$—NH-$A^2$-$X^1$—, $R^1$—NH—$S(O)_2$-$A^2$-$X^1$—, $R^1$—$C(O)$—NH-$A^2$-$X^1$— or $R^1$—NH—$C(O)$-$A^2$-$X^1$—.

According to a particular embodiment, the structural element —Y-$A^2$-$X^1$— comprises at least 2, 3 or 4 atoms in the main chain. According to further particular embodiments the structural element —Y-$A^2$-$X^1$— has up to 4, 5 or 6 atoms in the main chain, such as 2 to 6, 2 to 5 or 2 to 4 atoms in the main chain, especially 2, 3 or 4 atoms in the main chain.

According to a further particular embodiment, —Y-$A^2$-$X^1$— is —$C_1$-$C_4$-alkylene-O— or —$NR^9$—$C_1$-$C_4$-alkylene-O—, with —Y-$A^2$-$X^1$— preferably having 2 to 6, 3 to 5 and especially 4 atoms in the main chain. Particular examples of —Y-$A^2$-$X^1$— include —$(CH_2)_3$—O— and —$NR^9$—$(CH_2)_2$—O—. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl), or $R^9$ is $C_1$-$C_4$-alkylene that is bound to a carbon atom in $A^2$ which is $C_1$-$C_4$-alkylene.

According to a further particular embodiment, —Y-$A^2$-$X^1$— is —$NR^9$—$C_1$-$C_4$-alkylene- (e.g. —NH—$CH_2$—, —NH—$(CH_2)_2$— or —NH—$(CH_2)_3$—), with —Y-$A^2$-$X^1$— preferably having 2 to 6, 2 to 5, 2 to 4 and especially 2, 3 or 4 atoms in the main chain. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl); or $R^9$ is $C_1$-$C_4$-alkylene that is bound to a carbon atom in $X^1$ which is $C_1$-$C_4$-alkylene.

According to a further particular embodiment, —Y-$A^2$-$X^1$— is —$NR^9$—$C_2$-$C_4$-alkenylene- or —$NR^9$—$C_2$-$C_4$-alkynylene- (e.g. —NH—$CH_2$—C≡C—), with —Y-$A^2$-$X^1$— preferably having 2 to 6, 3 to 5 and especially 4 atoms in the main chain. In this particular embodiment, $R^9$ is as defined herein and preferably is $R^9$ is hydrogen, $C_1$-$C_6$-alkyl (e.g. methyl or ethyl) or $C_3$-$C_{12}$-cycloalkyl (e.g. cyclopropyl or cyclobutyl). If A is a heterocyclic ring, this embodiment of —Y-$A^2$-$X^1$— is particularly suitable.

According to a further particular embodiment, —Y-$A^2$-$X^1$— is —$C_1$-$C_4$-alkylene- (e.g. —$(CH_2)_2$—), with —Y-$A^2$-$X^1$— preferably having 2 to 6, 2 to 5, 2 to 4 and especially 2 atoms in the main chain. If A is a heterocyclic ring, this embodiment of —Y-$A^2$-$X^1$— is particularly suitable.

According to a further particular embodiment, the structural motif —Y-$A^2$-$X^1$ as disclosed herein is bound to Q being —$S(O)_2$— or —$C(O)$—. Particular examples for this embodiment include heterocyclic compounds of the invention wherein R is $R^1$—$S(O)_2$—Y-$A^2$-$X^1$ or $R^1$—C(O)—Y-$A^2$-$X^1$.

The radical R and in particular the radical $R^1$—W-$A^1$-Q-Y-$A^2$-$X^1$— may, in principle, be bound to the 5-, 6-, 7- or 8-position of the skeleton of the compounds of the invention:

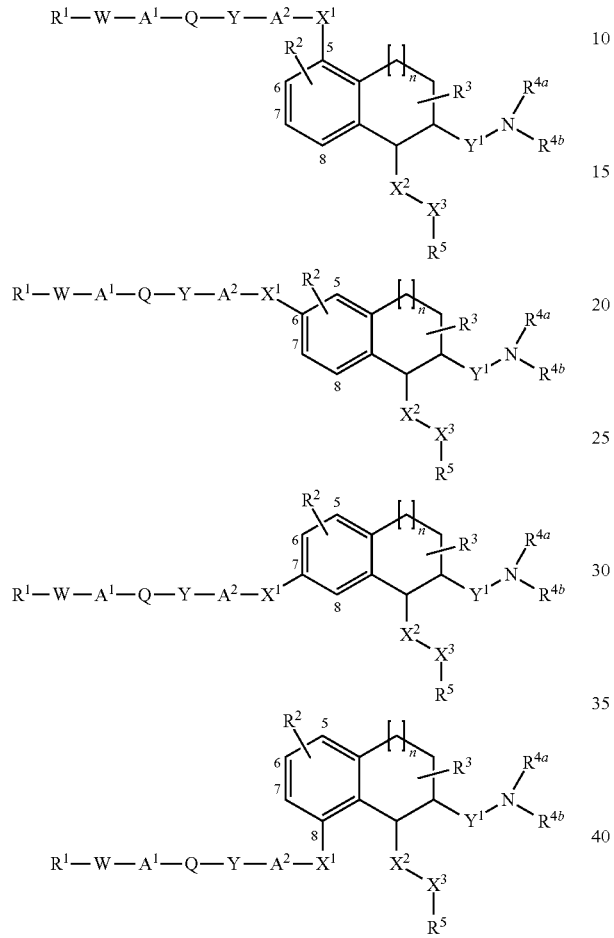

In said formulae, $R^1$, W, $A^1$, Q, Y, $A^2$, $X^1$, $R^2$, $R^3$, $Y^1$, $R^{4a}$, $R^{4b}$, $X^2$, $X^3$, $R^5$, n are as defined herein.

Further particular examples include compounds of the above formulae wherein the radical $R^1$—W-$A^1$-Q-Y-$A^2$-$X^1$— is replaced by the radical —CN.

Compounds of the invention having the radical $R^1$—W-$A^1$-O—Y-$A^2$-$X^1$— (or the radical —CN) in the 5-, 6-, 7-position are preferred.

Particularly preferred are compounds of the invention having the radical $R^1$—W-$A^1$-Q-Y-$A^2$-$X^1$— (or the radical —CN) in the 7-position.

In addition to the radical $R^1$—W-$A^1$-Q-Y-$A^2$-$X^1$— (or the radical —CN), the compounds of the invention may have one or more than one further substituent bound to the ring A. In these positions, the skeleton of the compounds of the invention may thus be substituted with one or more than one radical $R^2$. If there is more than one radical $R^2$, these may be the same or different radicals. In particular, in 5-, 6-, 7- and/or 8-position, the skeleton of the compounds of the invention may be substituted with one or more radical $R^2$. The compounds of the invention may therefore be represented by one of the following formulae:

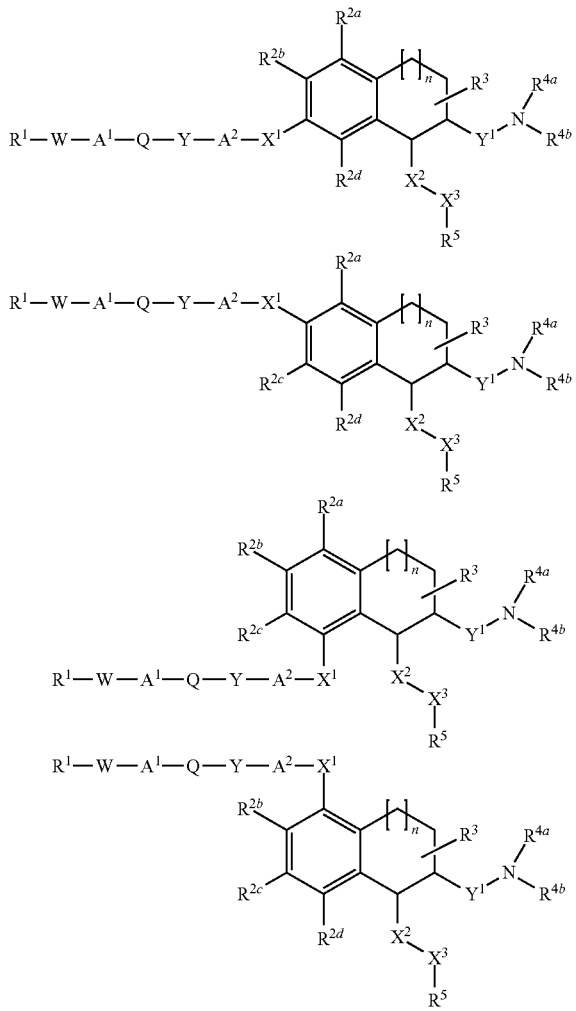

or by corresponding formulae wherein the radical $R^1$—W-$A^1$-Q-Y-$A^2$-$X^1$— is replaced by the radical —CN, wherein $R^{2a}$, $R^{2b}$, $R^{2c}$, $R^{2d}$ independently have one of the meanings given for $R^2$, and $R^1$, W, $A^1$, Q, Y, $A^2$, $X^1$, $R^2$, $R^3$, $Y^1$, $R^{4a}$, $R^{4b}$, $X^2$, $X^3$, $R^5$, n are as defined herein.

$R^2$ is hydrogen, halogen (e.g. fluorine), $C_1$-$C_6$-alkyl, halogenated $C_1$-$C_4$-alkyl, hydroxy-$C_1$-$C_4$ alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms to which they are bound form a 5- or 6 membered ring.

An optionally substituted 5- or 6-membered ring that is formed by two radicals $R^2$ together with the ring atoms of A to which they are bound is, for instance, a benzene ring.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen and $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $C_3$-$C_{12}$-heterocyclyl in particular includes $C_3$-$C_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

Preferably, $R^2$ is hydrogen, halogen (e.g. fluorine) or $C_1$-$C_6$-alkoxy. In particular, $R^2$ is hydrogen or halogen (e.g. fluorine).

According to a particular embodiment, the compounds of the invention have one of the following formulae:

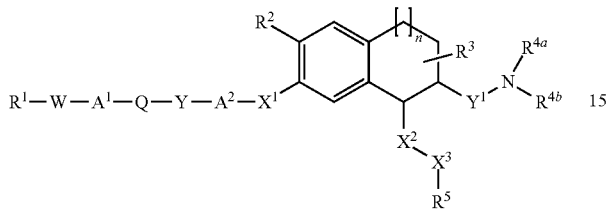

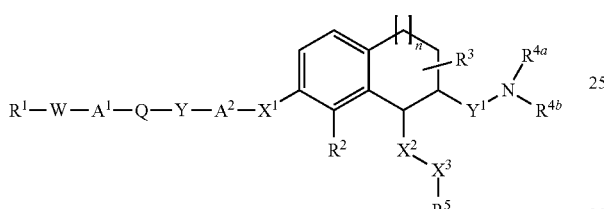

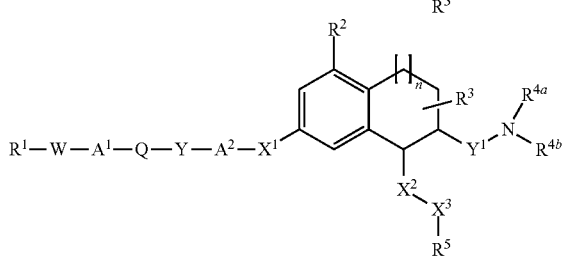

or by corresponding formulae wherein the radical $R^1$—W-$A^1$-Q-Y-$A^2$-$X^1$— is replaced by the radical —CN, wherein $R^1$, W, $A^1$, Q, Y, $A^2$, $X^1$, $R^2$, $R^3$, $Y^1$, $R^{4a}$, $R^{4b}$, $X^2$, $X^3$, $R^5$, n are as defined herein.

In 1-, 2-, 3- and/or 4-position, the compounds of the invention may be substituted with one or more than one radical $R^3$. If there is more than one radical $R^3$, these may be the same or different radicals. The compounds of the invention may therefore be represented by the following formula:

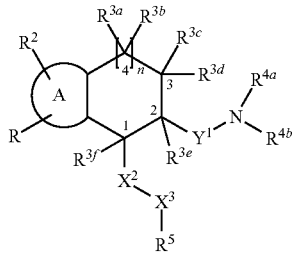

wherein $R^{3a}$, $R^{3b}$, $R^{3c}$, $R^{3d}$, $R^{3e}$, $R^{3f}$ independently have one of the meanings given for $R^3$, and A, R, $R^2$, $R^3$, $Y^1$, $R^{4a}$, $R^{4b}$, $X^2$, $X^3$, $R^5$, n are as defined herein.

According to a particular embodiment, the compounds of the invention have one of the following formulae:

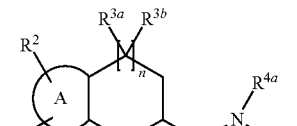

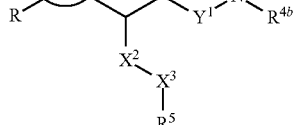

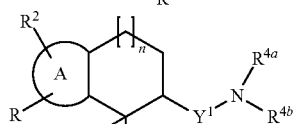

wherein $R^{3a}$, $R^{3b}$, $R^{3f}$ independently have the meaning of $R^3$ and A, R, $R^2$, $R^3$, $Y^1$, $R^{4a}$, $R^{4b}$, $X^2$, $X^3$, $R^5$, n are as defined herein.

$R^3$ is hydrogen, halogen, $C_1$-$C_6$-alkyl, $C_1$-$C_6$-alkoxy, or two radicals $R^3$ together with the carbon atom to which they are attached form a carbonyl group.

Preferably, $R^3$ is hydrogen or $C_1$-$C_6$-alkyl. In particular, $R^3$ is hydrogen.

$Y^1$ is optionally substituted $C_1$-$C_4$-alkylene (e.g. methylene or 1,2-ethylene). In connection with $Y^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, $C_3$-$C_{12}$-cycloalkyl and cyano. In particular, $Y^1$ is $C_1$-$C_4$-alkylene (e.g. methylene or 1,2-ethylene).

$R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), hydroxy-$C_1$-$C_4$-alkyl, $C_1$-$C_6$-alkoxy-$C_1$-$C_4$-alkyl, amino-$C_1$-$C_4$-alkyl, $CH_2CN$, $C_6$-$C_{12}$-aryl-$C_1$-$C_4$-alkyl (e.g. benzyl), $C_3$-$C_{12}$-cycloalkyl (e.g. cyclopropyl), —CHO, $C_1$-$C_4$-alkylcarbonyl (e.g. methylcarbonyl, ethylcarbonyl or isopropylcarbonyl), (halogenated $C_1$-$C_4$-alkyl)carbonyl (e.g. fluoromethylcarbonyl, difluoromethylcarbonyl, trifluoromethylcarbonyl, 1,1,1-trifluoroeth-2-ylcarbonyl or 1,1,1-trifluoroprop-3-ylcarbonyl), $C_6$-$C_{12}$-arylcarbonyl (e.g. phenylcarbonyl), $C_1$-$C_4$-alkoxycarbonyl (e.g. ethoxycarbonyl or tertbutyloxycarbonyl), $C_6$-$C_{12}$-aryloxycarbonyl (e.g. phenoxycarbonyl), $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl (e.g. 3-oxetanyl).

Preferably, $R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), amino-$C_1$-$C_4$-alkyl, $CH_2CN$, $C_6$-$C_{12}$-aryl-$C_1$-$C_4$-alkyl (e.g. benzyl), $C_3$-$C_{12}$-cycloalkyl (e.g. cyclopropyl), $C_1$-$C_4$-alkylcarbonyl (e.g. methylcarbonyl or isopropylcarbonyl), (halogenated $C_1$-$C_4$-alkyl) carbonyl (e.g. fluoromethylcarbonyl, difluoromethylcarbonyl or trifluoromethylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl), —C(=NH)NH$_2$, —C(=NH)NHCN, $C_1$-$C_6$-alkylsulfonyl, amino, —NO or $C_3$-$C_{12}$-heterocyclyl (e.g. 3-oxetanyl).

In particular, $R^{4a}$ is hydrogen; $C_1$-$C_6$-alkyl (e.g. methyl), $C_3$-$C_{12}$-cycloalkyl (e.g. cyclopropyl), or $C_3$-$C_{12}$-heterocyclyl (e.g. 3-oxetanyl).

Alternatively, $R^{4a}$ is optionally substituted $C_1$-$C_4$-alkylene (e.g. methylene or 1,2-ethylene) that is bound to a carbon atom in $Y^1$. In connection with $R^{4a}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, and cyano, with hydroxy and $C_1$-$C_4$-alkoxy being further substituents. In particular, $R^{4a}$ is $C_1$-$C_4$-alkylene (e.g. methylene or 1,2-ethylene) that is bound to a carbon atom in $Y^1$ with $Y^1$ being optionally substituted $C_1$-$C_4$-alkylene (e.g. 1,2-ethylene or 1,3-propylene) so that $R^{4a}$ and at least part of $Y^1$ together with the nitrogen atom to which $R^{4a}$ and $Y^1$ are bound form an N-containing heterocyclic ring having, in particular, 4, 5 or 6 ring member atoms (including the nitrogen atom). An alkylaminotetralin or indane derivative having such a ring may be represented by the following partial structure:

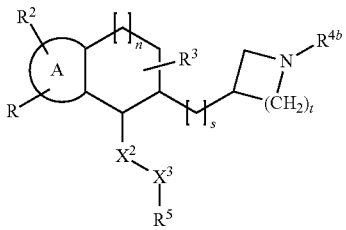

wherein A, R, $R^2$, $R^3$, $R^{4b}$, $X^2$, $X^3$, $R^5$, n are as defined herein, s is 0, 1 or 2, and t is 0, 1, 2, or 3. Particular combinations of s and t include s=1, t=1; s=0, t=1; s=1, t=2; and s=0, t=2.

$R^{4b}$ is hydrogen, $C_1$-$C_6$-alkyl (e.g. methyl, ethyl), halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl.

Preferably, $R^{4b}$ is hydrogen, $C_1$-$C_6$-alkyl (e.g. methyl). In particular, $R^{4b}$ is hydrogen.

Alternatively, $R^{4a}$, $R^{4b}$ together are optionally substituted $C_1$-$C_6$-alkylene (e.g. 1,4-butylene, 1,3-propylene, 2-fluorobut-1,4-ylene or 1-oxo-but-1,4-ylene), wherein one —$CH_2$— of $C_1$-$C_6$-alkylene may be replaced by an oxygen atom (e.g. —$CH_2$—$CH_2$—O—$CH_2$—$CH_2$—) or —$NR^{16}$.

In connection with $R^{4a}$ and $R^{4b}$, substituted $C_1$-$C_6$-alkylene in particular includes $C_1$-$C_6$-alkylene substituted with 1, 2 or 3 substituents selected from the group consisting of halogen (e.g. fluoro or chloro), $C_1$-$C_4$-alkyl, cyano, hydroxy and $C_1$-$C_4$-alkoxy.

$X^2$ is —O—, —$NR^6$—, —S—, >$CR^{12a}R^{12b}$ or a bond. Preferably, $X^2$ is >$CR^{12a}R^{12b}$.

$X^3$ is —O—, —S—, >$CR^{13a}R^{13b}$ or a bond. Preferably, $X^3$ is a bond.

Thus, it is preferred if $X^2$ is >$CR^{12a}R^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{12a}$ is hydrogen or $C_1$-$C_6$-alkyl.

$R^{13a}$ is hydrogen, optionally substituted $C_1$-$C_6$-alkyl, $C_1$-$C_6$ alkylamino $C_1$-$C_4$ alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{13a}$ is hydrogen or $C_1$-$C_6$-alkyl.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_4$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together are together are carbonyl or, preferably, optionally substituted $C_1$-$C_4$-alkylene (e.g. 1,3-propylene), wherein one —$CH_2$— of $C_1$-$C_4$-alkylene may be replaced by an oxygen atom or —$NR^{14}$—.

In connection with $R^{12a}$ and $R^{12b}$, or $R^{13a}$ and $R^{13b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is $C_1$-$C_6$-alkyl and $R^{12b}$ is hydrogen or $C_1$-$C_6$-alkyl, or $R^{13a}$ is $C_1$-$C_4$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted 1,3-propylene, or $R^{13a}$ and $R^{13b}$ together are optionally substituted 1,3-propylene.

$R^5$ is optionally substituted $C_6$-$C_{12}$-aryl (e.g. phenyl, 2-fluorophenyl, 2-chlorophenyl, 3-fluorophenyl, 3-chlorophenyl; 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 2,4-dichlorophenyl or 3,4-dichlorophenyl,), optionally substituted $C_3$-$C_{12}$-cycloalkyl (e.g. cyclohexyl) or optionally substituted $C_3$-$C_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_3$-$C_{12}$-heterocyclyl in particular includes $C_3$-$C_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, $C_3$-$C_{12}$-heterocyclyl in particular is $C_3$-$C_{12}$-heteroaryl.

Preferably, $R^5$ is optionally substituted $C_6$-$C_{12}$-aryl, in particular as in the compounds of the formula:

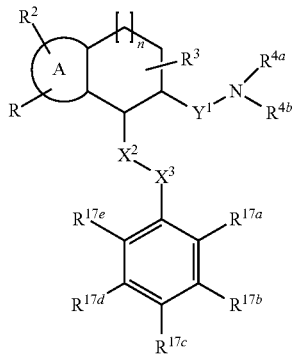

wherein A, R, $R^2$, $R^3$, $Y^1$, $R^{4a}$, $R^{4b}$, $X^2$, $X^3$, n are as defined herein, and
$R^{17a}$, $R^{17b}$, $R^{17c}$, $R^{17d}$, $R^{17e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

It is also preferred if $R^5$ is optionally substituted $C_6$-$C_{12}$-heteroaryl, in particular as in the aminoindane derivatives of the formula:

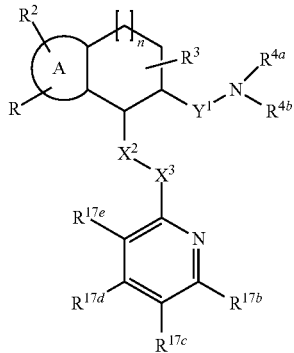

wherein A, R, $R^2$, $R^3$, $Y^1$, $R^{4a}$, $R^{4b}$, $X^2$, $X^3$, n are as defined herein, and $R^{17b}$, $R^{17c}$, $R^{17d}$, $R^{17e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

According to a particular embodiment, the invention relates to compounds of the formula:

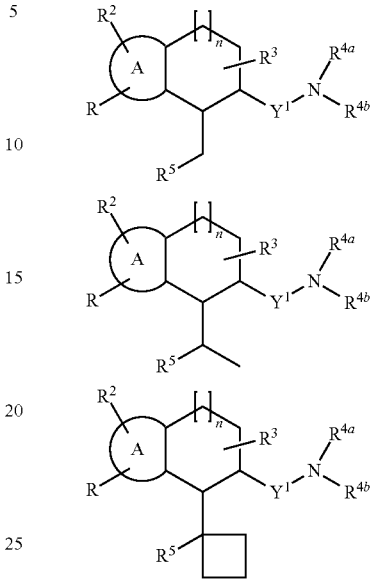

wherein A, R, $R^2$, $R^3$, $Y^1$, $R^{4a}$, $R^{4b}$, $R^5$, n are as defined herein, $R^5$ preferably being option ally substituted aryl and in particular optionally substituted phenyl as disclosed herein.

In connection with $R^5$ or $R^{17a}$, $R^{17c}$, $R^{17d}$, $R^{17e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $C_3$-$C_{12}$-heterocyclyl (e.g. morpholinyl or piperidinyl).

According to a particular embodiment, $R^{17a}$, $R^{17b}$, $R^{17d}$, $R^{17e}$ are hydrogen and $R^{17c}$ is different from hydrogen (para-mono-substitution).

According to a further particular embodiment, $R^{17a}$, $R^{17c}$, $R^{17d}$, $R^{17e}$ are hydrogen and $R^{17b}$ is different from hydrogen (meta-mono-substitution).

In connection with $R^{17a}$, $R^{17b}$, $R^{17c}$, $R^{17d}$, $R^{17e}$, $C_3$-$C_{12}$-heterocyclyl in particular includes morpholinyl, imidazolyl and pyrazolyl.

$R^6$ is hydrogen or $C_1$-$C_6$-alkyl. Preferably, $R^6$ is hydrogen.

$R^7$ is hydrogen or $C_1$-$C_6$-alkyl. Preferably, $R^7$ is hydrogen.

$R^8$ is hydrogen or $C_1$-$C_6$-alkyl. Preferably, $R^8$ is hydrogen.

$R^9$ is hydrogen, $C_1$-$C_6$-alkyl (e.g. methyl or ethyl), $C_3$-$C_{12}$-cycloalkyl (e.g. cyclopropyl), amino -$C_1$-$C_6$-alkyl, optionally substituted $C_6$-$C_{12}$-aryl-$C_1$-$C_4$-alkyl or $C_3$-$C_{12}$-heterocyclyl (e.g. 3-azetidinyl). Preferably, $R^9$ is hydrogen or $C_1$-$C_6$-alkyl (e.g. methyl or ethyl).

According to a particular embodiment, $R^9$ and $R^1$ together are $C_1$-$C_4$-alkylene (e.g. 1, 3-1,2-ethylene or propylene) so as that $R^9$ and $R^1$ together with the atom in Q to which $R^1$ is bound and the nitrogen atom to which $R^9$ is bound form an heterocyclic ring having, in particular, 4, 5 or 6 ring member atoms (including the nitrogen atom and Q). With W and $A^1$ both being a bond, such a ring may be represented by the following partial structure:

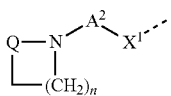

wherein Q, $A^2$, $X^1$, are as defined herein (e.g. $S(O)_2$) and n is 0, 1, 2, 3 or 4.

According to a further particular embodiment, $R^9$ is $C_1$-$C_4$-alkylene (e.g. methylene or 1,3-propylene) that is bound to a carbon atom in $A^2$ and $A^2$ is $C_1$-$C_4$-alkylene so that $R^9$ and at least part of $A^2$ together with the nitrogen atom to which $R^9$ is bound form an N-containing heterocyclic ring having, in particular, 4, 5, 6 or 7 ring member atoms (including the nitrogen atom). Such a ring may be represented by the following partial structure:

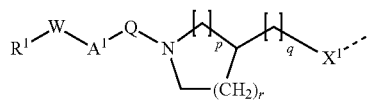

wherein $R^1$, W, $A^1$, Q and $X^1$ are as defined herein, p is 1 or 2, r is 0, 1 or 2 and q is 0, 1 or 2. In this particular embodiment, $X^1$ preferably is —O—. Particular combinations of p, r and q include p=1, r=0, q=1; and p=1, r=0, q=0. Alternatively, p is 0, r is 3 and q is 1, with $X^1$ preferably being —O—.

According to a further particular embodiment, $R^9$ is $C_1$-$C_4$-alkylene (e.g. methylene or 1,3-propylene) that is bound to a carbon atom in $X^1$ and $X^1$ is $C_1$-$C_4$-alkylene (e.g. 1,2-ethylene) so that $R^9$ and at least part of $X^1$ together with the nitrogen atom to which $R^9$ is bound form an N-containing heterocyclic ring having, in particular, 4, 5, 6 or 7 ring member atoms (including the nitrogen atom). With $A^2$ being a bond, such a ring may be represented by the following partial structure:

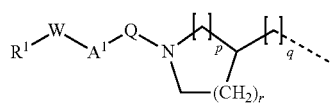

wherein $R^1$, W, $A^1$ and Q are as defined herein, p is 1 or 2, r is 0, 1 or 2 and q is 0, 1 or 2. Particular combinations of p, r and q include p=1, r=0, q=0.

$R^{10}$ is hydrogen, $C_1$-$C_6$-alkyl or $C_1$-$C_6$-alkylsulfonyl. Preferably, $R^{10}$ is hydrogen.

$R^{11}$ is hydrogen or $C_1$-$C_6$-alkyl. Preferably, $R^{11}$ is hydrogen. Alternatively, $R^9$, $R^{11}$ together are $C_1$-$C_4$-alkylene (e.g. ethylene).

$R^{14}$ is hydrogen or $C_1$-$C_6$-alkyl. Preferably, $R^{14}$ is hydrogen.
$R^{15}$ is hydrogen or $C_1$-$C_6$-alkyl. Preferably, $R^{15}$ is hydrogen.
$R^{16}$ is hydrogen or $C_1$-$C_6$-alkyl. Preferably, $R^{16}$ is hydrogen.

Particular embodiments of compounds of the invention result if
A is a benzene ring;
R is $R^1$-W-$A^1$-Q-Y-$A^2$-$X^1$—;
$R^1$ is $C_1$-$C_6$-alkyl (e.g. n-propyl), $C_3$-$C_{12}$-cycloalkyl-$C_1$-$C_4$-alkyl (e.g. cyclopropylmethyl), $C_3$-$C_{12}$-cycloalkyl (e.g. cyclobutyl), or optionally substituted $C_3$-$C_{12}$-heterocyclyl (e.g. 3-pyridyl, 1-methyl-1,2-diazol-4-yl, 1-methyl-1,3-diazol-4-yl, 3-oxetanyl, 1-methyl-pyrrol-3-yl);
W is a bond;
$A^1$ is a bond;
Q is —$S(O)_2$—;
Y is —$NR^9$— or a bond;
$A^2$ is $C_1$-$C_4$-alkylene (e.g. 1,2-ethylene) or a bond;
$X^1$ is —O— or optionally substituted $C_1$-$C_4$-alkylene (e.g. methylene, 1,2-ethylene);
$R^2$ is hydrogen or halogen (e.g. fluorine);
$R^3$ is hydrogen;
$Y^1$ is optionally substituted $C_1$-$C_4$-alkylene (e.g. methylene, 1,2-ethylene);
$R^{4a}$ is hydrogen, $C_1$-$C_6$-alkyl (e.g. methyl), $C_3$-$C_{12}$-cycloalkyl (e.g. cyclopropyl) or optionally substituted $C_3$-$C_{12}$-heterocyclyl (e.g. 3-oxetanyl); or
$R^{4a}$ is $C_1$-$C_4$-alkylene (e.g. methylene, 1,2-ethylene) that is bound to a carbon atom in $Y^1$ and $Y^1$ is optionally substituted $C_1$-$C_4$-alkylene (e.g. 1,2-ethylene, 1,3-propylene);
$R^{4b}$ is hydrogen; or
$R^{4a}$, $R^{4b}$ together are $C_1$-$C_6$-alkylene (e.g. 1,3-propylene, 1,4-butylene), wherein one —$CH_2$— of $C_1$-$C_6$-alkylene may be replaced by an oxygen atom (e.g. —$CH_2$—$CH_2$—O—$CH_2$—$CH_2$—);
$X^2$ is >$CR^{12a}R^{12b}$;
$X^3$ is a bond;
$R^5$ is optionally substituted phenyl (e.g. phenyl, 2-fluorophenyl, 2-chlorophenyl, 3-fluorophenyl, 3-chlorophenyl, 3-trifluoromethylphenyl);
n is 0 or 1;
$R^9$ is hydrogen, or
$R^9$ is $C_1$-$C_4$-alkylene (e.g. methylene) that is bound to a carbon atom in $X^1$ and $X^1$ is $C_1$-$C_4$-alkylene (e.g. 1,2-ethylene);
$R^{12a}$ is hydrogen;
$R^{12b}$ is hydrogen; or
$R^{12a}$, $R^{12b}$ together are $C_1$-$C_4$-alkylene (e.g. 1,3-propylene).

Further particular compounds of the present invention are the individual derivatives (in particular tetraline and indane derivatives) of the formula (Id) as listed in the following tables 1 to 24 and physiologically tolerated salts thereof:

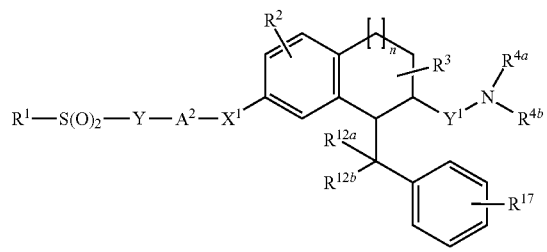

(Id)

Table 1

Compounds of the formula (Id) wherein —$Y^1$— is as defined herein and in particular represents —$CH_2$— or —$(CH_2)_2$—, $R^2$ is hydrogen, $R^3$ is as defined herein and in particular represents hydrogen, $R^{17}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 2

Compounds of the formula (Id) wherein —$Y^1$— is as defined herein and in particular represents —$CH_2$— or —$(CH_2)_2$—, $R^2$ is hydrogen, $R^3$ is as defined herein and in particular represents hydrogen, $R^{17}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 3

Compounds of the formula (Id) wherein —$Y^1$— is as defined herein and in particular represents —$CH_2$— or —$(CH_2)_2$—, $R^2$ is hydrogen, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 4

Compounds of the formula (Id) wherein —$Y^1$— is as defined herein and in particular represents —$CH_2$— or —$(CH_2)_2$—, $R^2$ is hydrogen, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 5

Compounds of the formula (Id) wherein —$Y^1$— is as defined herein and in particular represents —$CH_2$— or —$(CH_2)_2$—, $R^2$ is hydrogen, $R^3$ is as defined herein and in particular represents hydrogen, $R^{17}$ is 2-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 6

Compounds of the formula (Id) wherein —$Y^1$— is as defined herein and in particular represents —$CH_2$— or —$(CH_2)_2$—, $R^2$ is hydrogen, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 7

Compounds of the formula (Id) wherein —$Y^1$— is as defined herein and in particular represents —$CH_2$— or —$(CH_2)_2$—, $R^2$ is 5-F, $R^3$ is as defined herein and in particular represents hydrogen, $R^{17}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 8

Compounds of the formula (Id) wherein —$Y^1$— is as defined herein and in particular represents —$CH_2$— or —$(CH_2)_2$—, $R^2$ is 5-F, $R^3$ is as defined herein and in particular represents hydrogen, $R^{17}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 9

Compounds of the formula (Id) wherein —$Y^1$— is as defined herein and in particular represents —$CH_2$— or —$(CH_2)_2$—, $R^2$ is 5-F, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 10

Compounds of the formula (Id) wherein —$Y^1$— is as defined herein and in particular represents —$CH_2$— or —$(CH_2)_2$—, $R^2$ is 5-F, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 11

Compounds of the formula (Id) wherein —$Y^1$— is as defined herein and in particular represents —$CH_2$— or —$(CH_2)_2$—, $R^2$ is 5-F, $R^3$ is as defined herein and in particular represents hydrogen, $R^{17}$ is 2-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 12

Compounds of the formula (Id) wherein —$Y^1$— is as defined herein and in particular represents —$CH_2$— or —$(CH_2)_2$—, $R^2$ is 5-F, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 13

Compounds of the formula (Id) wherein —$Y^1$— is as defined herein and in particular represents —$CH_2$— or —$(CH_2)_2$—, $R^2$ is 6-F, $R^3$ is as defined herein and in particular represents hydrogen, $R^{17}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 14

Compounds of the formula (Id) wherein —$Y^1$— is as defined herein and in particular represents —$CH_2$— or —$(CH_2)_2$—, $R^2$ is 6-F, $R^3$ is as defined herein and in particular represents hydrogen, $R^{17}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 15

Compounds of the formula (Id) wherein —$Y^1$— is as defined herein and in particular represents —$CH_2$— or —$(CH_2)_2$—, $R^2$ is 6-F, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 16

Compounds of the formula (Id) wherein is as defined herein and in particular represents —$CH_2$— or —$(CH_2)_2$—, $R^2$ is 6-F, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 17

Compounds of the formula (Id) wherein —$Y^1$— is as defined herein and in particular represents —$CH_2$— or —$(CH_2)_2$—, $R^2$ is 6-F, $R^3$ is as defined herein and in particular represents hydrogen, $R^{17}$ is 2-F and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 18

Compounds of the formula (Id) wherein —$Y^1$— is as defined herein and in particular represents —$CH_2$— or —$(CH_2)_2$—, $R^2$ is 6-F, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 19

Compounds of the formula (Id) wherein —$Y^1$— is as defined herein and in particular represents —$CH_2$— or —$(CH_2)_2$—, $R^2$ is 8-F, $R^3$ is as defined herein and in particular represents hydrogen, $R^{17}$ is hydrogen and the combination of $R^1$, —Y-$A^2$-$X^1$—, >$CR^{12a}R^{12b}$, $R^{4a}$, $R^{4b}$ for a compound in each case corresponds to one line of Table A (A-1 to A-480).

Table 20

Compounds of the formula (Id) wherein —$Y^1$— is as defined herein and in particular represents —$CH_2$— or —$(CH_2)_2$—, $R^2$ is 8-F, $R^3$ is as defined herein and in particular represents hydrogen, $R^{17}$ is 3-F and the combination of $R^1$, —Y-A²-X¹—, >CR$^{12a}$R$^{12b}$, R$^{4a}$, R$^{4b}$ for a compound in each case corresponds to one line of Table A (A-1 to A-480).

Table 21

Compounds of the formula (Id) wherein —Y¹— is as defined herein and in particular represents —CH$_2$— or —(CH$_2$)$_2$—, R² is 8-F, R³ is as defined herein and in particular represents hydrogen, R$^{17}$ is 3-Cl and the combination of R¹, —Y-A²-X¹—, >CR$^{12a}$R$^{12b}$, R$^{4a}$, R$^{4b}$ for a compound in each case corresponds to one line of Table A (A-1 to A-480).

Table 22

Compounds of the formula (Id) wherein —Y¹— is as defined herein and in particular represents —CH$_2$— or —(CH$_2$)$_2$—, R² is 8-F, R³ is as defined herein and in particular represents hydrogen, R$^{17}$ is 3-CF$_3$ and the combination of R¹, —Y-A²-X¹—, >CR$^{12a}$R$^{12b}$, R$^{4a}$, R$^{4b}$ for a compound in each case corresponds to one line of Table A (A-1 to A-480).

Table 23

Compounds of the formula (Id) wherein —Y¹— is as defined herein and in particular represents —CH$_2$— or —(CH$_2$)$_2$—, R² is 8-F, R³ is as defined herein and in particular represents hydrogen, R$^{17}$ is 2-F and the combination of R¹, —Y-A²-X¹—, >CR$^{12a}$R$^{12b}$, R$^{4a}$, R$^{4b}$ for a compound in each case corresponds to one line of Table A (A-1 to A-480).

Table 24

Compounds of the formula (Id) wherein —Y¹— is as defined herein and in particular represents —CH$_2$— or —(CH$_2$)$_2$—, R² is 8-F, R³ is as defined herein and in particular represents hydrogen, R$^{17}$ is 2-Cl and the combination of R¹, —Y-A²-X¹—, >CR$^{12a}$R$^{12b}$, R$^{4a}$, R$^{4b}$ for a compound in each case corresponds to one line of Table A (A-1 to A-480).

|  | R¹ | —Y—A²—X¹— | >CR$^{12a}$R$^{12b}$ | R$^{4a}$, R$^{4b}$ |
|---|---|---|---|---|
| A-1. | cyclopropylmethyl | —NH—(CH$_2$)$_2$—O— | —CH$_2$— | —CH$_3$, H |
| A-2. | cyclobutyl | —NH—(CH$_2$)$_2$—O— | —CH$_2$— | —CH$_3$, H |
| A-3. | oxetanyl | —NH—(CH$_2$)$_2$—O— | —CH$_2$— | —CH$_3$, H |
| A-4. | propyl | —NH—(CH$_2$)$_2$—O— | —CH$_2$— | —CH$_3$, H |
| A-5. | pyridin-3-yl | —NH—(CH$_2$)$_2$—O— | —CH$_2$— | —CH$_3$, H |
| A-6. | 1-methylimidazol-4-yl | —NH—(CH$_2$)$_2$—O— | —CH$_2$— | —CH$_3$, H |
| A-7. | 1-methylpyrazol-4-yl | —NH—(CH$_2$)$_2$—O— | —CH$_2$— | —CH$_3$, H |

-continued
| | R¹ | —Y—A²—X¹— | >CR¹²ᵃR¹²ᵇ | R⁴ᵃ, R⁴ᵇ |
|---|---|---|---|---|
| A-8. | 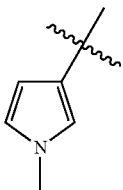 [SMILES: *c1ccn(C)c1] | —NH—(CH₂)₂—O— | —CH₂— | —CH₃, H |
| A-9. | 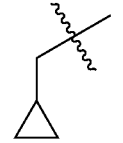 | —NH—(CH₂)₂— | —CH₂— | —CH₃, H |
| A-10. | 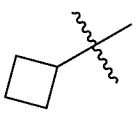 [SMILES: *C1CCC1] | —NH—(CH₂)₂— | —CH₂— | —CH₃, H |
| A-11. | 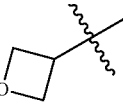 | —NH—(CH₂)₂— | —CH₂— | —CH₃, H |
| A-12. | 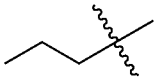 [SMILES: *CCC] | —NH—(CH₂)₂— | —CH₂— | —CH₃, H |
| A-13. | 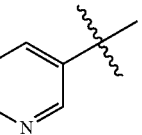 | —NH—(CH₂)₂— | —CH₂— | —CH₃, H |
| A-14. | 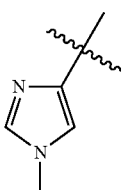 | —NH—(CH₂)₂— | —CH₂— | —CH₃, H |
| A-15. | 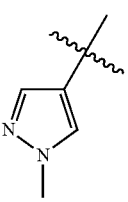 [SMILES: *c1cnn(C)c1] | —NH—(CH₂)₂— | —CH₂— | —CH₃, H |
| A-16. | 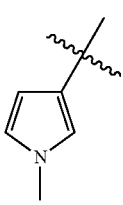 [SMILES: *c1ccn(C)c1] | —NH—(CH₂)₂— | —CH₂— | —CH₃, H |

-continued

| | R¹ | —Y—A²—X¹— | >CR$^{12a}$R$^{12b}$ | R$^{4a}$, R$^{4b}$ |
|---|---|---|---|---|
| A-17. | cyclopropylmethyl | —NH—CH$_2$— | —CH$_2$— | —CH$_3$, H |
| A-18. | cyclobutyl | —NH—CH$_2$— | —CH$_2$— | —CH$_3$, H |
| A-19. | oxetanyl | —NH—CH$_2$— | —CH$_2$— | —CH$_3$, H |
| A-20. | propyl | —NH—CH$_2$— | —CH$_2$— | —CH$_3$, H |
| A-21. | pyridin-3-yl | —NH—CH$_2$— | —CH$_2$— | —CH$_3$, H |
| A-22. | 1-methyl-1H-imidazol-4-yl | —NH—CH$_2$— | —CH$_2$— | —CH$_3$, H |
| A-23. | 1-methyl-1H-pyrazol-4-yl | —NH—CH$_2$— | —CH$_2$— | —CH$_3$, H |
| A-24. | 1-methyl-1H-pyrrol-3-yl | —NH—CH$_2$— | —CH$_2$— | —CH$_3$, H |
| A-25. | cyclopropylmethyl | azetidin-3-yl | —CH$_2$— | —CH$_3$, H |
| A-26. | cyclobutyl | azetidin-3-yl | —CH$_2$— | —CH$_3$, H |

-continued

| | R¹ | —Y—A²—X¹— | >CR$^{12a}$R$^{12b}$ | R$^{4a}$, R$^{4b}$ |
|---|---|---|---|---|
| A-27. | 3-oxetanyl | azetidinyl | —CH$_2$— | —CH$_3$, H |
| A-28. | sec-butyl | azetidinyl | —CH$_2$— | —CH$_3$, H |
| A-29. | 3-pyridyl | azetidinyl | —CH$_2$— | —CH$_3$, H |
| A-30. | 1-methyl-imidazol-4-yl | azetidinyl | —CH$_2$— | —CH$_3$, H |
| A-31. | 1-methyl-pyrazol-4-yl | azetidinyl | —CH$_2$— | —CH$_3$, H |
| A-32. | 1-methyl-pyrrol-3-yl | azetidinyl | —CH$_2$— | —CH$_3$, H |
| A-33. | cyclopropylmethyl | —(CH$_2$)$_2$— | —CH$_2$— | —CH$_3$, H |
| A-34. | cyclobutyl | —(CH$_2$)$_2$— | —CH$_2$— | —CH$_3$, H |
| A-35. | 3-oxetanyl | —(CH$_2$)$_2$— | —CH$_2$— | —CH$_3$, H |

-continued

| | R¹ | —Y—A²—X¹— | >CR$^{12a}$R$^{12b}$ | R$^{4a}$, R$^{4b}$ |
|---|---|---|---|---|
| A-36. | (butyl group) | —(CH$_2$)$_2$— | —CH$_2$— | —CH$_3$, H |
| A-37. | (pyridin-3-yl) | —(CH$_2$)$_2$— | —CH$_2$— | —CH$_3$, H |
| A-38. | (1-methylimidazol-4-yl) | —(CH$_2$)$_2$— | —CH$_2$— | —CH$_3$, H |
| A-39. | (1-methylpyrazol-4-yl) | —(CH$_2$)$_2$— | —CH$_2$— | —CH$_3$, H |
| A-40. | (1-methylpyrrol-3-yl) | —(CH$_2$)$_2$— | —CH$_2$— | —CH$_3$, H |
| A-41. | (cyclopropylmethyl) | —NH—(CH$_2$)$_2$—O— | (cyclobutylidene) | —CH$_3$, H |
| A-42. | (cyclobutyl) | —NH—(CH$_2$)$_2$—O— | (cyclobutylidene) | —CH$_3$, H |
| A-43. | (oxetan-3-yl) | —NH—(CH$_2$)$_2$—O— | (cyclobutylidene) | —CH$_3$, H |
| A-44. | (propyl) | —NH—(CH$_2$)$_2$—O— | (cyclobutylidene) | —CH$_3$, H |

-continued

| | R¹ | —Y—A²—X¹— | >CR¹²ᵃR¹²ᵇ | R⁴ᵃ, R⁴ᵇ |
|---|---|---|---|---|
| A-45. | 3-pyridyl | —NH—(CH₂)₂—O— | cyclobutyl | —CH₃, H |
| A-46. | 1-methyl-imidazol-4-yl | —NH—(CH₂)₂—O— | cyclobutyl | —CH₃, H |
| A-47. | 1-methyl-pyrazol-4-yl | —NH—(CH₂)₂—O— | cyclobutyl | —CH₃, H |
| A-48. | 1-methyl-pyrrol-3-yl | —NH—(CH₂)₂—O— | cyclobutyl | —CH₃, H |
| A-49. | cyclopropylmethyl | —NH—(CH₂)₂— | cyclobutyl | —CH₃, H |
| A-50. | cyclobutyl | —NH—(CH₂)₂— | cyclobutyl | —CH₃, H |
| A-51. | oxetan-3-yl | —NH—(CH₂)₂— | cyclobutyl | —CH₃, H |
| A-52. | n-propyl | —NH—(CH₂)₂— | cyclobutyl | —CH₃, H |
| A-53. | 3-pyridyl | —NH—(CH₂)₂— | cyclobutyl | —CH₃, H |

-continued
| | R¹ | —Y—A²—X¹— | >CR¹²ᵃR¹²ᵇ | R⁴ᵃ, R⁴ᵇ |
|---|---|---|---|---|
| A-54. | 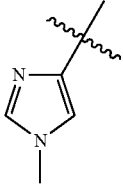 [SMILES: *c1cn(C)cn1] | —NH—(CH₂)₂— | 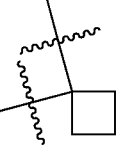 | —CH₃, H |
| A-55. | 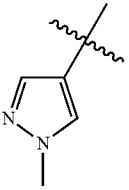 | —NH—(CH₂)₂— | 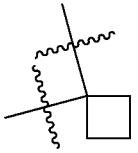 [SMILES: *C1(*)CCC1] | —CH₃, H |
| A-56. | 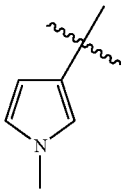 [SMILES: *c1ccn(C)c1] | —NH—(CH₂)₂— | 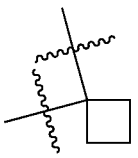 [SMILES: *C1(*)CCC1] | —CH₃, H |
| A-57. | 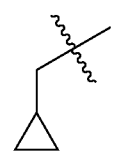 | —NH—CH₂— | 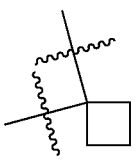 | —CH₃, H |
| A-58. | 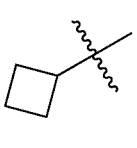 [SMILES: *C1CCC1] | —NH—CH₂— | 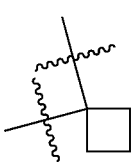 | —CH₃, H |
| A-59. | 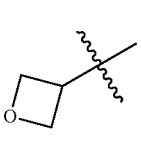 [SMILES: *C1COC1] | —NH—CH₂— | 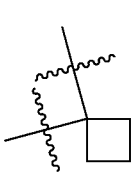 [SMILES: *C1(*)CCC1] | —CH₃, H |
| A-60. | 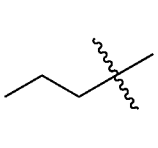 | —NH—CH₂— | 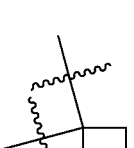 | —CH₃, H |
| A-61. | 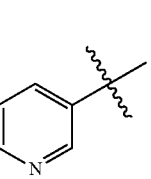 | —NH—CH₂— | 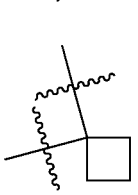 | —CH₃, H |

-continued

| | R¹ | —Y—A²—X¹— | >CR$^{12a}$R$^{12b}$ | R$^{4a}$, R$^{4b}$ |
|---|---|---|---|---|
| A-62. | 1-methylimidazol-4-yl | —NH—CH$_2$— | cyclobutylidene | —CH$_3$, H |
| A-63. | 1-methylpyrazol-4-yl | —NH—CH$_2$— | cyclobutylidene | —CH$_3$, H |
| A-64. | 1-methylpyrrol-3-yl | —NH—CH$_2$— | cyclobutylidene | —CH$_3$, H |
| A-65. | cyclopropylmethyl | azetidin-3-yl | cyclobutylidene | —CH$_3$, H |
| A-66. | cyclobutyl | azetidin-3-yl | cyclobutylidene | —CH$_3$, H |
| A-67. | oxetan-3-yl | azetidin-3-yl | cyclobutylidene | —CH$_3$, H |
| A-68. | n-propyl | azetidin-3-yl | cyclobutylidene | —CH$_3$, H |
| A-69. | pyridin-3-yl | azetidin-3-yl | cyclobutylidene | —CH$_3$, H |

-continued

| | R[1] | —Y—A[2]—X[1]— | >CR[12a]R[12b] | R[4a], R[4b] |
|---|---|---|---|---|
| A-70. | 1-methylimidazol-4-yl | azetidine-1,3-diyl | cyclobutylidene | —CH₃, H |
| A-71. | 1-methylpyrazol-4-yl | azetidine-1,3-diyl | cyclobutylidene | —CH₃, H |
| A-72. | 1-methylpyrrol-3-yl | azetidine-1,3-diyl | cyclobutylidene | —CH₃, H |
| A-73. | cyclopropylmethyl | —(CH₂)₂— | cyclobutylidene | —CH₃, H |
| A-74. | cyclobutyl | —(CH₂)₂— | cyclobutylidene | —CH₃, H |
| A-75. | oxetan-3-yl | —(CH₂)₂— | cyclobutylidene | —CH₃, H |
| A-76. | n-propyl | —(CH₂)₂— | cyclobutylidene | —CH₃, H |
| A-77. | pyridin-3-yl | —(CH₂)₂— | cyclobutylidene | —CH₃, H |

-continued

| | R¹ | —Y—A²—X¹— | >CR¹²ᵃR¹²ᵇ | R⁴ᵃ, R⁴ᵇ |
|---|---|---|---|---|
| A-78. | 1-methylimidazol-4-yl | —(CH₂)₂— | cyclobutylidene | —CH₃, H |
| A-79. | 1-methylpyrazol-4-yl | —(CH₂)₂— | cyclobutylidene | —CH₃, H |
| A-80. | 1-methylpyrrol-3-yl | —(CH₂)₂— | cyclobutylidene | —CH₃, H |
| A-81. | cyclopropylmethyl | —NH—(CH₂)₂—O— | —CH₂— | cyclopropyl, H |
| A-82. | cyclobutyl | —NH—(CH₂)₂—O— | —CH₂— | cyclopropyl, H |
| A-83. | oxetan-3-yl | —NH—(CH₂)₂—O— | —CH₂— | cyclopropyl, H |
| A-84. | propyl | —NH—(CH₂)₂—O— | —CH₂— | cyclopropyl, H |
| A-85. | pyridin-3-yl | —NH—(CH₂)₂—O— | —CH₂— | cyclopropyl, H |
| A-86. | 1-methylimidazol-5-yl | —NH—(CH₂)₂—O— | —CH₂— | cyclopropyl, H |

-continued

| | R¹ | —Y—A²—X¹— | >CR¹²ᵃR¹²ᵇ | R⁴ᵃ, R⁴ᵇ |
|---|---|---|---|---|
| A-87. | 1-methylpyrazol-4-yl | —NH—(CH₂)₂—O— | —CH₂— | cyclopropyl, H |
| A-88. | 1-methylpyrrol-3-yl | —NH—(CH₂)₂—O— | —CH₂— | cyclopropyl, H |
| A-89. | cyclopropylmethyl | —NH—(CH₂)₂— | —CH₂— | cyclopropyl, H |
| A-90. | cyclobutyl | —NH—(CH₂)₂— | —CH₂— | cyclopropyl, H |
| A-91. | oxetan-3-yl | —NH—(CH₂)₂— | —CH₂— | cyclopropyl, H |
| A-92. | sec-butyl | —NH—(CH₂)₂— | —CH₂— | cyclopropyl, H |
| A-93. | pyridin-3-yl | —NH—(CH₂)₂— | —CH₂— | cyclopropyl, H |
| A-94. | 1-methylimidazol-5-yl | —NH—(CH₂)₂— | —CH₂— | cyclopropyl, H |
| A-95. | 1-methylpyrazol-4-yl | —NH—(CH₂)₂— | —CH₂— | cyclopropyl, H |

-continued
| | R¹ | —Y—A²—X¹— | >CR$^{12a}$R$^{12b}$ | R$^{4a}$, R$^{4b}$ |
|---|---|---|---|---|
| A-96. | 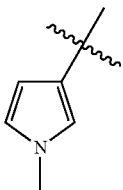 [SMILES: *c1ccn(C)c1] | —NH—(CH$_2$)$_2$— | —CH$_2$— | 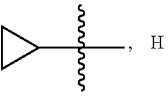, H |
| A-97. | 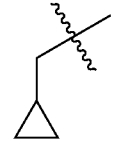 | —NH—CH$_2$— | —CH$_2$— | 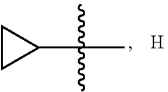, H |
| A-98. | 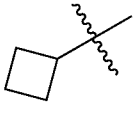 [SMILES: *C1CCC1] | —NH—CH$_2$— | —CH$_2$— | 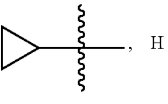, H |
| A-99. | 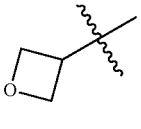 [SMILES: *C1COC1] | —NH—CH$_2$— | —CH$_2$— | 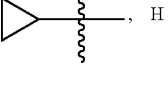, H |
| A-100. | 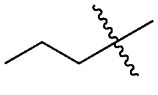 [SMILES: *CCC] | —NH—CH$_2$— | —CH$_2$— | 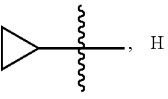, H |
| A-101. | 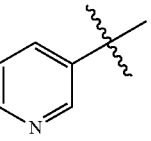 | —NH—CH$_2$— | —CH$_2$— | 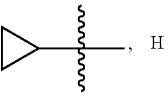, H |
| A-102. | 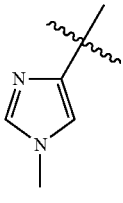 [SMILES: *c1cn(C)cn1] | —NH—CH$_2$— | —CH$_2$— | 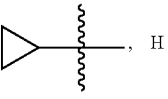, H |
| A-103. | 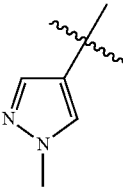 [SMILES: *c1cnn(C)c1] | —NH—CH$_2$— | —CH$_2$— | 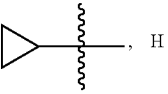, H |
| A-104. | 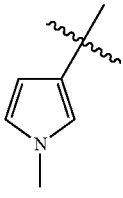 [SMILES: *c1ccn(C)c1] | —NH—CH$_2$— | —CH$_2$— | 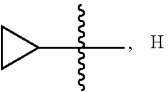, H |

-continued

| | R¹ | —Y—A²—X¹— | >CR^{12a}R^{12b} | R^{4a}, R^{4b} |
|---|---|---|---|---|
| A-105. | cyclopropylmethyl | azetidine (N-linked, 3-linked) | —CH₂— | cyclopropyl, H |
| A-106. | cyclobutylmethyl | azetidine (N-linked, 3-linked) | —CH₂— | cyclopropyl, H |
| A-107. | oxetan-3-ylmethyl | azetidine (N-linked, 3-linked) | —CH₂— | cyclopropyl, H |
| A-108. | n-butyl | azetidine (N-linked, 3-linked) | —CH₂— | cyclopropyl, H |
| A-109. | pyridin-3-ylmethyl | azetidine (N-linked, 3-linked) | —CH₂— | cyclopropyl, H |
| A-110. | (1-methyl-1H-imidazol-5-yl)methyl | azetidine (N-linked, 3-linked) | —CH₂— | cyclopropyl, H |
| A-111. | (1-methyl-1H-pyrazol-4-yl)methyl | azetidine (N-linked, 3-linked) | —CH₂— | cyclopropyl, H |
| A-112. | (1-methyl-1H-pyrrol-3-yl)methyl | azetidine (N-linked, 3-linked) | —CH₂— | cyclopropyl, H |

-continued

| | R¹ | —Y—A²—X¹— | >CR¹²ᵃR¹²ᵇ | R⁴ᵃ, R⁴ᵇ | |
|---|---|---|---|---|---|
| A-113. | (cyclopropylmethyl) | —(CH₂)₂— | —CH₂— | (cyclopropyl) | , H |
| A-114. | (cyclobutyl-methyl) | —(CH₂)₂— | —CH₂— | (cyclopropyl) | , H |
| A-115. | (oxetan-3-yl-methyl) | —(CH₂)₂— | —CH₂— | (cyclopropyl) | , H |
| A-116. | (propyl-methyl) | —(CH₂)₂— | —CH₂— | (cyclopropyl) | , H |
| A-117. | (pyridin-3-yl-methyl) | —(CH₂)₂— | —CH₂— | (cyclopropyl) | , H |
| A-118. | (1-methyl-imidazol-4-yl-methyl) | —(CH₂)₂— | —CH₂— | (cyclopropyl) | , H |
| A-119. | (1-methyl-pyrazol-4-yl-methyl) | —(CH₂)₂— | —CH₂— | (cyclopropyl) | , H |
| A-120. | (1-methyl-pyrrol-3-yl-methyl) | —(CH₂)₂— | —CH₂— | (cyclopropyl) | , H |
| A-121. | (cyclopropylmethyl) | —NH—(CH₂)₂—O— | (cyclobutylidene) | (cyclopropyl) | , H |

-continued
| | R¹ | —Y—A²—X¹— | >CR¹²ᵃR¹²ᵇ | R⁴ᵃ, R⁴ᵇ |
|---|---|---|---|---|
| A-122. | 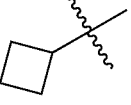 | —NH—(CH₂)₂—O— | 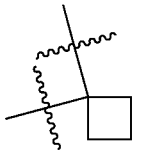 | 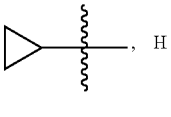, H |
| A-123. | 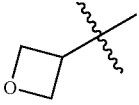 [SMILES: *C1COC1] | —NH—(CH₂)₂—O— | 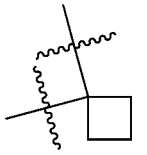 [SMILES: *C1(*)CCC1] | 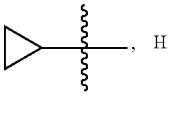, H |
| A-124. | 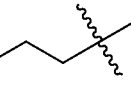 | —NH—(CH₂)₂—O— | 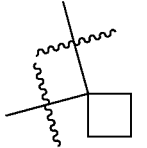 [SMILES: *C1(*)CCC1] | 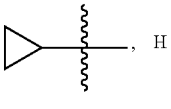, H |
| A-125. | 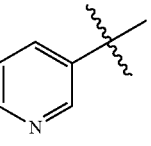 | —NH—(CH₂)₂—O— | 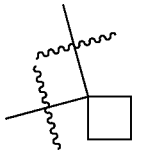 [SMILES: *C1(*)CCC1] | 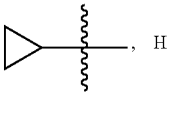, H |
| A-126. | 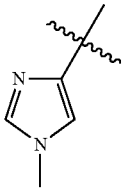 [SMILES: *c1cn(C)cn1] | —NH—(CH₂)₂—O— | 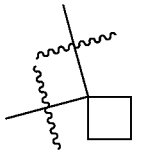 [SMILES: *C1(*)CCC1] | 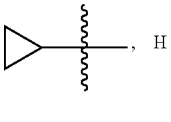, H |
| A-127. | 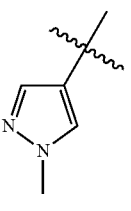 [SMILES: *c1cnn(C)c1] | —NH—(CH₂)₂—O— | 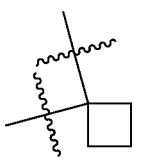 | 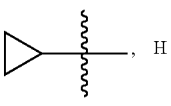, H |
| A-128. | 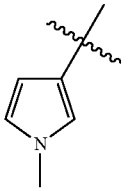 [SMILES: *c1ccn(C)c1] | —NH—(CH₂)₂—O— | 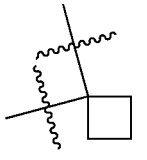 [SMILES: *C1(*)CCC1] | 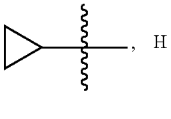, H |
| A-129. | 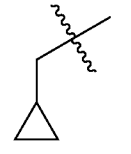 | —NH—(CH₂)₂— | 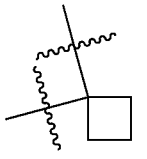 | 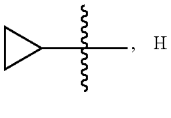, H |
| A-130. | 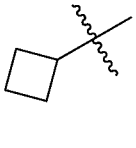 [SMILES: *C1CCC1] | —NH—(CH₂)₂— | 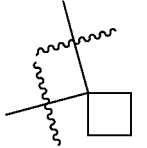 [SMILES: *C1(*)CCC1] | 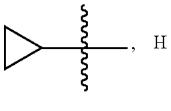, H |

-continued
| | R¹ | —Y—A²—X¹— | >CR$^{12a}$R$^{12b}$ | R$^{4a}$, R$^{4b}$ |
|---|---|---|---|---|
| A-131. | 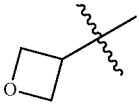 [SMILES: *C1COC1] | —NH—(CH$_2$)$_2$— | 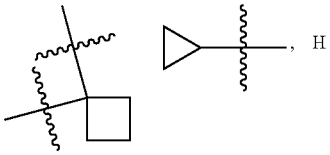 | 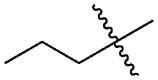 [SMILES: *CCC], H |
| A-132. | 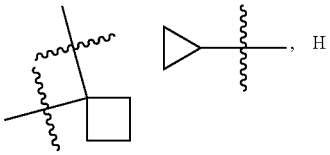 | —NH—(CH$_2$)$_2$— | 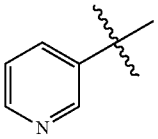 | 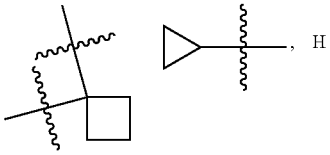, H |
| A-133. | 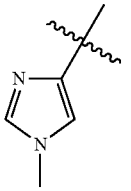 [SMILES: *c1cn(C)cn1] | —NH—(CH$_2$)$_2$— | 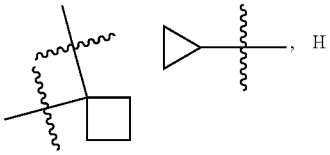 | 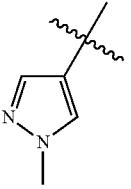 [SMILES: *c1cnn(C)c1], H |
| A-134. | 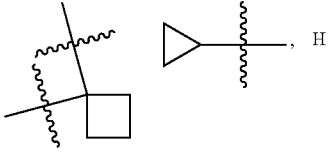 | —NH—(CH$_2$)$_2$— | 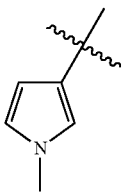 [SMILES: *c1ccn(C)c1] | 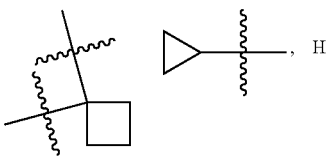, H |
| A-135. | 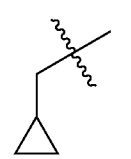 | —NH—(CH$_2$)$_2$— | 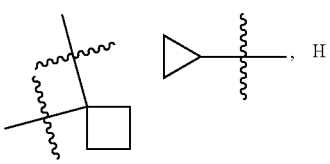 | 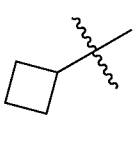 [SMILES: *C1CCC1], H |
| A-136. | 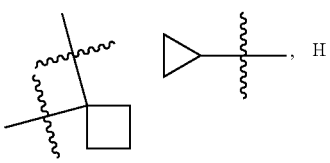 | —NH—(CH$_2$)$_2$— | | , H |
| A-137. | | —NH—CH$_2$— | | , H |
| A-138. | | —NH—CH$_2$— | | , H |

US 9,051,280 B2
-continued
| | R¹ | —Y—A²—X¹— | >CR¹²ᵃR¹²ᵇ | R⁴ᵃ, R⁴ᵇ |
|---|---|---|---|---|
| A-139. | 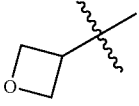 | —NH—CH₂— | 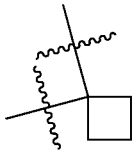 [SMILES: *C1(*)CCC1] | 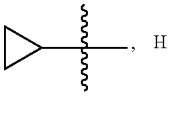, H |
| A-140. | 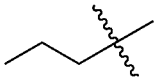 [SMILES: *CCC] | —NH—CH₂— | 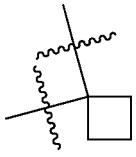 [SMILES: *C1(*)CCC1] | 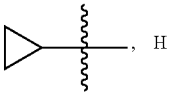, H |
| A-141. | 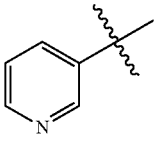 | —NH—CH₂— | 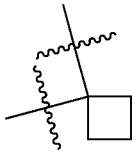 | , H |
| A-142. | 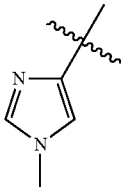 [SMILES: *c1cn(C)cn1] | —NH—CH₂— | 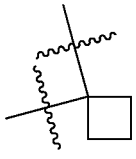 [SMILES: *C1(*)CCC1] | 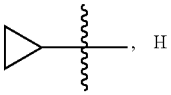, H |
| A-143. | 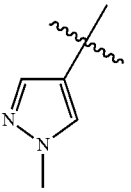 [SMILES: *c1cnn(C)c1] | —NH—CH₂— | 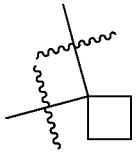 [SMILES: *C1(*)CCC1] | 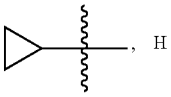, H |
| A-144. | 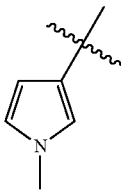 [SMILES: *c1ccn(C)c1] | —NH—CH₂— | 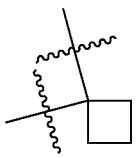 [SMILES: *C1(*)CCC1] | 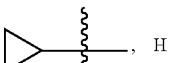, H |
| A-145. | 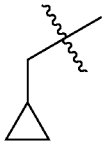 | 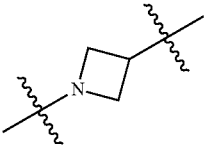 | 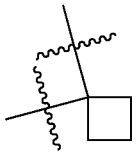 | 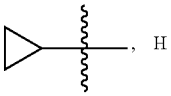, H |
| A-146. | 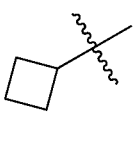 [SMILES: *C1CCC1] | 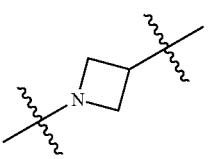 | 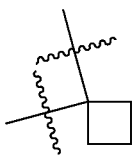 [SMILES: *C1(*)CCC1] | 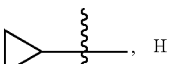, H |

-continued

| | R¹ | —Y—A²—X¹— | >CR$^{12a}$R$^{12b}$ | R$^{4a}$, R$^{4b}$ |
|---|---|---|---|---|
| A-147. | | | | , H |
| A-148. | | | | , H |
| A-149. | | | | , H |
| A-150. | | | | , H |
| A-151. | | | | , H |
| A-152. | | | | , H |
| A-153. | | —(CH$_2$)$_2$— | | , H |
| A-154. | | —(CH$_2$)$_2$— | | , H |

-continued

| | R¹ | —Y—A²—X¹— | >CR¹²ᵃR¹²ᵇ | R⁴ᵃ, R⁴ᵇ |
|---|---|---|---|---|
| A-155. | (oxetanyl) | —(CH₂)₂— | (cyclobutylidene) | (cyclopropyl), H |
| A-156. | (n-propyl) | —(CH₂)₂— | (cyclobutylidene) | (cyclopropyl), H |
| A-157. | (pyridin-3-yl) | —(CH₂)₂— | (cyclobutylidene) | (cyclopropyl), H |
| A-158. | (1-methylimidazol-4-yl) | —(CH₂)₂— | (cyclobutylidene) | (cyclopropyl), H |
| A-159. | (1-methylpyrazol-4-yl) | —(CH₂)₂— | (cyclobutylidene) | (cyclopropyl), H |
| A-160. | (1-methylpyrrol-3-yl) | —(CH₂)₂— | (cyclobutylidene) | (cyclopropyl), H |
| A-161. | (cyclopropylmethyl) | —NH—(CH₂)₂—O— | —CH₂— | (oxetanyl), H |
| A-162. | (cyclobutyl) | —NH—(CH₂)₂—O— | —CH₂— | (oxetanyl), H |
| A-163. | (oxetanyl) | —NH—(CH₂)₂—O— | —CH₂— | (oxetanyl), H |

-continued
| | R¹ | —Y—A²—X¹— | >CR¹²ᵃR¹²ᵇ | R⁴ᵃ, R⁴ᵇ |
|---|---|---|---|---|
| A-164. | 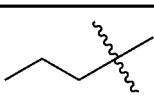 | —NH—(CH₂)₂—O— | —CH₂— | 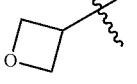, H |
| A-165. | 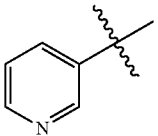 | —NH—(CH₂)₂—O— | —CH₂— | , H |
| A-166. | 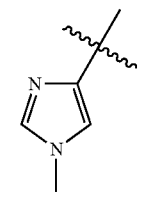 [SMILES: *c1cn(C)cn1] | —NH—(CH₂)₂—O— | —CH₂— | , H |
| A-167. | 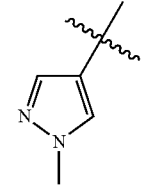 [SMILES: *c1cnn(C)c1] | —NH—(CH₂)₂—O— | —CH₂— | , H |
| A-168. | 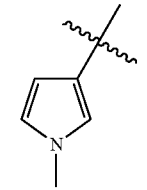 [SMILES: *c1ccn(C)c1] | —NH—(CH₂)₂—O— | —CH₂— | , H |
| A-169. | 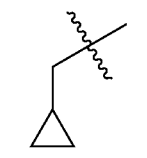 | —NH—(CH₂)₂— | —CH₂— | , H |
| A-170. | 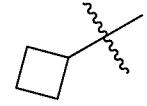 [SMILES: *C1CCC1] | —NH—(CH₂)₂— | —CH₂— | , H |
| A-171. | 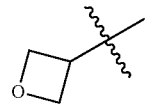 [SMILES: *C1COC1] | —NH—(CH₂)₂— | —CH₂— | , H |
| A-172. | 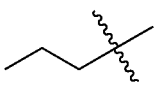 [SMILES: *CCC] | —NH—(CH₂)₂— | —CH₂— | , H |
| A-173. | 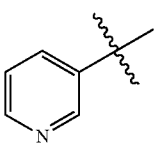 | —NH—(CH₂)₂— | —CH₂— | , H |

-continued

| | R¹ | —Y—A²—X¹— | >CR¹²ᵃR¹²ᵇ | R⁴ᵃ, R⁴ᵇ |
|---|---|---|---|---|
| A-174. | 1-methylimidazol-4-yl | —NH—(CH₂)₂— | —CH₂— | oxetan-3-yl, H |
| A-175. | 1-methylpyrazol-4-yl | —NH—(CH₂)₂— | —CH₂— | oxetan-3-yl, H |
| A-176. | 1-methylpyrrol-3-yl | —NH—(CH₂)₂— | —CH₂— | oxetan-3-yl, H |
| A-177. | cyclopropylmethyl | —NH—CH₂— | —CH₂— | oxetan-3-yl, H |
| A-178. | cyclobutyl | —NH—CH₂— | —CH₂— | oxetan-3-yl, H |
| A-179. | oxetan-3-yl | —NH—CH₂— | —CH₂— | oxetan-3-yl, H |
| A-180. | n-propyl | —NH—CH₂— | —CH₂— | oxetan-3-yl, H |
| A-181. | pyridin-3-yl | —NH—CH₂— | —CH₂— | oxetan-3-yl, H |
| A-182. | 1-methylimidazol-5-yl | —NH—CH₂— | —CH₂— | oxetan-3-yl, H |

-continued
| | R¹ | —Y—A²—X¹— | >CR¹²ᵃR¹²ᵇ | R⁴ᵃ, R⁴ᵇ |
|---|---|---|---|---|
| A-183. | 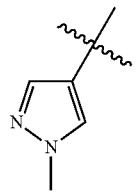 [SMILES: *c1cnn(C)c1] | —NH—CH₂— | —CH₂— | 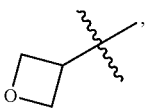, H |
| A-184. | 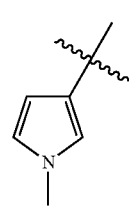 [SMILES: *c1ccn(C)c1] | —NH—CH₂— | —CH₂— | , H |
| A-185. | 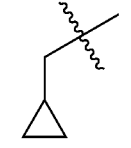 | 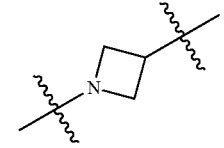 [SMILES: *C1CN(*)C1] | —CH₂— | 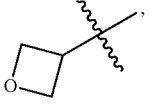, H |
| A-186. | 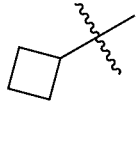 [SMILES: *C1CCC1] | 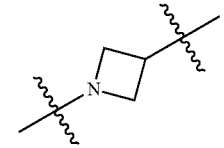 | —CH₂— | 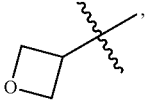, H |
| A-187. | 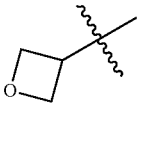 [SMILES: *C1COC1] | 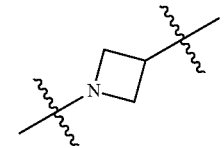 [SMILES: *C1CN(*)C1] | —CH₂— | 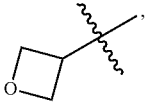, H |
| A-188. | 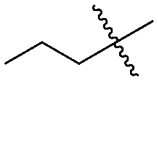 [SMILES: *CCC] | 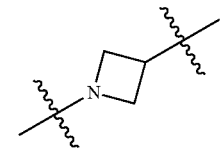 | —CH₂— | 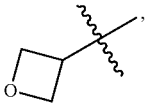, H |
| A-189. | 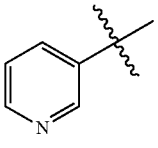 | 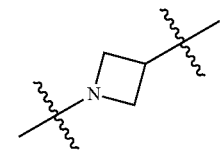 | —CH₂— | 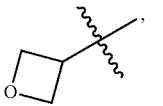, H |
| A-190. | 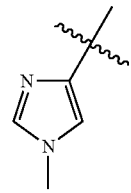 [SMILES: *c1cn(C)cn1] | 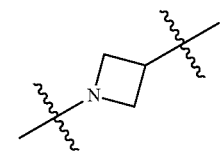 [SMILES: *C1CN(*)C1] | —CH₂— | 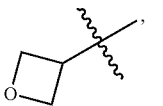, H |

-continued

| | R¹ | —Y—A²—X¹— | >CR¹²ᵃR¹²ᵇ | R⁴ᵃ, R⁴ᵇ |
|---|---|---|---|---|
| A-191. | 1-methylpyrazol-4-yl | azetidin-3-yl (N-linked) | —CH₂— | oxetan-3-yl, H |
| A-192. | 1-methylpyrrol-3-yl | azetidin-3-yl (N-linked) | —CH₂— | oxetan-3-yl, H |
| A-193. | cyclopropylmethyl | —(CH₂)₂— | —CH₂— | oxetan-3-yl, H |
| A-194. | cyclobutyl | —(CH₂)₂— | —CH₂— | oxetan-3-yl, H |
| A-195. | oxetan-3-yl | —(CH₂)₂— | —CH₂— | oxetan-3-yl, H |
| A-196. | n-propyl | —(CH₂)₂— | —CH₂— | oxetan-3-yl, H |
| A-197. | pyridin-3-yl | —(CH₂)₂— | —CH₂— | oxetan-3-yl, H |
| A-198. | 1-methylimidazol-5-yl | —(CH₂)₂— | —CH₂— | oxetan-3-yl, H |
| A-199. | 1-methylpyrazol-4-yl | —(CH₂)₂— | —CH₂— | oxetan-3-yl, H |

-continued

| | R¹ | —Y—A²—X¹— | >CR¹²ᵃR¹²ᵇ | R⁴ᵃ, R⁴ᵇ |
|---|---|---|---|---|
| A-200. | (N-methylpyrrol-3-yl) | —(CH₂)₂— | —CH₂— | (oxetan-3-yl), H |
| A-201. | (cyclopropylmethyl) | —NH—(CH₂)₂—O— | (cyclobutylidene) | (oxetan-3-yl), H |
| A-202. | (cyclobutyl) | —NH—(CH₂)₂—O— | (cyclobutylidene) | (oxetan-3-yl), H |
| A-203. | (oxetan-3-yl) | —NH—(CH₂)₂—O— | (cyclobutylidene) | (oxetan-3-yl), H |
| A-204. | (n-propyl) | —NH—(CH₂)₂—O— | (cyclobutylidene) | (oxetan-3-yl), H |
| A-205. | (pyridin-3-yl) | —NH—(CH₂)₂—O— | (cyclobutylidene) | (oxetan-3-yl), H |
| A-206. | (1-methylimidazol-5-yl) | —NH—(CH₂)₂—O— | (cyclobutylidene) | (oxetan-3-yl), H |
| A-207. | (1-methylpyrazol-4-yl) | —NH—(CH₂)₂—O— | (cyclobutylidene) | (oxetan-3-yl), H |

-continued

| | R¹ | —Y—A²—X¹— | >CR¹²ᵃR¹²ᵇ | R⁴ᵃ, R⁴ᵇ |
|---|---|---|---|---|
| A-208. | N-methyl pyrrole | —NH—(CH₂)₂—O— | cyclobutane | oxetane, H |
| A-209. | cyclopropylmethyl | —NH—(CH₂)₂— | cyclobutane | oxetane, H |
| A-210. | cyclobutyl | —NH—(CH₂)₂— | cyclobutane | oxetane, H |
| A-211. | oxetanyl | —NH—(CH₂)₂— | cyclobutane | oxetane, H |
| A-212. | propyl | —NH—(CH₂)₂— | cyclobutane | oxetane, H |
| A-213. | pyridin-3-yl | —NH—(CH₂)₂— | cyclobutane | oxetane, H |
| A-214. | N-methyl imidazole | —NH—(CH₂)₂— | cyclobutane | oxetane, H |
| A-215. | N-methyl pyrazole | —NH—(CH₂)₂— | cyclobutane | oxetane, H |

-continued

| | R¹ | —Y—A²—X¹— | >CR¹²ᵃR¹²ᵇ | R⁴ᵃ, R⁴ᵇ |
|---|---|---|---|---|
| A-216. | N-methylpyrrol-3-yl | —NH—(CH₂)₂— | cyclobutylidene | oxetan-3-yl, H |
| A-217. | cyclopropylmethyl | —NH—CH₂— | cyclobutylidene | oxetan-3-yl, H |
| A-218. | cyclobutyl | —NH—CH₂— | cyclobutylidene | oxetan-3-yl, H |
| A-219. | oxetan-3-yl | —NH—CH₂— | cyclobutylidene | oxetan-3-yl, H |
| A-220. | sec-butyl | —NH—CH₂— | cyclobutylidene | oxetan-3-yl, H |
| A-221. | pyridin-3-yl | —NH—CH₂— | cyclobutylidene | oxetan-3-yl, H |
| A-222. | 1-methylimidazol-5-yl | —NH—CH₂— | cyclobutylidene | oxetan-3-yl, H |
| A-223. | 1-methylpyrazol-4-yl | —NH—CH₂— | cyclobutylidene | oxetan-3-yl, H |

|       | R¹ | —Y—A²—X¹— | >CR¹²ᵃR¹²ᵇ | R⁴ᵃ, R⁴ᵇ |
|---|---|---|---|---|
| A-224. | N-methylpyrrole | —NH—CH₂— | cyclobutyl | oxetanyl, H |
| A-225. | cyclopropylmethyl | azetidinyl | cyclobutyl | oxetanyl, H |
| A-226. | cyclobutyl | azetidinyl | cyclobutyl | oxetanyl, H |
| A-227. | oxetanyl | azetidinyl | cyclobutyl | oxetanyl, H |
| A-228. | propyl | azetidinyl | cyclobutyl | oxetanyl, H |
| A-229. | pyridin-3-yl | azetidinyl | cyclobutyl | oxetanyl, H |
| A-230. | 1-methylimidazol-5-yl | azetidinyl | cyclobutyl | oxetanyl, H |
| A-231. | 1-methylpyrazol-4-yl | azetidinyl | cyclobutyl | oxetanyl, H |

|  | R¹ | —Y—A²—X¹— | >CR¹²ᵃR¹²ᵇ | R⁴ᵃ, R⁴ᵇ |
|---|---|---|---|---|
| A-232. | 1-methylpyrrol-3-yl | azetidine-3-yl (N-linked) | cyclobutylidene | oxetan-3-yl, H |
| A-233. | cyclopropylmethyl | —(CH₂)₂— | cyclobutylidene | oxetan-3-yl, H |
| A-234. | cyclobutyl | —(CH₂)₂— | cyclobutylidene | oxetan-3-yl, H |
| A-235. | oxetan-3-yl | —(CH₂)₂— | cyclobutylidene | oxetan-3-yl, H |
| A-236. | n-propyl | —(CH₂)₂— | cyclobutylidene | oxetan-3-yl, H |
| A-237. | pyridin-3-yl | —(CH₂)₂— | cyclobutylidene | oxetan-3-yl, H |
| A-238. | 1-methylimidazol-5-yl | —(CH₂)₂— | cyclobutylidene | oxetan-3-yl, H |
| A-239. | 1-methylpyrazol-4-yl | —(CH₂)₂— | cyclobutylidene | oxetan-3-yl, H |

-continued

| | R$^1$ | —Y—A$^2$—X$^1$— | >CR$^{12a}$R$^{12b}$ | R$^{4a}$, R$^{4b}$ |
|---|---|---|---|---|
| A-240. | 1-methylpyrrol-3-yl | —(CH$_2$)$_2$— | cyclobutylidene | oxetan-3-yl, H |
| A-241. | cyclopropylmethyl | —NH—(CH$_2$)$_2$—O— | —CH$_2$— | —(CH$_2$)$_3$— |
| A-242. | cyclobutyl | —NH—(CH$_2$)$_2$—O— | —CH$_2$— | —(CH$_2$)$_3$— |
| A-243. | oxetan-3-yl | —NH—(CH$_2$)$_2$—O— | —CH$_2$— | —(CH$_2$)$_3$— |
| A-244. | butan-2-yl | —NH—(CH$_2$)$_2$—O— | —CH$_2$— | —(CH$_2$)$_3$— |
| A-245. | pyridin-3-yl | —NH—(CH$_2$)$_2$—O— | —CH$_2$— | —(CH$_2$)$_3$— |
| A-246. | 1-methylimidazol-4-yl | —NH—(CH$_2$)$_2$—O— | —CH$_2$— | —(CH$_2$)$_3$— |
| A-247. | 1-methylpyrazol-4-yl | —NH—(CH$_2$)$_2$—O— | —CH$_2$— | —(CH$_2$)$_3$— |
| A-248. | 1-methylpyrrol-3-yl | —NH—(CH$_2$)$_2$—O— | —CH$_2$— | —(CH$_2$)$_3$— |

-continued

| | R¹ | —Y—A²—X¹— | >CR¹²ᵃR¹²ᵇ | R⁴ᵃ, R⁴ᵇ |
|---|---|---|---|---|
| A-249. | (cyclopropylmethyl) | —NH—(CH₂)₂— | —CH₂— | —(CH₂)₃— |
| A-250. | (cyclobutyl) | —NH—(CH₂)₂— | —CH₂— | —(CH₂)₃— |
| A-251. | (oxetan-3-yl) | —NH—(CH₂)₂— | —CH₂— | —(CH₂)₃— |
| A-252. | (n-propyl branched) | —NH—(CH₂)₂— | —CH₂— | —(CH₂)₃— |
| A-253. | (pyridin-3-yl) | —NH—(CH₂)₂— | —CH₂— | —(CH₂)₃— |
| A-254. | (1-methyl-1H-imidazol-4-yl) | —NH—(CH₂)₂— | —CH₂— | —(CH₂)₃— |
| A-255. | (1-methyl-1H-pyrazol-4-yl) | —NH—(CH₂)₂— | —CH₂— | —(CH₂)₃— |
| A-256. | (1-methyl-1H-pyrrol-3-yl) | —NH—(CH₂)₂— | —CH₂— | —(CH₂)₃— |
| A-257. | (cyclopropylmethyl) | —NH—CH₂— | —CH₂— | —(CH₂)₃— |
| A-258. | (cyclobutyl) | —NH—CH₂— | —CH₂— | —(CH₂)₃— |

-continued

| | R¹ | —Y—A²—X¹— | >CR$^{12a}$R$^{12b}$ | R$^{4a}$, R$^{4b}$ |
|---|---|---|---|---|
| A-259. | (oxetan-3-yl methyl) | —NH—CH$_2$— | —CH$_2$— | —(CH$_2$)$_3$— |
| A-260. | (n-butyl) | —NH—CH$_2$— | —CH$_2$— | —(CH$_2$)$_3$— |
| A-261. | (pyridin-3-yl methyl) | —NH—CH$_2$— | —CH$_2$— | —(CH$_2$)$_3$— |
| A-262. | (1-methyl-imidazol-4-yl methyl) | —NH—CH$_2$— | —CH$_2$— | —(CH$_2$)$_3$— |
| A-263. | (1-methyl-pyrazol-4-yl methyl) | —NH—CH$_2$— | —CH$_2$— | —(CH$_2$)$_3$— |
| A-264. | (1-methyl-pyrrol-3-yl methyl) | —NH—CH$_2$— | —CH$_2$— | —(CH$_2$)$_3$— |
| A-265. | (cyclopropylmethyl) | (azetidin-3-yl) | —CH$_2$— | —(CH$_2$)$_3$— |
| A-266. | (cyclobutylmethyl) | (azetidin-3-yl) | —CH$_2$— | —(CH$_2$)$_3$— |
| A-267. | (oxetan-3-yl methyl) | (azetidin-3-yl) | —CH$_2$— | —(CH$_2$)$_3$— |

-continued

| | R$^1$ | —Y—A$^2$—X$^1$— | >CR$^{12a}$R$^{12b}$ | R$^{4a}$, R$^{4b}$ |
|---|---|---|---|---|
| A-268. | (butyl group) | (azetidine) | —CH$_2$— | —(CH$_2$)$_3$— |
| A-269. | (pyridin-3-yl) | (azetidine) | —CH$_2$— | —(CH$_2$)$_3$— |
| A-270. | (1-methylimidazol-4-yl) | (azetidine) | —CH$_2$— | —(CH$_2$)$_3$— |
| A-271. | (1-methylpyrazol-4-yl) | (azetidine) | —CH$_2$— | —(CH$_2$)$_3$— |
| A-272. | (1-methylpyrrol-3-yl) | (azetidine) | —CH$_2$— | —(CH$_2$)$_3$— |
| A-273. | (cyclopropylmethyl) | —(CH$_2$)$_2$— | —CH$_2$— | —(CH$_2$)$_3$— |
| A-274. | (cyclobutyl) | —(CH$_2$)$_2$— | —CH$_2$— | —(CH$_2$)$_3$— |
| A-275. | (oxetan-3-yl) | —(CH$_2$)$_2$— | —CH$_2$— | —(CH$_2$)$_3$— |
| A-276. | (propyl) | —(CH$_2$)$_2$— | —CH$_2$— | —(CH$_2$)$_3$— |
| A-277. | (pyridin-3-yl) | —(CH$_2$)$_2$— | —CH$_2$— | —(CH$_2$)$_3$— |

-continued
| | R¹ | —Y—A²—X¹— | >CR¹²ᵃR¹²ᵇ | R⁴ᵃ, R⁴ᵇ |
|---|---|---|---|---|
| A-278. | 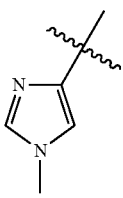 [SMILES: *c1cn(C)cn1] | —(CH₂)₂— | —CH₂— | —(CH₂)₃— |
| A-279. | 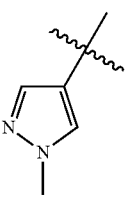 | —(CH₂)₂— | —CH₂— | —(CH₂)₃— |
| A-280. | 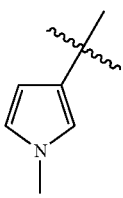 [SMILES: *c1ccn(C)c1] | —(CH₂)₂— | —CH₂— | —(CH₂)₃— |
| A-281. | 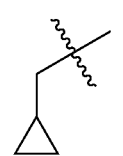 | —NH—(CH₂)₂—O— |  | —(CH₂)₃— |
| A-282. | 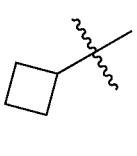 [SMILES: *C1CCC1] | —NH—(CH₂)₂—O— |  | —(CH₂)₃— |
| A-283. | 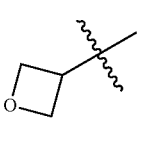 [SMILES: *C1COC1] | —NH—(CH₂)₂—O— |  | —(CH₂)₃— |
| A-284. | 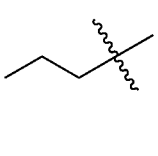 | —NH—(CH₂)₂—O— |  | —(CH₂)₃— |
| A-285. | 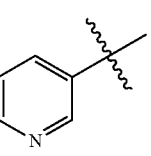 | —NH—(CH₂)₂—O— | 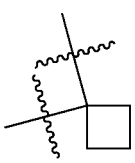 | —(CH₂)₃— |

-continued

| | R¹ | —Y—A²—X¹— | >CR¹²ᵃR¹²ᵇ | R⁴ᵃ, R⁴ᵇ |
|---|---|---|---|---|
| A-286. | (1-methyl-imidazol-4-yl) | —NH—(CH₂)₂—O— | | —(CH₂)₃— |
| A-287. | (1-methyl-pyrazol-4-yl) | —NH—(CH₂)₂—O— | | —(CH₂)₃— |
| A-288. | (1-methyl-pyrrol-3-yl) | —NH—(CH₂)₂—O— | | —(CH₂)₃— |
| A-289. | cyclopropylmethyl | —NH—(CH₂)₂— | | —(CH₂)₃— |
| A-290. | cyclobutyl | —NH—(CH₂)₂— | | —(CH₂)₃— |
| A-291. | oxetan-3-yl | —NH—(CH₂)₂— | | —(CH₂)₃— |
| A-292. | sec-butyl | —NH—(CH₂)₂— | | —(CH₂)₃— |
| A-293. | pyridin-3-yl | —NH—(CH₂)₂— | | —(CH₂)₃— |

-continued
| | R¹ | —Y—A²—X¹— | >CR$^{12a}$R$^{12b}$ | R$^{4a}$, R$^{4b}$ |
|---|---|---|---|---|
| A-294. | 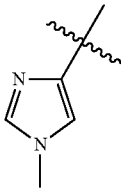 [SMILES: *c1cn(C)cn1] | —NH—(CH$_2$)$_2$— | 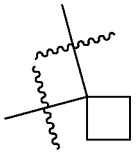 [SMILES: *C1(*)CCC1] | —(CH$_2$)$_3$— |
| A-295. | 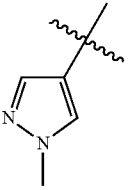 [SMILES: *c1cnn(C)c1] | —NH—(CH$_2$)$_2$— | 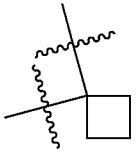 [SMILES: *C1(*)CCC1] | —(CH$_2$)$_3$— |
| A-296. | 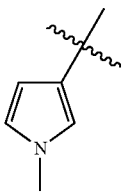 [SMILES: *c1ccn(C)c1] | —NH—(CH$_2$)$_2$— | 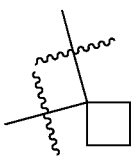 [SMILES: *C1(*)CCC1] | —(CH$_2$)$_3$— |
| A-297. | 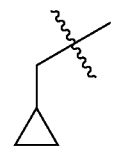 | —NH—CH$_2$— | 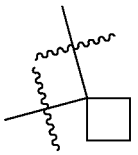 [SMILES: *C1(*)CCC1] | —(CH$_2$)$_3$— |
| A-298. | 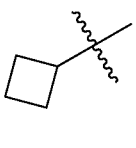 [SMILES: *C1CCC1] | —NH—CH$_2$— | 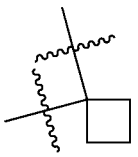 | —(CH$_2$)$_3$— |
| A-299. | 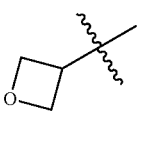 [SMILES: *C1COC1] | —NH—CH$_2$— | 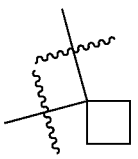 [SMILES: *C1(*)CCC1] | —(CH$_2$)$_3$— |
| A-300. | 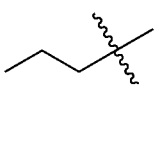 [SMILES: *CCC] | —NH—CH$_2$— | 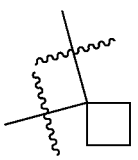 [SMILES: *C1(*)CCC1] | —(CH$_2$)$_3$— |
| A-301. | 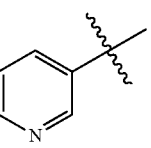 | —NH—CH$_2$— | 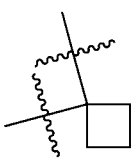 [SMILES: *C1(*)CCC1] | —(CH$_2$)$_3$— |

-continued

| | R¹ | —Y—A²—X¹— | >CR¹²ᵃR¹²ᵇ | R⁴ᵃ, R⁴ᵇ |
|---|---|---|---|---|
| A-302. | 1-methyl-imidazol-4-yl | —NH—CH₂— | cyclobutylidene | —(CH₂)₃— |
| A-303. | 1-methyl-pyrazol-4-yl | —NH—CH₂— | cyclobutylidene | —(CH₂)₃— |
| A-304. | 1-methyl-pyrrol-3-yl | —NH—CH₂— | cyclobutylidene | —(CH₂)₃— |
| A-305. | cyclopropylmethyl | azetidin-1,3-diyl | cyclobutylidene | —(CH₂)₃— |
| A-306. | cyclobutyl | azetidin-1,3-diyl | cyclobutylidene | —(CH₂)₃— |
| A-307. | oxetan-3-yl | azetidin-1,3-diyl | cyclobutylidene | —(CH₂)₃— |
| A-308. | n-propyl | azetidin-1,3-diyl | cyclobutylidene | —(CH₂)₃— |
| A-309. | pyridin-3-yl | azetidin-1,3-diyl | cyclobutylidene | —(CH₂)₃— |

-continued

| | R¹ | —Y—A²—X¹— | >CR$^{12a}$R$^{12b}$ | R$^{4a}$, R$^{4b}$ |
|---|---|---|---|---|
| A-310. | N-methylimidazol-4-yl | azetidin-3-yl (N-linked) | cyclobutylidene | —(CH$_2$)$_3$— |
| A-311. | N-methylpyrazol-4-yl | azetidin-3-yl (N-linked) | cyclobutylidene | —(CH$_2$)$_3$— |
| A-312. | N-methylpyrrol-3-yl | azetidin-3-yl (N-linked) | cyclobutylidene | —(CH$_2$)$_3$— |
| A-313. | cyclopropylmethyl | —(CH$_2$)$_2$— | cyclobutylidene | —(CH$_2$)$_3$— |
| A-314. | cyclobutyl | —(CH$_2$)$_2$— | cyclobutylidene | —(CH$_2$)$_3$— |
| A-315. | oxetan-3-yl | —(CH$_2$)$_2$— | cyclobutylidene | —(CH$_2$)$_3$— |
| A-316. | sec-butyl | —(CH$_2$)$_2$— | cyclobutylidene | —(CH$_2$)$_3$— |
| A-317. | pyridin-3-yl | —(CH$_2$)$_2$— | cyclobutylidene | —(CH$_2$)$_3$— |

| | R¹ | —Y—A²—X¹— | >CR¹²ᵃR¹²ᵇ | R⁴ᵃ, R⁴ᵇ |
|---|---|---|---|---|
| A-318. | 1-methylimidazol-4-yl | —(CH₂)₂— | cyclobutylidene | —(CH₂)₃— |
| A-319. | 1-methylpyrazol-4-yl | —(CH₂)₂— | cyclobutylidene | —(CH₂)₃— |
| A-320. | 1-methylpyrrol-3-yl | —(CH₂)₂— | cyclobutylidene | —(CH₂)₃— |
| A-321. | cyclopropylmethyl | —NH—(CH₂)₂—O— | —CH₂— | —(CH₂)₄— |
| A-322. | cyclobutyl | —NH—(CH₂)₂—O— | —CH₂— | —(CH₂)₄— |
| A-323. | oxetan-3-yl | —NH—(CH₂)₂—O— | —CH₂— | —(CH₂)₄— |
| A-324. | n-propyl | —NH—(CH₂)₂—O— | —CH₂— | —(CH₂)₄— |
| A-325. | pyridin-3-yl | —NH—(CH₂)₂—O— | —CH₂— | —(CH₂)₄— |
| A-326. | 1-methylimidazol-5-yl | —NH—(CH₂)₂—O— | —CH₂— | —(CH₂)₄— |

-continued

| | R¹ | —Y—A²—X¹— | >CR¹²ᵃR¹²ᵇ | R⁴ᵃ, R⁴ᵇ |
|---|---|---|---|---|
| A-327. | (1-methylpyrazol-4-yl) | —NH—(CH₂)₂—O— | —CH₂— | —(CH₂)₄— |
| A-328. | (1-methylpyrrol-3-yl) | —NH—(CH₂)₂—O— | —CH₂— | —(CH₂)₄— |
| A-329. | (cyclopropylmethyl) | —NH—(CH₂)₂— | —CH₂— | —(CH₂)₄— |
| A-330. | (cyclobutyl) | —NH—(CH₂)₂— | —CH₂— | —(CH₂)₄— |
| A-331. | (oxetan-3-yl) | —NH—(CH₂)₂— | —CH₂— | —(CH₂)₄— |
| A-332. | (butan-2-yl) | —NH—(CH₂)₂— | —CH₂— | —(CH₂)₄— |
| A-333. | (pyridin-3-yl) | —NH—(CH₂)₂— | —CH₂— | —(CH₂)₄— |
| A-334. | (1-methylimidazol-5-yl) | —NH—(CH₂)₂— | —CH₂— | —(CH₂)₄— |
| A-335. | (1-methylpyrazol-4-yl) | —NH—(CH₂)₂— | —CH₂— | —(CH₂)₄— |

-continued

| | R¹ | —Y—A²—X¹— | >CR$^{12a}$R$^{12b}$ | R$^{4a}$, R$^{4b}$ |
|---|---|---|---|---|
| A-336. | (1-methylpyrrol-3-yl) | —NH—(CH$_2$)$_2$— | —CH$_2$— | —(CH$_2$)$_4$— |
| A-337. | (cyclopropylmethyl) | —NH—CH$_2$— | —CH$_2$— | —(CH$_2$)$_4$— |
| A-338. | (cyclobutyl) | —NH—CH$_2$— | —CH$_2$— | —(CH$_2$)$_4$— |
| A-339. | (oxetan-3-yl) | —NH—CH$_2$— | —CH$_2$— | —(CH$_2$)$_4$— |
| A-340. | (sec-butyl) | —NH—CH$_2$— | —CH$_2$— | —(CH$_2$)$_4$— |
| A-341. | (pyridin-3-yl) | —NH—CH$_2$— | —CH$_2$— | —(CH$_2$)$_4$— |
| A-342. | (1-methylimidazol-4-yl) | —NH—CH$_2$— | —CH$_2$— | —(CH$_2$)$_4$— |
| A-343. | (1-methylpyrazol-4-yl) | —NH—CH$_2$— | —CH$_2$— | —(CH$_2$)$_4$— |
| A-344. | (1-methylpyrrol-3-yl) | —NH—CH$_2$— | —CH$_2$— | —(CH$_2$)$_4$— |

-continued
| | R$^1$ | —Y—A$^2$—X$^1$— | >CR$^{12a}$R$^{12b}$ | R$^{4a}$, R$^{4b}$ |
|---|---|---|---|---|
| A-345. | 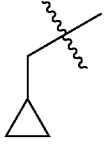 | 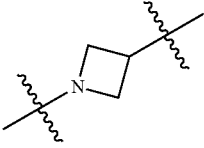 [SMILES: *C1CN(*)C1] | —CH$_2$— | —(CH$_2$)$_4$— |
| A-346. | 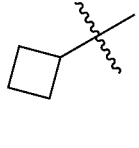 [SMILES: *C1CCC1] | 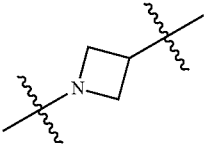 | —CH$_2$— | —(CH$_2$)$_4$— |
| A-347. | 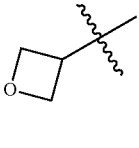 [SMILES: *C1COC1] | 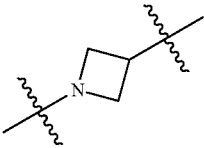 [SMILES: *C1CN(*)C1] | —CH$_2$— | —(CH$_2$)$_4$— |
| A-348. | 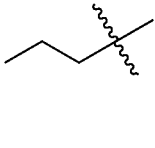 [SMILES: *CCC] | 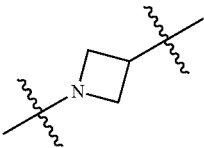 | —CH$_2$— | —(CH$_2$)$_4$— |
| A-349. | 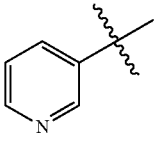 | 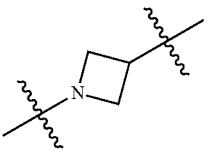 | —CH$_2$— | —(CH$_2$)$_4$— |
| A-350. | 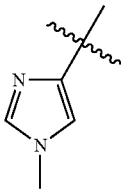 [SMILES: *c1cn(C)cn1] | 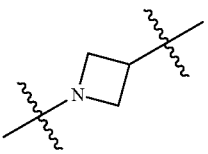 [SMILES: *C1CN(*)C1] | —CH$_2$— | —(CH$_2$)$_4$— |
| A-351. | 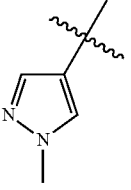 [SMILES: *c1cnn(C)c1] | 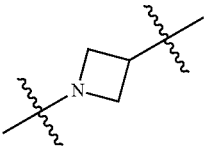 | —CH$_2$— | —(CH$_2$)$_4$— |
| A-352. | 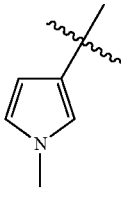 [SMILES: *c1ccn(C)c1] | 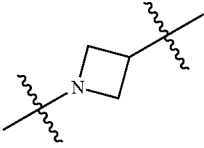 [SMILES: *C1CN(*)C1] | —CH$_2$— | —(CH$_2$)$_4$— |

| | R¹ | —Y—A²—X¹— | >CR¹²ᵃR¹²ᵇ | R⁴ᵃ, R⁴ᵇ |
|---|---|---|---|---|
| A-353. | 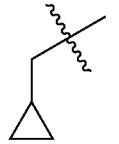 | —(CH₂)₂— | —CH₂— | —(CH₂)₄— |
| A-354. | 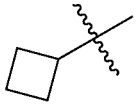 [SMILES: *C1CCC1] | —(CH₂)₂— | —CH₂— | —(CH₂)₄— |
| A-355. | 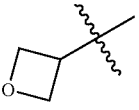 [SMILES: *C1COC1] | —(CH₂)₂— | —CH₂— | —(CH₂)₄— |
| A-356. | 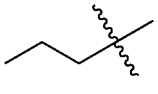 [SMILES: *CCC] | —(CH₂)₂— | —CH₂— | —(CH₂)₄— |
| A-357. | 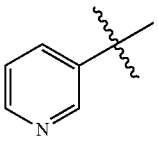 [SMILES: *c1cccnc1] | —(CH₂)₂— | —CH₂— | —(CH₂)₄— |
| A-358. | 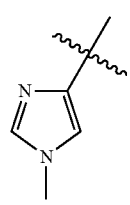 [SMILES: *c1cn(C)cn1] | —(CH₂)₂— | —CH₂— | —(CH₂)₄— |
| A-359. | 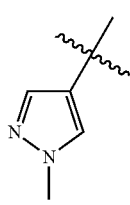 [SMILES: *c1cnn(C)c1] | —(CH₂)₂— | —CH₂— | —(CH₂)₄— |
| A-360. | 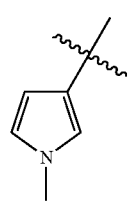 [SMILES: *c1ccn(C)c1] | —(CH₂)₂— | —CH₂— | —(CH₂)₄— |
| A-361. | 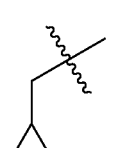 | —NH—(CH₂)₂—O— | 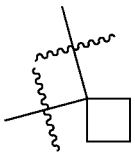 [SMILES: *C1(*)CCC1] | —(CH₂)₄— |
| A-362. | 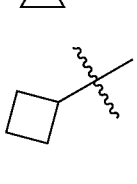 | —NH—(CH₂)₂—O— | 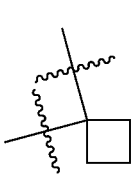 | —(CH₂)₄— |

-continued
| | R¹ | —Y—A²—X¹— | >CR¹²ᵃR¹²ᵇ | R⁴ᵃ, R⁴ᵇ |
|---|---|---|---|---|
| A-363. | 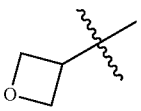 [SMILES: *C1COC1] | —NH—(CH₂)₂—O— | 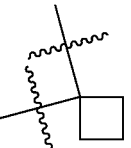 | —(CH₂)₄— |
| A-364. | 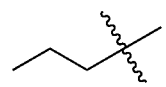 | —NH—(CH₂)₂—O— | 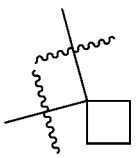 [SMILES: *C1(*)CCC1] | —(CH₂)₄— |
| A-365. | 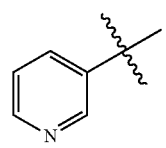 [SMILES: *c1cccnc1] | —NH—(CH₂)₂—O— | 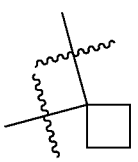 [SMILES: *C1(*)CCC1] | —(CH₂)₄— |
| A-366. | 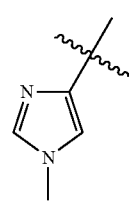 [SMILES: *c1cn(C)cn1] | —NH—(CH₂)₂—O— | 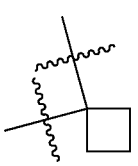 [SMILES: *C1(*)CCC1] | —(CH₂)₄— |
| A-367. | 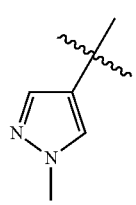 [SMILES: *c1cnn(C)c1] | —NH—(CH₂)₂—O— | 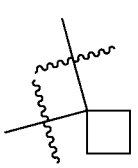 [SMILES: *C1(*)CCC1] | —(CH₂)₄— |
| A-368. | 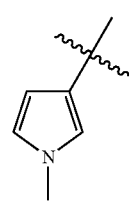 [SMILES: *c1ccn(C)c1] | —NH—(CH₂)₂—O— | 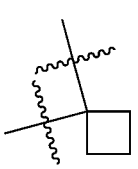 | —(CH₂)₄— |
| A-369. | 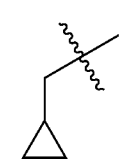 | —NH—(CH₂)₂— | 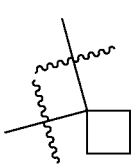 [SMILES: *C1(*)CCC1] | —(CH₂)₄— |
| A-370. | 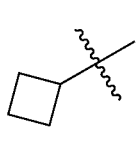 [SMILES: *C1CCC1] | —NH—(CH₂)₂— | 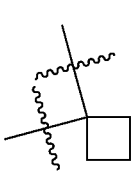 | —(CH₂)₄— |
| A-371. | 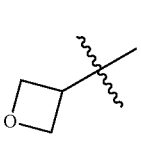 [SMILES: *C1COC1] | —NH—(CH₂)₂— | 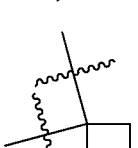 | —(CH₂)₄— |

-continued
| | R¹ | —Y—A²—X¹— | >CR¹²ᵃR¹²ᵇ | R⁴ᵃ, R⁴ᵇ |
|---|---|---|---|---|
| A-372. | 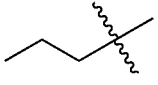 [SMILES: *CCC] | —NH—(CH₂)₂— | 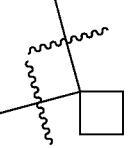 | —(CH₂)₄— |
| A-373. | 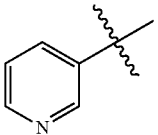 [SMILES: *c1cccnc1] | —NH—(CH₂)₂— | 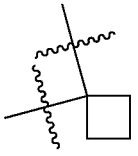 | —(CH₂)₄— |
| A-374. | 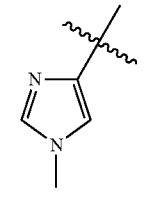 [SMILES: *c1cn(C)cn1] | —NH—(CH₂)₂— | 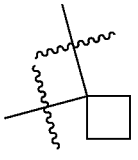 [SMILES: *C1(*)CCC1] | —(CH₂)₄— |
| A-375. | 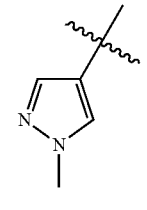 [SMILES: *c1cnn(C)c1] | —NH—(CH₂)₂— | 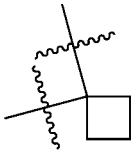 [SMILES: *C1(*)CCC1] | —(CH₂)₄— |
| A-376. | 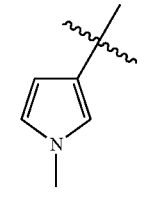 [SMILES: *c1ccn(C)c1] | —NH—(CH₂)₂— | 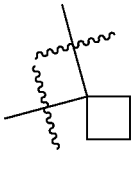 | —(CH₂)₄— |
| A-377. | 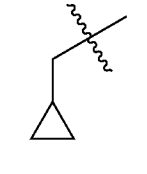 | —NH—CH₂— | 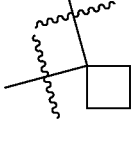 | —(CH₂)₄— |
| A-378. | 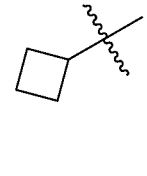 [SMILES: *C1CCC1] | —NH—CH₂— | 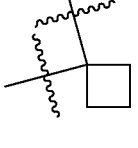 | —(CH₂)₄— |
| A-379. | 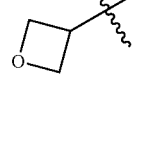 | —NH—CH₂— | 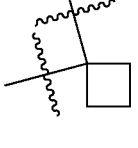 | —(CH₂)₄— |

-continued

| | R¹ | —Y—A²—X¹— | >CR¹²ᵃR¹²ᵇ | R⁴ᵃ, R⁴ᵇ |
|---|---|---|---|---|
| A-380. | (sec-butyl group) | —NH—CH₂— | (cyclobutyl) | —(CH₂)₄— |
| A-381. | (pyridin-3-yl) | —NH—CH₂— | (cyclobutyl) | —(CH₂)₄— |
| A-382. | (1-methylimidazol-4-yl) | —NH—CH₂— | (cyclobutyl) | —(CH₂)₄— |
| A-383. | (1-methylpyrazol-4-yl) | —NH—CH₂— | (cyclobutyl) | —(CH₂)₄— |
| A-384. | (1-methylpyrrol-3-yl) | —NH—CH₂— | (cyclobutyl) | —(CH₂)₄— |
| A-385. | (cyclopropylmethyl) | (azetidin-3-yl) | (cyclobutyl) | —(CH₂)₄— |
| A-386. | (cyclobutyl) | (azetidin-3-yl) | (cyclobutyl) | —(CH₂)₄— |
| A-387. | (oxetan-3-yl) | (azetidin-3-yl) | (cyclobutyl) | —(CH₂)₄— |

US 9,051,280 B2

139                                                                                                                      140

-continued

| | R¹ | —Y—A²—X¹— | >CR¹²ᵃR¹²ᵇ | R⁴ᵃ, R⁴ᵇ |
|---|---|---|---|---|
| A-388. | (n-butyl) | azetidine | cyclobutyl | —(CH₂)₄— |
| A-389. | (pyridin-3-yl) | azetidine | cyclobutyl | —(CH₂)₄— |
| A-390. | (1-methylimidazol-5-yl) | azetidine | cyclobutyl | —(CH₂)₄— |
| A-391. | (1-methylpyrazol-4-yl) | azetidine | cyclobutyl | —(CH₂)₄— |
| A-392. | (1-methylpyrrol-3-yl) | azetidine | cyclobutyl | —(CH₂)₄— |
| A-393. | (cyclopropylmethyl) | —(CH₂)₂— | cyclobutyl | —(CH₂)₄— |
| A-394. | (cyclobutyl) | —(CH₂)₂— | cyclobutyl | —(CH₂)₄— |
| A-395. | (oxetan-3-yl) | —(CH₂)₂— | cyclobutyl | —(CH₂)₄— |
| A-396. | (n-propyl) | —(CH₂)₂— | cyclobutyl | —(CH₂)₄— |

-continued

| | R¹ | —Y—A²—X¹— | >CR¹²ᵃR¹²ᵇ | R⁴ᵃ, R⁴ᵇ |
|---|---|---|---|---|
| A-397. | 3-pyridyl | —(CH₂)₂— | cyclobutylidene | —(CH₂)₄— |
| A-398. | 1-methyl-imidazol-4-yl | —(CH₂)₂— | cyclobutylidene | —(CH₂)₄— |
| A-399. | 1-methyl-pyrazol-4-yl | —(CH₂)₂— | cyclobutylidene | —(CH₂)₄— |
| A-400. | 1-methyl-pyrrol-3-yl | —(CH₂)₂— | cyclobutylidene | —(CH₂)₄— |
| A-401. | cyclopropylmethyl | —NH—(CH₂)₂—O— | —CH₂— | —(CH₂)₂—O—(CH₂)₂— |
| A-402. | cyclobutyl | —NH—(CH₂)₂—O— | —CH₂— | —(CH₂)₂—O—(CH₂)₂— |
| A-403. | oxetan-3-yl | —NH—(CH₂)₂—O— | —CH₂— | —(CH₂)₂—O—(CH₂)₂— |
| A-404. | n-propyl | —NH—(CH₂)₂—O— | —CH₂— | —(CH₂)₂—O—(CH₂)₂— |
| A-405. | 3-pyridyl | —NH—(CH₂)₂—O— | —CH₂— | —(CH₂)₂—O—(CH₂)₂— |

-continued
| | R¹ | —Y—A²—X¹— | >CR$^{12a}$R$^{12b}$ | R$^{4a}$, R$^{4b}$ |
|---|---|---|---|---|
| A-406. | 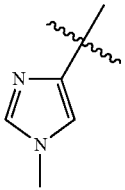 [SMILES: *c1cn(C)cn1] | —NH—(CH$_2$)$_2$—O— | —CH$_2$— | —(CH$_2$)$_2$—O—(CH$_2$)$_2$— |
| A-407. | 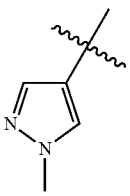 | —NH—(CH$_2$)$_2$—O— | —CH$_2$— | —(CH$_2$)$_2$—O—(CH$_2$)$_2$— |
| A-408. | 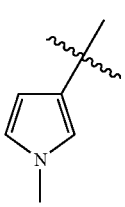 [SMILES: *c1ccn(C)c1] | —NH—(CH$_2$)$_2$—O— | —CH$_2$— | —(CH$_2$)$_2$—O—(CH$_2$)$_2$— |
| A-409. | 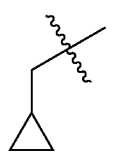 | —NH—(CH$_2$)$_2$— | —CH$_2$— | —(CH$_2$)$_2$—O—(CH$_2$)$_2$— |
| A-410. | 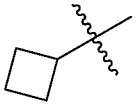 [SMILES: *C1CCC1] | —NH—(CH$_2$)$_2$— | —CH$_2$— | —(CH$_2$)$_2$—O—(CH$_2$)$_2$— |
| A-411. | 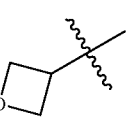 | —NH—(CH$_2$)$_2$— | —CH$_2$— | —(CH$_2$)$_2$—O—(CH$_2$)$_2$— |
| A-412. | 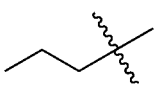 | —NH—(CH$_2$)$_2$— | —CH$_2$— | —(CH$_2$)$_2$—O—(CH$_2$)$_2$— |
| A-413. | 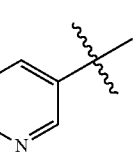 | —NH—(CH$_2$)$_2$— | —CH$_2$— | —(CH$_2$)$_2$—O—(CH$_2$)$_2$— |
| A-414. | 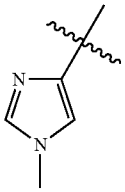 [SMILES: *c1cn(C)cn1] | —NH—(CH$_2$)$_2$— | —CH$_2$— | —(CH$_2$)$_2$—O—(CH$_2$)$_2$— |

-continued

| | R¹ | —Y—A²—X¹— | >CR$^{12a}$R$^{12b}$ | R$^{4a}$, R$^{4b}$ |
|---|---|---|---|---|
| A-415. | 1-methyl-1H-pyrazol-4-yl | —NH—(CH$_2$)$_2$— | —CH$_2$— | —(CH$_2$)$_2$—O—(CH$_2$)$_2$— |
| A-416. | 1-methyl-1H-pyrrol-3-yl | —NH—(CH$_2$)$_2$— | —CH$_2$— | —(CH$_2$)$_2$—O—(CH$_2$)$_2$— |
| A-417. | cyclopropylmethyl | —NH—CH$_2$— | —CH$_2$— | —(CH$_2$)$_2$—O—(CH$_2$)$_2$— |
| A-418. | cyclobutyl | —NH—CH$_2$— | —CH$_2$— | —(CH$_2$)$_2$—O—(CH$_2$)$_2$— |
| A-419. | oxetan-3-yl | —NH—CH$_2$— | —CH$_2$— | —(CH$_2$)$_2$—O—(CH$_2$)$_2$— |
| A-420. | butan-2-yl | —NH—CH$_2$— | —CH$_2$— | —(CH$_2$)$_2$—O—(CH$_2$)$_2$— |
| A-421. | pyridin-3-yl | —NH—CH$_2$— | —CH$_2$— | —(CH$_2$)$_2$—O—(CH$_2$)$_2$— |
| A-422. | 1-methyl-1H-imidazol-5-yl | —NH—CH$_2$— | —CH$_2$— | —(CH$_2$)$_2$—O—(CH$_2$)$_2$— |
| A-423. | 1-methyl-1H-pyrazol-4-yl | —NH—CH$_2$— | —CH$_2$— | —(CH$_2$)$_2$—O—(CH$_2$)$_2$— |

-continued
| | R[1] | —Y—A[2]—X[1]— | >CR[12a]R[12b] | R[4a], R[4b] |
|---|---|---|---|---|
| A-424. | 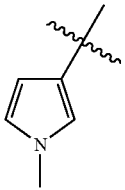 [SMILES: *c1ccn(C)c1] | —NH—CH$_2$— | —CH$_2$— | —(CH$_2$)$_2$—O—(CH$_2$)$_2$— |
| A-425. | 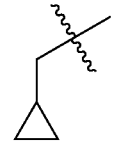 | 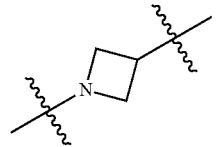 [SMILES: *C1CN(*)C1] | —CH$_2$— | —(CH$_2$)$_2$—O—(CH$_2$)$_2$— |
| A-426. | 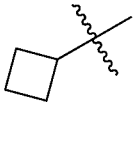 [SMILES: *C1CCC1] | 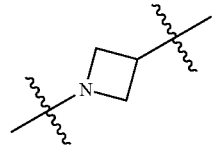 | —CH$_2$— | —(CH$_2$)$_2$—O—(CH$_2$)$_2$— |
| A-427. | 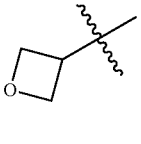 [SMILES: *C1COC1] | 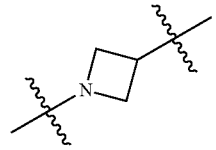 [SMILES: *C1CN(*)C1] | —CH$_2$— | —(CH$_2$)$_2$—O—(CH$_2$)$_2$— |
| A-428. | 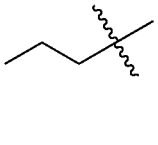 [SMILES: *CCC] | 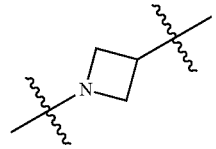 [SMILES: *C1CN(*)C1] | —CH$_2$— | —(CH$_2$)$_2$—O—(CH$_2$)$_2$— |
| A-429. | 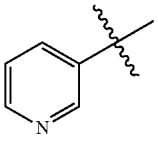 | 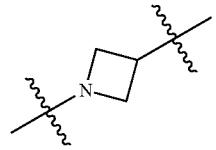 [SMILES: *C1CN(*)C1] | —CH$_2$— | —(CH$_2$)$_2$—O—(CH$_2$)$_2$— |
| A-430. | 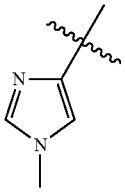 [SMILES: *c1cn(C)cn1] | 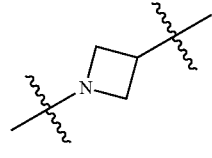 [SMILES: *C1CN(*)C1] | —CH$_2$— | —(CH$_2$)$_2$—O—(CH$_2$)$_2$— |
| A-431. | 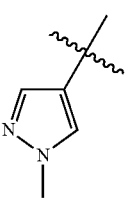 [SMILES: *c1cnn(C)c1] | 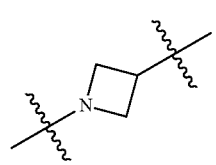 [SMILES: *C1CN(*)C1] | —CH$_2$— | —(CH$_2$)$_2$—O—(CH$_2$)$_2$— |

-continued
| | R¹ | —Y—A²—X¹— | >CR$^{12a}$R$^{12b}$ | R$^{4a}$, R$^{4b}$ |
|---|---|---|---|---|
| A-432. | 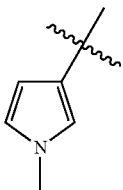 [SMILES: *c1ccn(C)c1] | 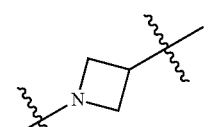 | —CH$_2$— | —(CH$_2$)$_2$—O—(CH$_2$)$_2$— |
| A-433. | 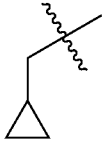 | —(CH$_2$)$_2$— | —CH$_2$— | —(CH$_2$)$_2$—O—(CH$_2$)$_2$— |
| A-434. | 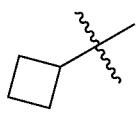 [SMILES: *C1CCC1] | —(CH$_2$)$_2$— | —CH$_2$— | —(CH$_2$)$_2$—O—(CH$_2$)$_2$— |
| A-435. | 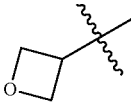 | —(CH$_2$)$_2$— | —CH$_2$— | —(CH$_2$)$_2$—O—(CH$_2$)$_2$— |
| A-436. | 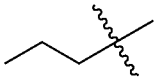 [SMILES: *CCC] | —(CH$_2$)$_2$— | —CH$_2$— | —(CH$_2$)$_2$—O—(CH$_2$)$_2$— |
| A-437. | 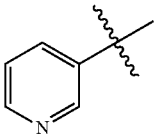 [SMILES: *c1cccnc1] | —(CH$_2$)$_2$— | —CH$_2$— | —(CH$_2$)$_2$—O—(CH$_2$)$_2$— |
| A-438. | 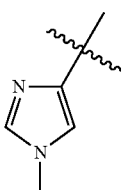 | —(CH$_2$)$_2$— | —CH$_2$— | —(CH$_2$)$_2$—O—(CH$_2$)$_2$— |
| A-439. | 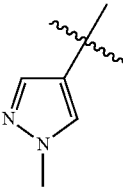 [SMILES: *c1cnn(C)c1] | —(CH$_2$)$_2$— | —CH$_2$— | —(CH$_2$)$_2$—O—(CH$_2$)$_2$— |
| A-440. | 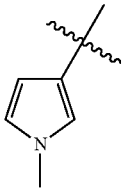 [SMILES: *c1ccn(C)c1] | —(CH$_2$)$_2$— | —CH$_2$— | —(CH$_2$)$_2$—O—(CH$_2$)$_2$— |

-continued
| | R¹ | —Y—A²—X¹— | >CR¹²ᵃR¹²ᵇ | R⁴ᵃ, R⁴ᵇ |
|---|---|---|---|---|
| A-441. | 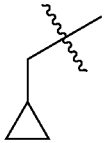 | —NH—(CH₂)₂—O— | 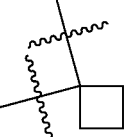 | —(CH₂)₂—O—(CH₂)₂— |
| A-442. | 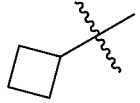 [SMILES: *C1CCC1] | —NH—(CH₂)₂—O— | 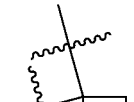 | —(CH₂)₂—O—(CH₂)₂— |
| A-443. | 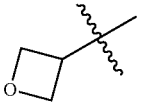 | —NH—(CH₂)₂—O— |  | —(CH₂)₂—O—(CH₂)₂— |
| A-444. | 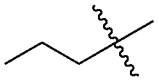 [SMILES: *CCC] | —NH—(CH₂)₂—O— |  | —(CH₂)₂—O—(CH₂)₂— |
| A-445. | 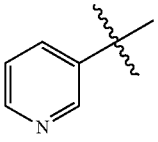 [SMILES: *c1cccnc1] | —NH—(CH₂)₂—O— | 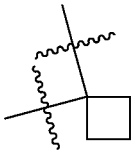 [SMILES: *C1(*)CCC1] | —(CH₂)₂—O—(CH₂)₂— |
| A-446. | 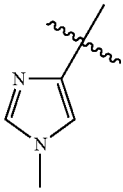 [SMILES: *c1cn(C)cn1] | —NH—(CH₂)₂—O— | 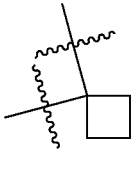 [SMILES: *C1(*)CCC1] | —(CH₂)₂—O—(CH₂)₂— |
| A-447. | 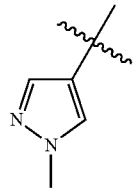 [SMILES: *c1cnn(C)c1] | —NH—(CH₂)₂—O— | 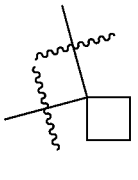 | —(CH₂)₂—O—(CH₂)₂— |
| A-448. | 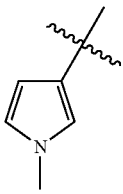 [SMILES: *c1ccn(C)c1] | —NH—(CH₂)₂—O— | 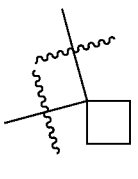 [SMILES: *C1(*)CCC1] | —(CH₂)₂—O—(CH₂)₂— |
| A-449. | 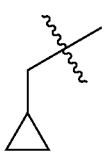 | —NH—(CH₂)₂— | 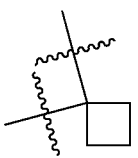 [SMILES: *C1(*)CCC1] | —(CH₂)₂—O—(CH₂)₂— |

-continued
| | R¹ | —Y—A²—X¹— | >CR$^{12a}$R$^{12b}$ | R$^{4a}$, R$^{4b}$ |
|---|---|---|---|---|
| A-450. | 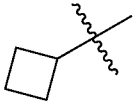 [SMILES: *C1CCC1] | —NH—(CH$_2$)$_2$— | 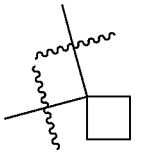 [SMILES: *C1(*)CCC1] | —(CH$_2$)$_2$—O—(CH$_2$)$_2$— |
| A-451. | 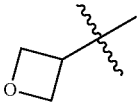 [SMILES: *C1COC1] | —NH—(CH$_2$)$_2$— | 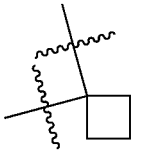 | —(CH$_2$)$_2$—O—(CH$_2$)$_2$— |
| A-452. | 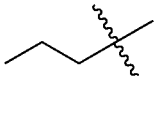 [SMILES: *CCC] | —NH—(CH$_2$)$_2$— | 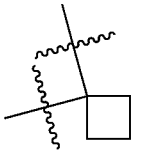 [SMILES: *C1(*)CCC1] | —(CH$_2$)$_2$—O—(CH$_2$)$_2$— |
| A-453. | 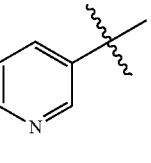 | —NH—(CH$_2$)$_2$— | 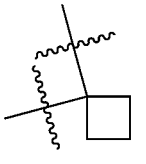 | —(CH$_2$)$_2$—O—(CH$_2$)$_2$— |
| A-454. | 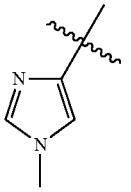 [SMILES: *c1cn(C)cn1] | —NH—(CH$_2$)$_2$— | 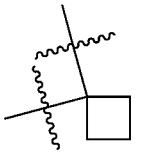 | —(CH$_2$)$_2$—O—(CH$_2$)$_2$— |
| A-455. | 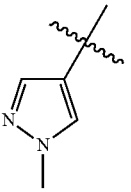 [SMILES: *c1cnn(C)c1] | —NH—(CH$_2$)$_2$— | 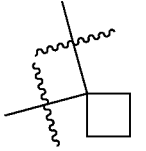 [SMILES: *C1(*)CCC1] | —(CH$_2$)$_2$—O—(CH$_2$)$_2$— |
| A-456. | 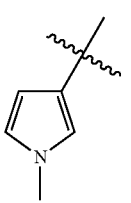 [SMILES: *c1ccn(C)c1] | —NH—(CH$_2$)$_2$— | 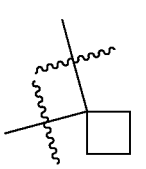 | —(CH$_2$)$_2$—O—(CH$_2$)$_2$— |
| A-457. | 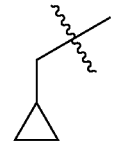 | —NH—CH$_2$— | 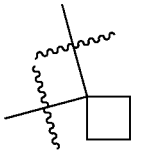 | —(CH$_2$)$_2$—O—(CH$_2$)$_2$— |

-continued
| | R[1] | —Y—A[2]—X[1]— | >CR[12a]R[12b] | R[4a], R[4b] |
|---|---|---|---|---|
| A-458. | 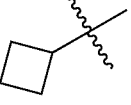 | —NH—CH$_2$— | 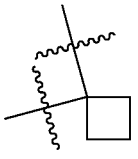 | —(CH$_2$)$_2$—O—(CH$_2$)$_2$— |
| A-459. | 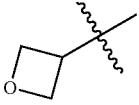 [SMILES: *C1COC1] | —NH—CH$_2$— | 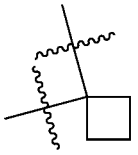 [SMILES: *C1(*)CCC1] | —(CH$_2$)$_2$—O—(CH$_2$)$_2$— |
| A-460. | 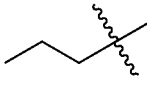 | —NH—CH$_2$— | 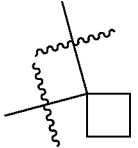 [SMILES: *C1(*)CCC1] | —(CH$_2$)$_2$—O—(CH$_2$)$_2$— |
| A-461. | 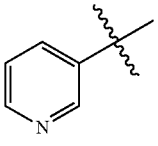 | —NH—CH$_2$— | 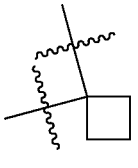 [SMILES: *C1(*)CCC1] | —(CH$_2$)$_2$—O—(CH$_2$)$_2$— |
| A-462. | 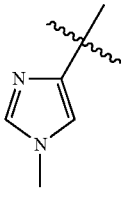 [SMILES: *c1cn(C)cn1] | —NH—CH$_2$— | 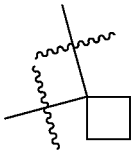 [SMILES: *C1(*)CCC1] | —(CH$_2$)$_2$—O—(CH$_2$)$_2$— |
| A-463. | 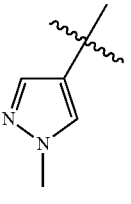 [SMILES: *c1cnn(C)c1] | —NH—CH$_2$— | 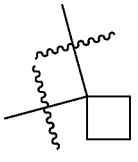 | —(CH$_2$)$_2$—O—(CH$_2$)$_2$— |
| A-464. | 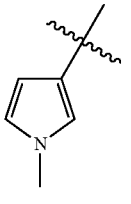 [SMILES: *c1ccn(C)c1] | —NH—CH$_2$— | 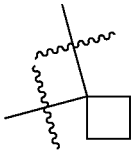 [SMILES: *C1(*)CCC1] | —(CH$_2$)$_2$—O—(CH$_2$)$_2$— |
| A-465. | 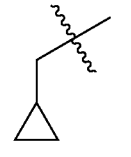 | 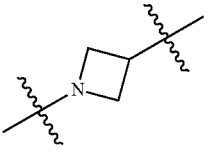 | 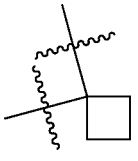 | —(CH$_2$)$_2$—O—(CH$_2$)$_2$— |
| A-466. | 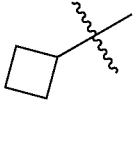 [SMILES: *C1CCC1] | 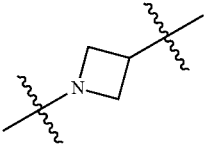 [SMILES: *C1CN(*)C1] | 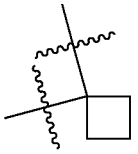 | —(CH$_2$)$_2$—O—(CH$_2$)$_2$— |

-continued
| | R$^1$ | —Y—A$^2$—X$^1$— | >CR$^{12a}$R$^{12b}$ | R$^{4a}$, R$^{4b}$ |
|---|---|---|---|---|
| A-467. | 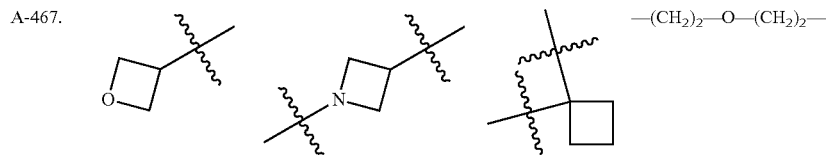 | | | —(CH$_2$)$_2$—O—(CH$_2$)$_2$— |
| A-468. | 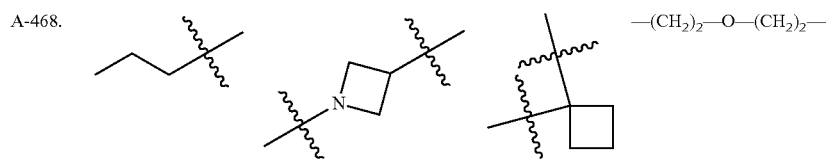 | | | —(CH$_2$)$_2$—O—(CH$_2$)$_2$— |
| A-469. | 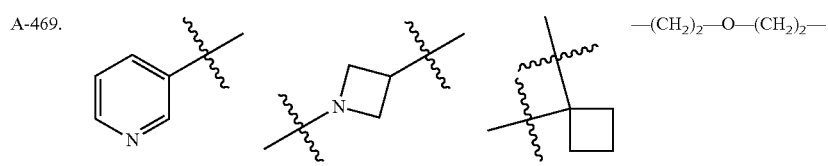 | | | —(CH$_2$)$_2$—O—(CH$_2$)$_2$— |
| A-470. | 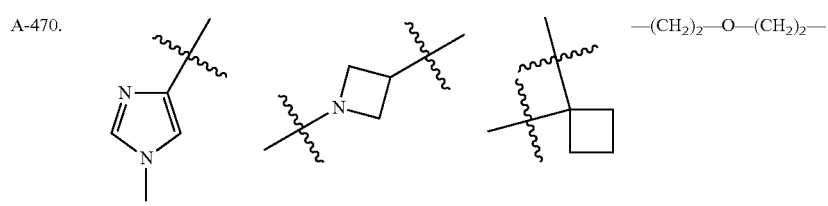 | | | —(CH$_2$)$_2$—O—(CH$_2$)$_2$— |
| A-471. | 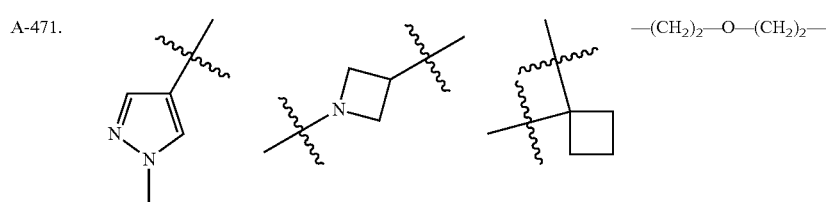 | | | —(CH$_2$)$_2$—O—(CH$_2$)$_2$— |
| A-472. | 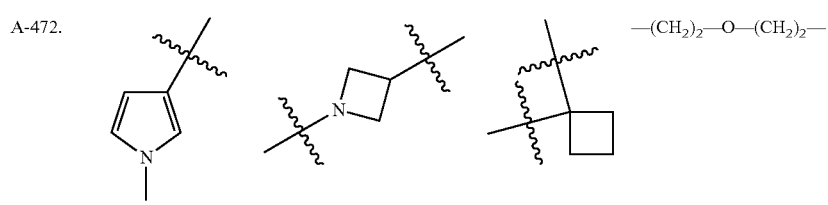 | | | —(CH$_2$)$_2$—O—(CH$_2$)$_2$— |
| A-473. | 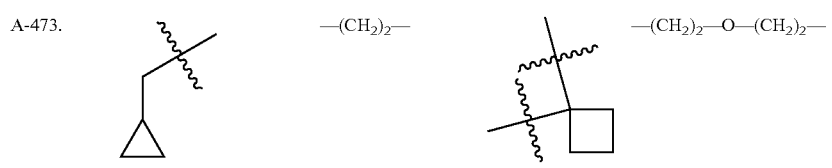 | —(CH$_2$)$_2$— | | —(CH$_2$)$_2$—O—(CH$_2$)$_2$— |
| A-474. | 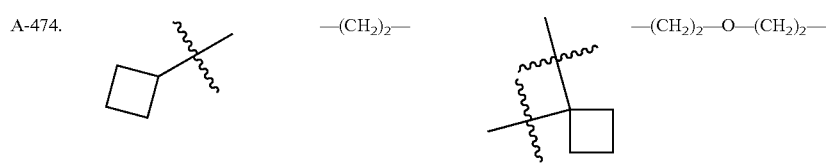 | —(CH$_2$)$_2$— | | —(CH$_2$)$_2$—O—(CH$_2$)$_2$— |

-continued

| | R¹ | —Y—A²—X¹— | >CR¹²ᵃR¹²ᵇ | R⁴ᵃ, R⁴ᵇ |
|---|---|---|---|---|
| A-475. | (3-oxetanyl) | —(CH₂)₂— | (cyclobutylidene) | —(CH₂)₂—O—(CH₂)₂— |
| A-476. | (n-butyl, attached at C2) | —(CH₂)₂— | (cyclobutylidene) | —(CH₂)₂—O—(CH₂)₂— |
| A-477. | (pyridin-3-yl) | —(CH₂)₂— | (cyclobutylidene) | —(CH₂)₂—O—(CH₂)₂— |
| A-478. | (1-methyl-1H-imidazol-4-yl) | —(CH₂)₂— | (cyclobutylidene) | —(CH₂)₂—O—(CH₂)₂— |
| A-479. | (1-methyl-1H-pyrazol-4-yl) | —(CH₂)₂— | (cyclobutylidene) | —(CH₂)₂—O—(CH₂)₂— |
| A-480. | (1-methyl-1H-pyrrol-3-yl) | —(CH₂)₂— | (cyclobutylidene) | —(CH₂)₂—O—(CH₂)₂— |

Further particular compounds of the present invention are the individual derivatives (in particular tetraline and indane derivatives) of the formula (Id) as listed in the following tables 25 to 48 and physiologically tolerated salts thereof:

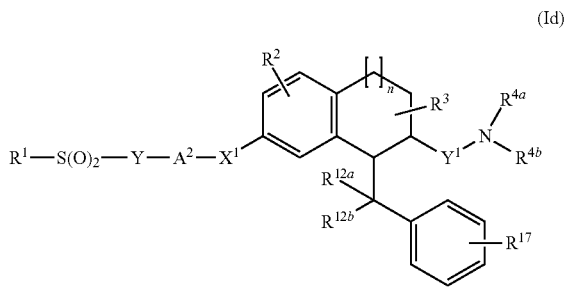

(Id)

Table 25

Compounds of the formula (Id) wherein —$Y^1$—$NR^{4a}R^{4b}$ is as defined herein and in particular represents one of the partial structures P1, P2, P3 or P4, $R^2$ is hydrogen, $R^3$ is as defined herein and in particular represents hydrogen, $R^{17}$ is hydrogen and the combination of $R^1$, —Y-$A^2$-$X^1$—, >$CR^{12a}R^{12b}$, $R^{4b}$ for a compound in each case corresponds to one line of Table A (A-481 to A-640).

Table 26

Compounds of the formula (Id) wherein —$Y^1$—$NR^{4a}R^{4b}$ is as defined herein and in particular represents one of the partial structures P1, P2, P3 or P4, $R^2$ is hydrogen, $R^3$ is as defined herein and in particular represents hydrogen, $R^{17}$ is 3-F and the combination of $R^1$, —Y-$A^2$-$X^1$—, >$CR^{12a}R^{12b}$, $R^{4b}$ for a compound in each case corresponds to one line of Table A (A-481 to A-640).

Table 27

Compounds of the formula (Id) wherein —$Y^1$—$NR^{4a}R^{4b}$ is as defined herein and in particular represents one of the partial structures P1, P2, P3 or P4-, $R^2$ is hydrogen, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4b}$ for a compound in each case corresponds to one line of Table A (A-1 to A-512).

Table 28

Compounds of the formula (Id) wherein —$Y^1$—$NR^{4a}R^{4b}$ is as defined herein and in particular represents one of the partial structures P1, P2, P3 or P4, $R^2$ is hydrogen, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4b}$ for a compound in each case corresponds to one line of Table A (A-481 to A-640).

Table 29

Compounds of the formula (Id) wherein —$Y^1$—$NR^{4a}R^{4b}$ is as defined herein and in particular represents one of the partial structures P1, P2, P3 or P4, $R^2$ is hydrogen, $R^3$ is as defined herein and in particular represents hydrogen, $R^{17}$ is 2-F and the combination of $R^1$, —Y-$A^2$-$X^1$—, >$CR^{12a}R^{12b}$, $R^{4b}$ for a compound in each case corresponds to one line of Table A (A-481 to A-640).

Table 30

Compounds of the formula (Id) wherein —$Y^1$—$NR^{4a}R^{4b}$ is as defined herein and in particular represents one of the partial structures P1, P2, P3 or P4, $R^2$ is hydrogen, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4b}$ for a compound in each case corresponds to one line of Table A (A-481 to A-640).

Table 31

Compounds of the formula (Id) wherein —$Y^1$—$NR^{4a}R^{4b}$ is as defined herein and in particular represents one of the partial structures P1, P2, P3 or P4, $R^2$ is 5-F, $R^3$ is as defined herein and in particular represents hydrogen, $R^{17}$ is hydrogen and the combination of $R^1$, —Y-$A^2$-$X^1$—, >$CR^{12a}R^{12b}$, $R^{4b}$ for a compound in each case corresponds to one line of Table A (A-481 to A-640).

Table 32

Compounds of the formula (Id) wherein —Y—$NR^{4a}R^{4b}$ is as defined herein and in particular represents one of the partial structures P1, P2, P3 or P4, $R^2$ is 5-F, $R^3$ is as defined herein and in particular represents hydrogen, $R^{17}$ is 3-F and the combination of $R^1$, —Y-$A^2$-$X^1$—, >$CR^{12a}R^{12b}$, $R^{4b}$ for a compound in each case corresponds to one line of Table A (A-481 to A-640).

Table 33

Compounds of the formula (Id) wherein —$Y^1$—$NR^{4a}R^{4b}$ is as defined herein and in particular represents one of the partial structures P1, P2, P3 or P4, $R^2$ is 5-F, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4b}$ for a compound in each case corresponds to one line of Table A (A-481 to A-640).

Table 34

Compounds of the formula (Id) wherein —$Y^1$—$NR^{4a}R^{4b}$ is as defined herein and in particular represents one of the partial structures P1, P2, P3 or P4, $R^2$ is 5-F, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4b}$ for a compound in each case corresponds to one line of Table A (A-481 to A-640).

Table 35

Compounds of the formula (Id) wherein —$Y^1$—$NR^{4a}R^{4b}$ is as defined herein and in particular represents one of the partial structures P1, P2, P3 or P4, $R^2$ is 5-F, $R^3$ is as defined herein and in particular represents hydrogen, $R^{17}$ is 2-F and the combination of $R^1$, —Y-$A^2$-$X^1$—, >$CR^{12a}R^{12b}$, $R^{4b}$ for a compound in each case corresponds to one line of Table A (A-481 to A-640).

Table 36

Compounds of the formula (Id) wherein —$Y^1$—$NR^{4a}R^{4b}$ is as defined herein and in particular represents one of the partial structures P1, P2, P3 or P4, $R^2$ is 5-F, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4b}$ for a compound in each case corresponds to one line of Table A (A-481 to A-640).

Table 37

Compounds of the formula (Id) wherein —$Y^1$—$NR^{4a}R^{4b}$ is as defined herein and in particular represents one of the partial structures P1, P2, P3 or P4, $R^2$ is 6-F, $R^3$ is as defined herein and in particular represents hydrogen, $R^{17}$ is hydrogen and the combination of $R^1$, —Y-$A^2$-$X^1$—, >$CR^{12a}R^{12b}$, $R^{4b}$ for a compound in each case corresponds to one line of Table A (A-481 to A-640).

Table 38

Compounds of the formula (Id) wherein —$Y^1$—$NR^{4a}R^{4b}$ is as defined herein and in particular represents one of the partial structures P1, P2, P3 or P4, $R^2$ is 6-F, $R^3$ is as defined herein and in particular represents hydrogen, $R^{17}$ is 3-F and the combination of $R^1$, —Y-$A^2$-$X^1$—, >$CR^{12a}R^{12b}$, $R^{4b}$ for a compound in each case corresponds to one line of Table A (A-481 to A-640).

Table 39

Compounds of the formula (Id) wherein —$Y^1$—$NR^{4a}R^{4b}$ is as defined herein and in particular represents one of the partial structures P1, P2, P3 or P4, $R^2$ is 6-F, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4b}$ for a compound in each case corresponds to one line of Table A (A-481 to A-640).

Table 40

Compounds of the formula (Id) wherein —$Y^1$—$NR^{4a}R^{4b}$ is as defined herein and in particular represents one of the partial structures P1, P2, P3 or P4, $R^2$ is 6-F, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4a}$, $R^{4b}$ for a compound in each case corresponds to one line of Table A (A-481 to A-640).

Table 41

Compounds of the formula (Id) wherein —$Y^1$—$NR^{4a}R^{4b}$ is as defined herein and in particular represents one of the partial structures P1, P2, P3 or P4, $R^2$ is 6-F, $R^3$ is as defined herein and in particular represents hydrogen, $R^{17}$ is 2-F and the combination of $R^1$, —Y-$A^2$-$X^1$—, >$CR^{12a}R^{12b}$, $R^{4b}$ for a compound in each case corresponds to one line of Table A (A-481 to A-640).

Table 42

Compounds of the formula (Id) wherein —$Y^1$—$NR^{4a}R^{4b}$ is as defined herein and in particular represents one of the partial structures P1, P2, P3 or P4, $R^2$ is 6-F, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4b}$ for a compound in each case corresponds to one line of Table A (A-481 to A-640).

Table 43

Compounds of the formula (Id) wherein —Y—$NR^{4a}R^{4b}$ is as defined herein and in particular represents one of the partial structures P1, P2, P3 or P4, $R^2$ is 8-F, $R^3$ is as defined herein and in particular represents hydrogen, $R^{17}$ is hydrogen and the combination of $R^1$, —Y-$A^2$-$X^1$—, >$CR^{12a}R^{12b}$, $R^{4b}$ for a compound in each case corresponds to one line of Table A (A-481 to A-640).

Table 44

Compounds of the formula (Id) wherein —$Y^1$—$NR^{4a}R^{4b}$ is as defined herein and in particular represents one of the partial structures P1, P2, P3 or P4, $R^2$ is 8-F, $R^3$ is as defined herein and in particular represents hydrogen, $R^{17}$ is 3-F and the combination of $R^1$, —Y-$A^2$-$X^1$—, >$CR^{12a}R^{12b}$, $R^{4a}$, $R^{4b}$ for a compound in each case corresponds to one line of Table A (A-481 to A-640).

Table 45

Compounds of the formula (Id) wherein —$Y^1$—$NR^{4a}R^{4b}$ is as defined herein and in particular represents one of the partial structures P1, P2, P3 or P4, $R^2$ is 8-F, $R^3$ is as defined herein and in particular represents hydrogen, $R^{17}$ is 3-Cl and the combination of $R^1$, —Y-$A^2$-$X^1$—, >$CR^{12a}R^{12b}$, $R^{4b}$ for a compound in each case corresponds to one line of Table A (A-481 to A-640).

Table 46

Compounds of the formula (Id) wherein —$Y^1$—$NR^{4a}R^{4b}$ is as defined herein and in particular represents one of the partial structures P1, P2, P3 or P4, $R^2$ is 8-F, $R^3$ is as defined herein and in particular represents hydrogen, $R^{17}$ is 3-$CF_3$ and the combination of $R^1$, —Y-$A^2$-$X^1$—, >$CR^{12a}R^{12b}$, $R^{4b}$ for a compound in each case corresponds to one line of Table A (A-481 to A-640).

Table 47

Compounds of the formula (Id) wherein —$Y^1$—$NR^{4a}R^{4b}$ is as defined herein and in particular represents one of the partial structures P1, P2, P3 or P4, $R^2$ is 8-F, $R^3$ is as defined herein and in particular represents hydrogen, $R^{17}$ is 2-F and the combination of $R^1$, —Y-$A^2$-$X^1$—, >$CR^{12a}R^{12b}$, $R^{4b}$ for a compound in each case corresponds to one line of Table A (A-481 to A-640).

Table 48

Compounds of the formula (Id) wherein —$Y^1$—$NR^{4a}R^{4b}$ is as defined herein and in particular represents one of the partial structures P1, P2, P3 or P4, $R^2$ is 8-F, $R^3$ is as defined herein and in particular represents hydrogen, $R^{17}$ is 2-Cl and the combination of $R^1$, —Y-$A^2$-$X^1$—, >$CR^{12a}R^{12b}$, $R^{4b}$ for a compound in each case corresponds to one line of Table A (A-481 to A-640).

Partial structures P1, P2, P3, and P4:
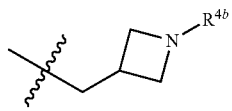
P1
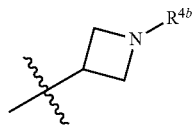
P2
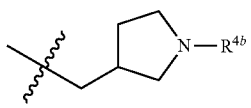
P3
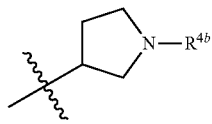
P4
| | $R^1$ | -Y-$A^2$-$X^1$- | >$CR^{12a}R^{12b}$ | $R^{4b}$ |
|---|---|---|---|---|
| A-481. | 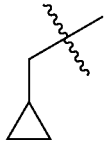 | —NH—$(CH_2)_2$—O— | —$CH_2$— | —H |
| A-482. |  | —NH—$(CH_2)_2$—O— | —$CH_2$— | —H |
| A-483. | 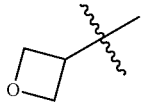 [SMILES: *C1COC1] | —NH—$(CH_2)_2$—O— | —$CH_2$— | —H |
| A-484. | 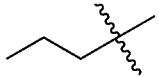 [SMILES: *CCC] | —NH—$(CH_2)_2$—O— | —$CH_2$— | —H |
| A-485. | 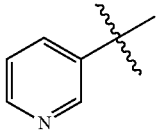 [SMILES: *c1cccnc1] | —NH—$(CH_2)_2$—O— | —$CH_2$— | —H |
| A-486. | 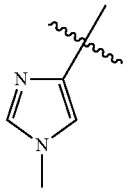 [SMILES: *c1cn(C)cn1] | —NH—$(CH_2)_2$—O— | —$CH_2$— | —H |

-continued
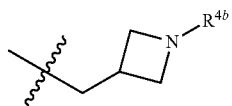 P1
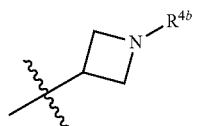 P2
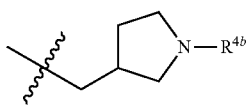 P3
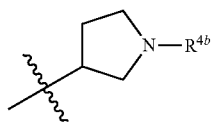 P4
| | R¹ | -Y-A²-X¹- | >CR$^{12a}$R$^{12b}$ | R$^{4b}$ |
|---|---|---|---|---|
| A-487. | 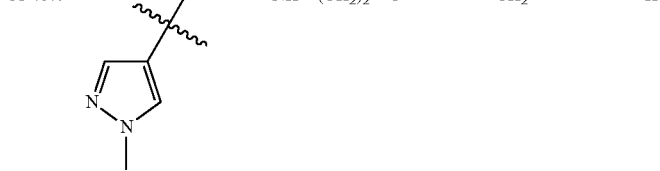 | —NH—(CH$_2$)$_2$—O— | —CH$_2$— | —H |
| A-488. | 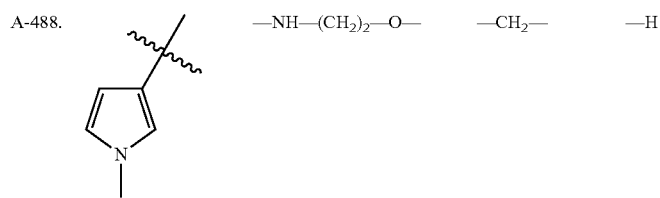 | —NH—(CH$_2$)$_2$—O— | —CH$_2$— | —H |
| A-489. | 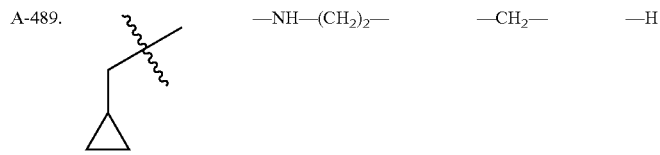 | —NH—(CH$_2$)$_2$— | —CH$_2$— | —H |
| A-490. | 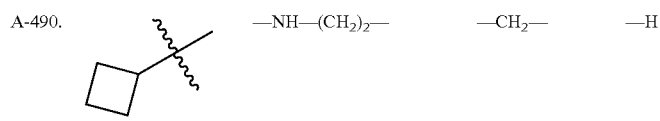 | —NH—(CH$_2$)$_2$— | —CH$_2$— | —H |
| A-491. | 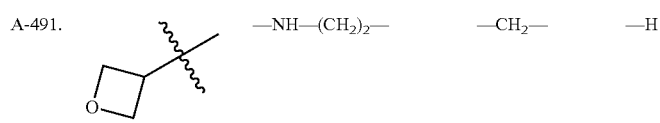 | —NH—(CH$_2$)$_2$— | —CH$_2$— | —H |
| A-492. | 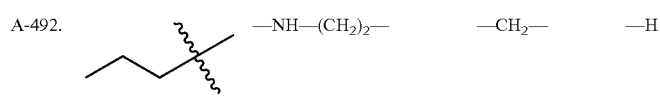 | —NH—(CH$_2$)$_2$— | —CH$_2$— | —H |

-continued
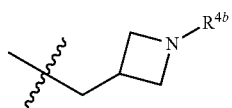
P1
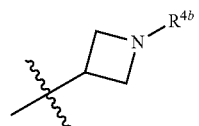
P2
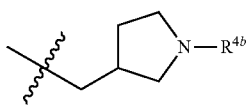
P3
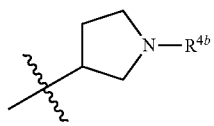
P4
| | R¹ | -Y-A²-X¹- | >CR$^{12a}$R$^{12b}$ | R$^{4b}$ |
|---|---|---|---|---|
| A-493. | (3-pyridyl) | —NH—(CH$_2$)$_2$— | —CH$_2$— | —H |
| A-494. | (1-methyl-imidazol-4-yl) | —NH—(CH$_2$)$_2$— | —CH$_2$— | —H |
| A-495. | (1-methyl-pyrazol-4-yl) | —NH—(CH$_2$)$_2$— | —CH$_2$— | —H |
| A-496. | (1-methyl-pyrrol-3-yl) | —NH—(CH$_2$)$_2$— | —CH$_2$— | —H |
| A-497. | (cyclopropylmethyl) | —NH—CH$_2$— | —CH$_2$— | —H |

-continued
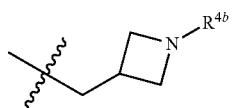 P1
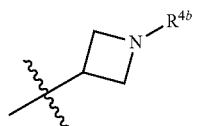 P2
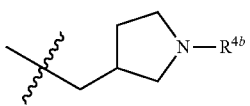 P3
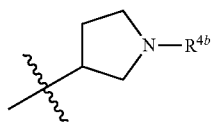 P4
| | $R^1$ | $-Y-A^2-X^1-$ | $>CR^{12a}R^{12b}$ | $R^{4b}$ |
|---|---|---|---|---|
| A-498. | cyclobutyl | —NH—CH$_2$— | —CH$_2$— | —H |
| A-499. | oxetanyl | —NH—CH$_2$— | —CH$_2$— | —H |
| A-500. | propyl | —NH—CH$_2$— | —CH$_2$— | —H |
| A-501. | pyridin-3-yl | —NH—CH$_2$— | —CH$_2$— | —H |
| A-502. | 1-methylimidazol-4-yl | —NH—CH$_2$— | —CH$_2$— | —H |
| A-503. | 1-methylpyrazol-4-yl (Na) | —NH—CH$_2$— | —CH$_2$— | —H |

-continued
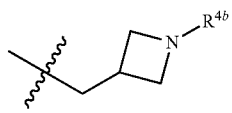
P1
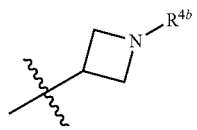
P2
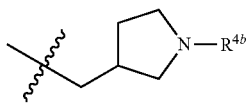
P3
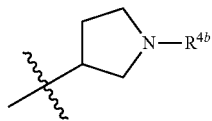
P4
| | $R^1$ | -Y-$A^2$-$X^1$- | >$CR^{12a}R^{12b}$ | $R^{4b}$ |
|---|---|---|---|---|
| A-504. | 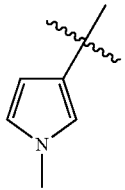 [SMILES: *c1ccn(C)c1] | —NH—$CH_2$— | —$CH_2$— | —H |
| A-505. | 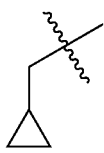 [SMILES: *CC1CC1] | 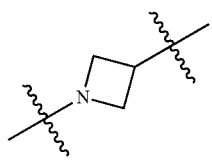 | —$CH_2$— | —H |
| A-506. | 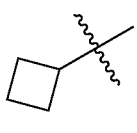 [SMILES: *C1CCC1] | 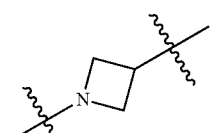 | —$CH_2$— | —H |
| A-507. | 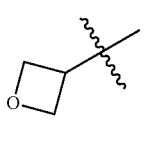 | 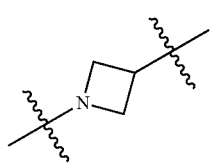 | —$CH_2$— | —H |
| A-508. | 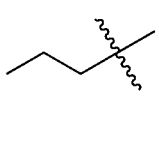 | 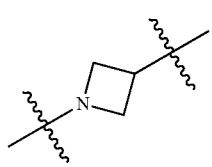 [SMILES: *C1CN(*)C1] | —$CH_2$— | —H |

-continued
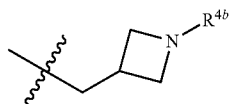   P1
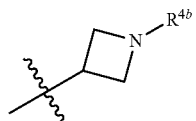   P2
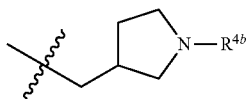   P3
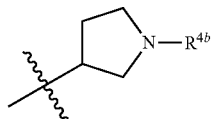   P4
| | R¹ | -Y-A²-X¹- | >CR$^{12a}$R$^{12b}$ | R$^{4b}$ |
|---|---|---|---|---|
| A-509. | 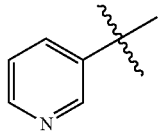 [SMILES: *c1cccnc1] | 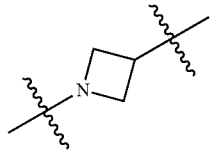 | —CH$_2$— | —H |
| A-510. | 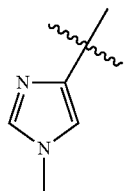 [SMILES: *c1cn(C)cn1] | 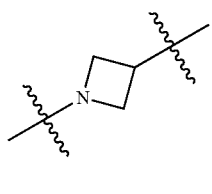 [SMILES: *C1CN(*)C1] | —CH$_2$— | —H |
| A-511. | 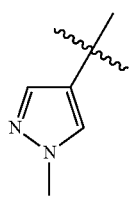 | 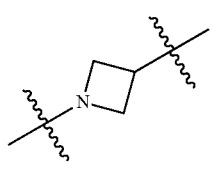 [SMILES: *C1CN(*)C1] | —CH$_2$— | —H |
| A-512. | 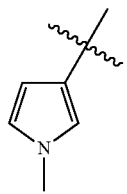 [SMILES: *c1ccn(C)c1] | 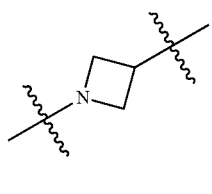 [SMILES: *C1CN(*)C1] | —CH$_2$— | —H |
| A-513. | 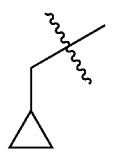 [SMILES: *CC1CC1] | —(CH$_2$)$_2$— | —CH$_2$— | —H |

-continued
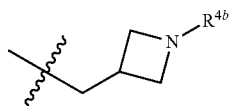 P1
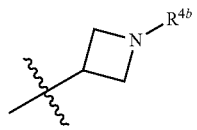 P2
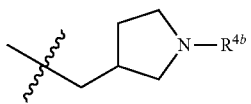 P3
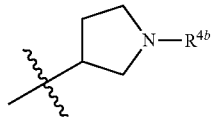 P4
| R¹ | -Y-A²-X¹- | >CR$^{12a}$R$^{12b}$ | R$^{4b}$ |
|---|---|---|---|
| A-514. ![cyclobutyl] | —(CH$_2$)$_2$— | —CH$_2$— | —H |
| A-515. ![oxetanyl] | —(CH$_2$)$_2$— | —CH$_2$— | —H |
| A-516. ![propyl] | —(CH$_2$)$_2$— | —CH$_2$— | —H |
| A-517. ![pyridin-3-yl] | —(CH$_2$)$_2$— | —CH$_2$— | —H |
| A-518. ![1-methylimidazol-4-yl] | —(CH$_2$)$_2$— | —CH$_2$— | —H |
| A-519. ![1-methylpyrazol-4-yl] | —(CH$_2$)$_2$— | —CH$_2$— | —H |

-continued
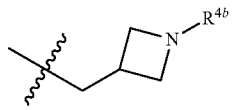
P1
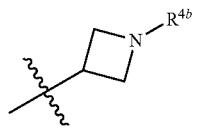
P2
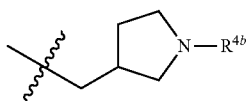
P3
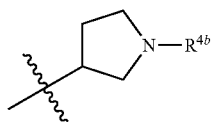
P4
| R$^1$ | -Y-A$^2$-X$^1$- | >CR$^{12a}$R$^{12b}$ | R$^{4b}$ |
|---|---|---|---|
| A-520. 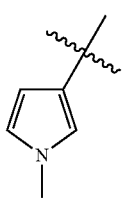 [SMILES: *c1ccn(C)c1] | —(CH$_2$)$_2$— | —CH$_2$— | —H |
| A-521. 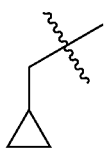 [SMILES: *CC1CC1] | —NH—(CH$_2$)$_2$—O— | 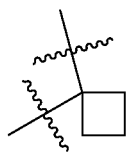 | —H |
| A-522. 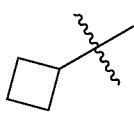 [SMILES: *C1CCC1] | —NH—(CH$_2$)$_2$—O— | 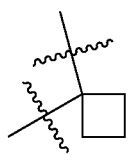 [SMILES: *C1(*)CCC1] | —H |
| A-523. 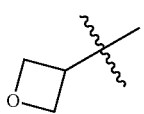 [SMILES: *C1COC1] | —NH—(CH$_2$)$_2$—O— | 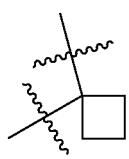 [SMILES: *C1(*)CCC1] | —H |
| A-524. 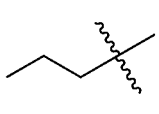 | —NH—(CH$_2$)$_2$—O— | 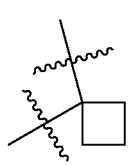 [SMILES: *C1(*)CCC1] | —H |

-continued
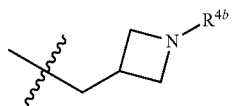 P1
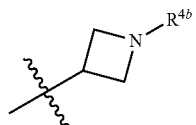 P2
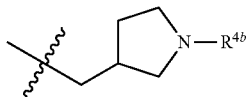 P3
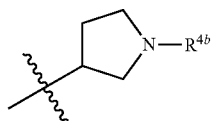 P4
| | R¹ | -Y-A²-X¹- | >CR¹²ᵃR¹²ᵇ | R⁴ᵇ |
|---|---|---|---|---|
| A-525. | 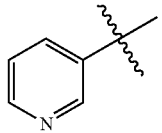 [SMILES: *c1cccnc1] | —NH—(CH₂)₂—O— | 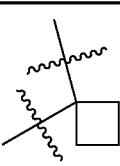 | —H |
| A-526. | 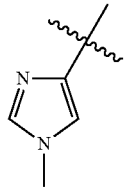 [SMILES: *c1cn(C)cn1] | —NH—(CH₂)₂—O— | 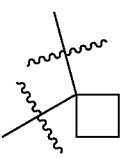 | —H |
| A-527. | 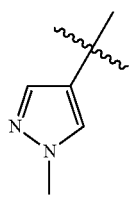 | —NH—(CH₂)₂—O— | 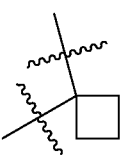 [SMILES: *C1(*)CCC1] | —H |
| A-528. | 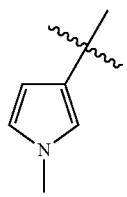 [SMILES: *c1ccn(C)c1] | —NH—(CH₂)₂—O— | 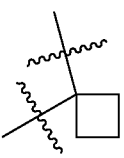 | —H |
| A-529. | 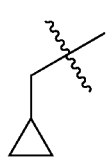 [SMILES: *CC1CC1] | —NH—(CH₂)₂— | 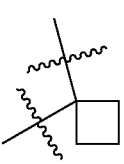 [SMILES: *C1(*)CCC1] | —H |

P1
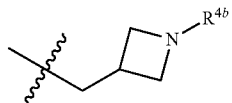
P2
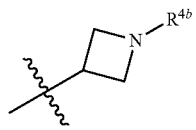
P3
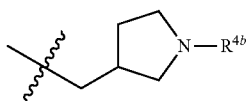
P4
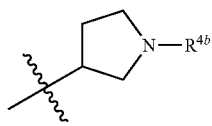
| | R$^1$ | -Y-A$^2$-X$^1$- | >CR$^{12a}$R$^{12b}$ | R$^{4b}$ |
|---|---|---|---|---|
| A-530. | 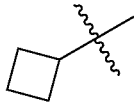 [SMILES: *C1CCC1] | —NH—(CH$_2$)$_2$— | 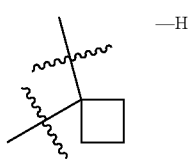 | —H |
| A-531. | 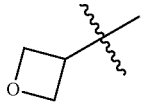 [SMILES: *C1COC1] | —NH—(CH$_2$)$_2$— | 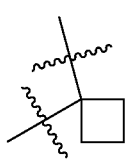 [SMILES: *C1(*)CCC1] | —H |
| A-532. | 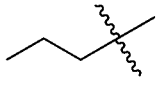 [SMILES: *CCC] | —NH—(CH$_2$)$_2$— | 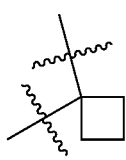 [SMILES: *C1(*)CCC1] | —H |
| A-533. | 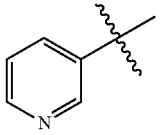 [SMILES: *c1cccnc1] | —NH—(CH$_2$)$_2$— | 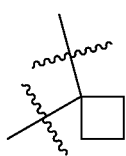 | —H |
| A-534. | 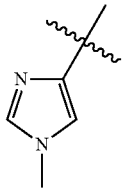 [SMILES: *c1cn(C)cn1] | —NH—(CH$_2$)$_2$— | 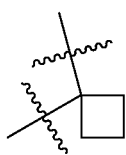 [SMILES: *C1(*)CCC1] | —H |

-continued
| | | P1 |
|---|---|---|
| 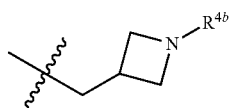 | | |
| | | P2 |
|---|---|---|
| 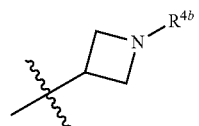 | | |
| | | P3 |
|---|---|---|
| 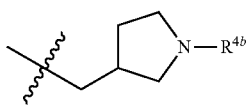 | | |
| | | P4 |
|---|---|---|
| 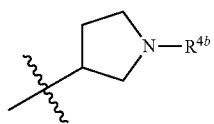 | | |
| | $R^1$ | -Y-A$^2$-X$^1$- | >CR$^{12a}$R$^{12b}$ | R$^{4b}$ |
|---|---|---|---|---|
| A-535. | 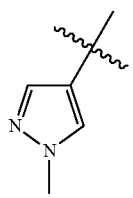 | —NH—(CH$_2$)$_2$— | 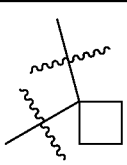 | —H |
| A-536. | 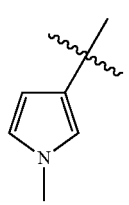 [SMILES: *c1ccn(C)c1] | —NH—(CH$_2$)$_2$— | 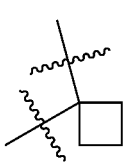 [SMILES: *C1(*)CCC1] | —H |
| A-537. | 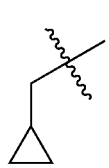 [SMILES: *CC1CC1] | —NH—CH$_2$— | 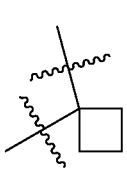 [SMILES: *C1(*)CCC1] | —H |
| A-538. | 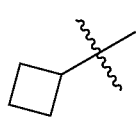 [SMILES: *C1CCC1] | —NH—CH$_2$— | 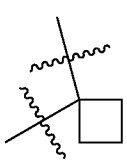 [SMILES: *C1(*)CCC1] | —H |
| A-539. | 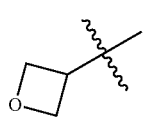 [SMILES: *C1COC1] | —NH—CH$_2$— | 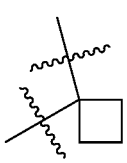 [SMILES: *C1(*)CCC1] | —H |

-continued
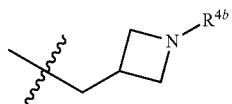 P1
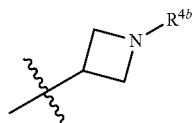 P2
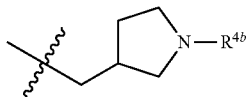 P3
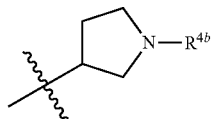 P4
| | R$^1$ | -Y-A$^2$-X$^1$- | >CR$^{12a}$R$^{12b}$ | R$^{4b}$ |
|---|---|---|---|---|
| A-540. | 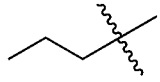 | —NH—CH$_2$— | 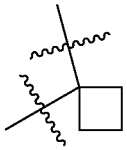 [SMILES: *C1(*)CCC1] | —H |
| A-541. | 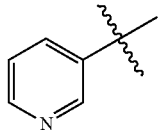 [SMILES: *c1cccnc1] | —NH—CH$_2$— | 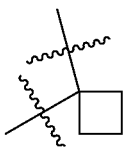 [SMILES: *C1(*)CCC1] | —H |
| A-542. | 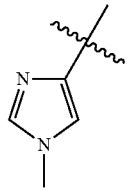 | —NH—CH$_2$— | 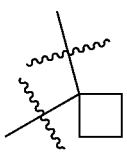 [SMILES: *C1(*)CCC1] | —H |
| A-543. | 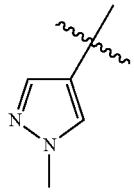 [SMILES: *c1cnn(C)c1] | —NH—CH$_2$— | 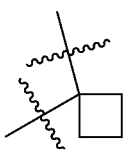 | —H |
| A-544. | 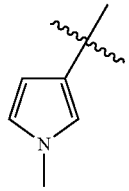 [SMILES: *c1ccn(C)c1] | —NH—CH$_2$— | 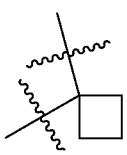 [SMILES: *C1(*)CCC1] | —H |

-continued
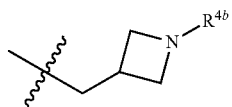 P1
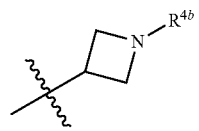 P2
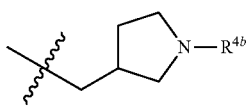 P3
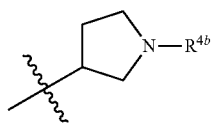 P4
| | $R^1$ | $-Y-A^2-X^1-$ | $>CR^{12a}R^{12b}$ | $R^{4b}$ |
|---|---|---|---|---|
| A-545. | 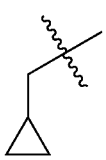 | 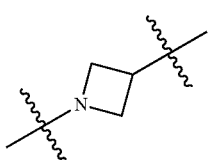 [SMILES: *C1CN(*)C1] | 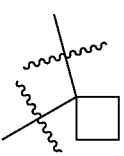 [SMILES: *C1(*)CCC1] | —H |
| A-546. | 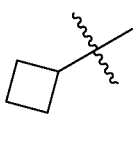 [SMILES: *C1CCC1] | 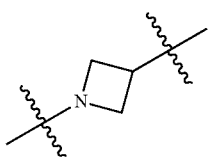 [SMILES: *C1CN(*)C1] |  | —H |
| A-547. | 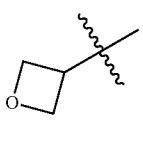 [SMILES: *C1COC1] | 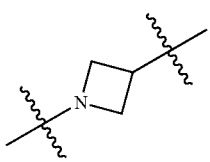 [SMILES: *C1CN(*)C1] | 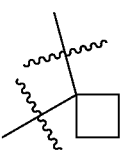 [SMILES: *C1(*)CCC1] | —H |
| A-548. | 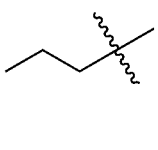 [SMILES: *CCC] | 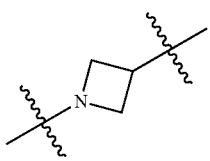 [SMILES: *C1CN(*)C1] | 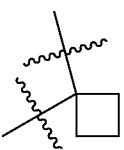 [SMILES: *C1(*)CCC1] | —H |
| A-549. | 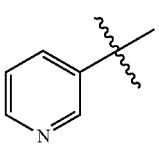 [SMILES: *c1cccnc1] | 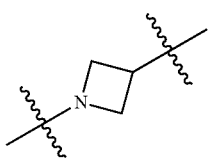 [SMILES: *C1CN(*)C1] |  | —H |

-continued
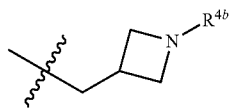
P1
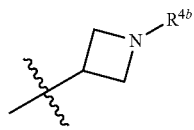
P2
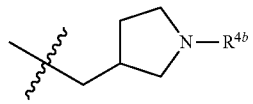
P3
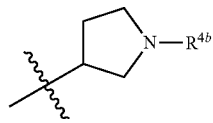
P4
| | R¹ | -Y-A²-X¹- | >CR$^{12a}$R$^{12b}$ | R$^{4b}$ |
|---|---|---|---|---|
| A-550. | 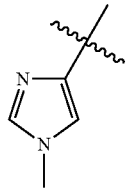 [SMILES: *c1cn(C)cn1] | 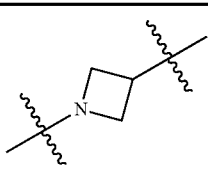 | 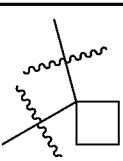 | —H |
| A-551. | 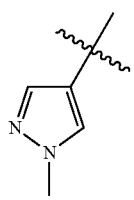 | 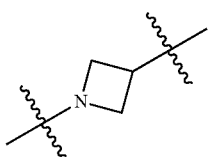 [SMILES: *C1CN(*)C1] | 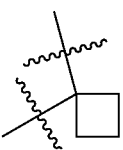 [SMILES: *C1(*)CCC1] | —H |
| A-552. | 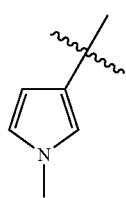 [SMILES: *c1ccn(C)c1] | 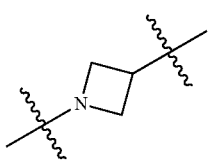 [SMILES: *C1CN(*)C1] | 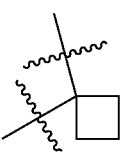 [SMILES: *C1(*)CCC1] | —H |
| A-553. | 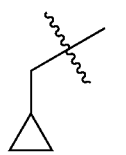 [SMILES: *CC1CC1] | —(CH₂)₂— | 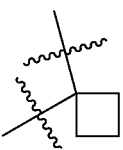 [SMILES: *C1(*)CCC1] | —H |
| A-554. | 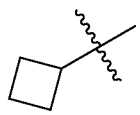 [SMILES: *C1CCC1] | —(CH₂)₂— | 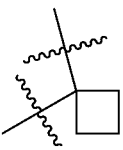 [SMILES: *C1(*)CCC1] | —H |

-continued
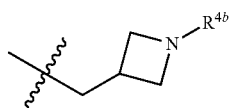
P1
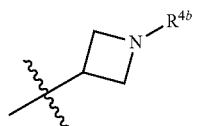
P2
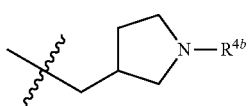
P3
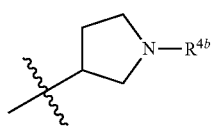
P4
| | $R^1$ | $-Y-A^2-X^1-$ | $>CR^{12a}R^{12b}$ | $R^{4b}$ |
|---|---|---|---|---|
| A-555. | 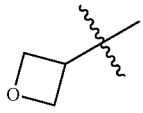 | —(CH$_2$)$_2$— | 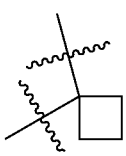 [SMILES: *C1(*)CCC1] | —H |
| A-556. | 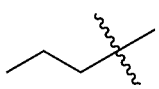 [SMILES: *CCC] | —(CH$_2$)$_2$— | 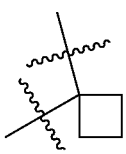 [SMILES: *C1(*)CCC1] | —H |
| A-557. | 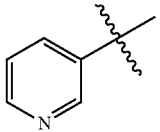 [SMILES: *c1cccnc1] | —(CH$_2$)$_2$— | 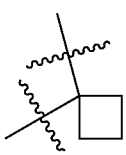 [SMILES: *C1(*)CCC1] | —H |
| A-558. | 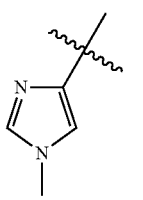 [SMILES: *c1cn(C)cn1] | —(CH$_2$)$_2$— | 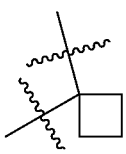 | —H |
| A-559. | 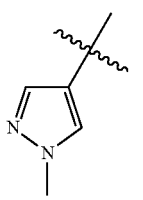 [SMILES: *c1cnn(C)c1] | —(CH$_2$)$_2$— | 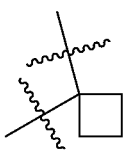 [SMILES: *C1(*)CCC1] | —H |

-continued
| | | | P1 |
|---|---|---|---|
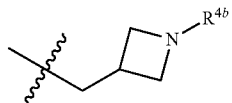
| | | | P2 |
|---|---|---|---|
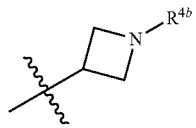
| | | | P3 |
|---|---|---|---|
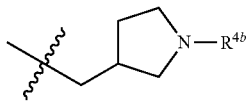
| | | | P4 |
|---|---|---|---|
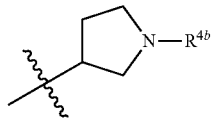
| | R¹ | -Y-A²-X¹- | >CR^{12a}R^{12b} | R^{4b} |
|---|---|---|---|---|
| A-560. | 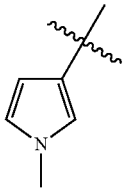 [SMILES: *c1ccn(C)c1] | —(CH₂)₂— | 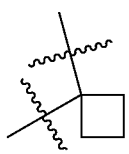 [SMILES: *C1(*)CCC1] | —H |
| A-561. | 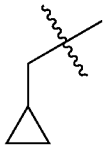 [SMILES: *CC1CC1] | —NH—(CH₂)₂—O— | —CH₂— | —CH₃ |
| A-562. | 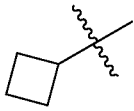 [SMILES: *C1CCC1] | —NH—(CH₂)₂—O— | —CH₂— | —CH₃ |
| A-563. |  | —NH—(CH₂)₂—O— | —CH₂— | —CH₃ |
| A-564. | 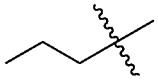 [SMILES: *CCC] | —NH—(CH₂)₂—O— | —CH₂— | —CH₃ |
| A-565. | 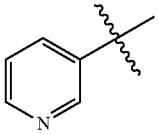 [SMILES: *c1cccnc1] | —NH—(CH₂)₂—O— | —CH₂— | —CH₃ |

-continued
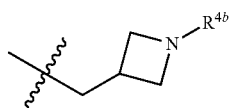  P1
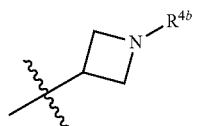  P2
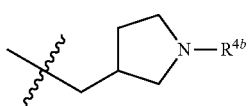  P3
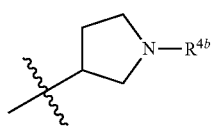  P4
| | R$^1$ | -Y-A$^2$-X$^1$- | >CR$^{12a}$R$^{12b}$ | R$^{4b}$ |
|---|---|---|---|---|
| A-566. | 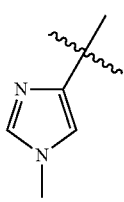 [SMILES: *c1cn(C)cn1] | —NH—(CH$_2$)$_2$—O— | —CH$_2$— | —CH$_3$ |
| A-567. | 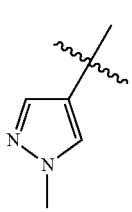 [SMILES: *c1cnn(C)c1] | —NH—(CH$_2$)$_2$—O— | —CH$_2$— | —CH$_3$ |
| A-568. | 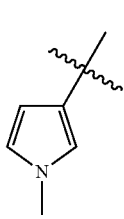 [SMILES: *c1ccn(C)c1] | —NH—(CH$_2$)$_2$—O— | —CH$_2$— | —CH$_3$ |
| A-569. | 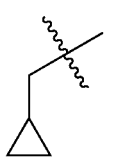 | —NH—(CH$_2$)$_2$— | —CH$_2$— | —CH$_3$ |
| A-570. | 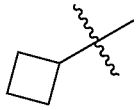 [SMILES: *C1CCC1] | —NH—(CH$_2$)$_2$— | —CH$_2$— | —CH$_3$ |

|   |   | P1 |
|---|---|---|
|   | 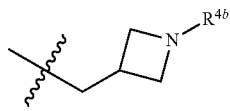 |   |
|   |   | P2 |
|   | 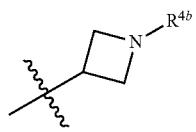 |   |
|   |   | P3 |
|   | 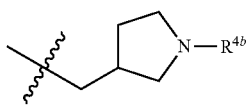 |   |
|   |   | P4 |
|   | 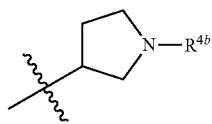 |   |
| | $R^1$ | -Y-$A^2$-$X^1$- | >$CR^{12a}R^{12b}$ | $R^{4b}$ |
|---|---|---|---|---|
| A-571. | 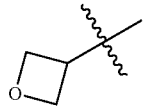 | —NH—(CH$_2$)$_2$— | —CH$_2$— | —CH$_3$ |
| A-572. | 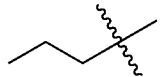 [SMILES: *CCC] | —NH—(CH$_2$)$_2$— | —CH$_2$— | —CH$_3$ |
| A-573. | 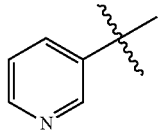 [SMILES: *c1cccnc1] | —NH—(CH$_2$)$_2$— | —CH$_2$— | —CH$_3$ |
| A-574. | 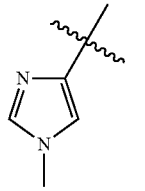 [SMILES: *c1cn(C)cn1] | —NH—(CH$_2$)$_2$— | —CH$_2$— | —CH$_3$ |
| A-575. | 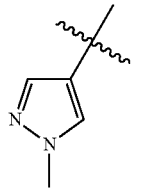 | —NH—(CH$_2$)$_2$— | —CH$_2$— | —CH$_3$ |
| A-576. | 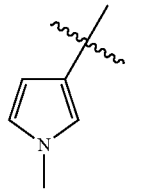 [SMILES: *c1ccn(C)c1] | —NH—(CH$_2$)$_2$— | —CH$_2$— | —CH$_3$ |

-continued
P1
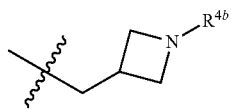
P2
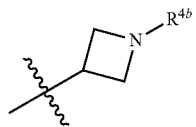
P3
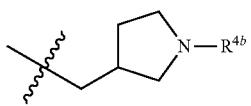
P4
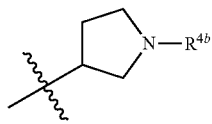
| | R¹ | -Y-A²-X¹- | >CR$^{12a}$R$^{12b}$ | R$^{4b}$ |
|---|---|---|---|---|
| A-577. | 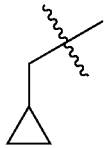 | —NH—CH$_2$— | —CH$_2$— | —CH$_3$ |
| A-578. | 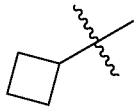 | —NH—CH$_2$— | —CH$_2$— | —CH$_3$ |
| A-579. | 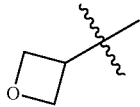 [SMILES: *C1COC1] | —NH—CH$_2$— | —CH$_2$— | —CH$_3$ |
| A-580. | 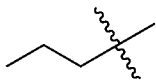 [SMILES: *CCC] | —NH—CH$_2$— | —CH$_2$— | —CH$_3$ |
| A-581. | 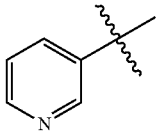 [SMILES: *c1cccnc1] | —NH—CH$_2$— | —CH$_2$— | —CH$_3$ |
| A-582. | 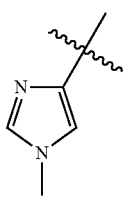 [SMILES: *c1cn(C)cn1] | —NH—CH$_2$— | —CH$_2$— | —CH$_3$ |

-continued
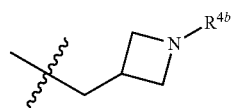 P1
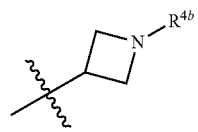 P2
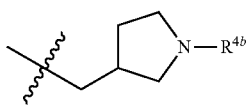 P3
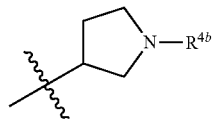 P4
| | R$^1$ | -Y-A$^2$-X$^1$- | >CR$^{12a}$R$^{12b}$ | R$^{4b}$ |
|---|---|---|---|---|
| A-583. | 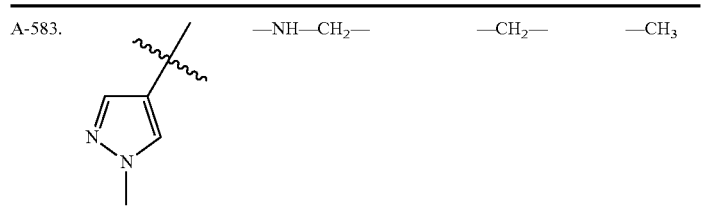 | —NH—CH$_2$— | —CH$_2$— | —CH$_3$ |
| A-584. | 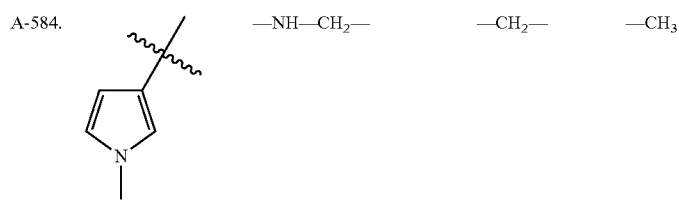 | —NH—CH$_2$— | —CH$_2$— | —CH$_3$ |
| A-585. | 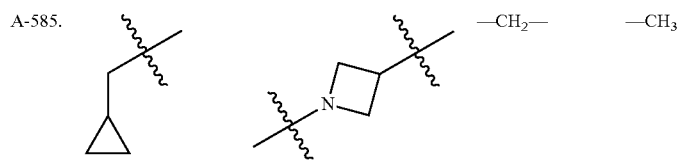 | | —CH$_2$— | —CH$_3$ |
| A-586. | 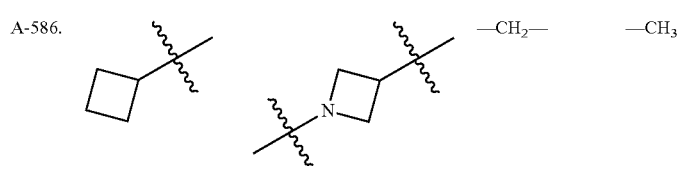 | | —CH$_2$— | —CH$_3$ |
| A-587. | 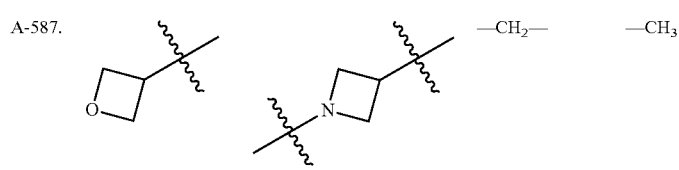 | | —CH$_2$— | —CH$_3$ |

-continued
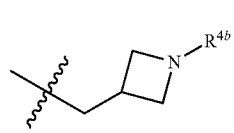
P1
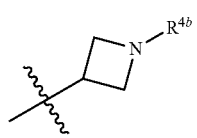
P2
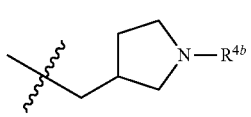
P3
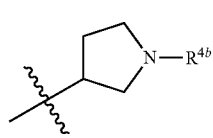
P4
| | R$^1$ | -Y-A$^2$-X$^1$- | >CR$^{12a}$R$^{12b}$ | R$^{4b}$ |
|---|---|---|---|---|
| A-588. | 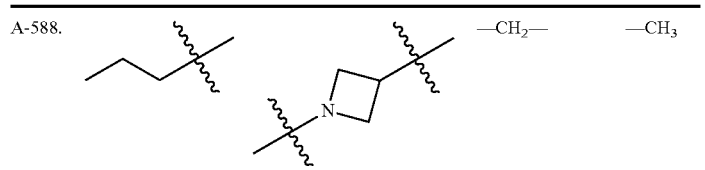 | | —CH$_2$— | —CH$_3$ |
| A-589. | 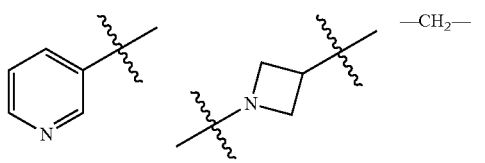 | | —CH$_2$— | —CH$_3$ |
| A-590. | 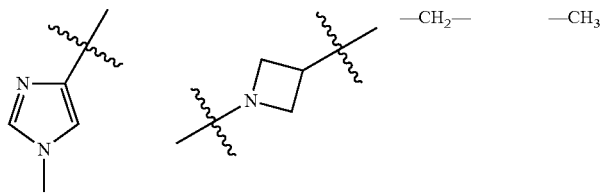 | | —CH$_2$— | —CH$_3$ |
| A-591. | 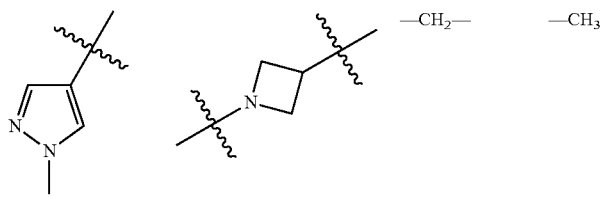 | | —CH$_2$— | —CH$_3$ |
| A-592. | 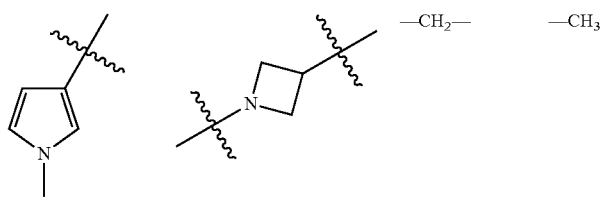 | | —CH$_2$— | —CH$_3$ |

-continued
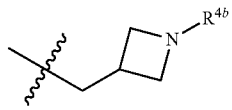
P1
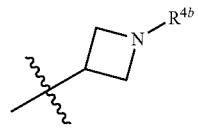
P2
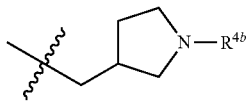
P3
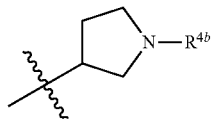
P4
| | R¹ | -Y-A²-X¹- | >CR$^{12a}$R$^{12b}$ | R$^{4b}$ |
|---|---|---|---|---|
| A-593. | 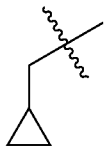 | —(CH$_2$)$_2$— | —CH$_2$— | —CH$_3$ |
| A-594. | 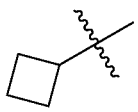 | —(CH$_2$)$_2$— | —CH$_2$— | —CH$_3$ |
| A-595. |  | —(CH$_2$)$_2$— | —CH$_2$— | —CH$_3$ |
| A-596. | 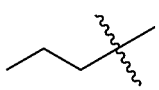 [SMILES: *CCC] | —(CH$_2$)$_2$— | —CH$_2$— | —CH$_3$ |
| A-597. | 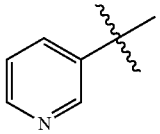 [SMILES: *c1cccnc1] | —(CH$_2$)$_2$— | —CH$_2$— | —CH$_3$ |
| A-598. | 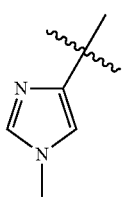 [SMILES: *c1cn(C)cn1] | —(CH$_2$)$_2$— | —CH$_2$— | —CH$_3$ |

-continued
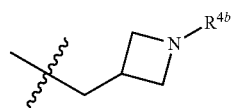
P1
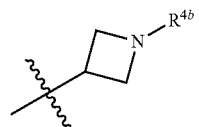
P2
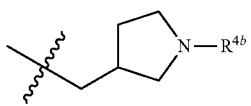
P3
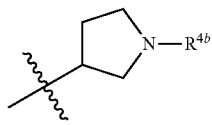
P4
| | R¹ | -Y-A²-X¹- | >CR$^{12a}$R$^{12b}$ | R$^{4b}$ |
|---|---|---|---|---|
| A-599. | 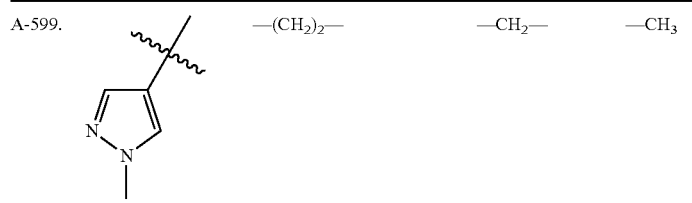 | —(CH$_2$)$_2$— | —CH$_2$— | —CH$_3$ |
| A-600. | 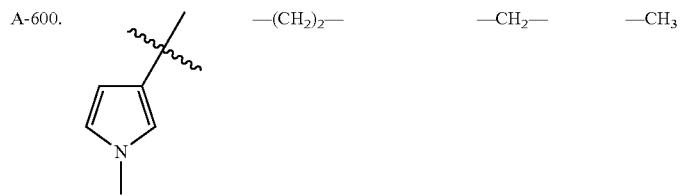 | —(CH$_2$)$_2$— | —CH$_2$— | —CH$_3$ |
| A-601. | | —NH—(CH$_2$)$_2$—O— | | —CH$_3$ |
| A-602. | 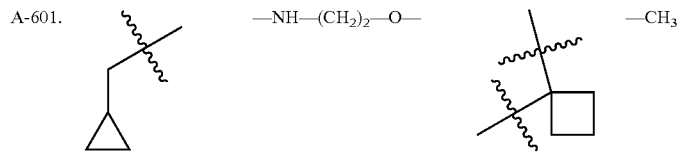 | —NH—(CH$_2$)$_2$—O— | | —CH$_3$ |
| A-603. | 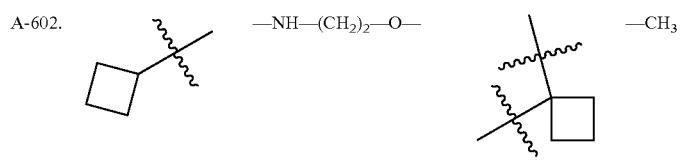 | —NH—(CH$_2$)$_2$—O— | | —CH$_3$ |
| | 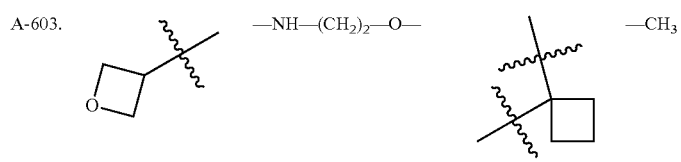 | | | |

-continued
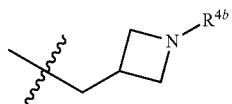
P1
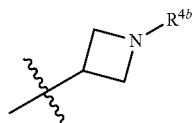
P2
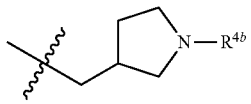
P3
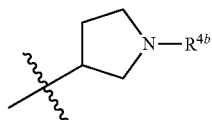
P4
| | R¹ | -Y-A²-X¹- | >CR$^{12a}$R$^{12b}$ | R$^{4b}$ |
|---|---|---|---|---|
| A-604. | 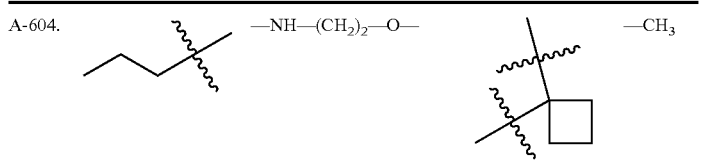 | —NH—(CH$_2$)$_2$—O— | | —CH$_3$ |
| A-605. | 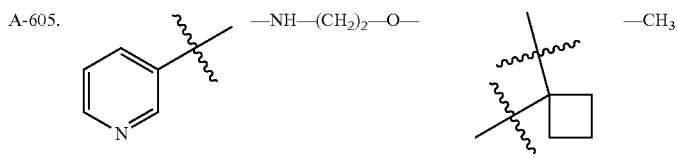 | —NH—(CH$_2$)$_2$—O— | | —CH$_3$ |
| A-606. | 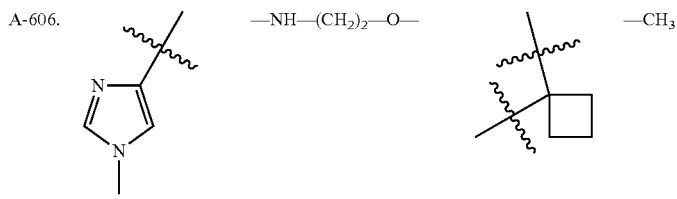 | —NH—(CH$_2$)$_2$—O— | | —CH$_3$ |
| A-607. | 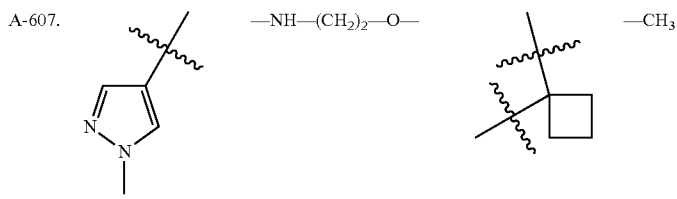 | —NH—(CH$_2$)$_2$—O— | | —CH$_3$ |
| A-608. | 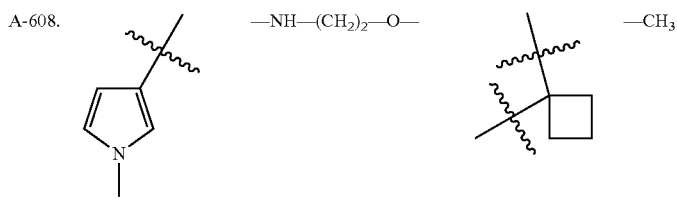 | —NH—(CH$_2$)$_2$—O— | | —CH$_3$ |

-continued
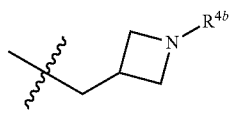 P1
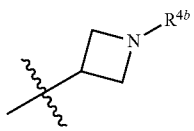 P2
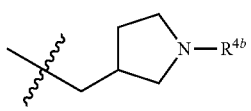 P3
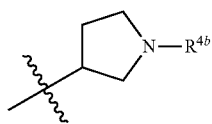 P4
| | R$^1$ | -Y-A$^2$-X$^1$- | >CR$^{12a}$R$^{12b}$ | R$^{4b}$ |
|---|---|---|---|---|
| A-609. | 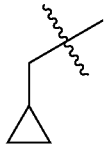 | —NH—(CH$_2$)$_2$— | 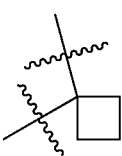 [SMILES: *C1(*)CCC1] | —CH$_3$ |
| A-610. | 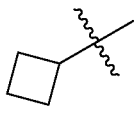 [SMILES: *C1CCC1] | —NH—(CH$_2$)$_2$— | 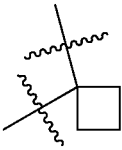 [SMILES: *C1(*)CCC1] | —CH$_3$ |
| A-611. | 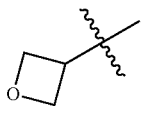 [SMILES: *C1COC1] | —NH—(CH$_2$)$_2$— | 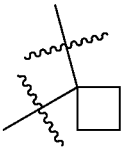 [SMILES: *C1(*)CCC1] | —CH$_3$ |
| A-612. | 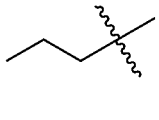 [SMILES: *CCC] | —NH—(CH$_2$)$_2$— | 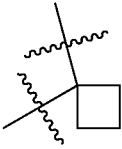 | —CH$_3$ |
| A-613. | 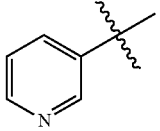 [SMILES: *c1cccnc1] | —NH—(CH$_2$)$_2$— | 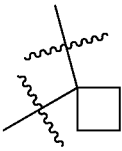 [SMILES: *C1(*)CCC1] | —CH$_3$ |

-continued
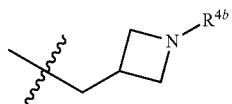
P1
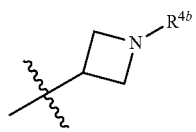
P2
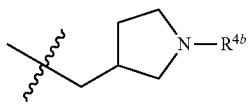
P3
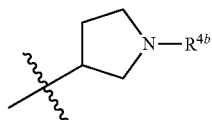
P4
| | $R^1$ | $-Y-A^2-X^1-$ | $>CR^{12a}R^{12b}$ | $R^{4b}$ |
|---|---|---|---|---|
| A-614. | 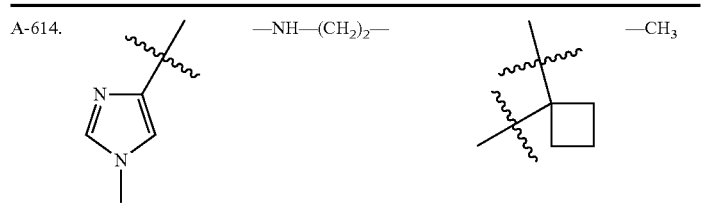 | —NH—(CH$_2$)$_2$— | | —CH$_3$ |
| A-615. | 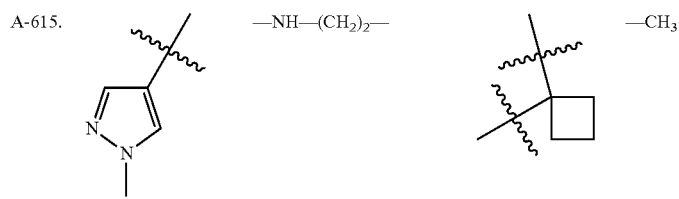 | —NH—(CH$_2$)$_2$— | | —CH$_3$ |
| A-616. | 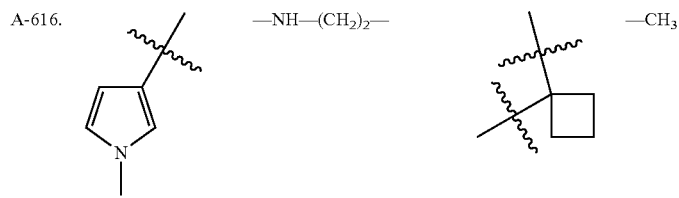 | —NH—(CH$_2$)$_2$— | | —CH$_3$ |
| A-617. | 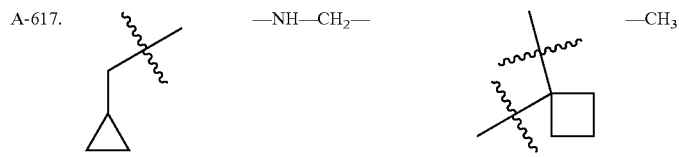 | —NH—CH$_2$— | | —CH$_3$ |
| A-618. | 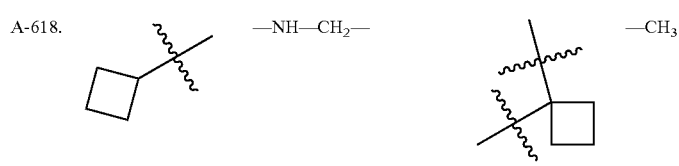 | —NH—CH$_2$— | | —CH$_3$ |

-continued
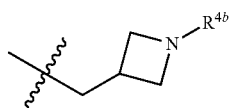 P1
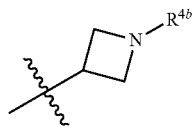 P2
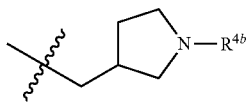 P3
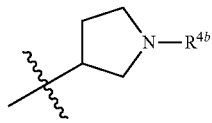 P4
| | $R^1$ | $-Y-A^2-X^1-$ | $>CR^{12a}R^{12b}$ | $R^{4b}$ |
|---|---|---|---|---|
| A-619. | 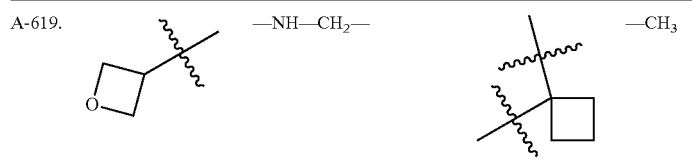 | —NH—CH$_2$— | | —CH$_3$ |
| A-620. | | —NH—CH$_2$— | | —CH$_3$ |
| A-621. | 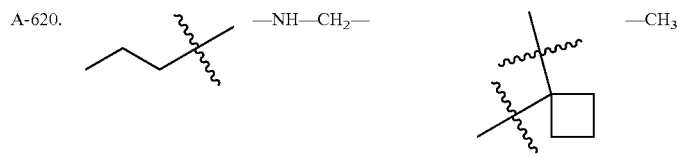 | —NH—CH$_2$— | | —CH$_3$ |
| A-622. | 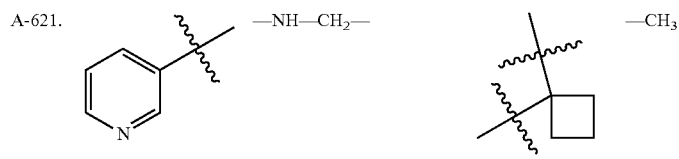 | —NH—CH$_2$— | | —CH$_3$ |
| A-623. | 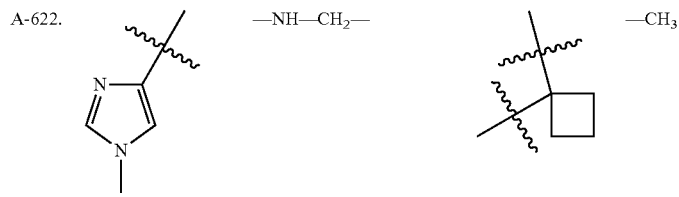 | —NH—CH$_2$— | | —CH$_3$ |

-continued
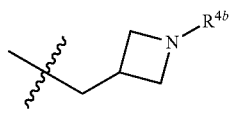  P1
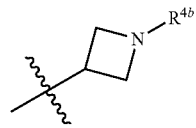  P2
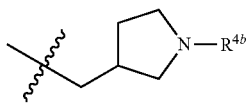  P3
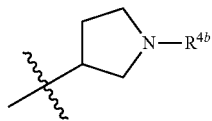  P4
| | R¹ | -Y-A²-X¹- | >CR$^{12a}$R$^{12b}$ | R$^{4b}$ |
|---|---|---|---|---|
| A-624. | 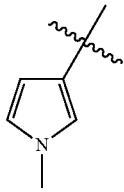 [SMILES: *c1ccn(C)c1] | —NH—CH$_2$— | 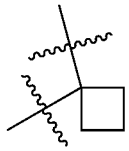 [SMILES: *C1(*)CCC1] | —CH$_3$ |
| A-625. | 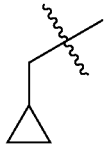 [SMILES: *CC1CC1] | 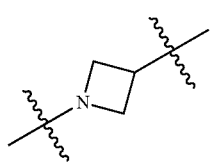 [SMILES: *C1CN(*)C1] | 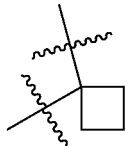 [SMILES: *C1(*)CCC1] | —CH$_3$ |
| A-626. | 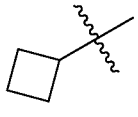 | 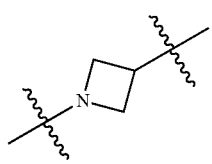 [SMILES: *C1CN(*)C1] | 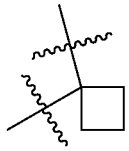 [SMILES: *C1(*)CCC1] | —CH$_3$ |
| A-627. | 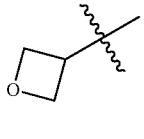 [SMILES: *C1COC1] | 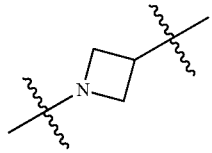 [SMILES: *C1CN(*)C1] | 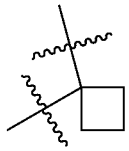 | —CH$_3$ |
| A-628. | 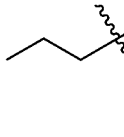 | 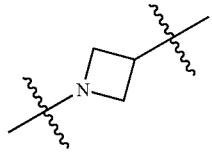 [SMILES: *C1CN(*)C1] | 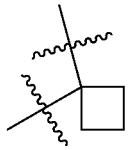 [SMILES: *C1(*)CCC1] | —CH$_3$ |

-continued
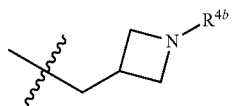 P1
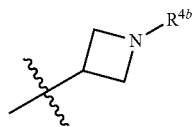 P2
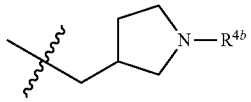 P3
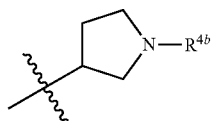 P4
| | R¹ | -Y-A²-X¹- | >CR$^{12a}$R$^{12b}$ | R$^{4b}$ |
|---|---|---|---|---|
| A-629. | 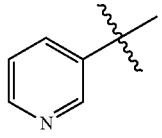 [SMILES: *c1cccnc1] | 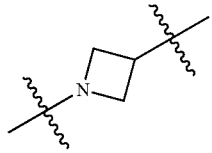 [SMILES: *C1CN(*)C1] | 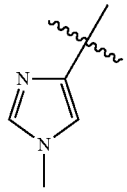 [SMILES: *c1cn(C)cn1] | —CH$_3$ |
| A-630. | 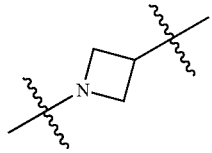 [SMILES: *C1CN(*)C1] | 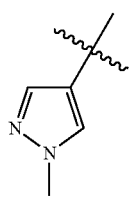 | 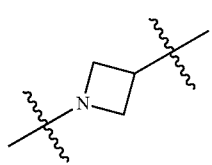 [SMILES: *C1CN(*)C1] | —CH$_3$ |
| A-631. | 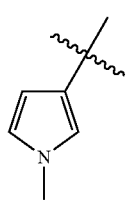 [SMILES: *c1ccn(C)c1] | 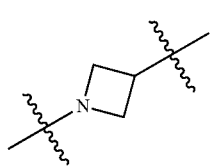 [SMILES: *C1CN(*)C1] | 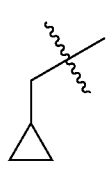 | —CH$_3$ |
| A-632. | 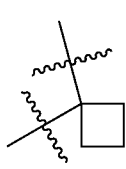 [SMILES: *C1(*)CCC1] | | | —CH$_3$ |
| A-633. | 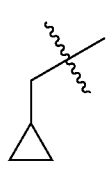 | —(CH$_2$)$_2$— | 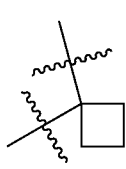 [SMILES: *C1(*)CCC1] | —CH$_3$ |

|  |  | P1 |
|---|---|---|
|  | 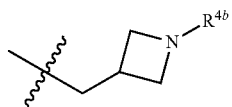 |  |
|  |  | P2 |
|---|---|---|
|  | 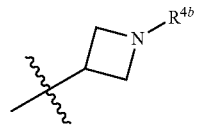 |  |
|  |  | P3 |
|---|---|---|
|  | 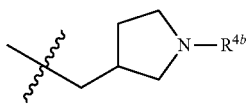 |  |
|  |  | P4 |
|---|---|---|
|  | 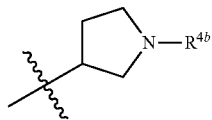 |  |
| | R$^1$ | -Y-A$^2$-X$^1$- | >CR$^{12a}$R$^{12b}$ | R$^{4b}$ |
|---|---|---|---|---|
| A-634. | 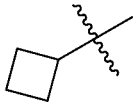 [SMILES: *C1CCC1] | —(CH$_2$)$_2$— | 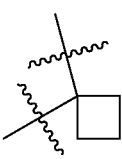 [SMILES: *C1(*)CCC1] | —CH$_3$ |
| A-635. | 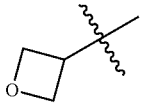 [SMILES: *C1COC1] | —(CH$_2$)$_2$— | 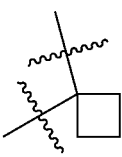 [SMILES: *C1(*)CCC1] | —CH$_3$ |
| A-636. | 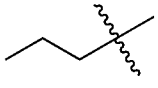 [SMILES: *CCC] | —(CH$_2$)$_2$— | 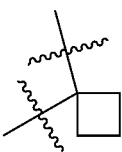 [SMILES: *C1(*)CCC1] | —CH$_3$ |
| A-637. | 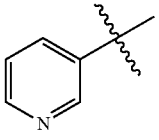 [SMILES: *c1cccnc1] | —(CH$_2$)$_2$— | 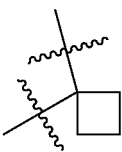 [SMILES: *C1(*)CCC1] | —CH$_3$ |
| A-638. | 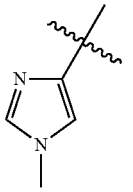 [SMILES: *c1cn(C)cn1] | —(CH$_2$)$_2$— | 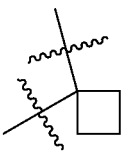 [SMILES: *C1(*)CCC1] | —CH$_3$ |

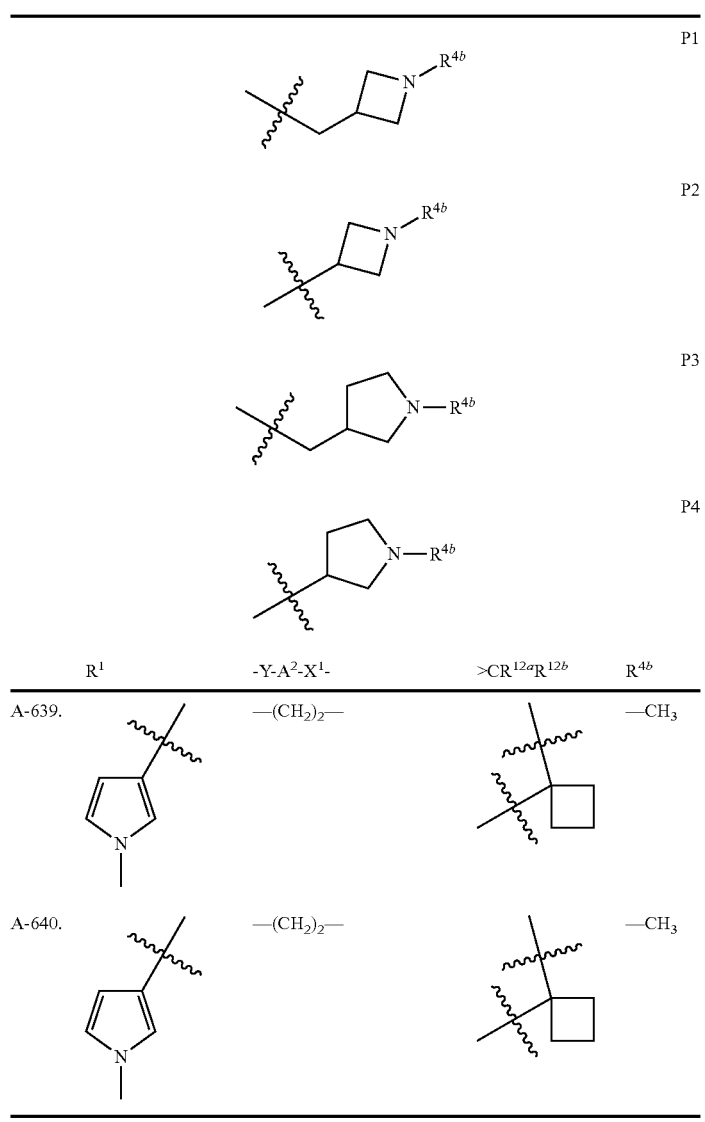

Still further particular compounds of the present invention are the compounds disclosed in preparation examples and physiologically tolerated salts thereof. These include for each preparation example the exemplified compound as well as the corresponding free base and any other physiologically tolerated salts of the free base (if the exemplified compound is a salt), or any physiologically tolerated salt of the free base (if the exemplified compound is a free base). These further include enantiomers, diastereomers, tautomers and any other isomeric forms of said compounds, be they explicitly or implicitly disclosed.

The compounds of the formula (I) can be prepared by analogy to methods which are well known in the art. Suitable methods for the preparation of compounds of formula (I) are outlined in the following schemes.

Scheme 1:

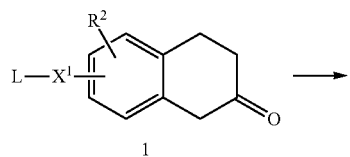

1

-continued

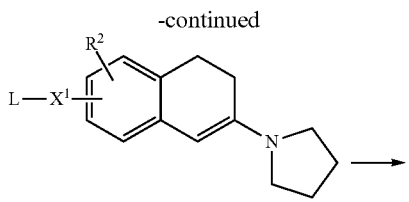

2

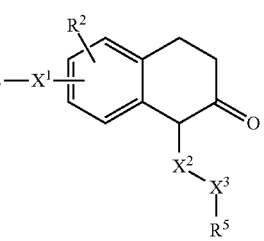

3

As shown in scheme 1, the compound of general formula 1 readily undergoes enamine alkylation to give the compound of general formula 3.

In scheme 1, the variables $X^1$, $R^2$, $X^2$, $X^3$, $R^5$ are as defined herein and L is a suitable protecting group (e.g. L=Me). The process depicted in scheme 1 is also useful for obtaining tetralines, wherein $X^1$ is optionally substituted alkylene or oxygen. In this case, L is a group that represents, or can be converted into, the desired side chain $R^1$—W-$A^1$-Q-Y-$A^2$-.

Alternatively, compounds of formula 3 can be prepared as described in scheme 2.

Scheme 2a:

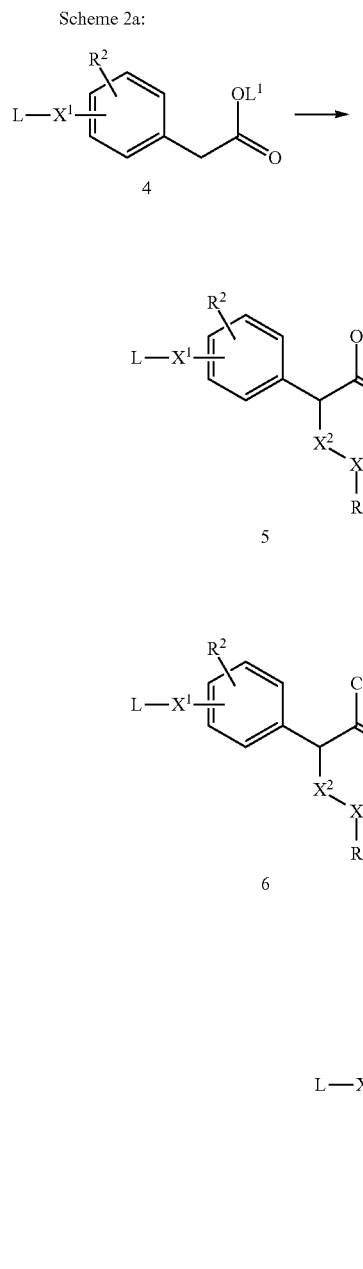

acid (e.g. $AlCl_3$) affords compound 3 (e.g. J. Het. Chem., 23 (2), 343, 1986 and Bioorg. Med. Chem. Let, 17 (22), 6160, 2007).

In scheme 2a, the variables $X^1$, $R^2$, $X^2$, $X^3$, $R^5$ are as defined herein and L, $L^1$ are a suitable protecting group (e.g. L, $L^1$=Me). Compounds 3 can be further converted to compounds of the general formula (I).

Scheme 2b:

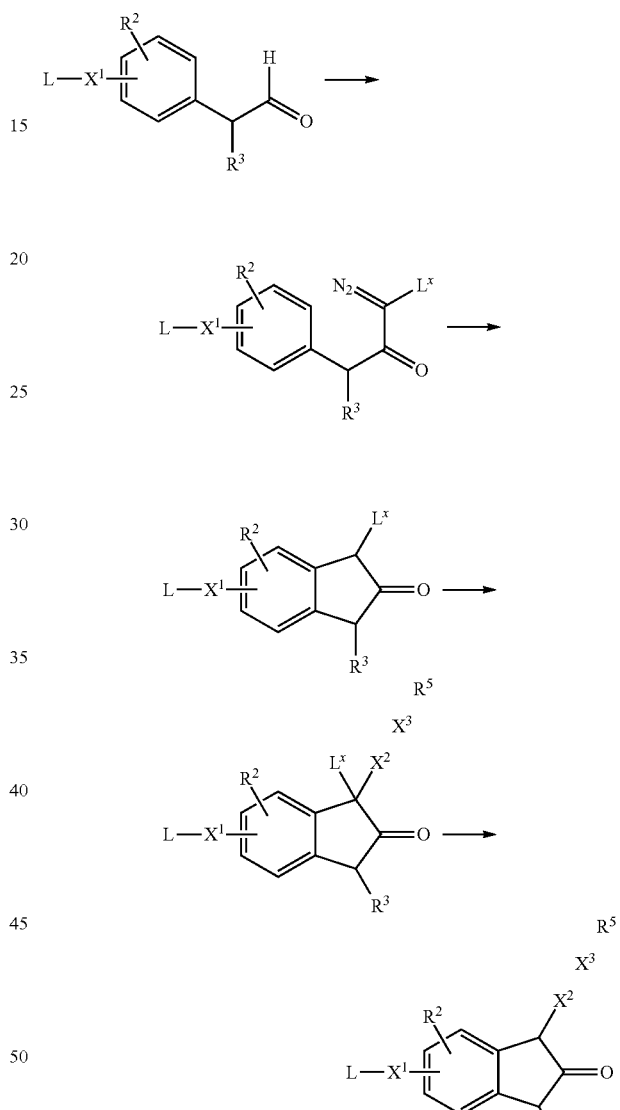

Scheme 2b depicts the general synthesis of indanones 3 using transition metal-catalyzed C,C-bond formation to synthesize the indanone from a diazoprecursor (cf. Tetrahedron Letters (2009), 50, 3568). $L^x$ is an ester moiety. The side chain containing $X^2$, $X^3$ and $R^5$ could be introduced by an alkylation of the 1,3-dicarboyl intermediate. Saponification of the ester moiety and decarboxylation could yield indanone 3.

In scheme 2b, the variables $X^1$, $R^2$, $X^2$, $X^3$, $R^3$, $R^5$ are as defined herein and L is a suitable protecting group (e.g. L=Me). Compounds 3 can be further converted to compounds of the general formula (I).

As shown in scheme 2a, the compound of general formula 4 readily undergoes alkylation to give the compound of general formula 5. Conversion to the acid chloride and subsequent ring closure with ethylene in the presence of a Lewis Scheme 2c:
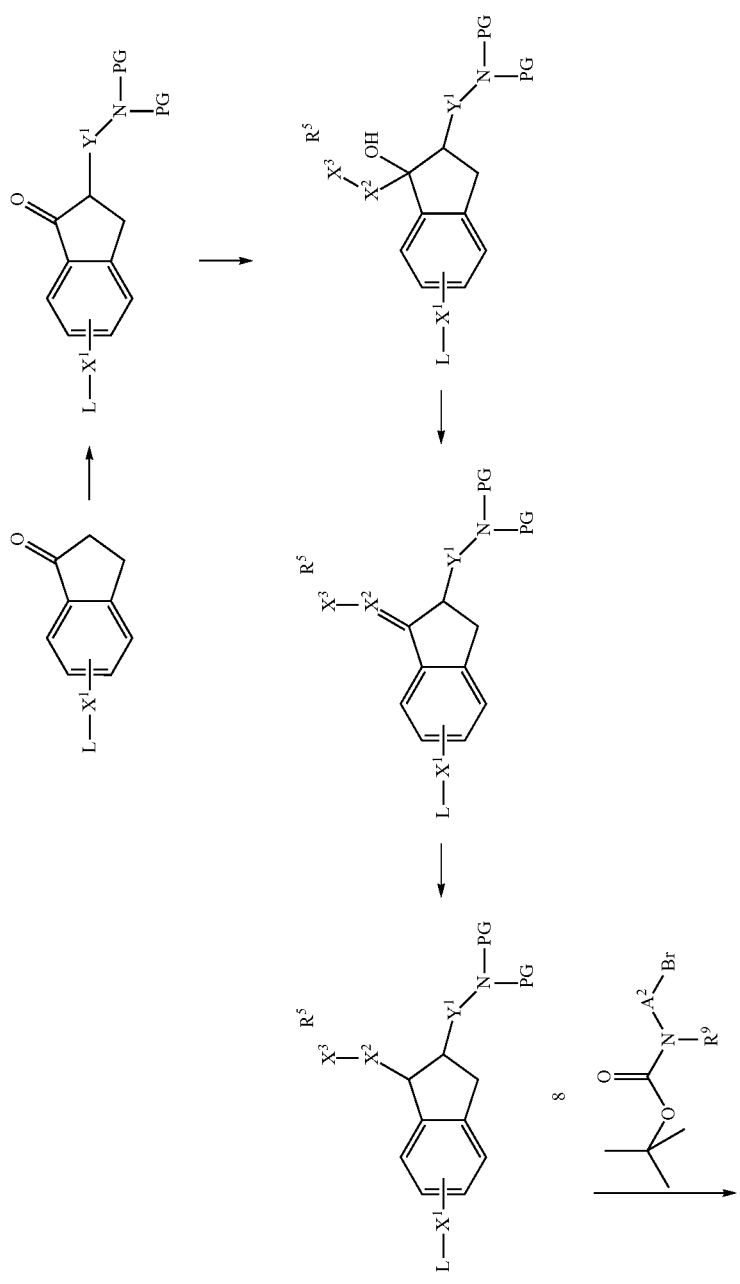

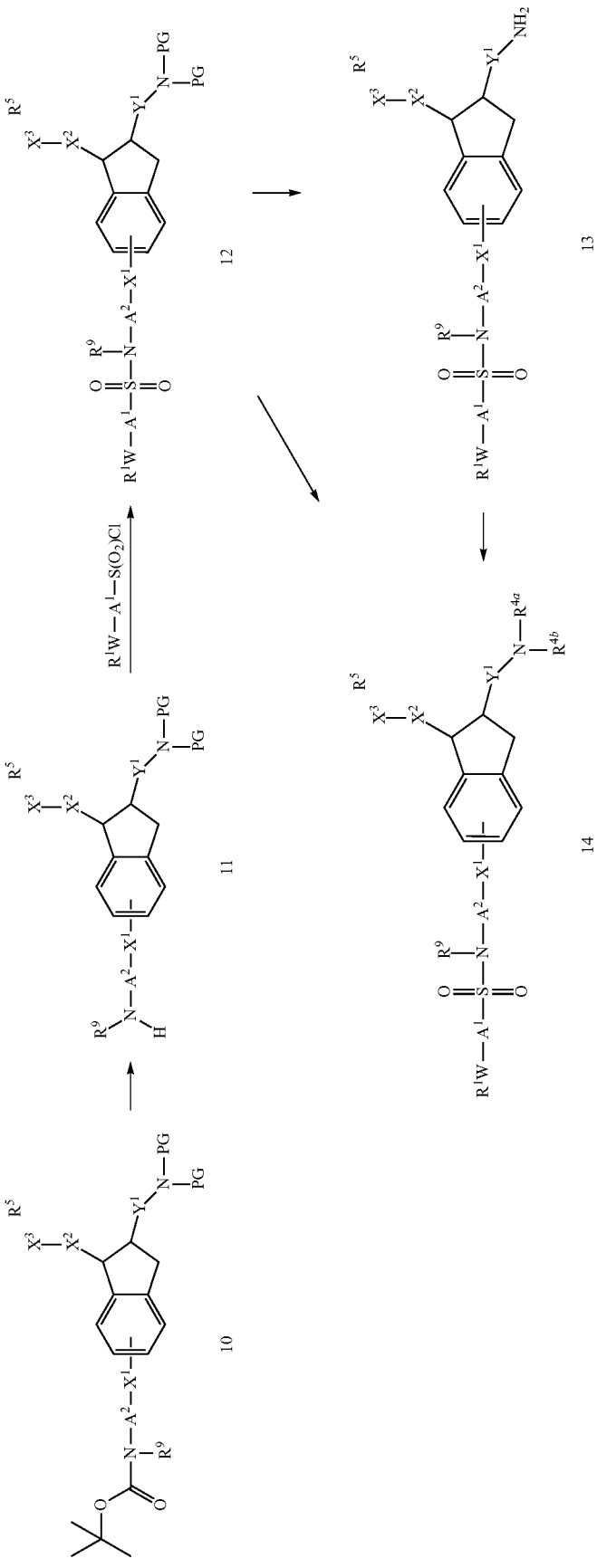

In scheme 2c, an alternative route to compounds 14 where n=0 is depicted. A substituted 1-indanone can be functionalized in the 2-position after deprotonation next to the carbonyl followed by alkylation with an electrophile bearing a protected nitrogen (PG=protective group; this includes $N(PG)_2$ being nitro and the adjacent carbon in $Y^1$ and $N(PG)_2$ being nitrile). Addition of a functionalized nucleophile (e.g. Li-organyl or Grignard reagent) to the carbonyl of the 1-indanone followed by elimination and hydrogenation can yield compound 8. Standard protective group chemistry followed by alkylation, deprotection of the amine attached to $A^2$ and reaction with a substituted sulfonyl chloride can yield intermediate 12.

When $N(PG)_2$ is a nitro group or when $N(PG)_2$ and the carbon in $Y^1$ adjacent to $N(PG)_2$ form a nitrile group the activated C—H bond next to the nitro or nitrile can be used for alkylation reactions with suitably functionalized electrophiles to yield compounds 14 in which $R^{4a}$ is an optionally substituted alkylene that is bound to a carbon atom in $Y^1$.

Alternatively the nitrogen attached to $Y^1$ in compound 12 can be deprotected and substituted to yield compound 14.

In scheme 2c, the variables $R^1$, W, $A^1$, $R^9$, $A^2$, $X^1$, $X^2$, $X^3$, $R^3$, $R^5$, $Y^1$, $R^{4a}$, $R^{4b}$ are as defined herein and L is a suitable protecting group (e.g. L=Me).

The process depicted in scheme 3 is useful for obtaining tetralines and indanes, wherein $X^1$ is —O— or —S—, $A^2$ is optionally substituted alkylene, Y is —$NR^9$—, and Q is —$S(O)_2$. $Y^1$ is optionally substituted methylene or ethylene.

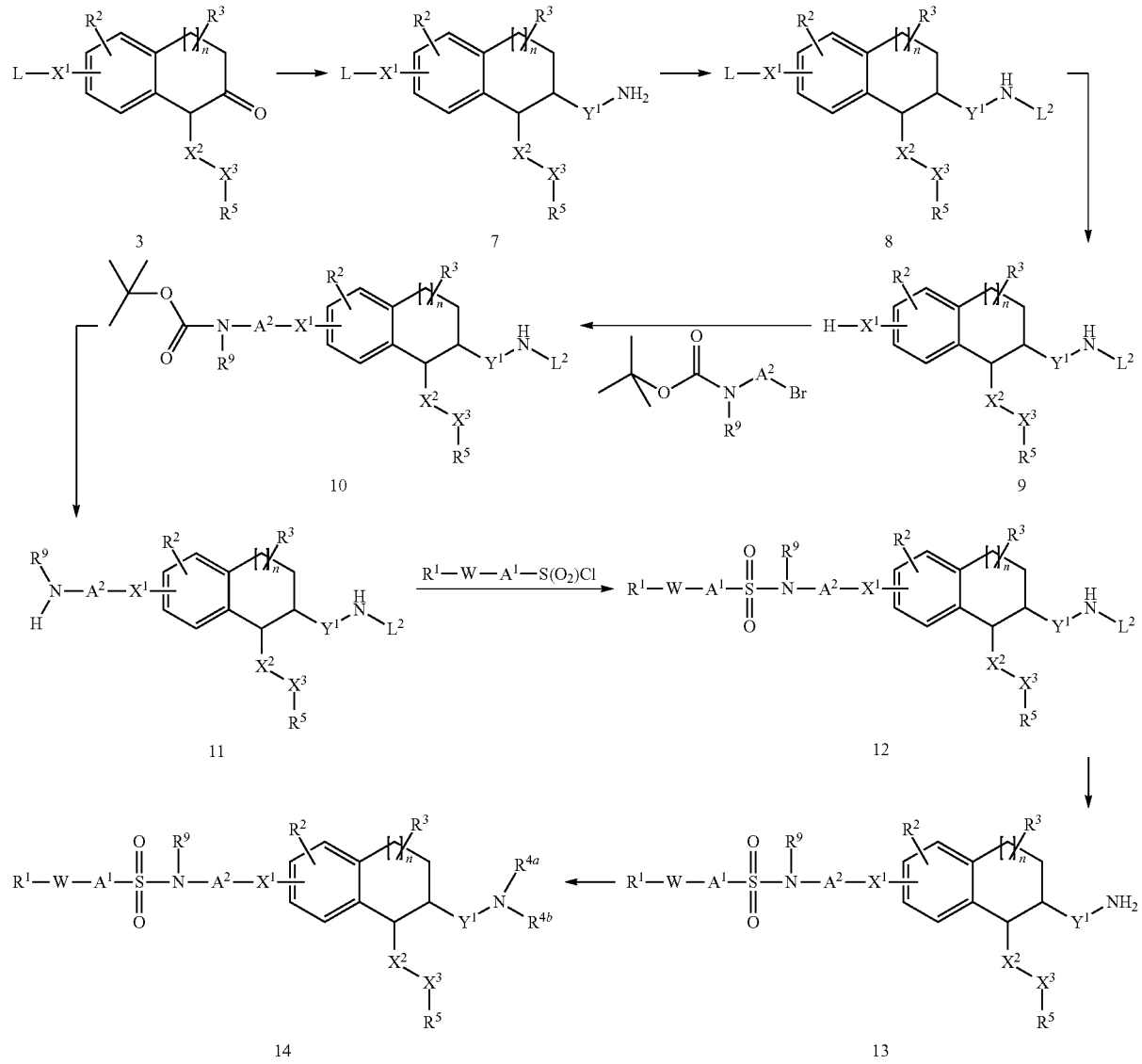

Scheme 3:

In scheme 3, the variables L, $R^1$, W, $A^1$, $R^2$, $R^3$, $R^{4a}$, $R^{4b}$, $R^5$, $R^9$, $X^2$, $X^3$ and n are as defined herein and $L^2$ is a suitable protecting group (e.g. $L^2$=COOEt).

Compounds 7 in which $Y^1$ is ethylene can be obtained from compounds 3 in analogy to the protocol described in Helv. Chim. Acta (1989), 72, 1463-70 or J. Med. Chem. (2000), 43, 4051-62 followed by reduction of the corresponding nitrile (e.g. with lithium aluminum hydride or borane tetrahydrofuran complex in tetrahydrofuran).

Compounds 7 in which $Y^1$ is methylene can be obtained from compounds 3 by Henry reaction in analogy to the protocol described in DE3901814 followed by reduction of the corresponding nitro group (e.g. catalytic hydrogenation with palladium on charcoal). Alternatively compounds 7 in which $Y^1$ is methylene can be obtained from compounds 3 in analogy to the protocol described in J. Med. Chem. (2000), 43, 4051-62 followed by Curtius rearrangement of the corresponding carboxylic acid to the amine 7.

Side chains containing $R^1$, W, $A^1$, $A^2$, $X^1$ and $R^9$ and $R^5$, $X^2$ and $X^3$ as well as the substituents $R^2$, $R^3$, $R^{4a}$ and $R^{4b}$ can be introduced analog to the protocols described in WO2009121872.

The process depicted in scheme 3a is useful for obtaining tetralines, wherein $X^1$ is —O— or —S—, and Y is a bond.

Scheme 3a:

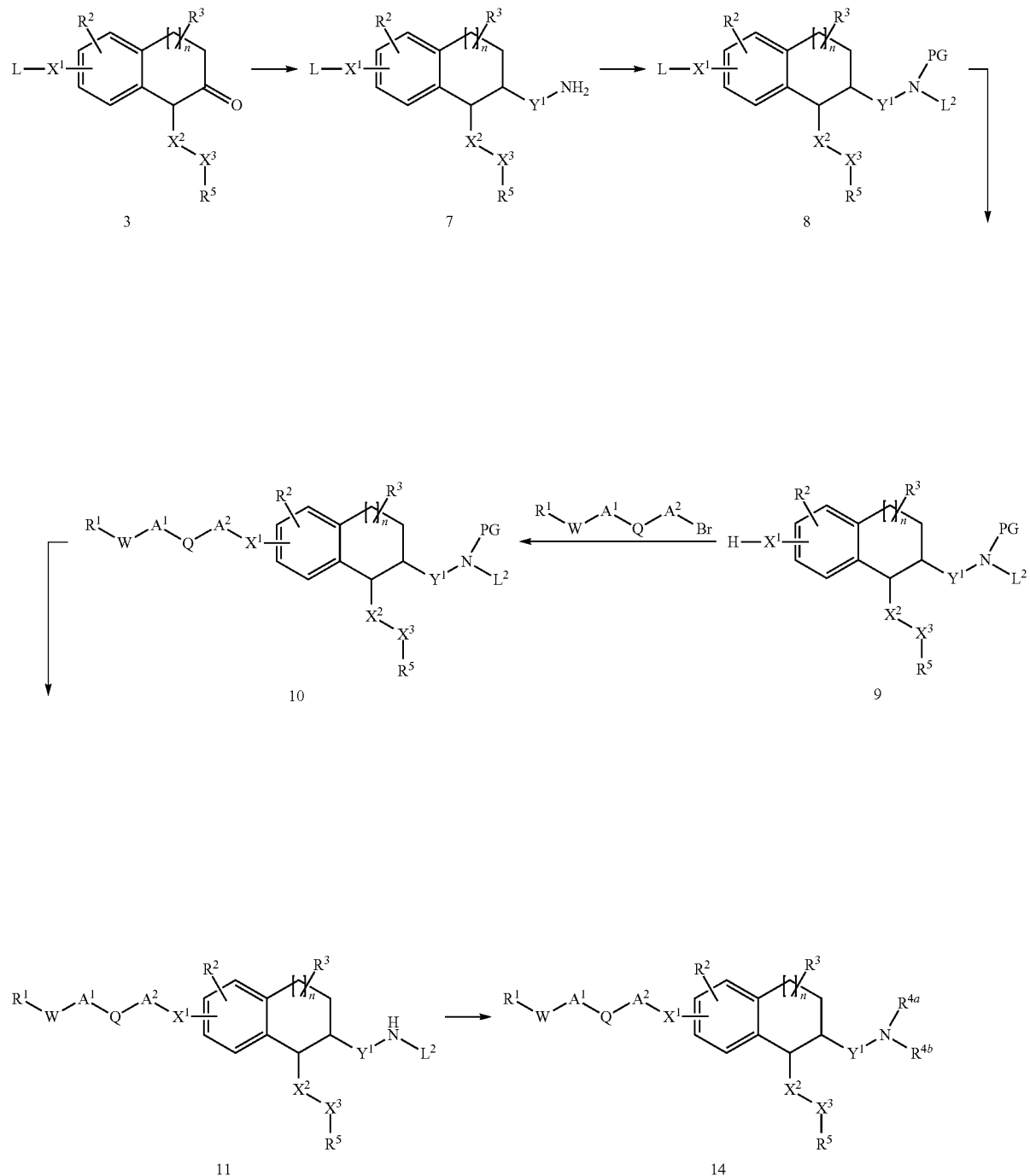

In scheme 3a, the variables L, $L^2$, $R^1$, W, $A^1$, Q, $A^2$, $R^2$, $R^3$, $R^{4a}$, $R^{4b}$, $R^5$, $X^2$, $X^3$, $Y^1$, n are as defined herein. One example for compound $R^1$—W-$A^1$-Q-$A^2$-Br could be $CH_3$—$SO_2$—$CH_2$—$CH_2$—Br.

Further protocols for the synthesis of compounds in which Y is a bond and W is $NR^8$ are described in WO 2009/121872.

Scheme 3b:

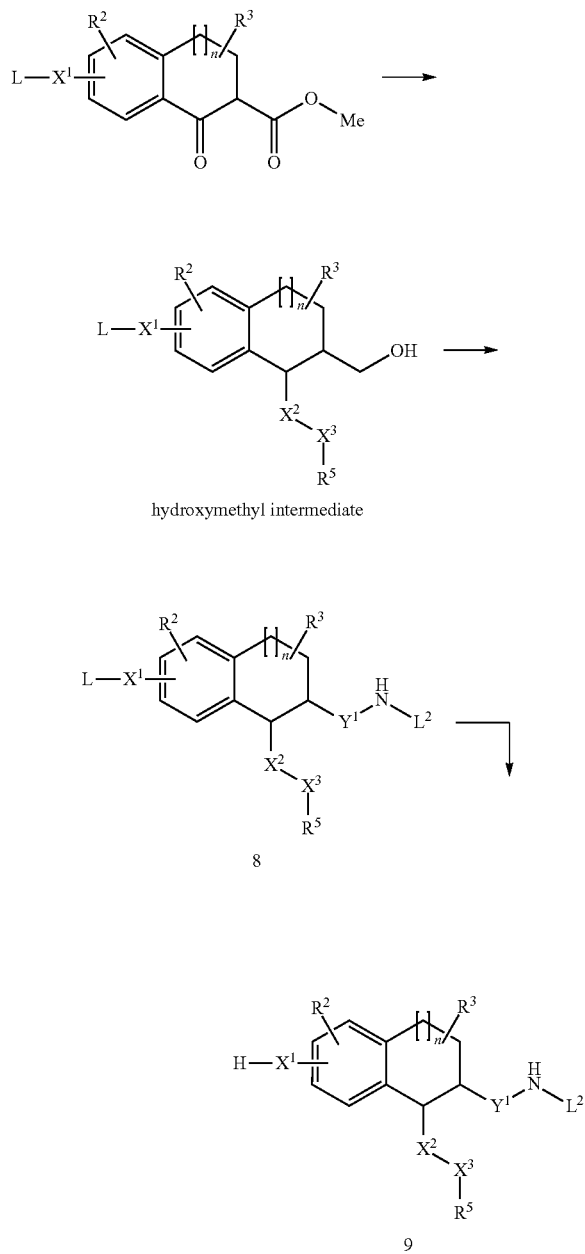

8

9

In scheme 3b, an alternative route to compound 9 is depicted. Starting from a functionalized beta-keto ester the hydroxymethyl intermediate can be obtained in analogy to the protocols described in Bioorg. Med. Chem. Lett. 2005, 15, 1375. Compound 8 wherein $Y^1$ is a linker containing one carbon atom can be obtained in analogy to the protocols described in Bioorg. Med. Chem. Lett. 2005, 15, 1375. To obtain longer linkers $Y^1$ with two or three carbon atoms the hydroxyl group in the hydroxymethyl intermediate can either be converted to a leaving group which then can be substituted by a cyanide or the hydroxymethyl intermediate can be oxydized to an aldehyde which can be converted in a Henry reaction to the corresponding nitro compound. Reduction (e.g. hydrogenation) of the above nitriles or nitro compounds followed by protection of the corresponding amine can give the compounds 9.

Scheme 3c:

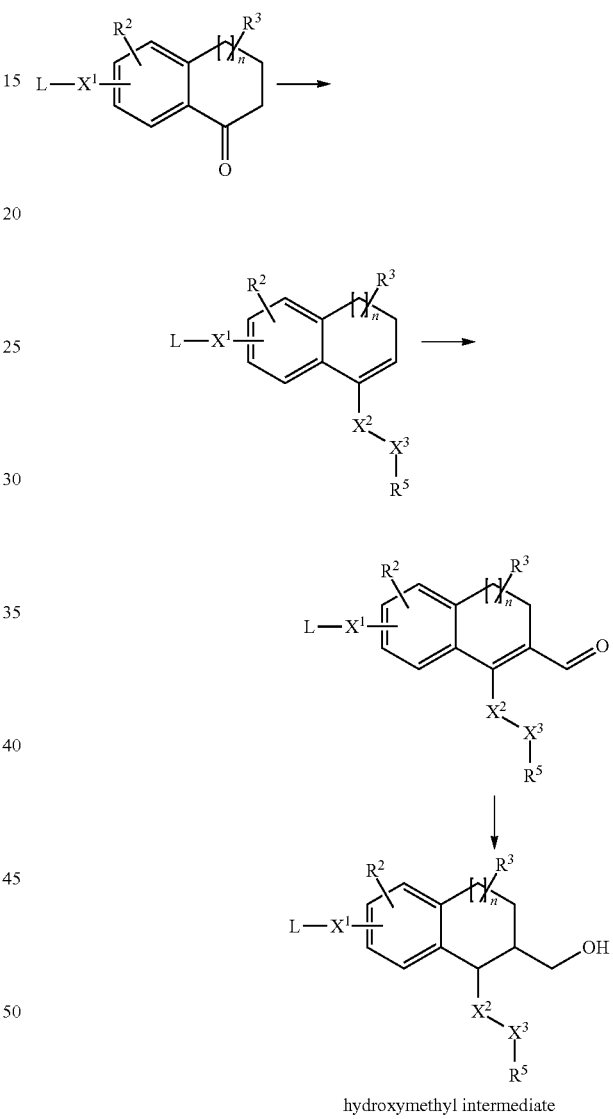

In scheme 3c, an alternative route to the hydroxmethyl intermediate described above is depicted. Analog to the protocols described in Journal of Organic Chemistry (1981), 46(26), 5371, U.S. Pat. No. 4,927,838 or http://www3.interscience.wiley.com/cqi-bin/mrwhome/107610747/HOME the aldehyde can be obtained which upon reduction (e.g. hydrogenation) can yield the hydroxmethyl intermediate.

The process depicted in scheme 4 is useful for obtaining tetralines and indanes, wherein $X^1$ is methylene, $A^2$ is a bond, Y is —$NR^9$—, and Q is —$S(O)_2$.

Scheme 4:

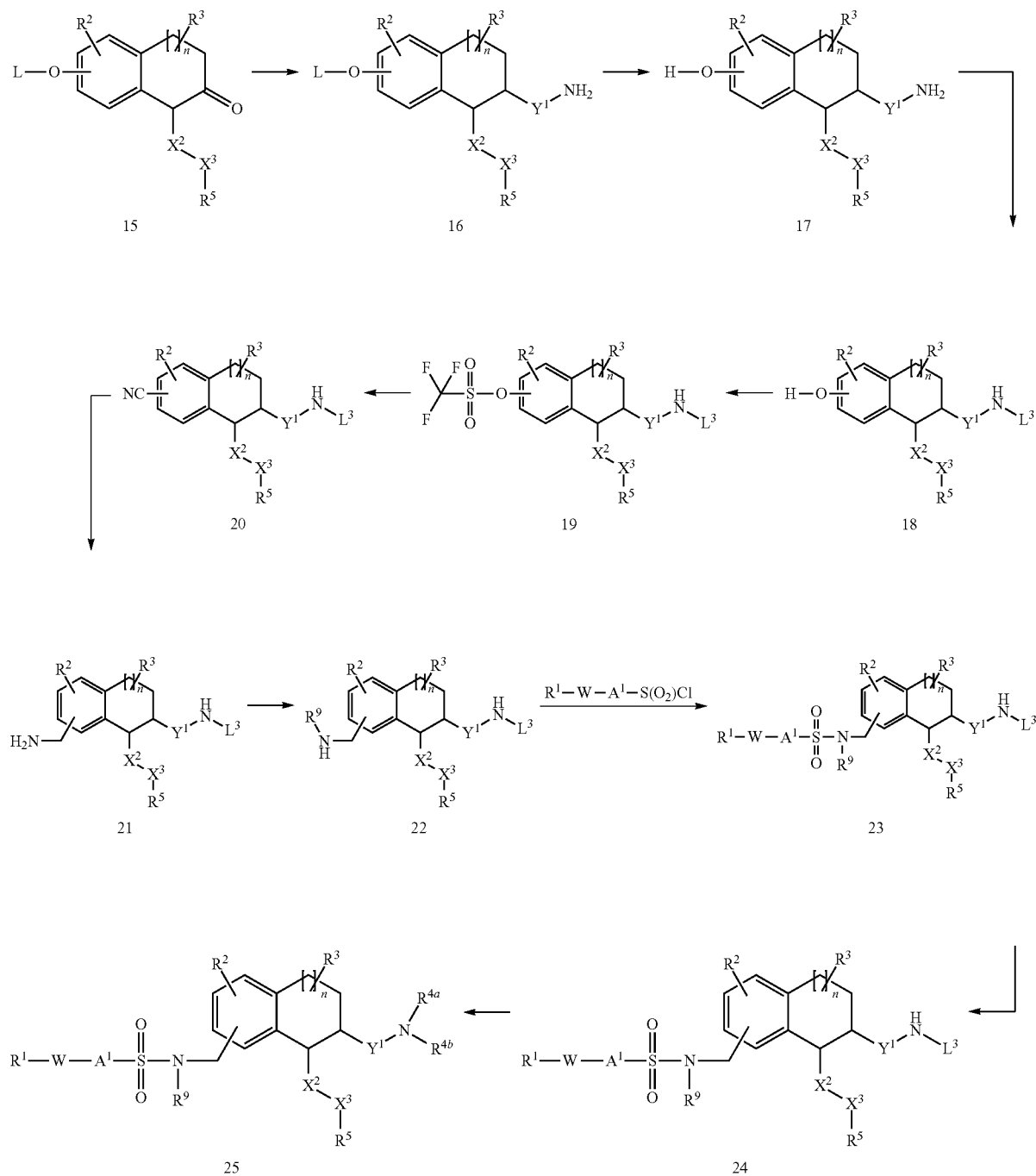

Alternatively to triflate 19, the corresponding bromide or iodide can be used to prepare compound 20.

In scheme 4, the variables $R^1$, W, $A^1$, $R^2$, $R^3$, $R^{4a}$, $R^{4b}$, $R^5$, $R^9$, $X^2$, $X^3$ and n are as defined herein, and $L^3$ is a suitable protecting group (e.g. $L^3$=COO$^t$Bu). $Y^1$ is optionally substituted methylene or ethylene.

Compounds 16 with $Y^1$ methylene or ethylene can be obtained from compound 15 in a similar fashion as compounds 7 from compounds 3.

Side chains containing $R^1$, W, $A^1$, $X^1$ and $R^9$ and $R^5$, $X^2$ and $X^3$ as well as the substituents $R^2$, $R^3$, $R^{4a}$ and $R^{4b}$ can be introduced in analogy to the protocols described in WO2009/121872.

The process depicted in scheme 5 is useful for obtaining tetralines and indanes, wherein $X^1$ is optionally substituted alkylene, $A^2$ is optionally substituted alkylene or a bond, Y is —$NR^9$—, and Q is —S(O)$_2$.

Scheme 5:

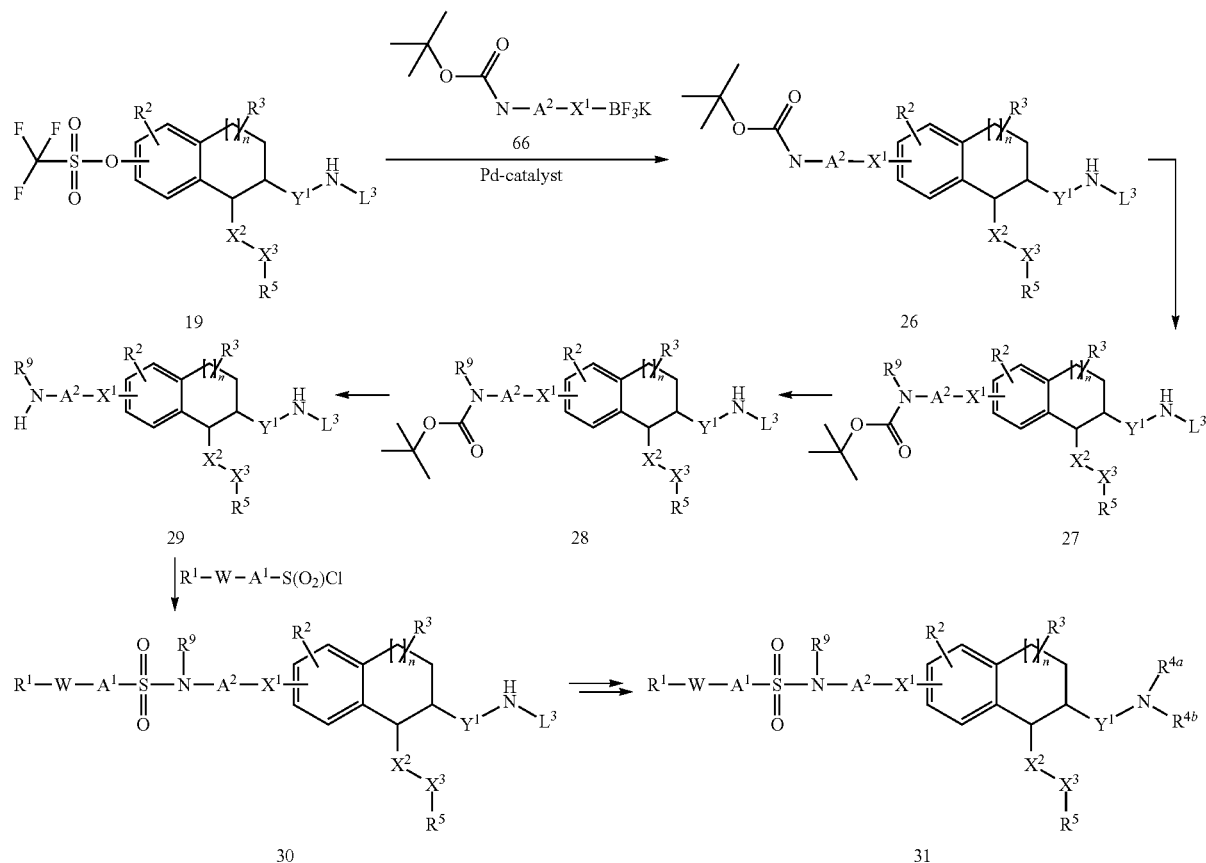

Instead of the trifluoroborate 66, the corresponding 9-borabicyclo[3.3.1]non-9-yl derivative can be used to prepare compound 26.

In scheme 5, the variables $R^1$, W, $A^1$, $R^2$, $R^3$, $R^{4a}$, $R^{4b}$, $R^5$, $R^9$, $X^2$, $X^3$, $A^2$ and n are as defined herein, and $L^3$ is a suitable protecting group (e.g. $L^3$=COO$^t$Bu). $Y^1$ is optionally substituted methylene or ethylene.

The process depicted in scheme 6 is useful for obtaining tetralines and indanes, wherein X is —$NR^{11}$—, $A^2$ is optionally substituted alkylene, Y is —$NR^9$—, and Q is —S(O)$_2$. $Y^1$ is optionally substituted methylene or ethylene.

Scheme 6:

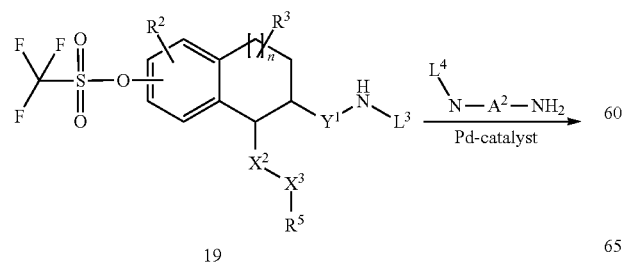

In scheme 6, the variables $R^1$, W, $A^1$, $R^2$, $R^3$, $R^{4a}$, $R^{4b}$, $R^5$, $R^9$, $X^2$, $X^3$, $A^2$ and n are as defined herein, and $L^4$ is a suitable protecting group. $Y^1$ is optionally substituted methylene or ethylene.

Compounds 33, wherein $R^{4a}$ is alkylene that is bound to a carbon atom in $Y^1$ can be synthesized by the processes depicted in Scheme 7 and Scheme 8.

Scheme 7:
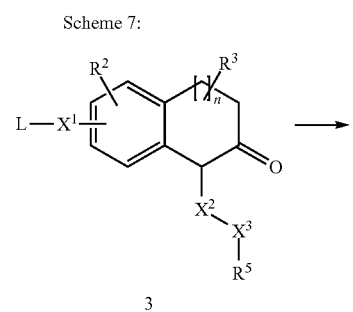
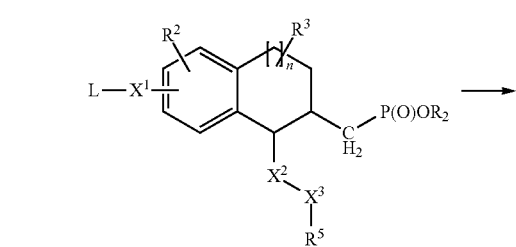
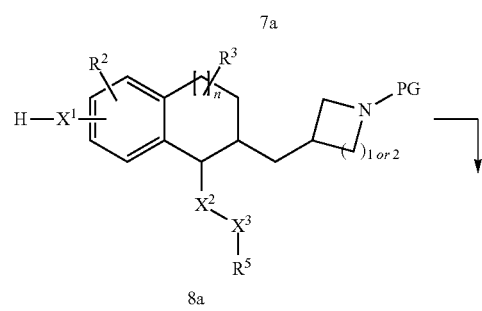
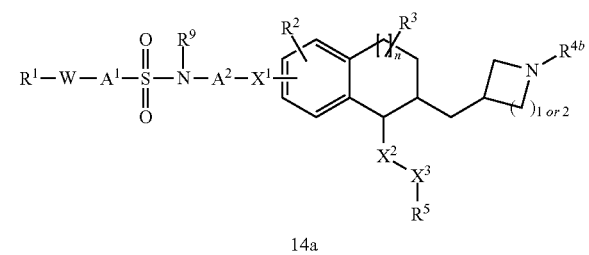
Scheme 8:
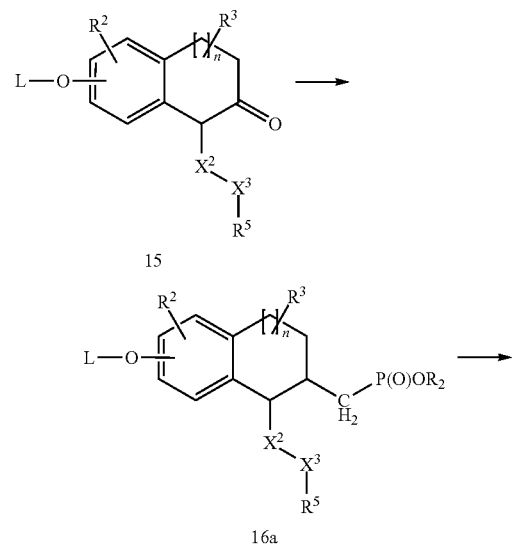
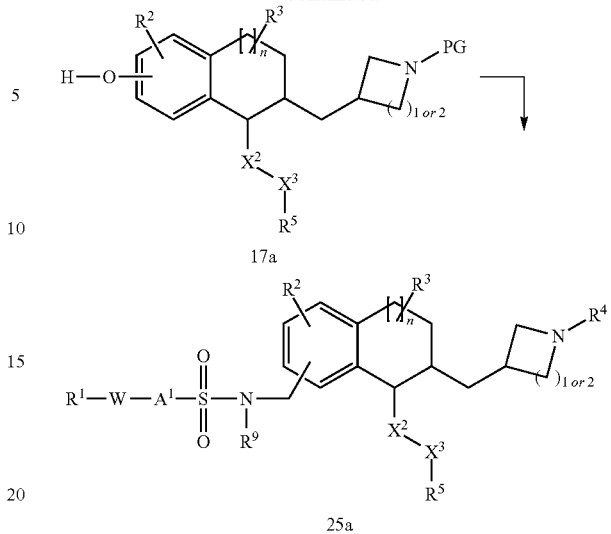
Compounds 8a and 17a can be obtained from compounds 3 and 15, respectively, in analogy to the following protocols: Wittig reagent 7a and 16a: c.f. J. Org. Chem. 2009, 74, 9191-9194, Organic Reactions 1990, 38 (http://www3.interscience.wiley.com/cgi-bin/mrwhome/107610747/HOME; CAN 149:555087); Olefination followed by hydrogenation introducing the heterocyclyl moiety yielding 8a and 17a: WO2007/143823 and WO2006/102760.
Scheme 9:
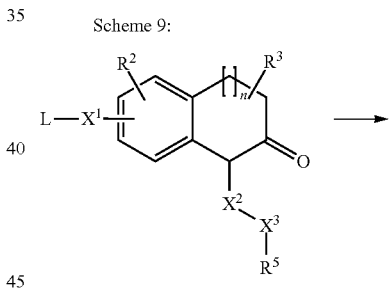
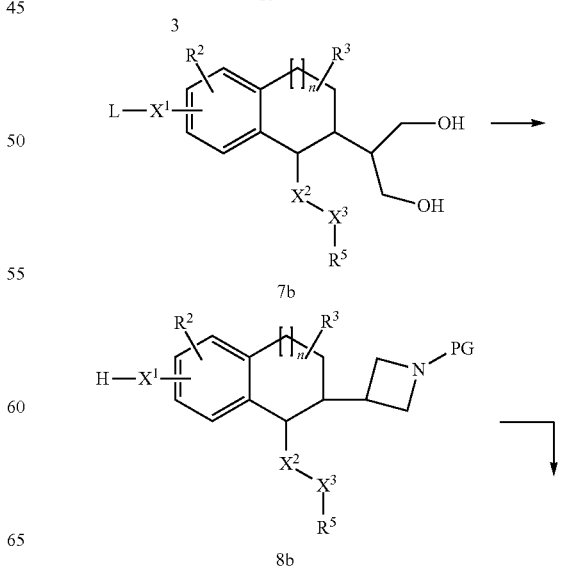

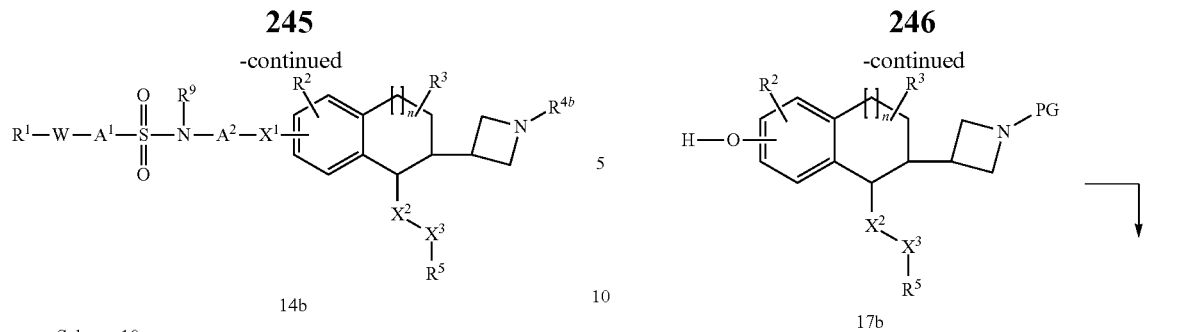
Scheme 10:
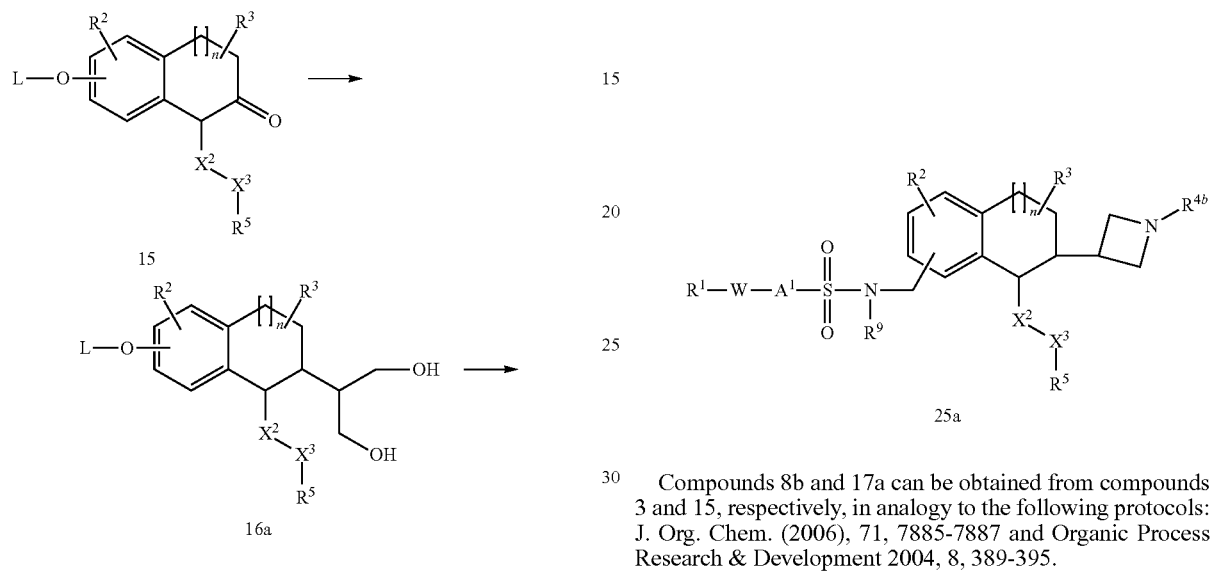
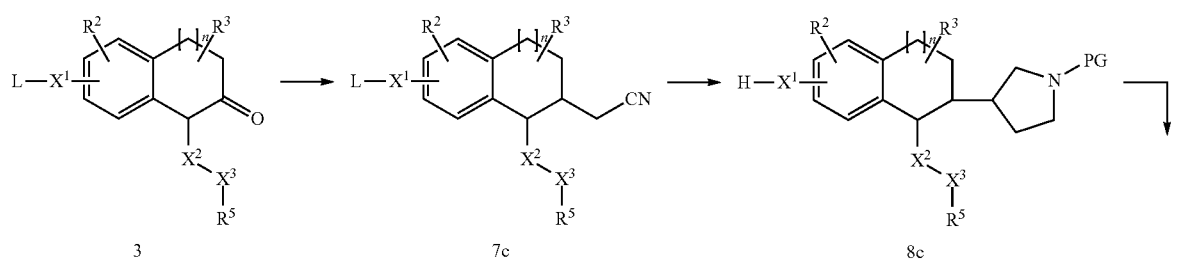
Compounds 8b and 17a can be obtained from compounds 3 and 15, respectively, in analogy to the following protocols: J. Org. Chem. (2006), 71, 7885-7887 and Organic Process Research & Development 2004, 8, 389-395.
Scheme 11:
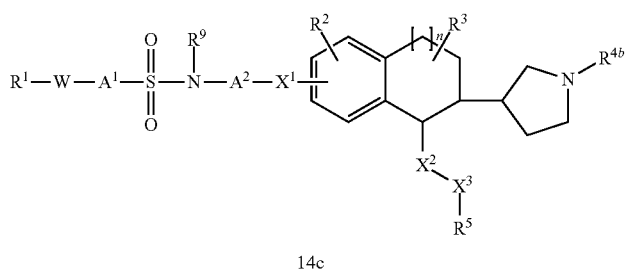

Scheme 12:

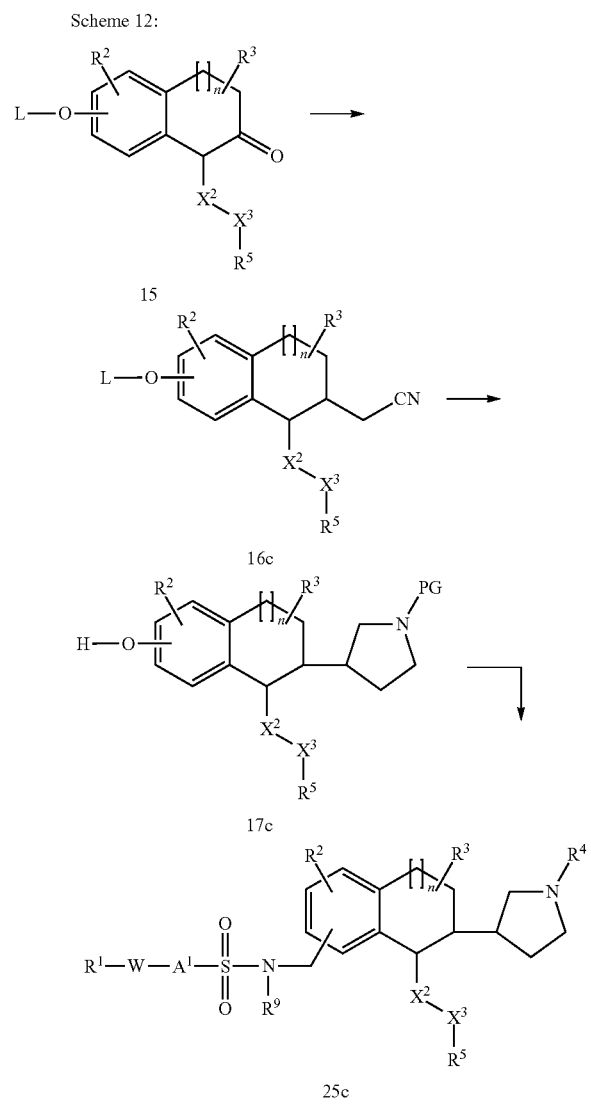

Compounds 8c and 17c can be obtained from compounds 3 and 15, respectively, in analogy to the following protocols: Pyrrolidinone synthesis: c.f. J. Med. Chem. 2005, 48, 2294-2307; reduction to pyrrolidine with lithium aluminium hydride: c.f. Tetrahedron Letters (2010), 51(11), 1459-1461.

The process depicted in the following schemes is useful for obtaining compounds of the general formula (I) in which A is a heterocycle.

Scheme 13:

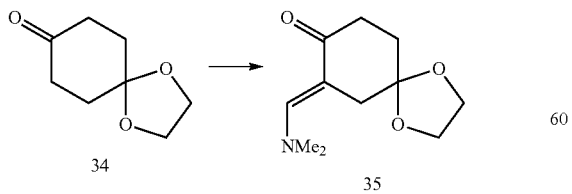

As shown in scheme 13, the compound of general formula 34 readily undergoes condensation with dimethylformamide dimethyl acetal to give the compound of general formula 35.

Scheme 14:

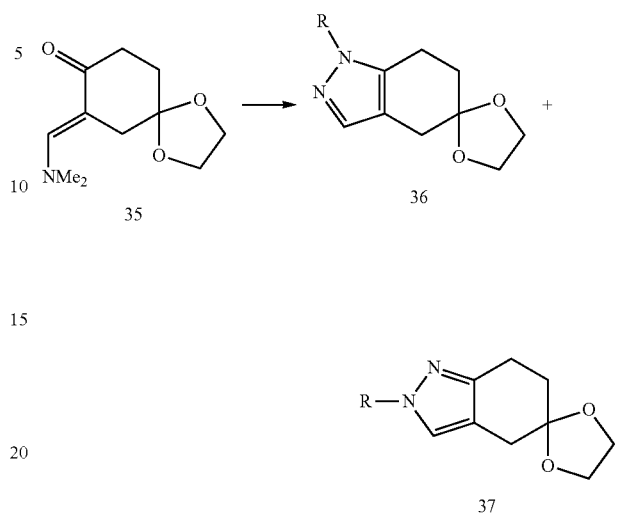

As shown in the above scheme 8, the intermediate of general formula 35 reacts with various nucleophiles of general formula $H_2N-NH-R$ in an alcoholic solvent preferably methanol or ethanol at a temperature of about 20° to 80° C. to obtain the compounds of general formulae 36 and 37. In case of monosubstituted hydrazines regioisomeric products are formed. Compounds 36 and 37 can be transformed to compounds of the general formula (I) as depicted in Scheme 15.

In schemes 14 the variable R is as defined herein.

Scheme 15:

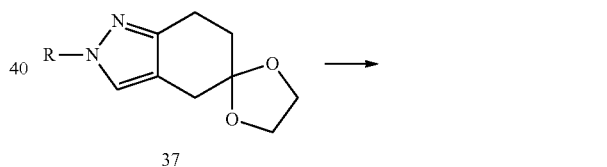

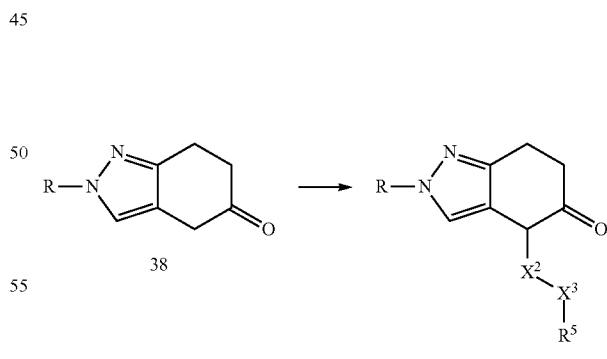

Alkylation of 38 can proceed via an enamine as described in scheme 1, or via an enolate. Compound 39 can be used in analogy to compound 3 to prepare heterocyclic analogs of formula (I) depicted in Schemes 3 to 12. In scheme 15, the variables R, $R^5$, $X^2$, $X^3$ are as defined herein.

Scheme 16:

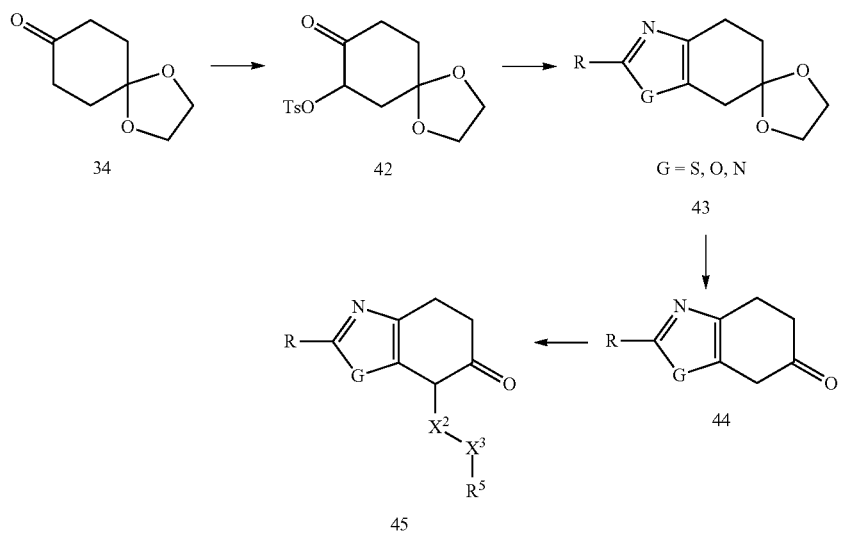

As shown in scheme 16, the reaction of compound of general formula 34 with hydroxyl (tosyloxy)iodobenzene gives the compound of formula 42. Reaction of compound of general formula 42 with 1,3-nucleophiles under appropriate conditions yield the compound of general formula 43. Compound 45 can be used in analogy to compound 3 to prepare heterocyclic analogs of formula (I) depicted in Schemes 3 to 12. In scheme 16, the variables R, $R^5$, $X^2$, $X^3$ are as defined herein.

Scheme 17:

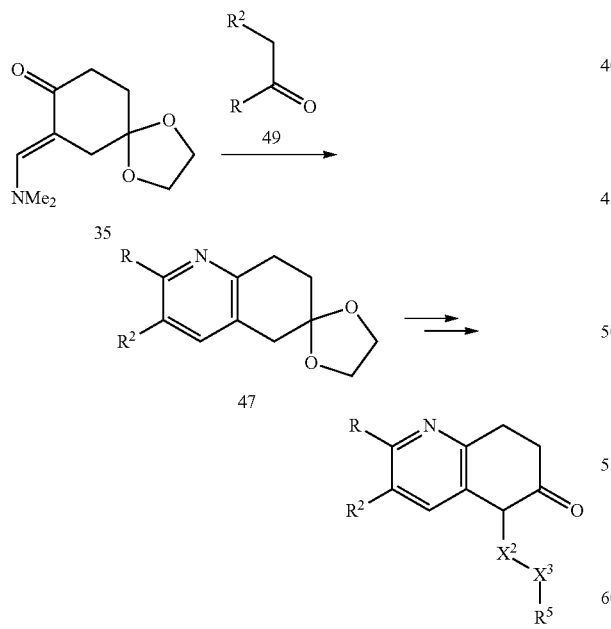

$R^2$ = —$CO_2Me$, —$CO_2Et$, —CN, $NO_2$ etc.

As shown in scheme 17, the condensation of compound of general formula 35 with reagent of general formula 49 and ammonia acetate in refluxing acetic acid give compound of general formula 47, which can be further transformed to compounds of general formula 48.

Compound 48 can be used in analogy to compound 3 to prepare heterocyclic analogs of formula (I) depicted in Schemes 3 to 12. In scheme 17, the variables R, $R^5$, $X^2$, $X^3$ are as defined herein.

Scheme 18:

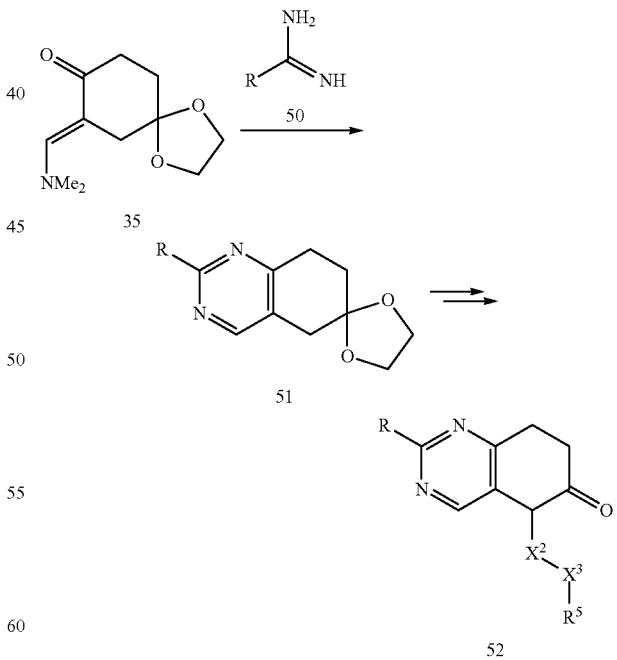

As shown in scheme 18, the cyclocondensation of intermediate of general formula 35 with the 1,3-nucleophiles of general formula 50 in the presence of suitable organic or inorganic bases such as KOH, NaOH, $NaHCO_3$, sodium ethoxide, sodium methoxide, triethyl amine and diisopropyl ethyl amine in an alcoholic solvent, preferably ethanol or methanol, at a temperature of about 20° to 80° C. yield the compound of general formula 51, which can be transformed further to give compounds of general formula 52. Compound 52 can be used in analogy to compound 3 to prepare heterocyclic analogs of formula (I) depicted in Schemes 3 to 12. In scheme 18, the variables R, $R^5$, $X^2$, $X^3$ are as defined herein.

Scheme 19:

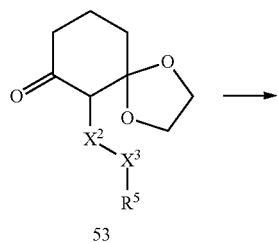

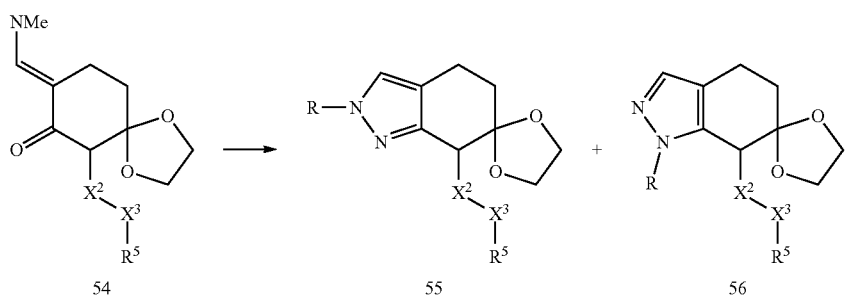

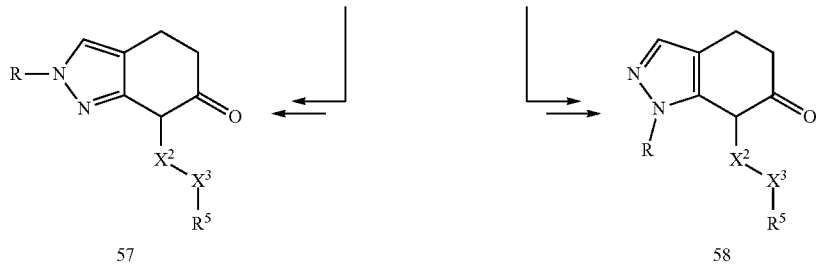

As shown in scheme 19, the intermediate of general formula 53 readily can undergo condensation with dimethylformamide dimethyl acetal to give the compound of general formula 54, which reacts with various nucleophiles of general formula H₂N—NH—R in an alcoholic solvent, preferably methanol or ethanol, at a temperature of about 20° to 80° C. to afford the compound of general formula 55 and 56. Compounds 57 and 58 can be used in analogy to compound 3 to prepare heterocyclic analogs of formula (I) depicted in Schemes 3 to 12. In scheme 19, the variables R, $R^5$, $X^2$, $X^3$ are as defined herein.

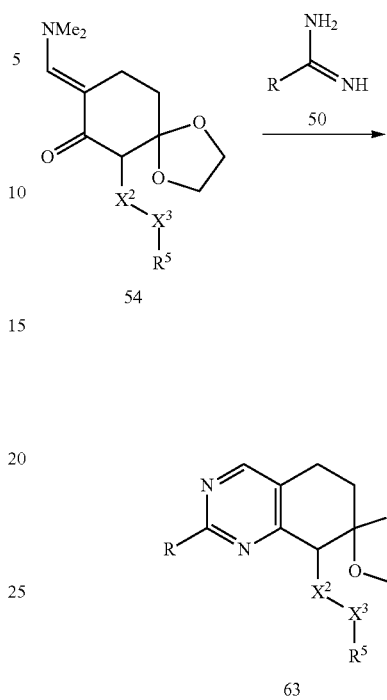

Scheme 21:

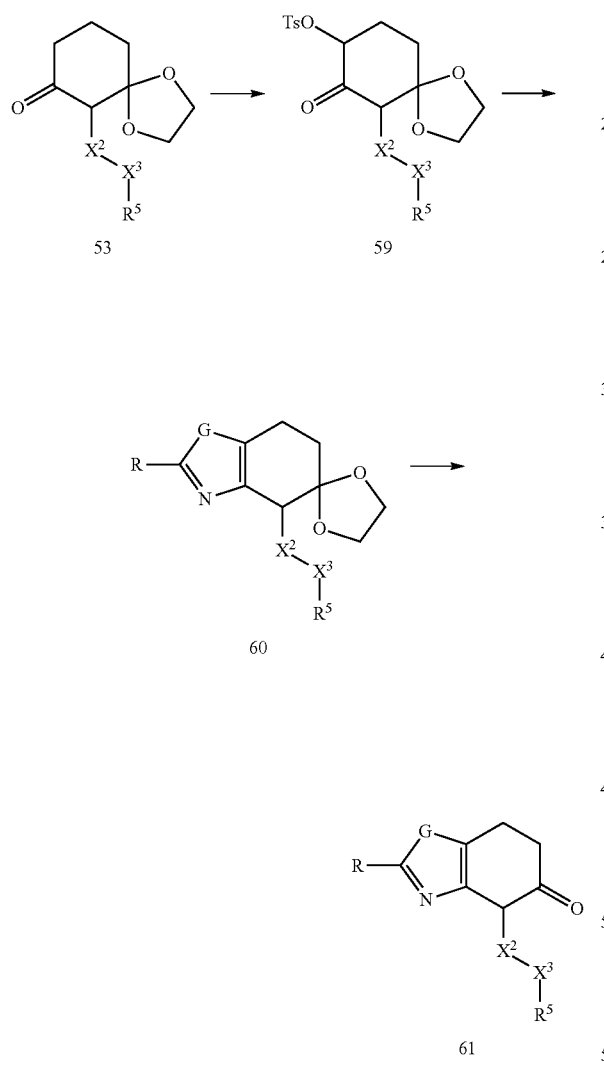

Scheme 20:

As shown in scheme 20, the reaction of compound of general formula 53 with hydroxyl (tosyloxy)iodobenzene gives the compound of formula 59, which reacts with 1,3-nucleophiles under appropriate conditions to yield the compound of general formula 60. Further transformation results in compounds of general formula 61. Compound 61 can be used analogous to compound 3 to prepare heterocyclic analogs of formula (I) depicted in Schemes 3 to 12. In scheme 20, the variables R, $R^5$, $X^2$, $X^3$ are as defined herein.

As shown in scheme 21, the cyclocondensation of intermediate of general formula 54 with the 1,3-nucleophiles of general formula 50 in the presence of suitable organic or inorganic bases such as KOH, NaOH, NaHCO₃, sodium ethoxide, sodium methoxide, triethyl amine and diisopropyl ethyl amine in an alcoholic solvent, preferably ethanol or methanol, at a temperature of about 20° to 80° C. yields the compound of general formula 63, which can be transformed further to give compounds of general formula 64. Compound 64 can be used in analogy to compound 3 to prepare heterocyclic analogs of formula (I) depicted in Schemes 3 to 12. In scheme 21, the variables R, $R^5$, $X^2$, $X^3$ are as defined herein.

The acid addition salts of the compounds of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of formula (II)

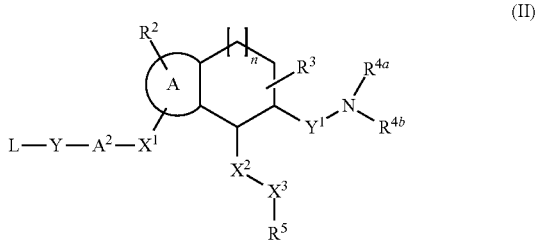

wherein L is an amino-protecting group, Y is $NR^9$, and $A^2$, $X^1$, A, $R^2$, $R^3$, $Y^1$, $R^{4a}$, $R^{4b}$, $X^2$, $X^3$, $R^5$, n are defined as above are useful as intermediates in the preparation of GlyT1 inhibitors, in particular those of formula (I).

Suitable amino-protecting groups are well known in the art such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991.

According to a particular embodiment, L is optionally substituted alkylcarbonyl (e.g., tert-butylcarbonyl), optionally substituted arylcarbonyl, optionally substituted arylalkylcarbonyl (e.g., benzylcarbonyl), optionally substituted alkoxycarbonyl (e.g., methoxycarbonyl or tert-butyloxycarbonyl), optionally substituted aryloxycarbonyl (e.g. phenoxycarbonyl) or optionally substituted arylalkoxycarbonyl.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}<1$ µMol, more preferably at a level of $IC_{50}<0.5$ µMol, particularly preferably at a level of $IC_{50}<0.2$ µMol and most preferably at a level of $IC_{50}<0.1$ µMol.

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine transport may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neurophysiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive suboptimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Cantor-Verlag, 1996.

The compounds of formula (I) may also be suitable for combination with other therapeutic agents.

Thus, the present invention also provides:
i) a combination comprising a compound of formula (I) with one or more further therapeutic agents;
ii) a pharmaceutical composition comprising a combination product as defined in i) above and at least one carrier, diluent or excipient;
iii) the use of a combination as defined in i) above in the manufacture of a medicament for treating or preventing a disorder, disease or condition as defined herein;
iv) a combination as defined in i) above for use in treating or preventing a disorder, disease or condition as defined herein;
v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration,
vi) a combination as defined in i) above for use in therapy;
vii) a method of treatment or prevention of a disorder, disease or condition as defined herein comprising administering an effective amount of a combination as defined in i) above;
viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilised on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilising or antimanic agent, a pharmaceutical composition comprising compounds of formula (I) and at least one mood stabilising or antimanic agent, the use of a pharmaceutical composition comprising compounds of formula (I) and at least one mood stabilising or antimanic agent in the manufacture of a medicament for the treatment of a psychotic disorder, and a pharmaceutical composition comprising compounds of formula (I) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benziso-thiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE (D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer. Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anti-convulsant drugs such as carbamazepine and gabapentin, sodium channel blockers, anti-depressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1 B antagonists, 5HT1 D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLC-MS in a fast gradient on C18-material (electrospray-ionisation (ESI) mode).

Preparation Examples

The following compounds were obtained or can be obtained using the procedures described herein.

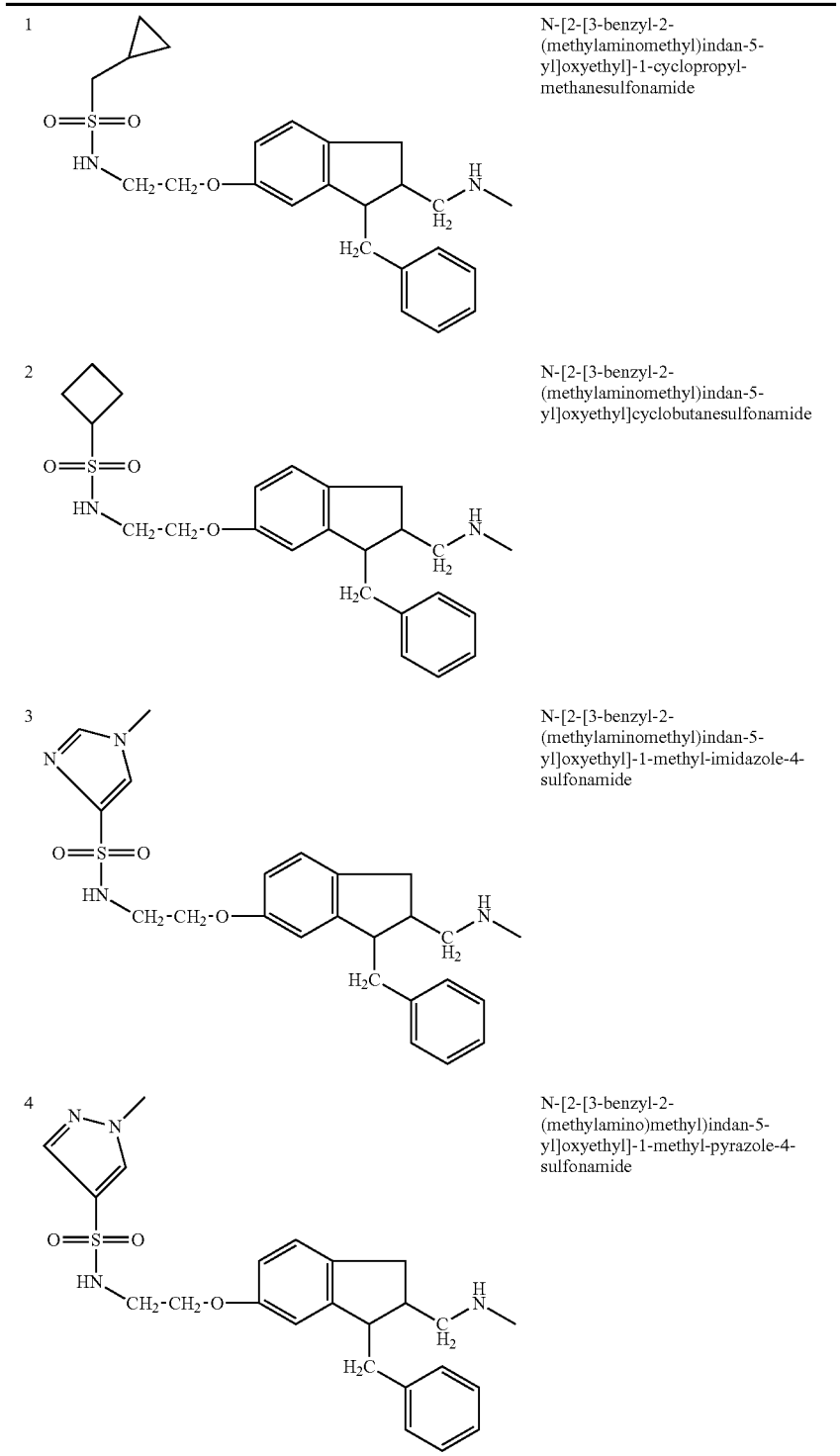

1  N-[2-[3-benzyl-2-(methylaminomethyl)indan-5-yl]oxyethyl]-1-cyclopropyl-methanesulfonamide 2  N-[2-[3-benzyl-2-(methylaminomethyl)indan-5-yl]oxyethyl]cyclobutanesulfonamide 3  N-[2-[3-benzyl-2-(methylaminomethyl)indan-5-yl]oxyethyl]-1-methyl-imidazole-4-sulfonamide 4  N-[2-[3-benzyl-2-(methylamino)methyl)indan-5-yl]oxyethyl]-1-methyl-pyrazole-4-sulfonamide

| | | |
|---|---|---|
| 5 | 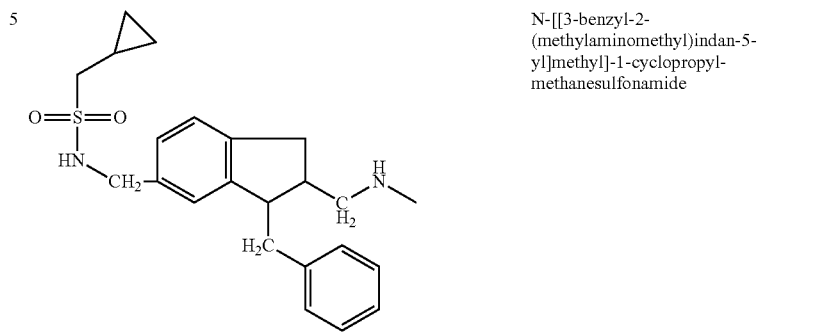 | N-[[3-benzyl-2-(methylaminomethyl)indan-5-yl]methyl]-1-cyclopropyl-methanesulfonamide |
| 6 | 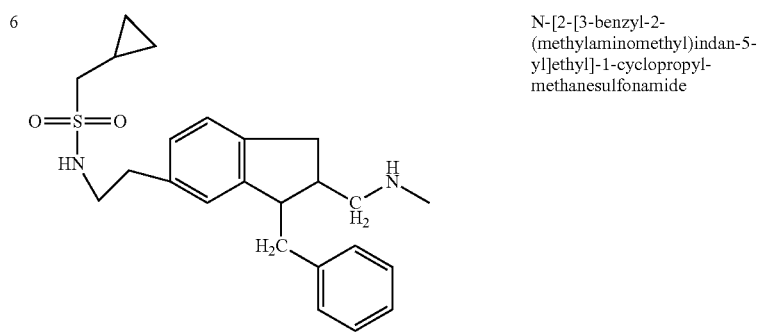 | N-[2-[3-benzyl-2-(methylaminomethyl)indan-5-yl]ethyl]-1-cyclopropyl-methanesulfonamide |
| 7 | 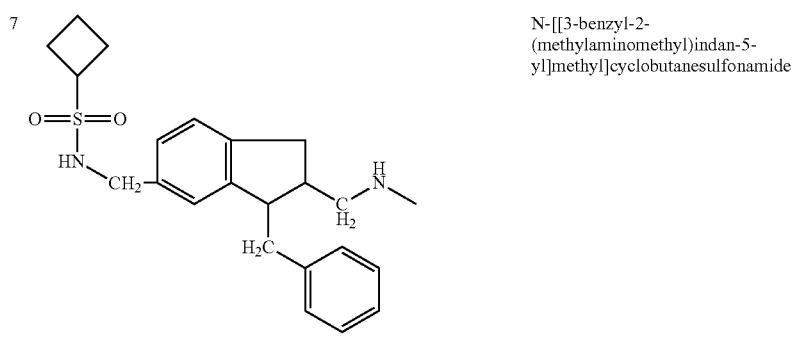 | N-[[3-benzyl-2-(methylaminomethyl)indan-5-yl]methyl]cyclobutanesulfonamide |
| 8 | 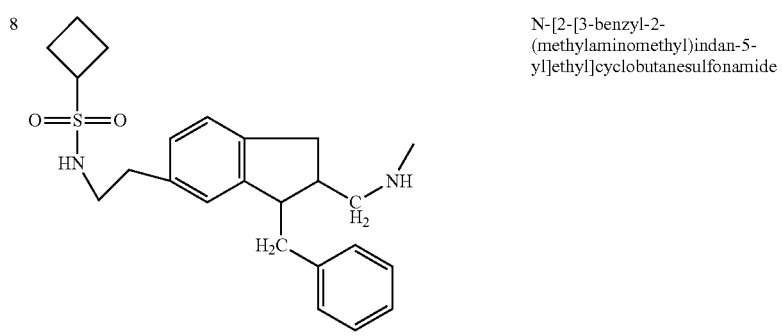 | N-[2-[3-benzyl-2-(methylaminomethyl)indan-5-yl]ethyl]cyclobutanesulfonamide |

-continued
| | | |
|---|---|---|
| 9 | 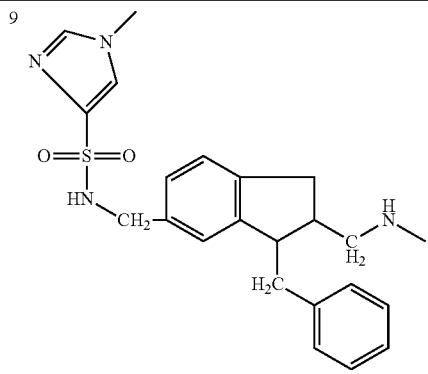 | N-[[3-benzyl-2-(methylaminomethyl)indan-5-yl]methyl]-1-methyl-imidazole-4-sulfonamide |
| 10 | 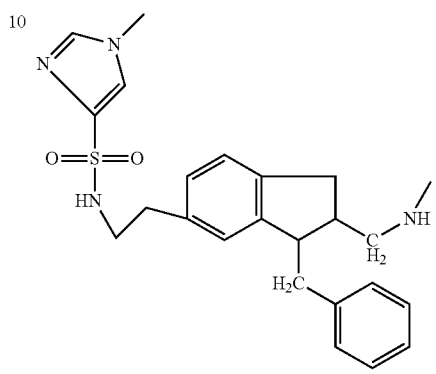 | N-[2-[3-benzyl-2-(methylaminomethyl)indan-5-yl]ethyl]-1-methyl-imidazole-4-sulfonamide |
| 11 | 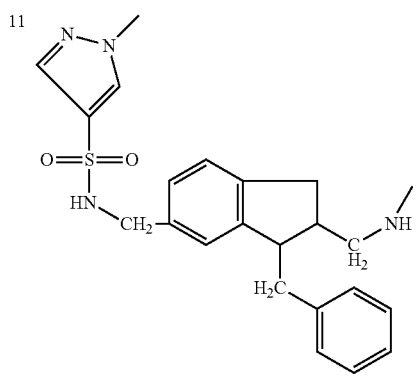 | N-[[3-benzyl-2-(methylaminomethyl)indan-5-yl]methyl]-1-methyl-pyrazole-4-sulfonamide |
| 12 | 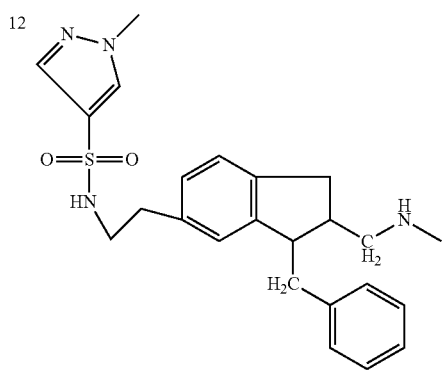 | N-[2-[3-benzyl-2-(methylaminomethyl)indan-5-yl]ethyl]-1-methyl-pyrazole-4-sulfonamide |

| # | Structure | Name |
|---|---|---|
| 13 | (cyclopropylmethyl-SO2-NH-CH2-CH2-O- attached to 5-fluoro-indan with 2-(methylaminomethyl) and 1-benzyl) | N-[2-[3-benzyl-6-fluoro-2-(methylaminomethyl)indan-5-yl]oxyethyl]-1-cyclopropyl-methanesulfonamide |
| 14 | (cyclobutyl-SO2-NH-CH2-CH2-O- attached to 5-fluoro-indan with 2-(methylaminomethyl) and 1-benzyl) | N-[2-[3-benzyl-6-fluoro-2-(methylaminomethyl)indan-5-yl]oxyethyl]cyclobutanesulfonamide |
| 15 | (1-methylimidazol-4-yl-SO2-NH-CH2-CH2-O- attached to 5-fluoro-indan with 2-(methylaminomethyl) and 1-benzyl) | N-[2-[3-benzyl-6-fluoro-2-(methylaminomethyl)indan-5-yl]oxyethyl]-1-methyl-imidazole-4-sulfonamide |
| 16 | (1-methylpyrazol-4-yl-SO2-NH-CH2-CH2-O- attached to 5-fluoro-indan with 2-(methylaminomethyl) and 1-benzyl) | N-[2-[3-benzyl-6-fluoro-2-(methylaminomethyl)indan-5-yl]oxyethyl]-1-methyl-pyrazole-4-sulfonamide |

| | | |
|---|---|---|
| 17 | 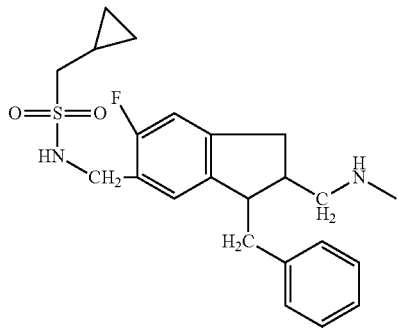 [SMILES: CNCC1Cc2cc(F)c(CNS(=O)(=O)CC3CC3)cc2C1Cc1ccccc1] | N-[[3-benzyl-6-fluoro-2-(methylaminomethyl)indan-5-yl]methyl]-1-cyclopropyl-methanesulfonamide |
| 18 | 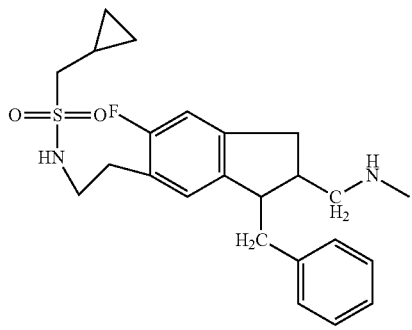 [SMILES: CNCC1Cc2cc(F)c(CCNS(=O)(=O)CC3CC3)cc2C1Cc1ccccc1] | N-[2-[3-benzyl-6-fluoro-2-(methylaminomethyl)indan-5-yl]ethyl]-1-cyclopropyl-methanesulfonamide |
| 19 | 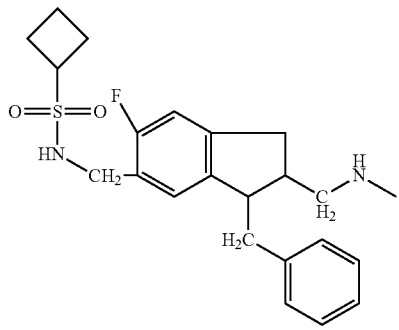 [SMILES: CNCC1Cc2cc(F)c(CNS(=O)(=O)C3CCC3)cc2C1Cc1ccccc1] | N-[[3-benzyl-6-fluoro-2-(methylaminomethyl)indan-5-yl]methyl]cyclobutanesulfonamide |
| 20 | 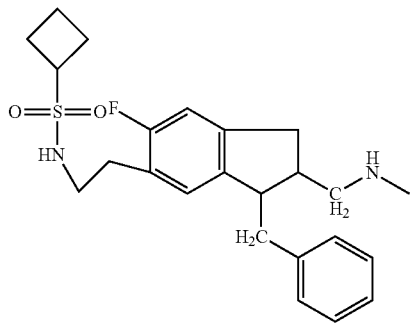 [SMILES: CNCC1Cc2cc(F)c(CCNS(=O)(=O)C3CCC3)cc2C1Cc1ccccc1] | N-[2-[3-benzyl-6-fluoro-2-(methylaminomethyl)indan-5-yl]ethyl]cyclobutanesulfonamide |

-continued
| | | |
|---|---|---|
| 21 | 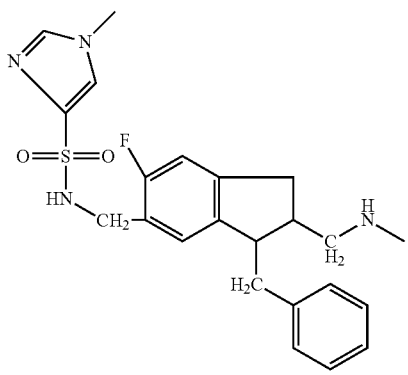 [SMILES: CNCC1Cc2cc(F)c(CNS(=O)(=O)c3cn(C)cn3)cc2C1Cc1ccccc1] | N-[[3-benzyl-6-fluoro-2-(methylaminomethyl)indan-5-yl]methyl]-1-methyl-imidazole-4-sulfonamide |
| 22 | 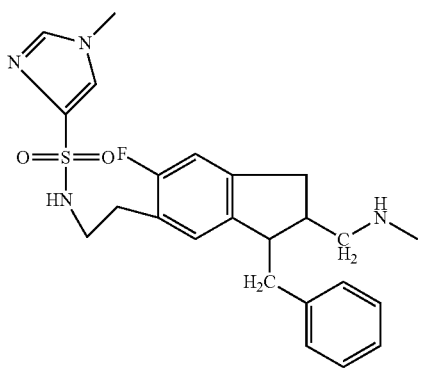 [SMILES: CNCC1Cc2cc(F)c(CCNS(=O)(=O)c3cn(C)cn3)cc2C1Cc1ccccc1] | N-[2-[3-benzyl-6-fluoro-2-(methylaminomethyl)indan-5-yl]ethyl]-1-methyl-imidazole-4-sulfonamide |
| 23 | 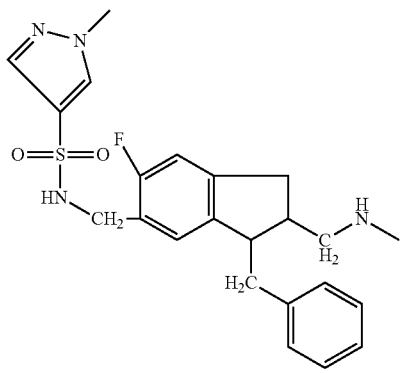 [SMILES: CNCC1Cc2cc(F)c(CNS(=O)(=O)c3cnn(C)c3)cc2C1Cc1ccccc1] | N-[[3-benzyl-6-fluoro-2-(methylaminomethyl)indan-5-yl]methyl]-1-methyl-pyrazole-4-sulfonamide |
| 24 | 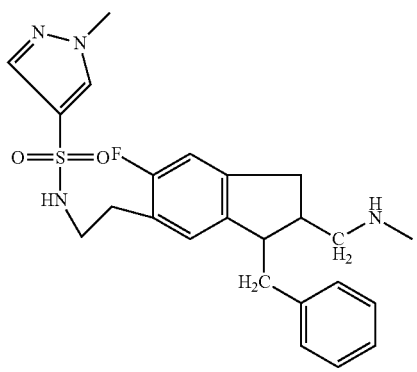 [SMILES: CNCC1Cc2cc(F)c(CCNS(=O)(=O)c3cnn(C)c3)cc2C1Cc1ccccc1] | N-[2-[3-benzyl-6-fluoro-2-(methylaminomethyl)indan-5-yl]ethyl]-1-methyl-pyrazole-4-sulfonamide |

| | | |
|---|---|---|
| 25 | 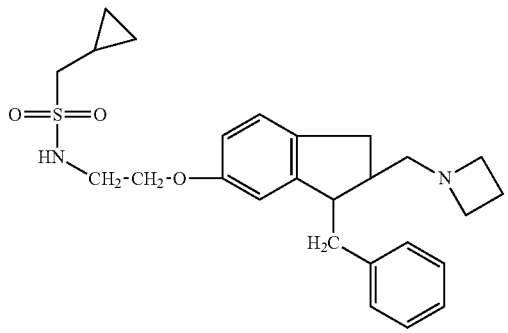 [SMILES: O=S(=O)(CC1CC1)NCCOc1ccc2c(c1)C(Cc1ccccc1)C(CN1CCC1)C2] | N-[2-[2-(azetidin-1-ylmethyl)-3-benzyl-indan-5-yl]oxyethyl]-1-cyclopropyl-methanesulfonamide |
| 26 | 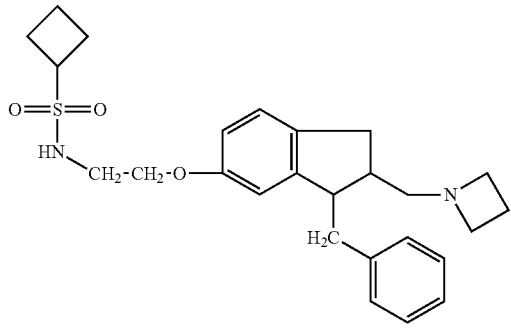 [SMILES: O=S(=O)(NCCOc1ccc2c(c1)C(Cc1ccccc1)C(CN1CCC1)C2)C1CCC1] | N-[2-[2-(azetidin-1-ylmethyl)-3-benzyl-indan-5-yl]oxyethyl]cyclobutanesulfonamide |
| 27 | 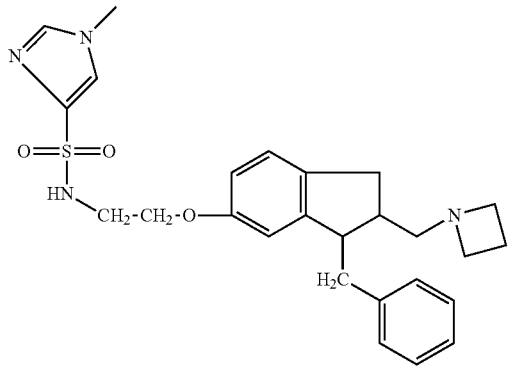 [SMILES: Cn1cnc(S(=O)(=O)NCCOc2ccc3c(c2)C(Cc2ccccc2)C(CN2CCC2)C3)c1] | N-[2-[2-(azetidin-1-ylmethyl)-3-benzyl-indan-5-yl]oxyethyl]-1-methyl-imidazole-4-sulfonamide |
| 28 | 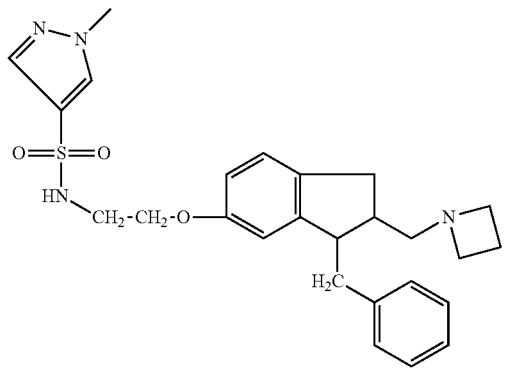 [SMILES: Cn1cc(S(=O)(=O)NCCOc2ccc3c(c2)C(Cc2ccccc2)C(CN2CCC2)C3)cn1] | N-[2-[2-(azetidin-1-ylmethyl)-3-benzyl-indan-5-yl]oxyethyl]-1-methyl-pyrazole-4-sulfonamide |

| | | |
|---|---|---|
| 29 | 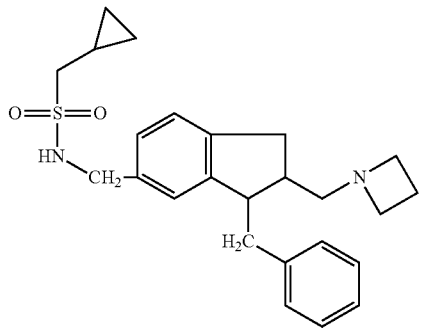 [SMILES: O=S(=O)(CC1CC1)NCc1ccc2c(c1)C(Cc1ccccc1)C(CN1CCC1)C2] | N-[[2-(azetidin-1-ylmethyl)-3-benzyl-indan-5-yl]methyl]-1-cyclopropyl-methanesulfonamide |
| 30 | 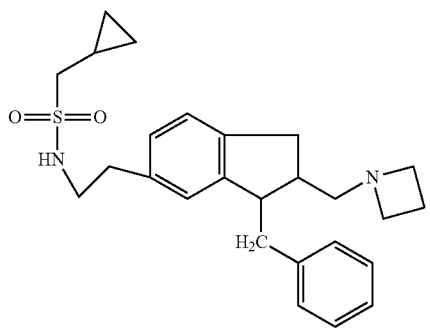 [SMILES: O=S(=O)(CC1CC1)NCCc1ccc2c(c1)C(Cc1ccccc1)C(CN1CCC1)C2] | N-[2-[2-(azetidin-1-ylmethyl)-3-benzyl-indan-5-yl]ethyl]-1-cyclopopyl-methanesulfonamide |
| 31 | 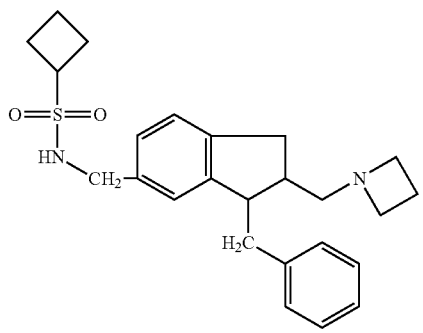 [SMILES: O=S(=O)(NCc1ccc2c(c1)C(Cc1ccccc1)C(CN1CCC1)C2)C1CCC1] | N-[[2-(azetidin-1-ylmethyl)-3-benzyl-indan-5-yl]methyl]cyclobutanesulfonamide |
| 32 | 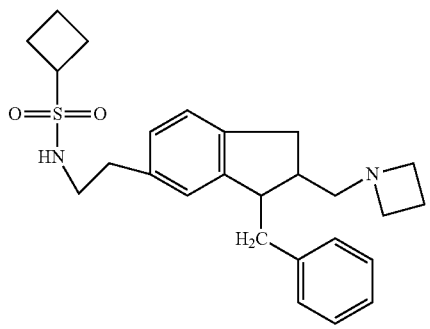 [SMILES: O=S(=O)(NCCc1ccc2c(c1)C(Cc1ccccc1)C(CN1CCC1)C2)C1CCC1] | N-[2-[2-(azetidin-1-ylmethyl)-3-benzyl-indan-5-yl]ethyl]cyclobutanesulfonamide |

-continued
| | | |
|---|---|---|
| 33 | 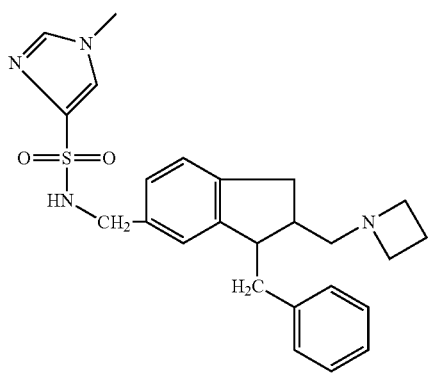 [SMILES: Cn1cnc(S(=O)(=O)NCc2ccc3c(c2)C(Cc2ccccc2)C(CN2CCC2)C3)c1] | N-[[2-(azetidin-1-ylmethyl)-3-benzyl-indan-5-yl]methyl]-1-methyl-imidazole-4-sulfonamide |
| 34 | 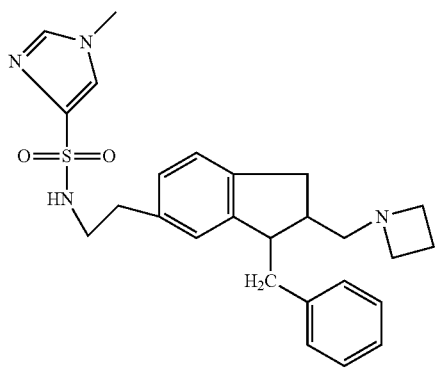 [SMILES: Cn1cnc(S(=O)(=O)NCCc2ccc3c(c2)C(Cc2ccccc2)C(CN2CCC2)C3)c1] | N-[2-[2-(azetidin-1-ylmethyl)-3-benzyl-indan-5-yl]ethyl]-1-methyl-imidazole-4-sulfonamide |
| 35 | 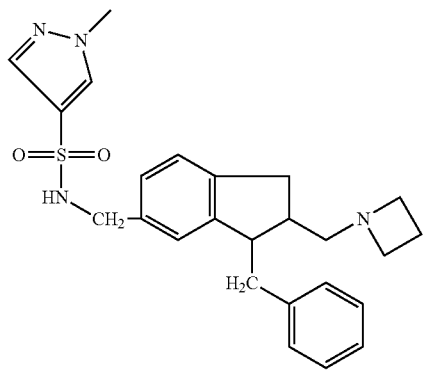 [SMILES: Cn1cc(S(=O)(=O)NCc2ccc3c(c2)C(Cc2ccccc2)C(CN2CCC2)C3)cn1] | N-[[2-(azetidin-1-ylmethyl)-3-benzyl-indan-5-yl]methyl]-1-methyl-pyrazole-4-sulfonamide |
| 36 | 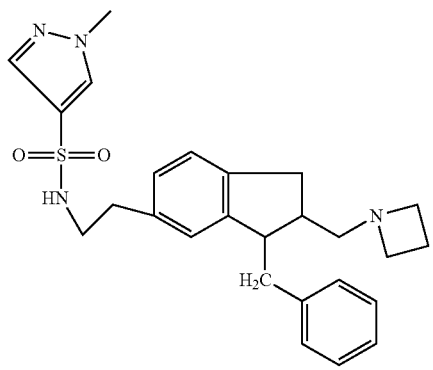 [SMILES: Cn1cc(S(=O)(=O)NCCc2ccc3c(c2)C(Cc2ccccc2)C(CN2CCC2)C3)cn1] | N-[2-[2-(azetidin-1-ylmethyl)-3-benzyl-indan-5-yl]ethyl]-1-methyl-pyrazole-4-sulfonamide |

-continued
| | | |
|---|---|---|
| 37 | 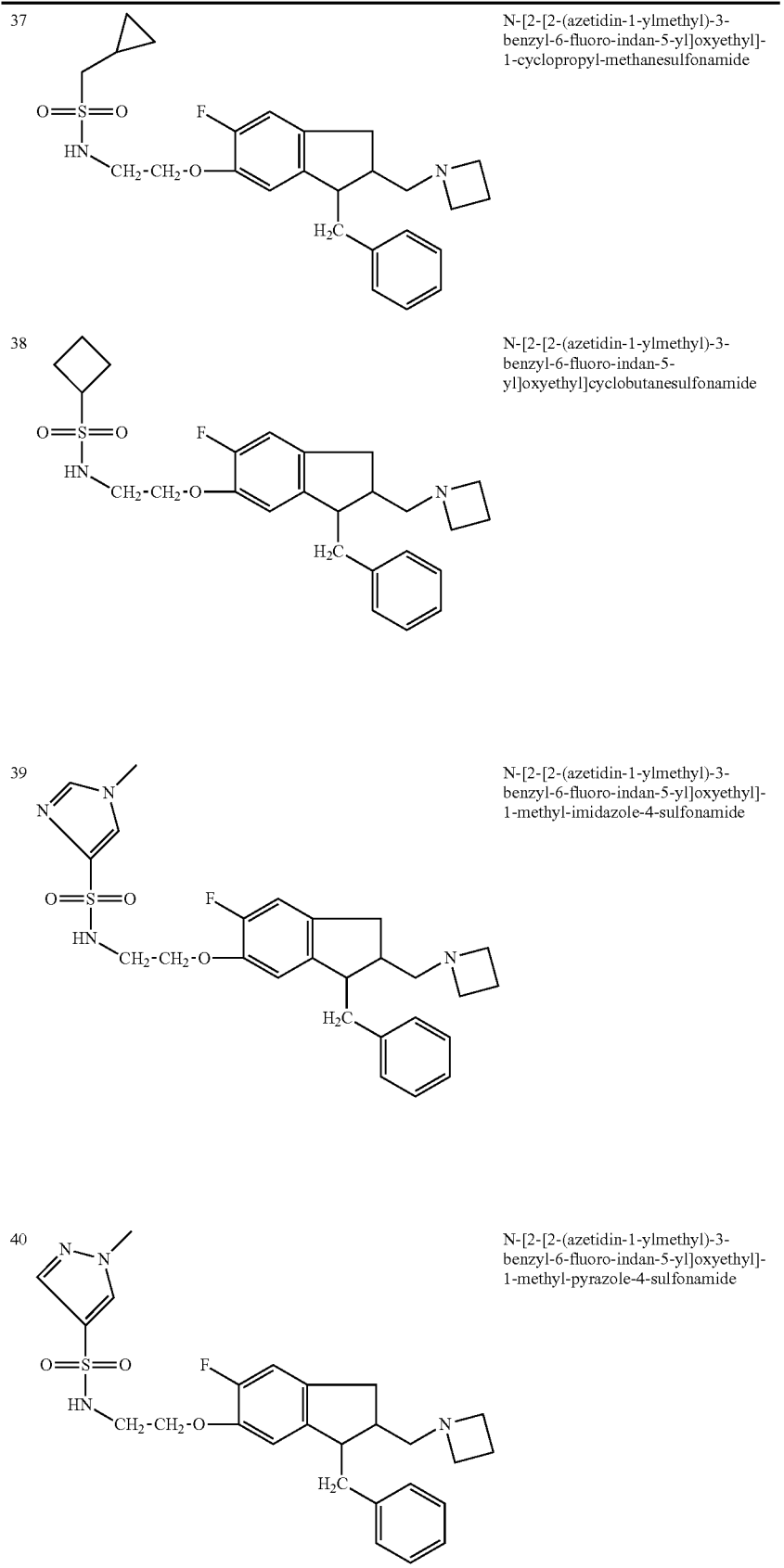 | N-[2-[2-(azetidin-1-ylmethyl)-3-benzyl-6-fluoro-indan-5-yl]oxyethyl]-1-cyclopropyl-methanesulfonamide |
| 38 | | N-[2-[2-(azetidin-1-ylmethyl)-3-benzyl-6-fluoro-indan-5-yl]oxyethyl]cyclobutanesulfonamide |
| 39 | | N-[2-[2-(azetidin-1-ylmethyl)-3-benzyl-6-fluoro-indan-5-yl]oxyethyl]-1-methyl-imidazole-4-sulfonamide |
| 40 | | N-[2-[2-(azetidin-1-ylmethyl)-3-benzyl-6-fluoro-indan-5-yl]oxyethyl]-1-methyl-pyrazole-4-sulfonamide |

-continued
| | | |
|---|---|---|
| 41 | 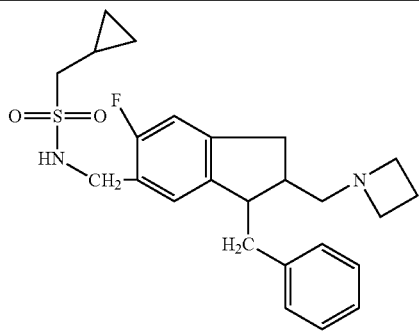 | N-[[2-(azetidin-1-ylmethyl)-3-benzyl-6-fluoro-indan-5-yl]methyl]-1-cyclopropyl-methanesulfonamide |
| 42 | 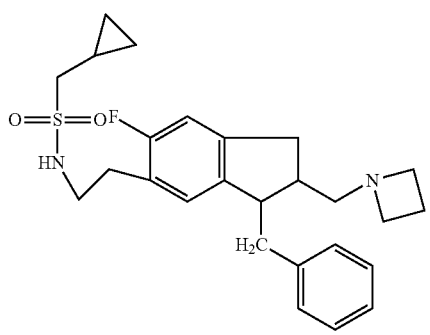 [SMILES: O=S(=O)(CC1CC1)NCCc1cc2c(cc1F)CC(CN1CCC1)C2Cc1ccccc1] | N-[2-[2-(azetidin-1-ylmethyl)-3-benzyl-6-fluoro-indan-5-yl]ethyl]-1-cyclopopyl-methanesulfonamide |
| 43 | 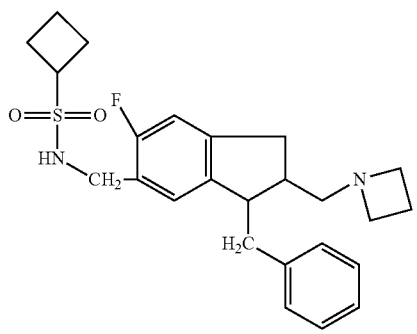 [SMILES: O=S(=O)(NCc1cc2c(cc1F)CC(CN1CCC1)C2Cc1ccccc1)C1CCC1] | N-[[2-(azetidin-1-ylmethyl)-3-benzyl-6-fluoro-indan-5-yl]methyl]cyclobutanesulfonamide |
| 44 | 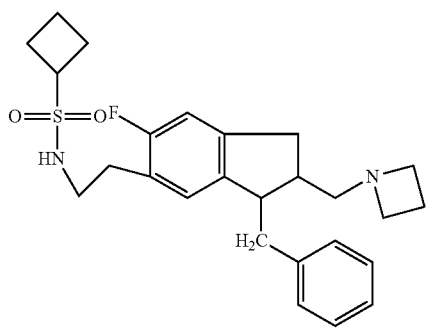 [SMILES: O=S(=O)(NCCc1cc2c(cc1F)CC(CN1CCC1)C2Cc1ccccc1)C1CCC1] | N-[2-[2-(azetidin-1-ylmethyl)-3-benzyl-6-fluoro-indan-5-yl]ethyl]cyclobutanesulfonamide |

| | | |
|---|---|---|
| 45 | 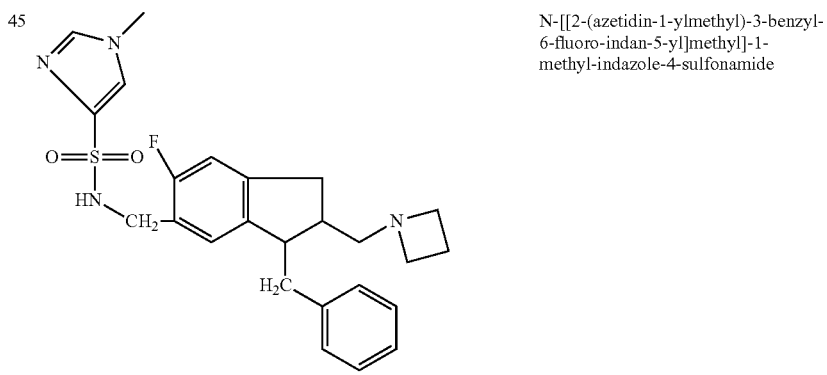 | N-[[2-(azetidin-1-ylmethyl)-3-benzyl-6-fluoro-indan-5-yl]methyl]-1-methyl-indazole-4-sulfonamide |
| 46 | 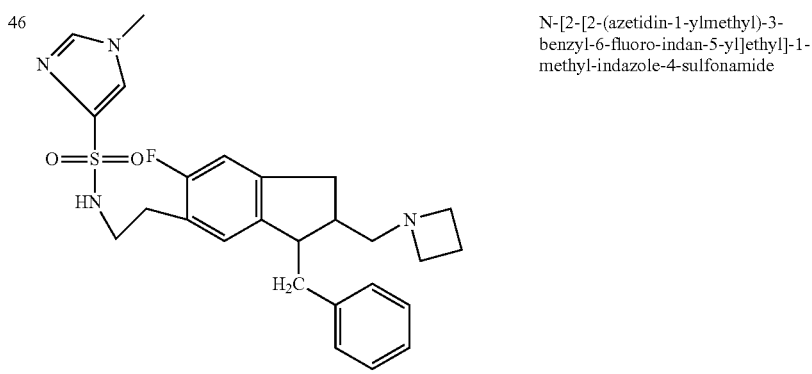 | N-[2-[2-(azetidin-1-ylmethyl)-3-benzyl-6-fluoro-indan-5-yl]ethyl]-1-methyl-indazole-4-sulfonamide |
| 47 | 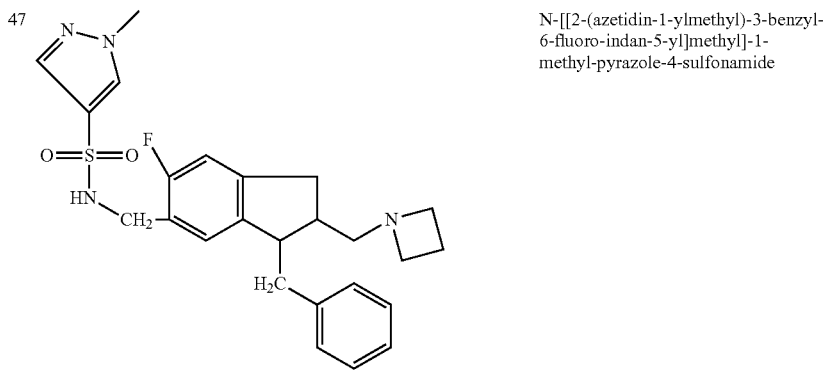 | N-[[2-(azetidin-1-ylmethyl)-3-benzyl-6-fluoro-indan-5-yl]methyl]-1-methyl-pyrazole-4-sulfonamide |
| 48 | 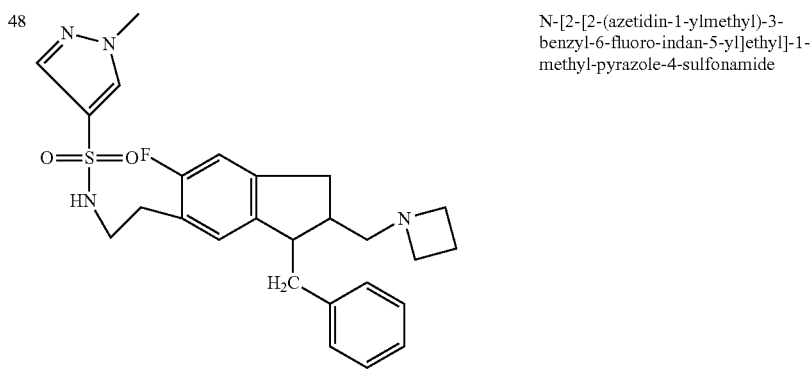 | N-[2-[2-(azetidin-1-ylmethyl)-3-benzyl-6-fluoro-indan-5-yl]ethyl]-1-methyl-pyrazole-4-sulfonamide |

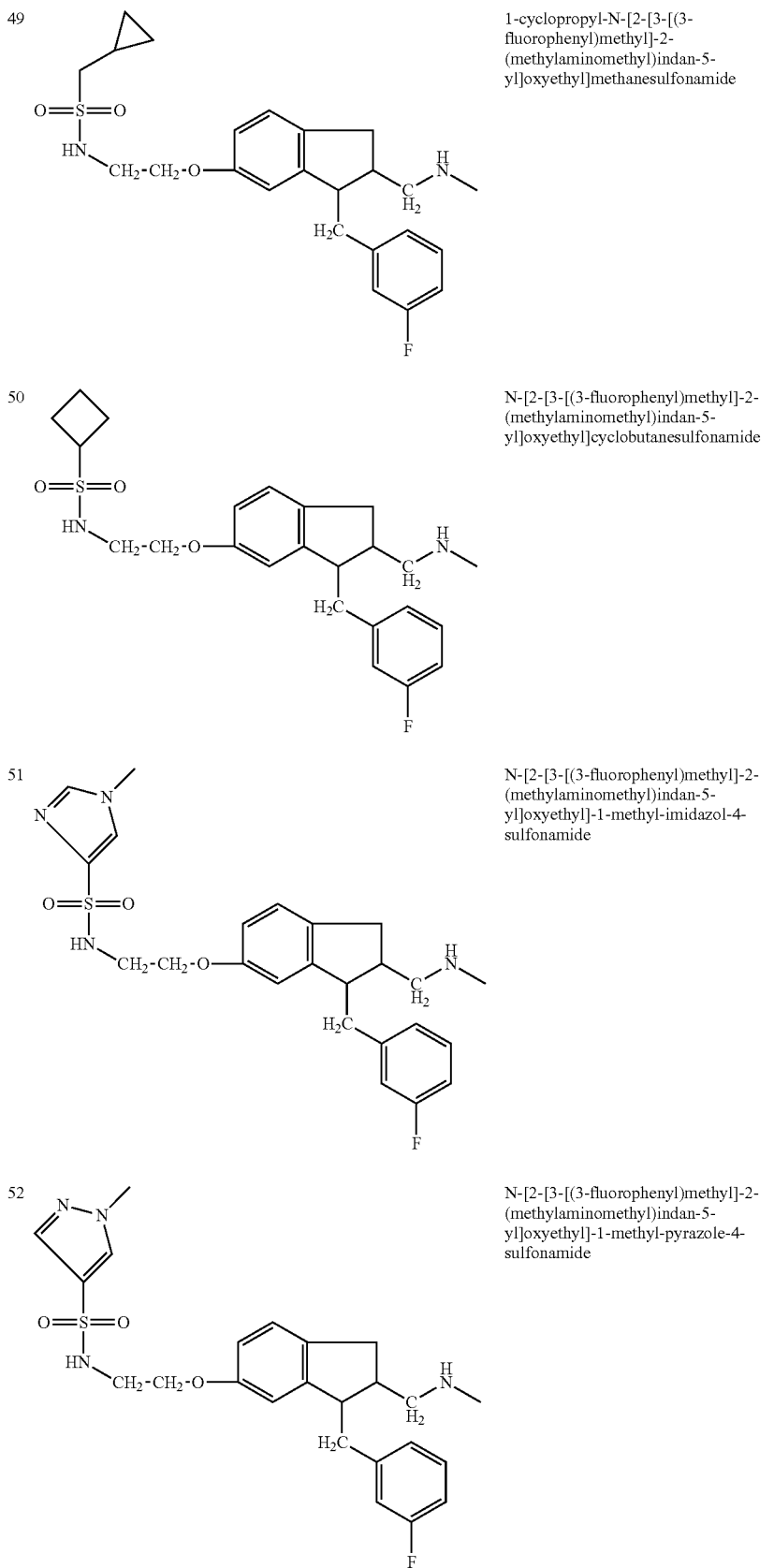

| | |
|---|---|
| 49 | 1-cyclopropyl-N-[2-[3-[(3-fluorophenyl)methyl]-2-(methylaminomethyl)indan-5-yl]oxyethyl]methanesulfonamide |
| 50 | N-[2-[3-[(3-fluorophenyl)methyl]-2-(methylaminomethyl)indan-5-yl]oxyethyl]cyclobutanesulfonamide |
| 51 | N-[2-[3-[(3-fluorophenyl)methyl]-2-(methylaminomethyl)indan-5-yl]oxyethyl]-1-methyl-imidazol-4-sulfonamide |
| 52 | N-[2-[3-[(3-fluorophenyl)methyl]-2-(methylaminomethyl)indan-5-yl]oxyethyl]-1-methyl-pyrazole-4-sulfonamide |

-continued

| | | |
|---|---|---|
| 53 | | 1-cyclopropyl-N-[[3-[(3-fluorophenyl)methyl]-2-(methylaminomethyl)indan-5-yl]methyl]methanesulfonamide |
| 54 | | 1-cyclopropyl-N-[2-[3-[(3-fluorophenyl)methyl]-2-(methylaminomethyl)indan-5-yl]ethyl]methanesulfonamide |
| 55 | | N-[[3-[(3-fluorophenyl)methyl]-2-(methylaminomethyl)indan-5-yl]methyl]cyclobutanesulfonamide |
| 56 | | N-[2-[3-[(3-fluorophenyl)methyl]-2-(methylaminomethyl)indan-5-yl]ethyl]cyclobutanesulfonamide |

-continued
| | | |
|---|---|---|
| 57 | 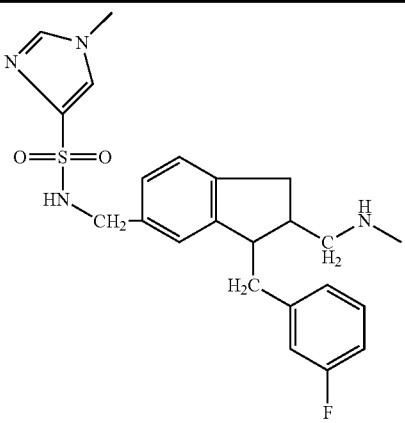 | N-[[3-[3-(fluorophenyl)methyl]-2-(methylaminomethyl)indan-5-yl]methyl]-1-methyl-imidazole-4-sulfonamide |
| 58 | 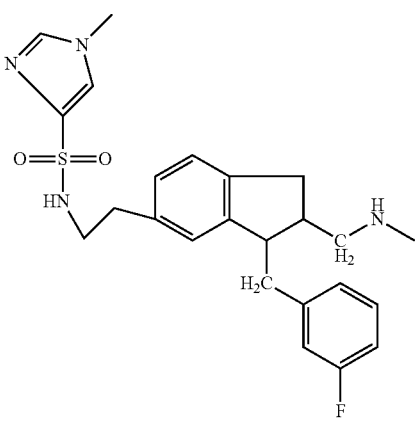 [SMILES: CNCC1Cc2ccc(CCNS(=O)(=O)c3cn(C)cn3)cc2C1Cc1cccc(F)c1] | N-[2-[3-[(3-fluorophenyl)methyl]-2-(methylaminomethyl)indan-5-yl]ethyl]-1-methyl-imidazole-4-sulfonamide |
| 59 | 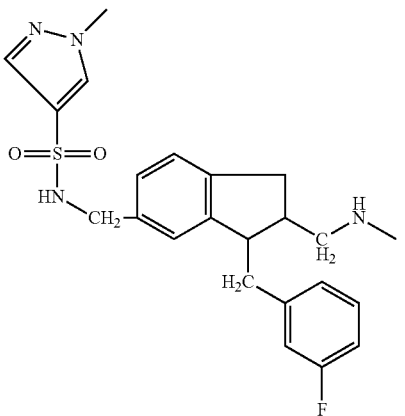 [SMILES: CNCC1Cc2ccc(CNS(=O)(=O)c3cnn(C)c3)cc2C1Cc1cccc(F)c1] | N-[[3-[(3-fluorophenyl)methyl]-2-(methylaminomethyl)indan-5-yl]methyl]-1-methyl-pyrazole-4-sulfonamide |

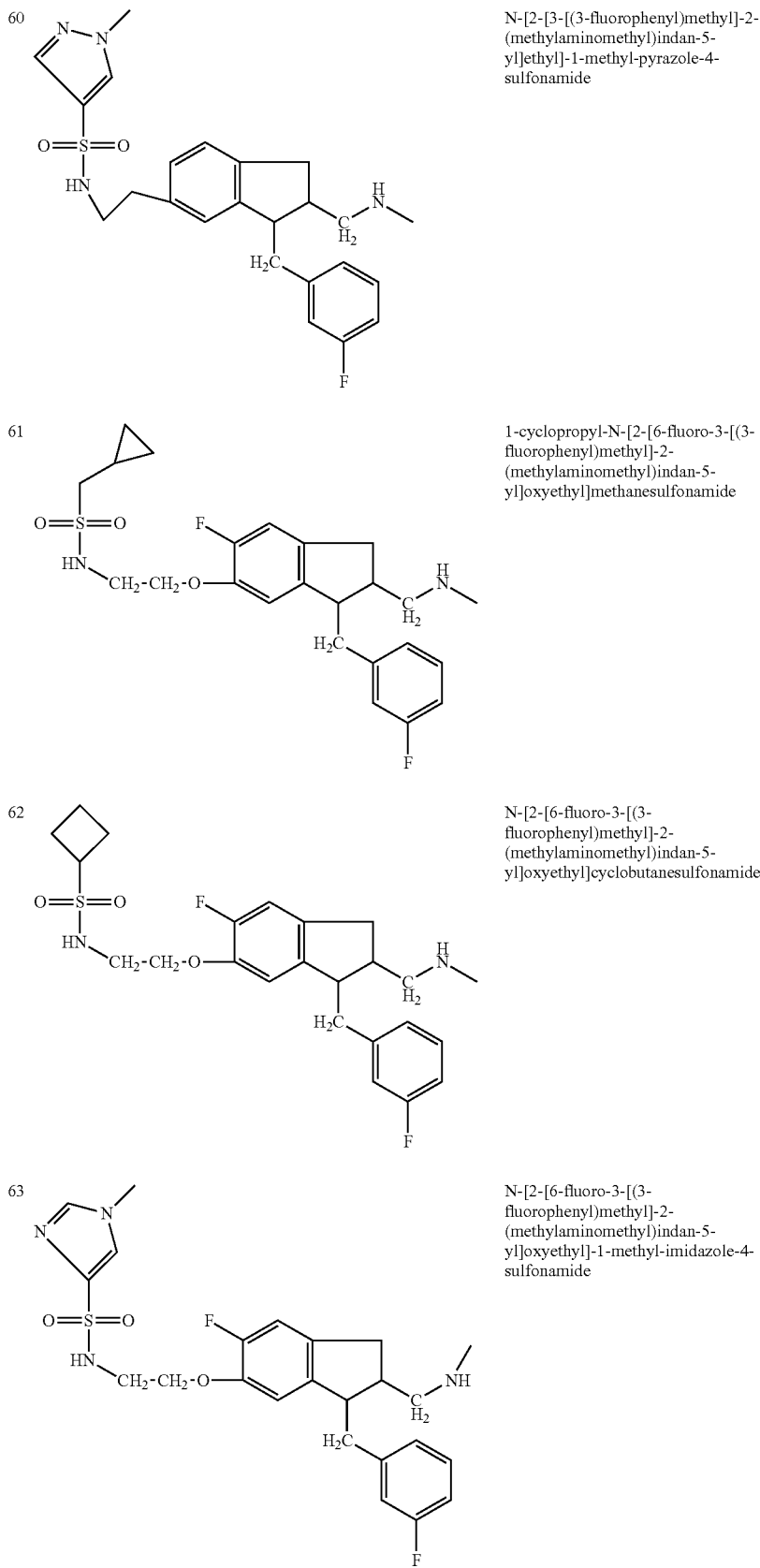

60    N-[2-[3-[(3-fluorophenyl)methyl]-2-(methylaminomethyl)indan-5-yl]ethyl]-1-methyl-pyrazole-4-sulfonamide 61    1-cyclopropyl-N-[2-[6-fluoro-3-[(3-fluorophenyl)methyl]-2-(methylaminomethyl)indan-5-yl]oxyethyl]methanesulfonamide 62    N-[2-[6-fluoro-3-[(3-fluorophenyl)methyl]-2-(methylaminomethyl)indan-5-yl]oxyethyl]cyclobutanesulfonamide 63    N-[2-[6-fluoro-3-[(3-fluorophenyl)methyl]-2-(methylaminomethyl)indan-5-yl]oxyethyl]-1-methyl-imidazole-4-sulfonamide

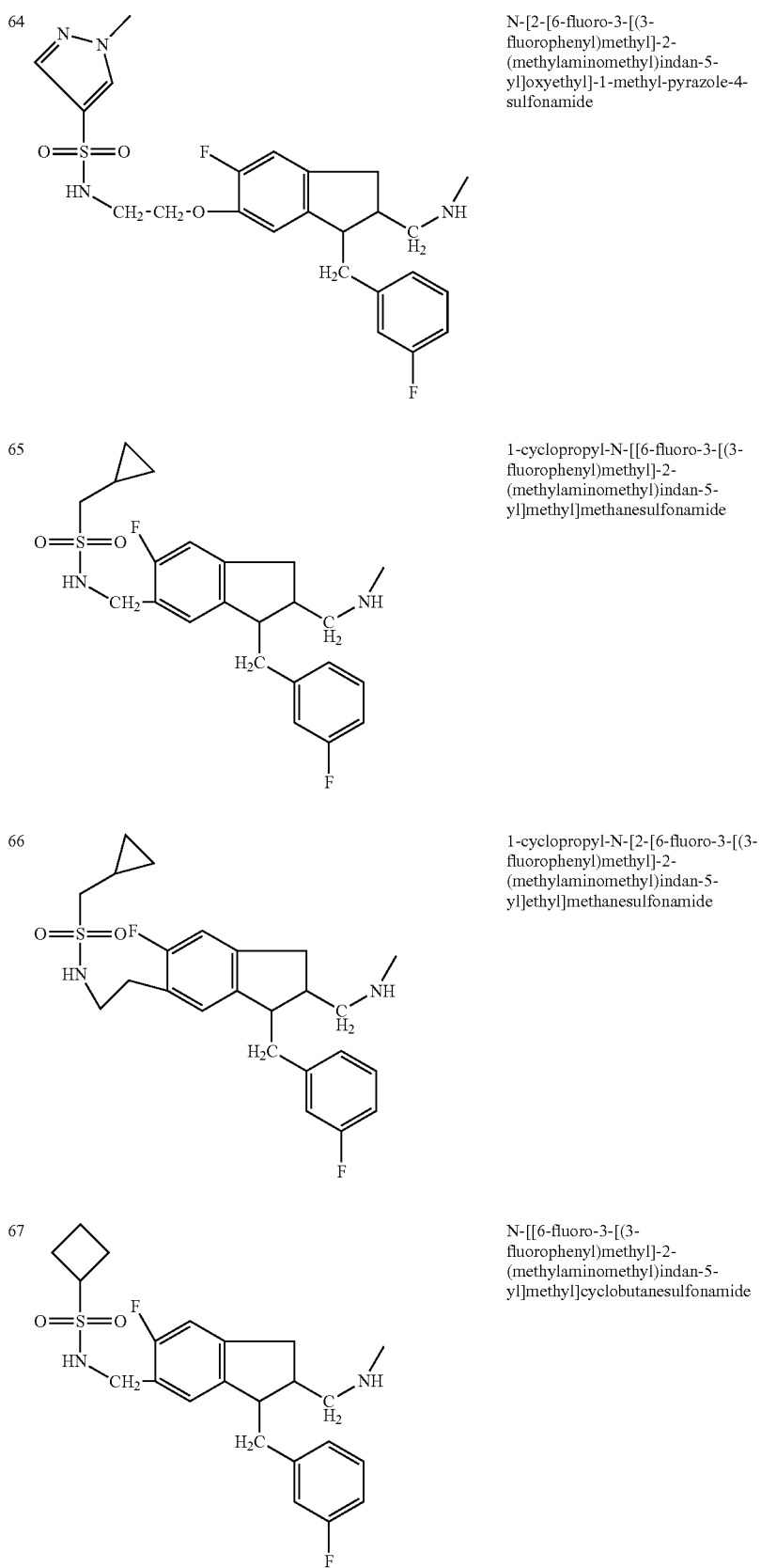

| 64 | N-[2-[6-fluoro-3-[(3-fluorophenyl)methyl]-2-(methylaminomethyl)indan-5-yl]oxyethyl]-1-methyl-pyrazole-4-sulfonamide |
| 65 | 1-cyclopropyl-N-[[6-fluoro-3-[(3-fluorophenyl)methyl]-2-(methylaminomethyl)indan-5-yl]methyl]methanesulfonamide |
| 66 | 1-cyclopropyl-N-[2-[6-fluoro-3-[(3-fluorophenyl)methyl]-2-(methylaminomethyl)indan-5-yl]ethyl]methanesulfonamide |
| 67 | N-[[6-fluoro-3-[(3-fluorophenyl)methyl]-2-(methylaminomethyl)indan-5-yl]methyl]cyclobutanesulfonamide |

| | | |
|---|---|---|
| 68 | | N-[2-[6-fluoro-3-[(3-fluorophenyl)methyl]-2-(methylaminomethyl)indan-5-yl]ethyl]cyclobutanesulfonamide |
| 69 | | N-[[6-fluoro-3-[(3-fluorophenyl)methyl]-2-(methylaminomethyl)indan-5-yl]methyl]-1-methyl-imidazole-4-sulfonamide |
| 70 | | N-[2-[6-fluoro-3-[(3-fluorophenyl)methyl]-2-(methylaminomethyl)indan-5-yl]ethyl]-1-methyl-imidazole-4-sulfonamide |
| 71 | | N-[[6-fluoro-3-[(3-fluorophenyl)methyl]-2-(methylaminomethyl)indan-5-yl]methyl]-1-methyl-pyrazole-4-sulfonamide |

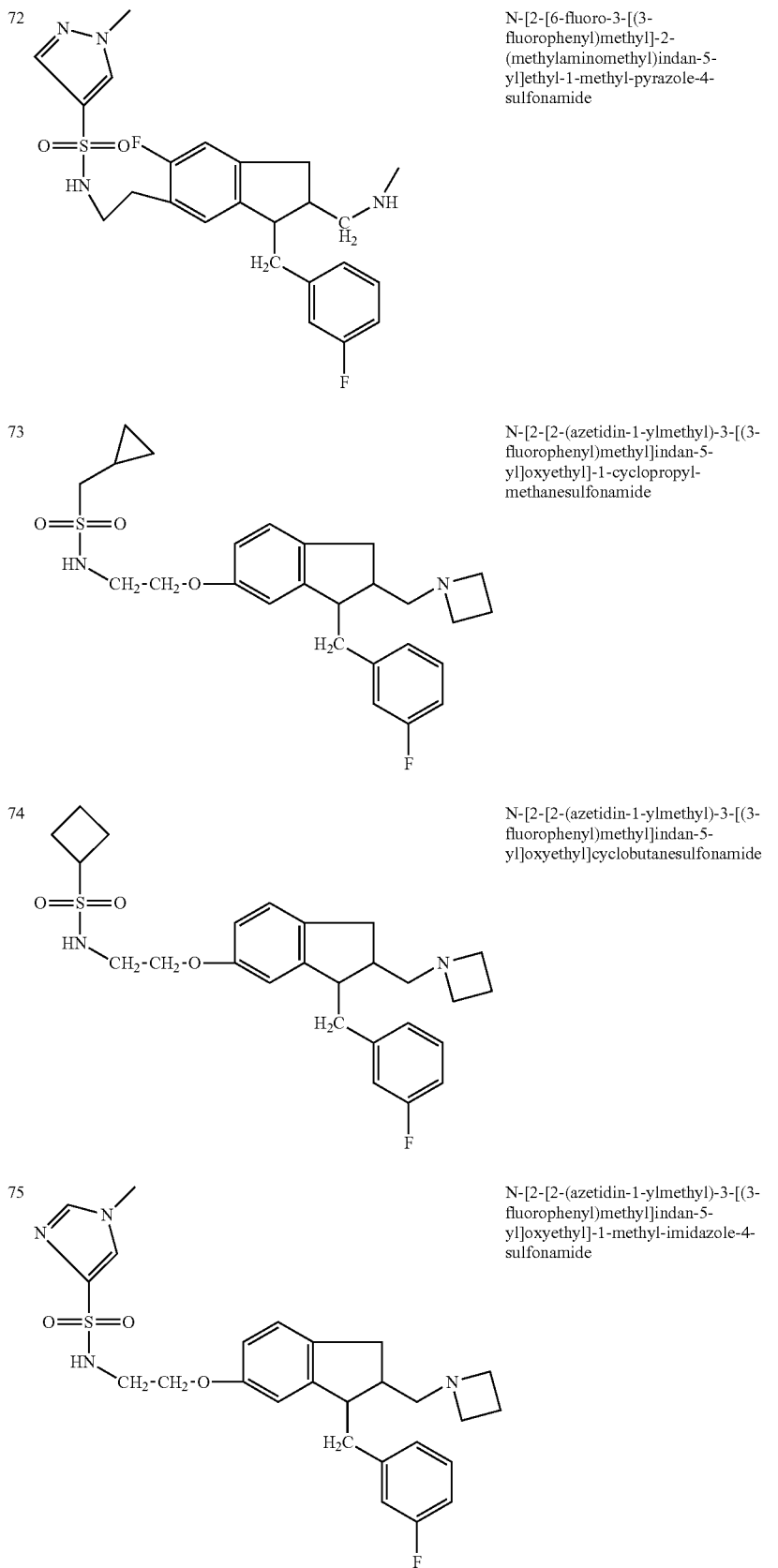

| | |
|---|---|
| 72 | N-[2-[6-fluoro-3-[(3-fluorophenyl)methyl]-2-(methylaminomethyl)indan-5-yl]ethyl-1-methyl-pyrazole-4-sulfonamide |
| 73 | N-[2-[2-(azetidin-1-ylmethyl)-3-[(3-fluorophenyl)methyl]indan-5-yl]oxyethyl]-1-cyclopropyl-methanesulfonamide |
| 74 | N-[2-[2-(azetidin-1-ylmethyl)-3-[(3-fluorophenyl)methyl]indan-5-yl]oxyethyl]cyclobutanesulfonamide |
| 75 | N-[2-[2-(azetidin-1-ylmethyl)-3-[(3-fluorophenyl)methyl]indan-5-yl]oxyethyl]-1-methyl-imidazole-4-sulfonamide |

-continued

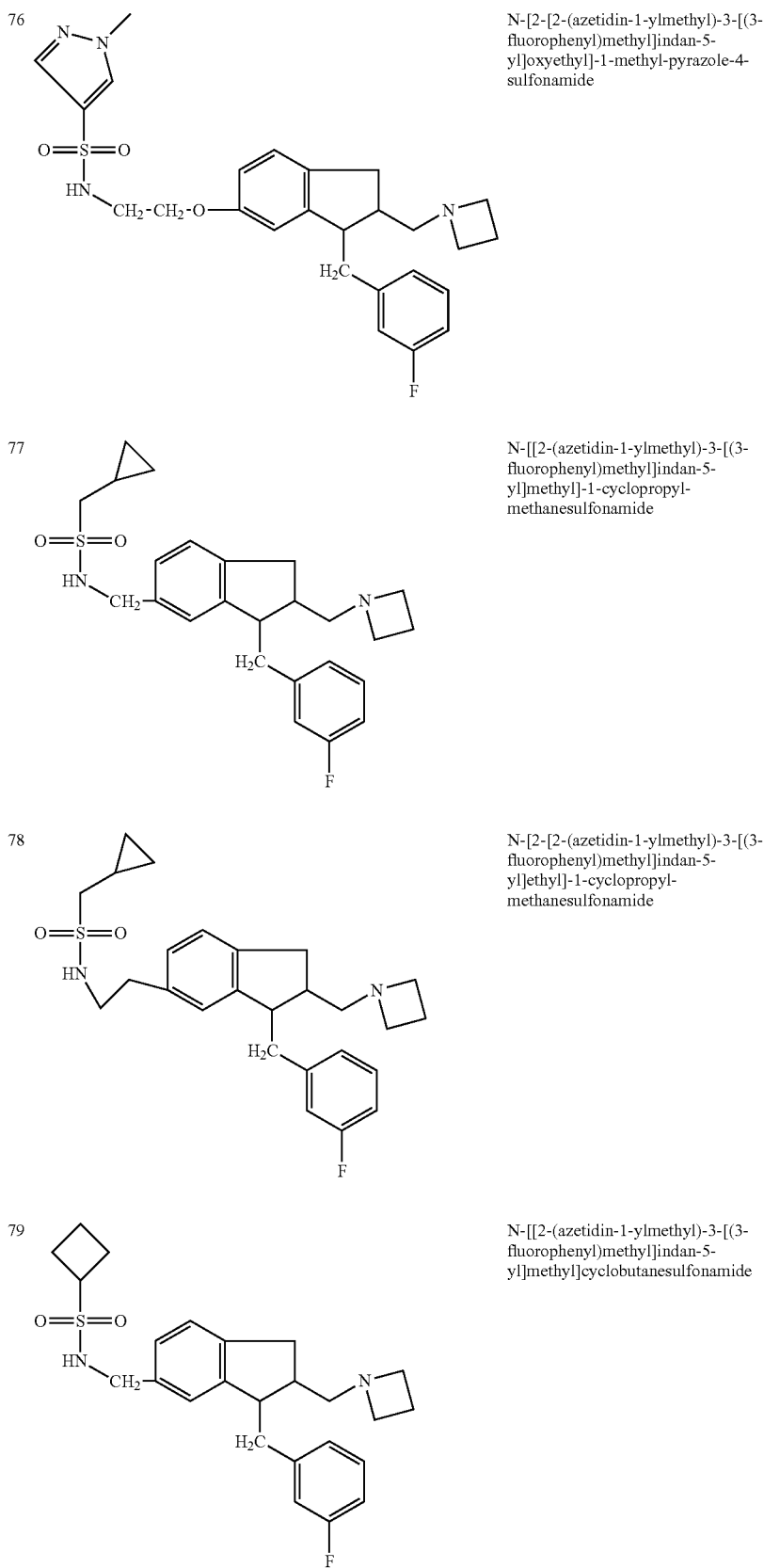

| 76 | N-[2-[2-(azetidin-1-ylmethyl)-3-[(3-fluorophenyl)methyl]indan-5-yl]oxyethyl]-1-methyl-pyrazole-4-sulfonamide |
| 77 | N-[[2-(azetidin-1-ylmethyl)-3-[(3-fluorophenyl)methyl]indan-5-yl]methyl]-1-cyclopropyl-methanesulfonamide |
| 78 | N-[2-[2-(azetidin-1-ylmethyl)-3-[(3-fluorophenyl)methyl]indan-5-yl]ethyl]-1-cyclopropyl-methanesulfonamide |
| 79 | N-[[2-(azetidin-1-ylmethyl)-3-[(3-fluorophenyl)methyl]indan-5-yl]methyl]cyclobutanesulfonamide |

| | | |
|---|---|---|
| 80 | 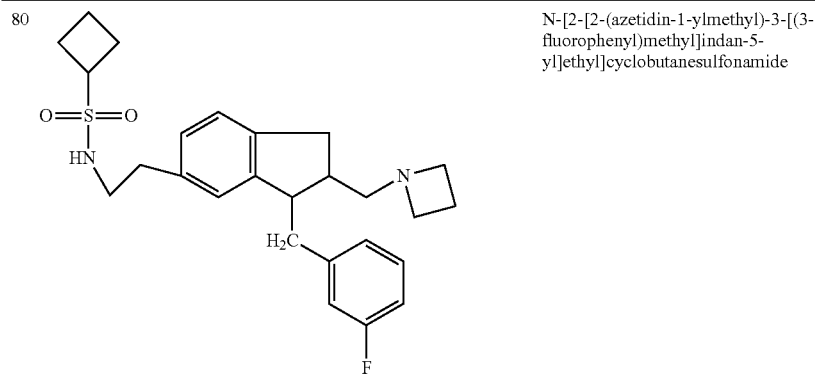 | N-[2-[2-(azetidin-1-ylmethyl)-3-[(3-fluorophenyl)methyl]indan-5-yl]ethyl]cyclobutanesulfonamide |
| 81 | 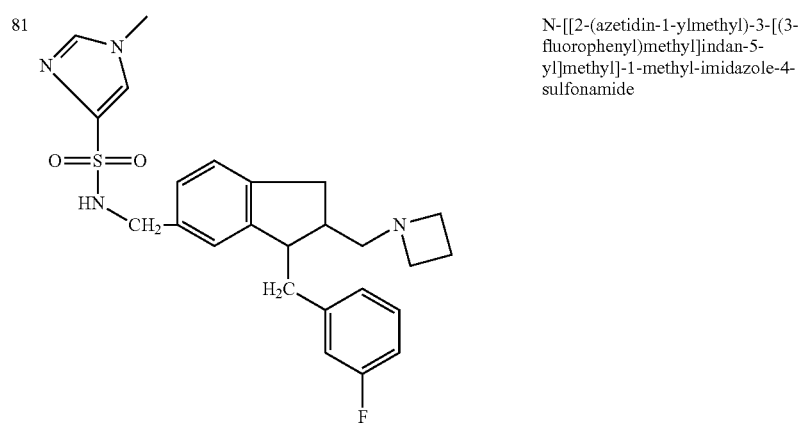 | N-[[2-(azetidin-1-ylmethyl)-3-[(3-fluorophenyl)methyl]indan-5-yl]methyl]-1-methyl-imidazole-4-sulfonamide |
| 82 | 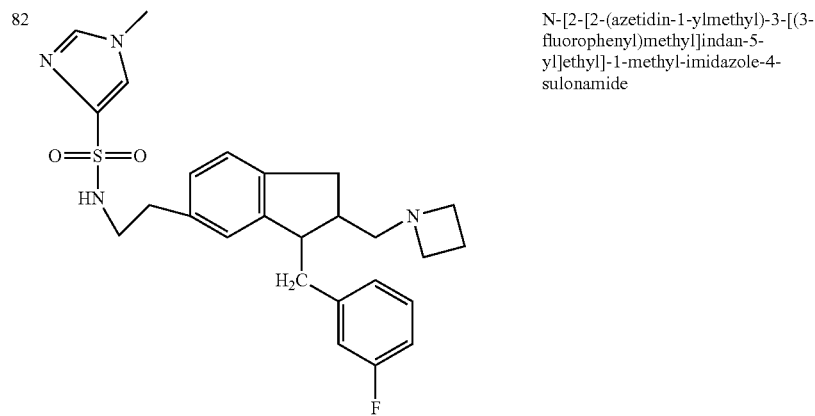 | N-[2-[2-(azetidin-1-ylmethyl)-3-[(3-fluorophenyl)methyl]indan-5-yl]ethyl]-1-methyl-imidazole-4-sulonamide |
| 83 | 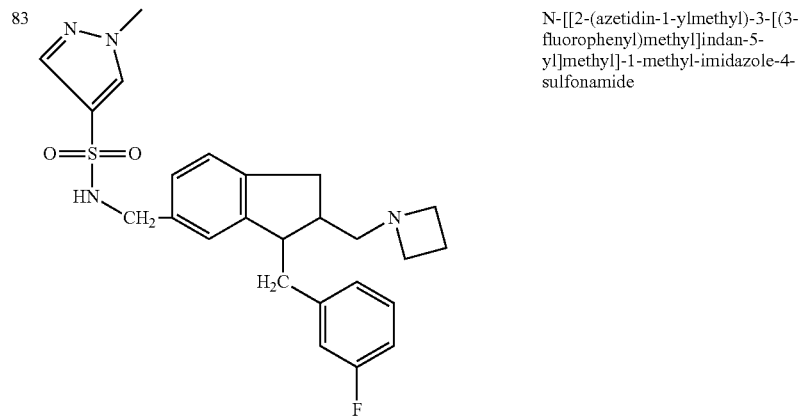 | N-[[2-(azetidin-1-ylmethyl)-3-[(3-fluorophenyl)methyl]indan-5-yl]methyl]-1-methyl-imidazole-4-sulfonamide |

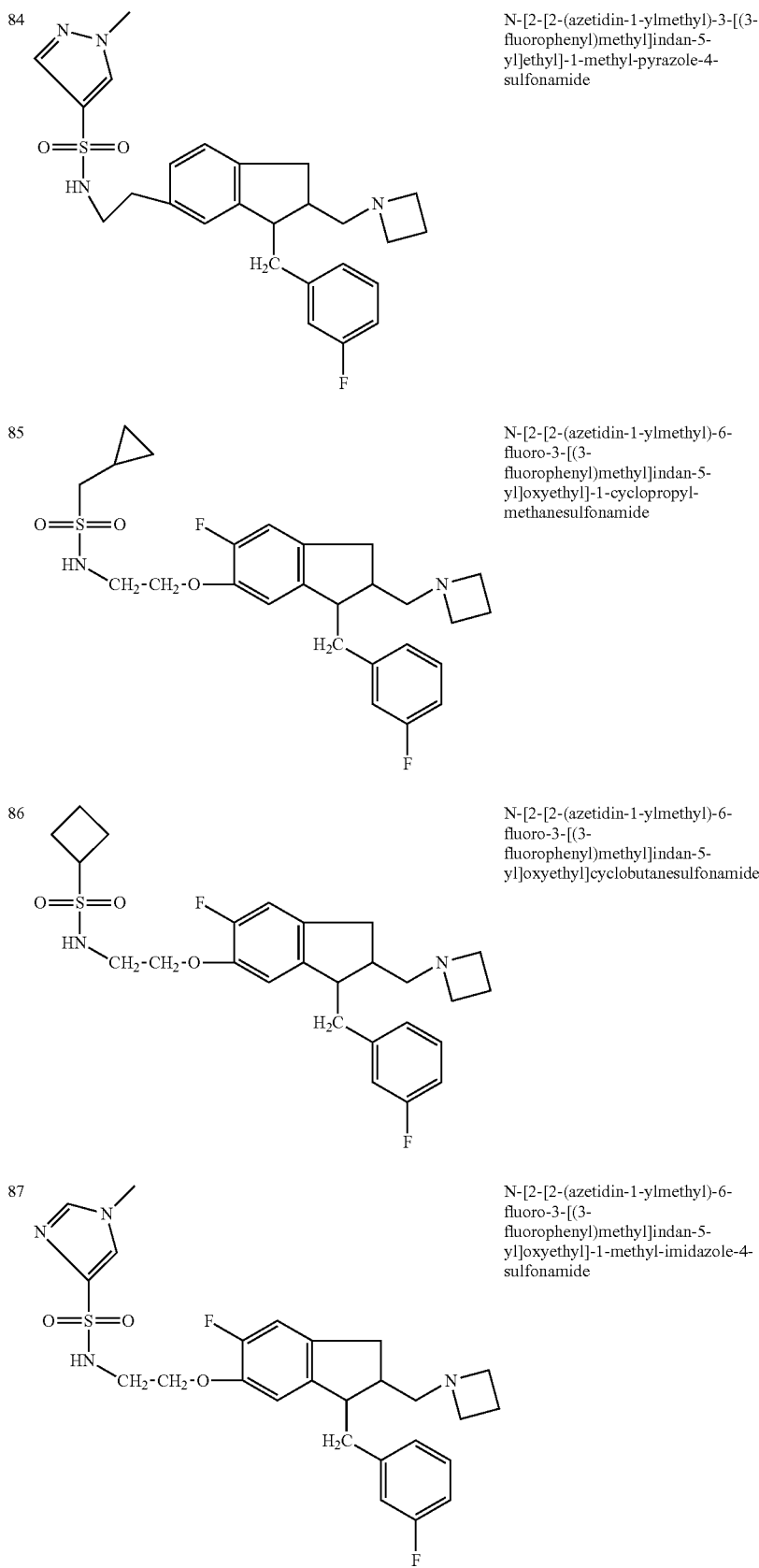

| | | |
|---|---|---|
| 84 | | N-[2-[2-(azetidin-1-ylmethyl)-3-[(3-fluorophenyl)methyl]indan-5-yl]ethyl]-1-methyl-pyrazole-4-sulfonamide |
| 85 | | N-[2-[2-(azetidin-1-ylmethyl)-6-fluoro-3-[(3-fluorophenyl)methyl]indan-5-yl]oxyethyl]-1-cyclopropyl-methanesulfonamide |
| 86 | | N-[2-[2-(azetidin-1-ylmethyl)-6-fluoro-3-[(3-fluorophenyl)methyl]indan-5-yl]oxyethyl]cyclobutanesulfonamide |
| 87 | | N-[2-[2-(azetidin-1-ylmethyl)-6-fluoro-3-[(3-fluorophenyl)methyl]indan-5-yl]oxyethyl]-1-methyl-imidazole-4-sulfonamide |

| | | |
|---|---|---|
| 88 |  | N-[2-[2-(azetidin-1-ylmethyl)-6-fluoro-3-[(3-fluorophenyl)methyl]indan-5-yl]oxyethyl]-1-methyl-pyrazole-4-sulfonamide |
| | 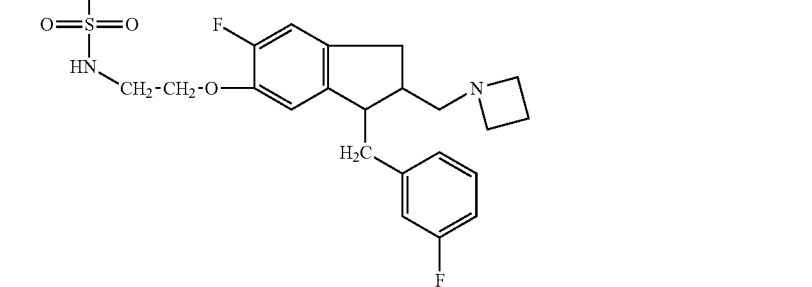 | |
| 89 | 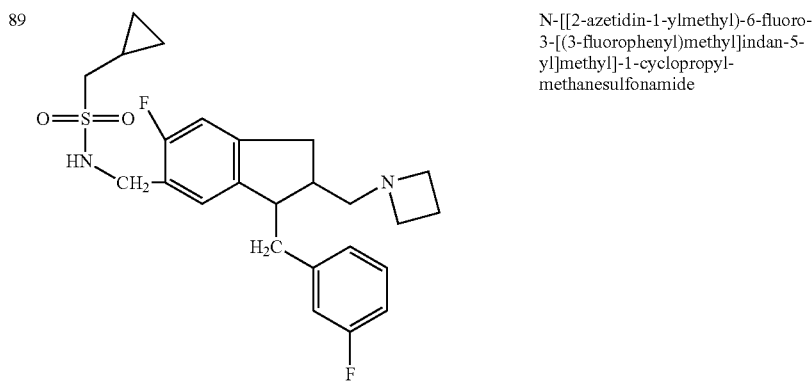 | N-[[2-azetidin-1-ylmethyl)-6-fluoro-3-[(3-fluorophenyl)methyl]indan-5-yl]methyl]-1-cyclopropyl-methanesulfonamide |
| 90 | 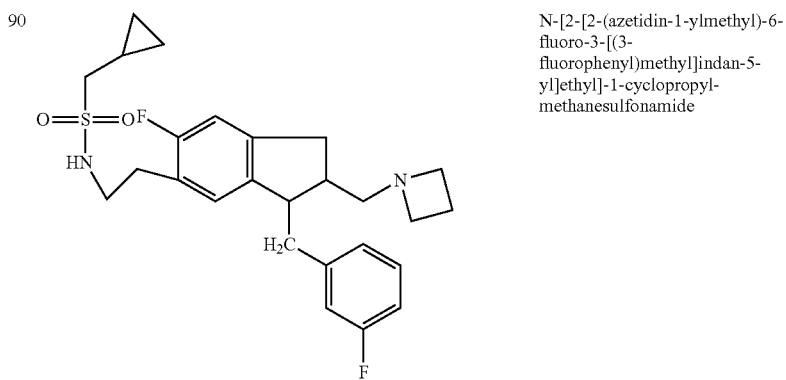 | N-[2-[2-(azetidin-1-ylmethyl)-6-fluoro-3-[(3-fluorophenyl)methyl]indan-5-yl]ethyl]-1-cyclopropyl-methanesulfonamide |
| 91 | 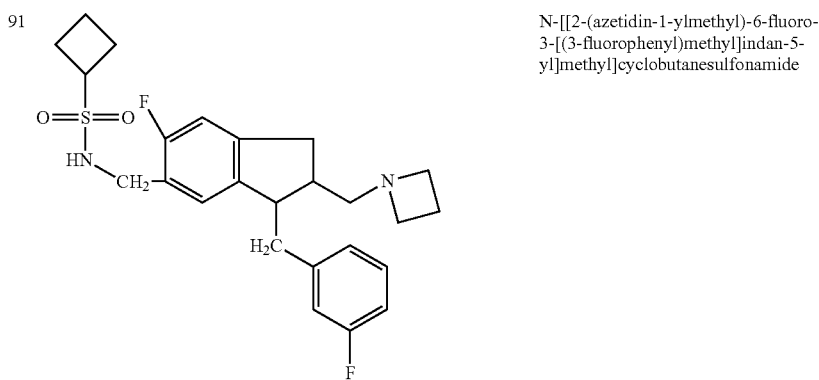 | N-[[2-(azetidin-1-ylmethyl)-6-fluoro-3-[(3-fluorophenyl)methyl]indan-5-yl]methyl]cyclobutanesulfonamide |

-continued

| | | |
|---|---|---|
| 92 | | N-[2-[2-(azetidin-1-ylmethyl)-6-fluoro-3-[(3-fluorophenyl)methyl]indan-5-yl]ethyl]cyclobutanesulfonamide |
| 93 | | N-[[2-(azetidin-1-ylmethyl)-6-fluoro-3-[(3-fluorophenyl)methyl]indan-5-yl]methyl]-1-methyl-imidazole-4-sulfonamide |
| 94 | | N-[2-[2-(azetidin-1-ylmethyl)-6-fluoro-3-[(3-fluorophenyl)methyl]indan-5-yl]ethyl]-1-methyl-imidazole-4-sulfonamide |
| 95 | | N-[[2-(azetidin-1-ylmethyl)-6-fluoro-3-[(3-fluorophenyl)methyl]indan-5-yl]methyl]-1-methyl-pyrazole-4-sulfonamide |

| | | |
|---|---|---|
| 96 | 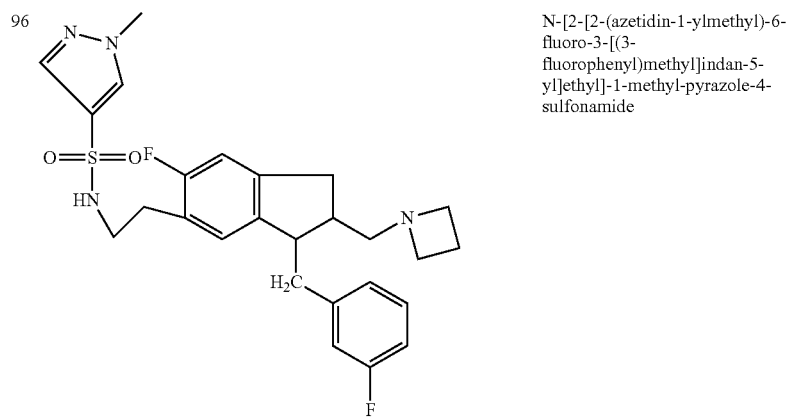 | N-[2-[2-(azetidin-1-ylmethyl)-6-fluoro-3-[(3-fluorophenyl)methyl]indan-5-yl]ethyl]-1-methyl-pyrazole-4-sulfonamide |
| 97 | 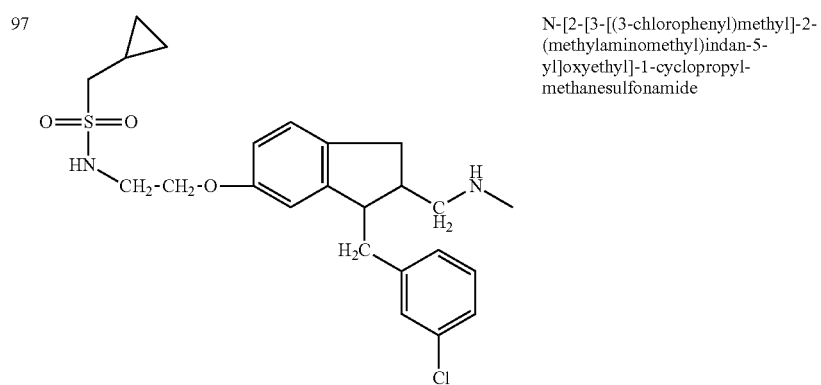 | N-[2-[3-[(3-chlorophenyl)methyl]-2-(methylaminomethyl)indan-5-yl]oxyethyl]-1-cyclopropyl-methanesulfonamide |
| 98 | 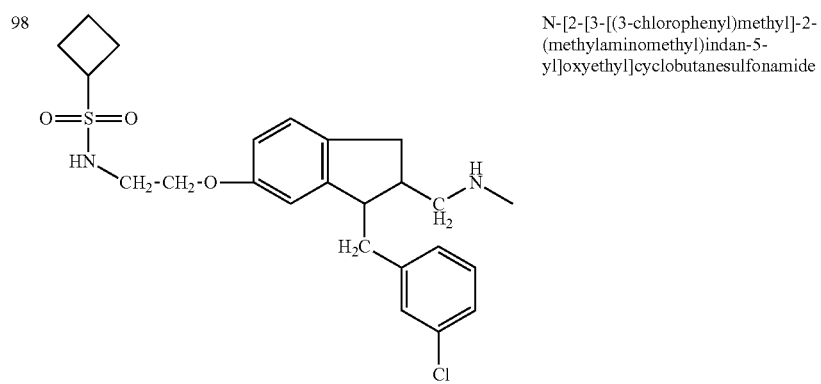 | N-[2-[3-[(3-chlorophenyl)methyl]-2-(methylaminomethyl)indan-5-yl]oxyethyl]cyclobutanesulfonamide |
| 99 | 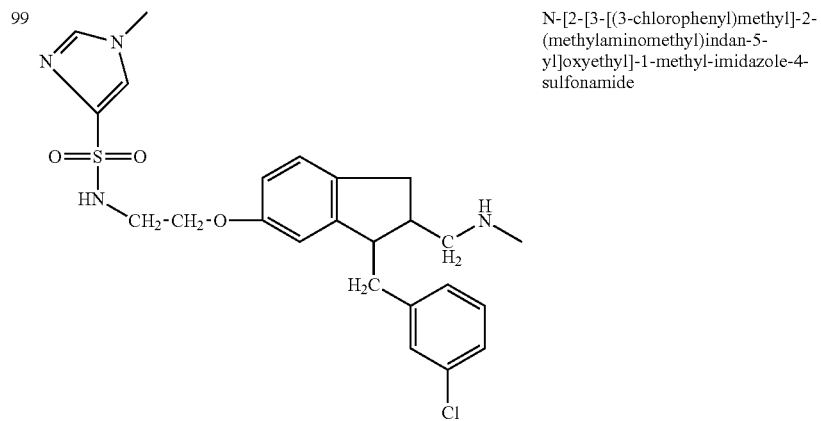 | N-[2-[3-[(3-chlorophenyl)methyl]-2-(methylaminomethyl)indan-5-yl]oxyethyl]-1-methyl-imidazole-4-sulfonamide |

-continued

| | | |
|---|---|---|
| 100 | 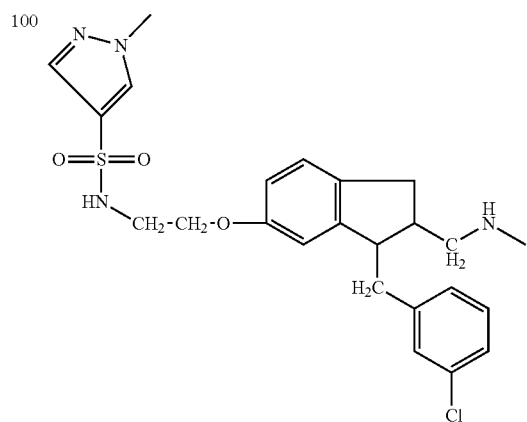 | N-[2-[3-[(3-chlorophenyl)methyl]-2-(methylaminomethyl)indan-5-yl]oxyethyl]-1-methyl-pyrazole-4-sulfonamide |
| 101 | 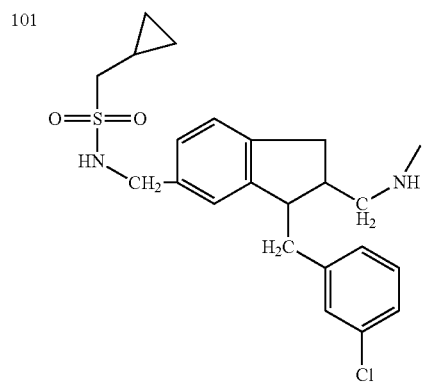 | N-[2-[3-[(3-chlorophenyl)methyl]-2-(methylaminomethyl)indan-5-yl]oxyethyl]-1-methyl-pyrazole-4-sulfonamide |
| 102 | 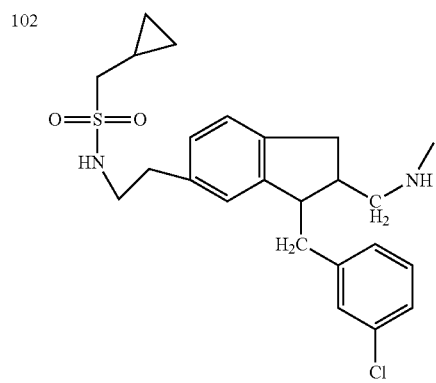 | N-[2-[3-[(3-chlorophenyl)methyl]-2-(methylaminomethyl)indan-5-yl]ethyl]-1-cyclopropyl-methanesulfonamide |
| 103 | 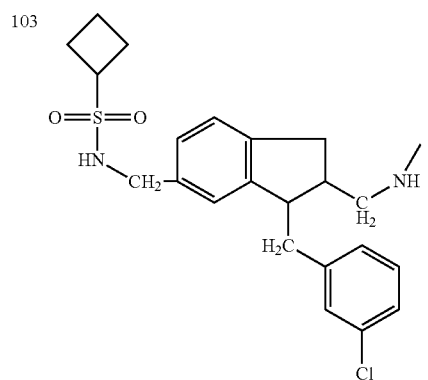 | N-[[3-[(3-chlorophenyl)methyl]-2-(methylaminomethyl)indan-5-yl]methyl]cyclobutanesulfonamide |

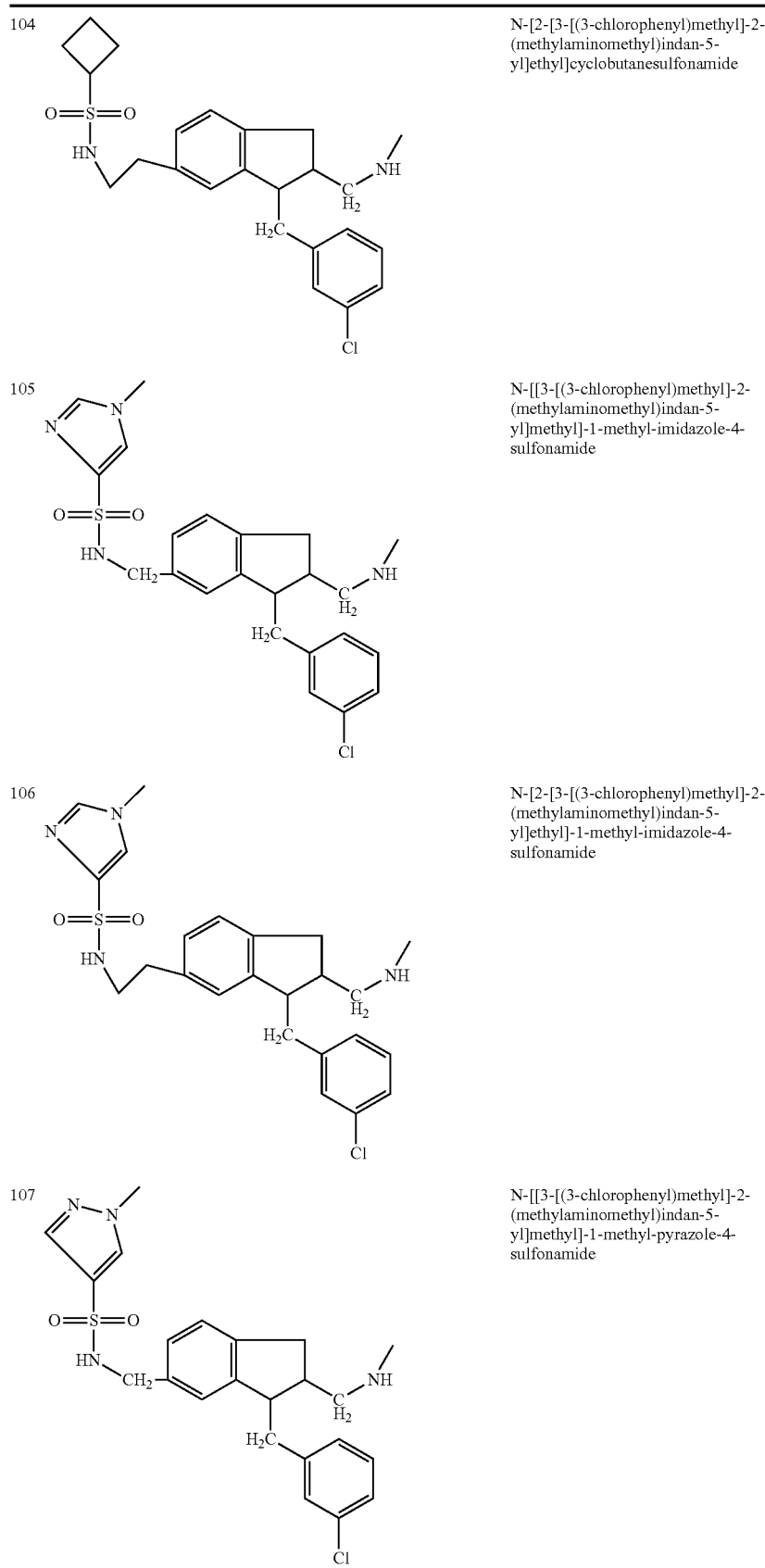
| | |
|---|---|
| 104 | N-[2-[3-[(3-chlorophenyl)methyl]-2-(methylaminomethyl)indan-5-yl]ethyl]cyclobutanesulfonamide |
| 105 | N-[[3-[(3-chlorophenyl)methyl]-2-(methylaminomethyl)indan-5-yl]methyl]-1-methyl-imidazole-4-sulfonamide |
| 106 | N-[2-[3-[(3-chlorophenyl)methyl]-2-(methylaminomethyl)indan-5-yl]ethyl]-1-methyl-imidazole-4-sulfonamide |
| 107 | N-[[3-[(3-chlorophenyl)methyl]-2-(methylaminomethyl)indan-5-yl]methyl]-1-methyl-pyrazole-4-sulfonamide |

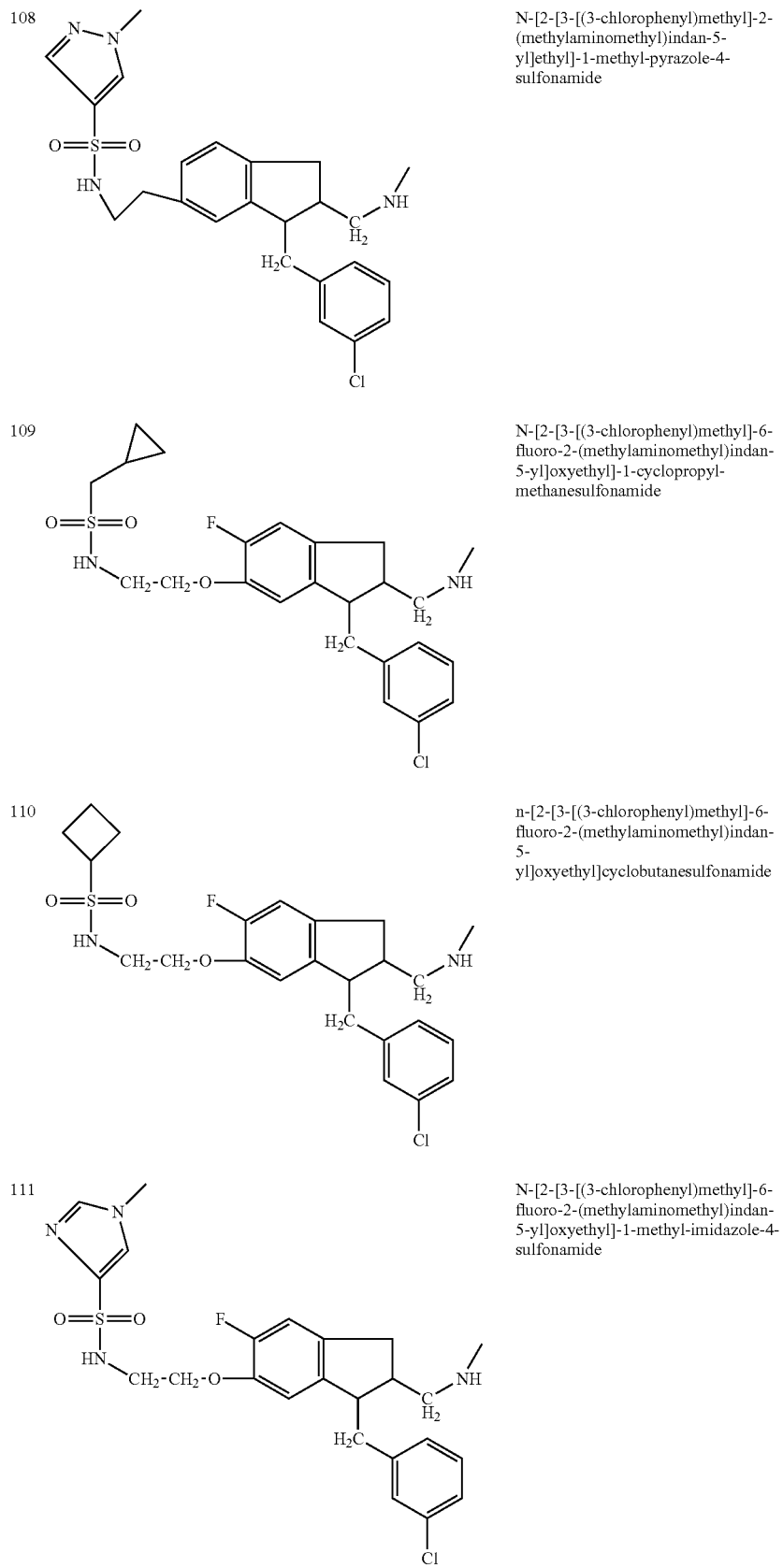

| 108 | N-[2-[3-[(3-chlorophenyl)methyl]-2-(methylaminomethyl)indan-5-yl]ethyl]-1-methyl-pyrazole-4-sulfonamide |
| 109 | N-[2-[3-[(3-chlorophenyl)methyl]-6-fluoro-2-(methylaminomethyl)indan-5-yl]oxyethyl]-1-cyclopropyl-methanesulfonamide |
| 110 | n-[2-[3-[(3-chlorophenyl)methyl]-6-fluoro-2-(methylaminomethyl)indan-5-yl]oxyethyl]cyclobutanesulfonamide |
| 111 | N-[2-[3-[(3-chlorophenyl)methyl]-6-fluoro-2-(methylaminomethyl)indan-5-yl]oxyethyl]-1-methyl-imidazole-4-sulfonamide |

| | | |
|---|---|---|
| 112 | 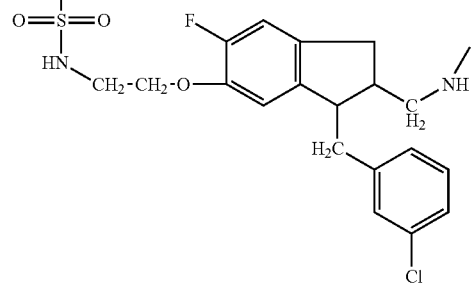 | N-[2-[3-[(3-chlorophenyl)methyl]-6-fluoro-2-(methylaminomethyl)indan-5-yl]oxyethyl]-1-methyl-pyrazole-4-sulfonamide |
| 113 | 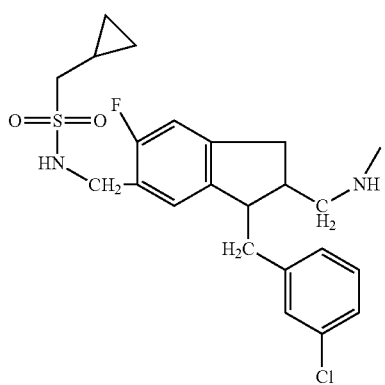 [SMILES: CNCC1Cc2cc(F)c(CNS(=O)(=O)CC3CC3)cc2C1Cc1cccc(Cl)c1] | N-[[3-[(3-chlorophenyl)methyl]-6-fluoro-2-(methylaminomethyl)indan-5-yl]methyl]-1-cyclopropyl-methanesulfonamide |
| 114 | 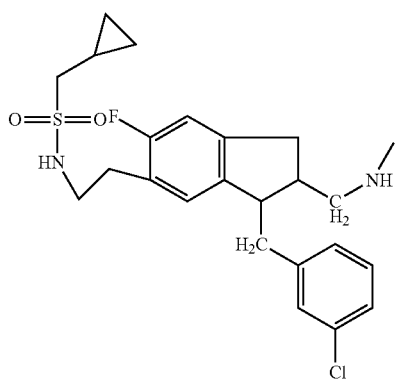 [SMILES: CNCC1Cc2cc(F)c(CCNS(=O)(=O)CC3CC3)cc2C1Cc1cccc(Cl)c1] | N-[2-[3-[(3-chlorophenyl)methyl]-6-fluoro-2-(methylaminomethyl)indan-5-yl]ethyl]-1-cyclopropyl-methanesulfonamide |
| 115 | | N-[[3-[(3-chlorophenyl)methyl]-6-fluoro-2-(methylaminomethyl)indan-5-yl]methyl]cyclobutanesulfonamide |

-continued

| | | |
|---|---|---|
| 116 | 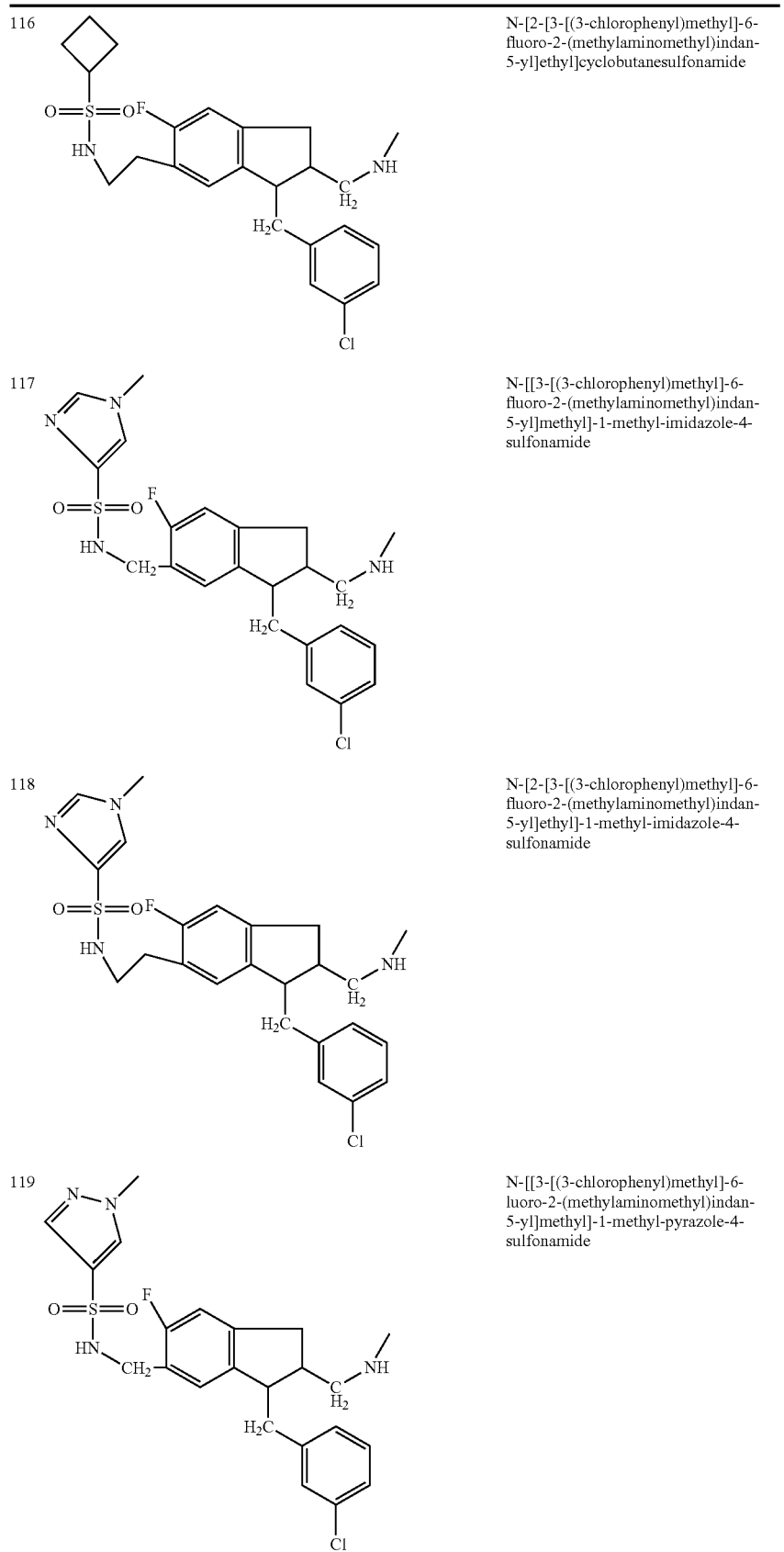 | N-[2-[3-[(3-chlorophenyl)methyl]-6-fluoro-2-(methylaminomethyl)indan-5-yl]ethyl]cyclobutanesulfonamide |
| 117 | | N-[[3-[(3-chlorophenyl)methyl]-6-fluoro-2-(methylaminomethyl)indan-5-yl]methyl]-1-methyl-imidazole-4-sulfonamide |
| 118 | | N-[2-[3-[(3-chlorophenyl)methyl]-6-fluoro-2-(methylaminomethyl)indan-5-yl]ethyl]-1-methyl-imidazole-4-sulfonamide |
| 119 | | N-[[3-[(3-chlorophenyl)methyl]-6-luoro-2-(methylaminomethyl)indan-5-yl]methyl]-1-methyl-pyrazole-4-sulfonamide |

| | | |
|---|---|---|
| 120 | 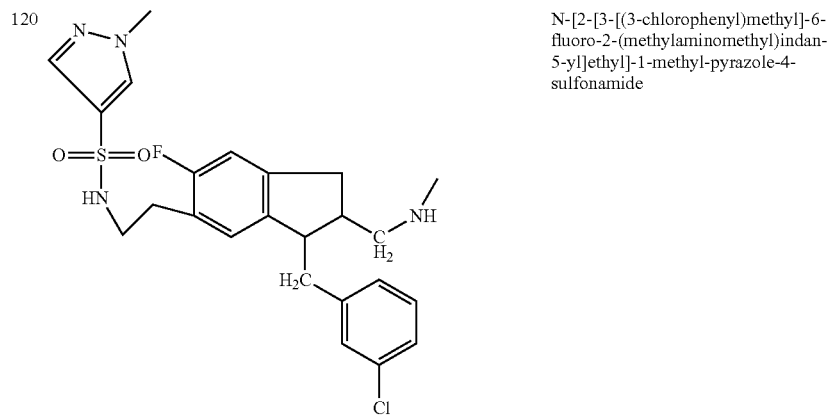 | N-[2-[3-[(3-chlorophenyl)methyl]-6-fluoro-2-(methylaminomethyl)indan-5-yl]ethyl]-1-methyl-pyrazole-4-sulfonamide |
| 121 | 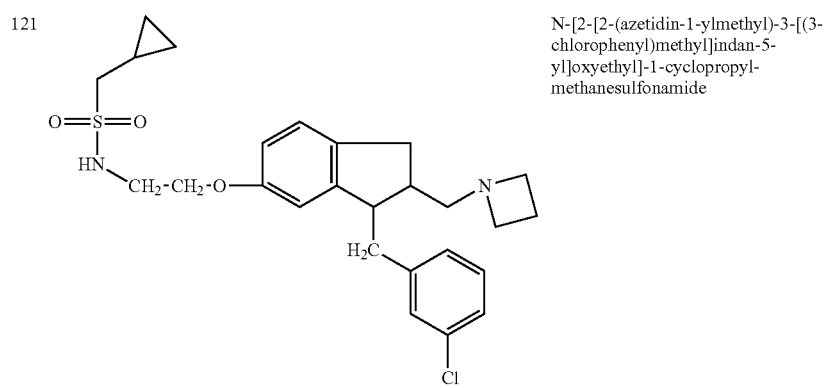 | N-[2-[2-(azetidin-1-ylmethyl)-3-[(3-chlorophenyl)methyl]indan-5-yl]oxyethyl]-1-cyclopropyl-methanesulfonamide |
| 122 | 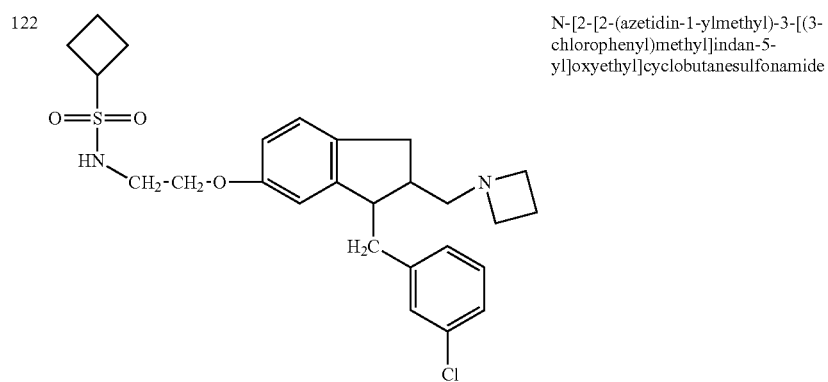 | N-[2-[2-(azetidin-1-ylmethyl)-3-[(3-chlorophenyl)methyl]indan-5-yl]oxyethyl]cyclobutanesulfonamide |
| 123 | 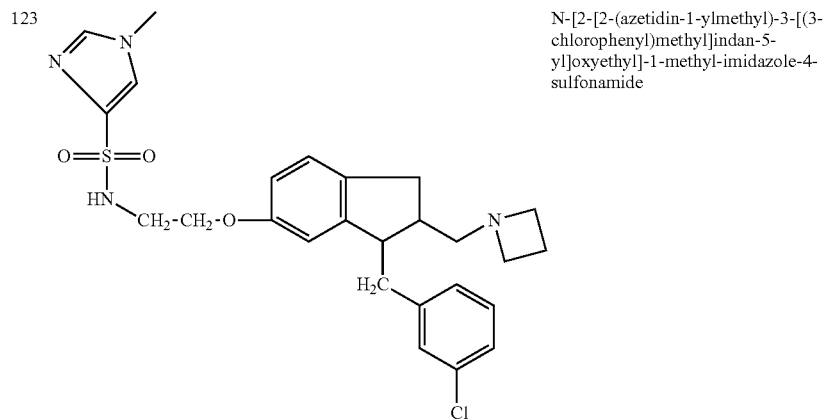 | N-[2-[2-(azetidin-1-ylmethyl)-3-[(3-chlorophenyl)methyl]indan-5-yl]oxyethyl]-1-methyl-imidazole-4-sulfonamide |

| | | |
|---|---|---|
| 124 | 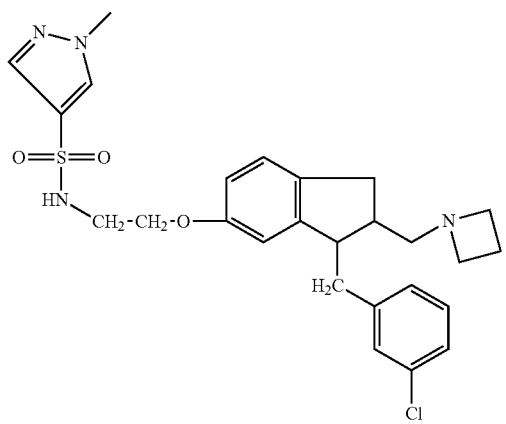 [SMILES: Cn1cc(S(=O)(=O)NCCOc2ccc3c(c2)C(Cc2cccc(Cl)c2)C(CN2CCC2)C3)cn1] | N-[2-[2-(azetidin-1-ylmethyl)-3-[(3-chlorophenyl)methyl]indan-5-yl]oxyethyl]-1-methyl-pyrazole-4-sulfonamide |
| 125 | 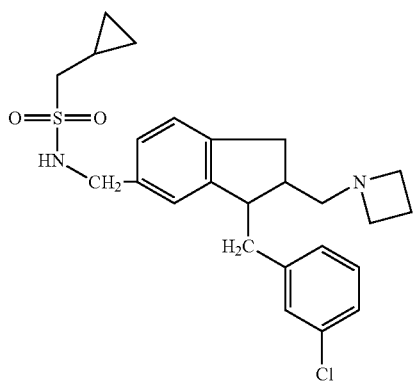 | N-[[2-(azetidin-1-ylmethyl)-3-[(3-chlorophenyl)methyl]indan-5-yl]methyl]-1-cyclopropyl-methanesulfonamide |
| 126 | 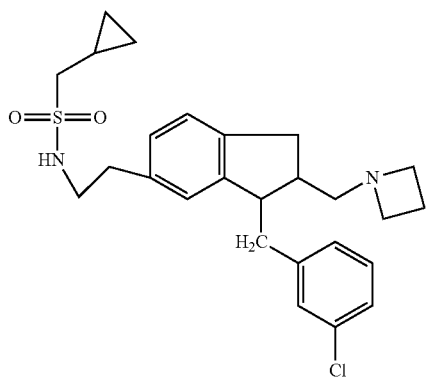 [SMILES: O=S(=O)(CC1CC1)NCCc1ccc2c(c1)C(Cc1cccc(Cl)c1)C(CN1CCC1)C2] | N-[2-[2-(azetidin-1-ylmethyl)-3-[(3-chlorophenyl)methyl]indan-5-yl]ethyl]-1-cyclopropyl-methanesulfonamide |
| 127 | 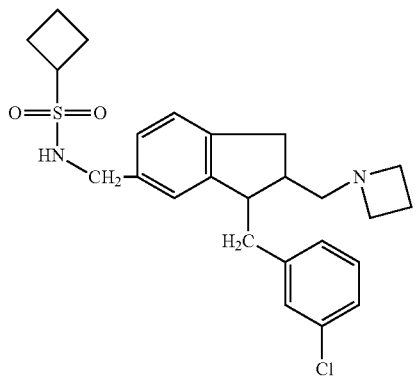 [SMILES: O=S(=O)(NCc1ccc2c(c1)C(Cc1cccc(Cl)c1)C(CN1CCC1)C2)C1CCC1] | N-[[2-(azetidin-1-ylmethyl)-3-[(3-chlorophenyl)methyl]indan-5-yl]methyl]cyclobutanesulfonamide |

| | | |
|---|---|---|
| 128 | 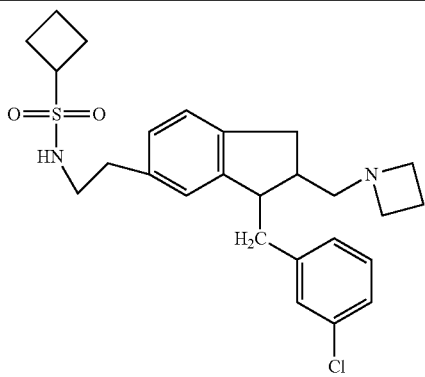 | N-[2-[2-(azetidin-1-ylmethyl)-3-[(3-chlorophenyl)methyl]indan-5-yl]ethyl]cyclobutanesulfonamide |
| 129 | 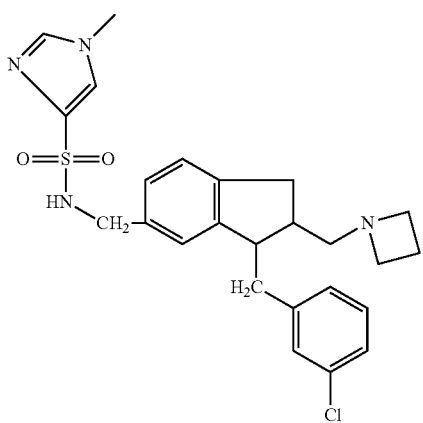 [SMILES: Cn1cnc(S(=O)(=O)NCc2ccc3c(c2)C(Cc2cccc(Cl)c2)C(CN2CCC2)C3)c1] | N-[[2-(azetidin-1-ylmethyl)-3-[(3-chlorophenyl)methyl]indan-5-yl]methyl]-1-methyl-imidazole-4-sulfonamide |
| 130 | 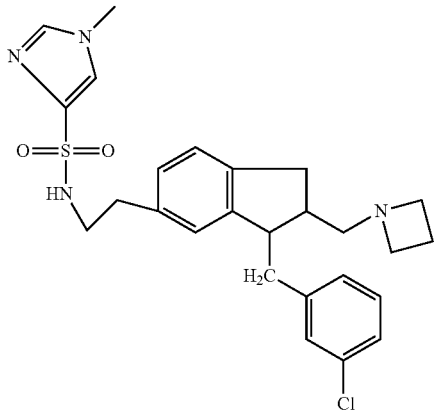 [SMILES: Cn1cnc(S(=O)(=O)NCCc2ccc3c(c2)C(Cc2cccc(Cl)c2)C(CN2CCC2)C3)c1] | N-[2-[2-(azetidin-1-ylmethyl)-3-[(3-chlorophenyl)methyl]indan-5-yl]ethyl]-1-methyl-imidazole-5-sulfonamide |
| 131 | 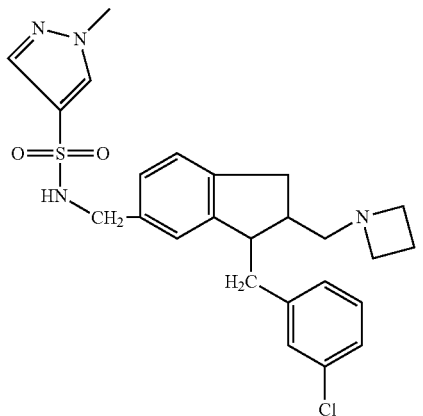 [SMILES: Cn1cc(S(=O)(=O)NCc2ccc3c(c2)C(Cc2cccc(Cl)c2)C(CN2CCC2)C3)cn1] | N-[[2-(azetidin-1-ylmethyl)-3-[(3-chlorophenyl)methyl]indan-5-yl]methyl]-1-methyl-pyrazole-4-sulfonamide |

-continued

| 132 | 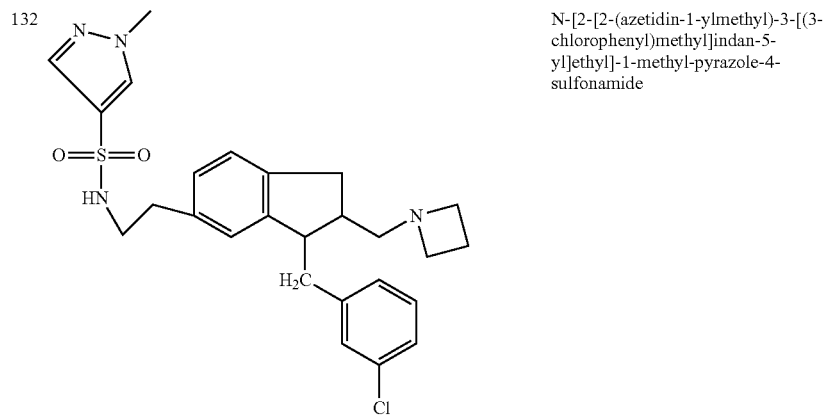 | N-[2-[2-(azetidin-1-ylmethyl)-3-[(3-chlorophenyl)methyl]indan-5-yl]ethyl]-1-methyl-pyrazole-4-sulfonamide |
| 133 | 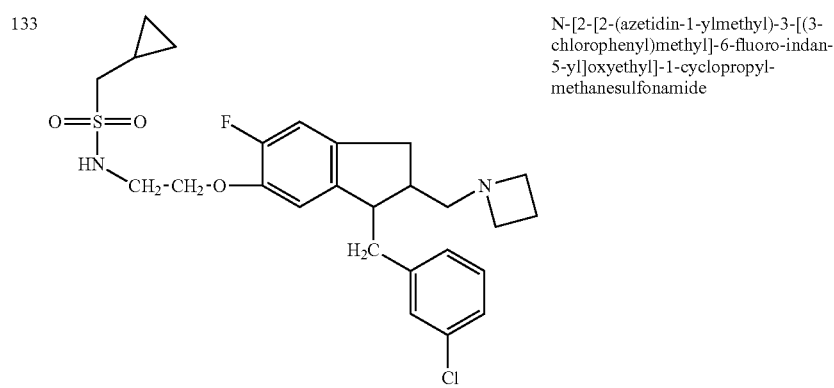 | N-[2-[2-(azetidin-1-ylmethyl)-3-[(3-chlorophenyl)methyl]-6-fluoro-indan-5-yl]oxyethyl]-1-cyclopropyl-methanesulfonamide |
| 134 | 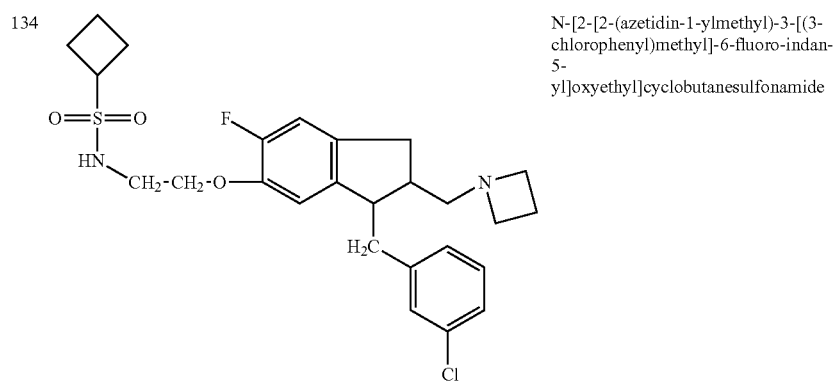 | N-[2-[2-(azetidin-1-ylmethyl)-3-[(3-chlorophenyl)methyl]-6-fluoro-indan-5-yl]oxyethyl]cyclobutanesulfonamide |
| 135 | 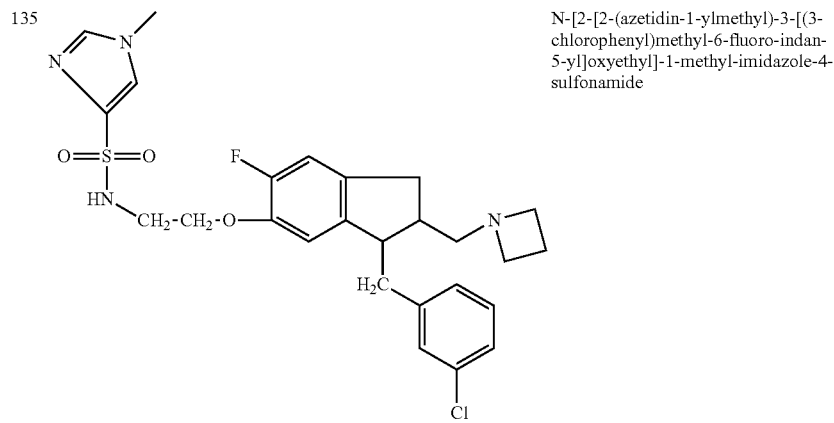 | N-[2-[2-(azetidin-1-ylmethyl)-3-[(3-chlorophenyl)methyl-6-fluoro-indan-5-yl]oxyethyl]-1-methyl-imidazole-4-sulfonamide |

-continued

| | | |
|---|---|---|
| 136 |  | N-[2-[2-(azetidin-1-ylmethyl)-3-[(3-chlorophenyl)methyl]-6-fluoro-indan-5-yl]oxyethyl]-1-methyl-pyrazole-4-sulfonamide |
| 137 |  | N-[[2-(azetidin-1-ylmethyl)-3-[(3-chlorophenyl)methyl]-6-fluoro-indan-5-yl]methyl]-1-cyclopropyl-methanesulfonamide |
| 138 |  | N-[2-[2-(azetidin-1-ylmethyl)-3-[(3-chlorophenyl)methyl]-6-fluoro-indan-5-yl]ethyl]-1-cyclopropyl-methanesulfonamide |
| 139 |  | N-[[2-(azetidin-1-ylmethyl)-3-[(3-chlorophenyl)methyl]-6-fluoro-indan-5-yl]methyl]cyclobutanesulfonamide |

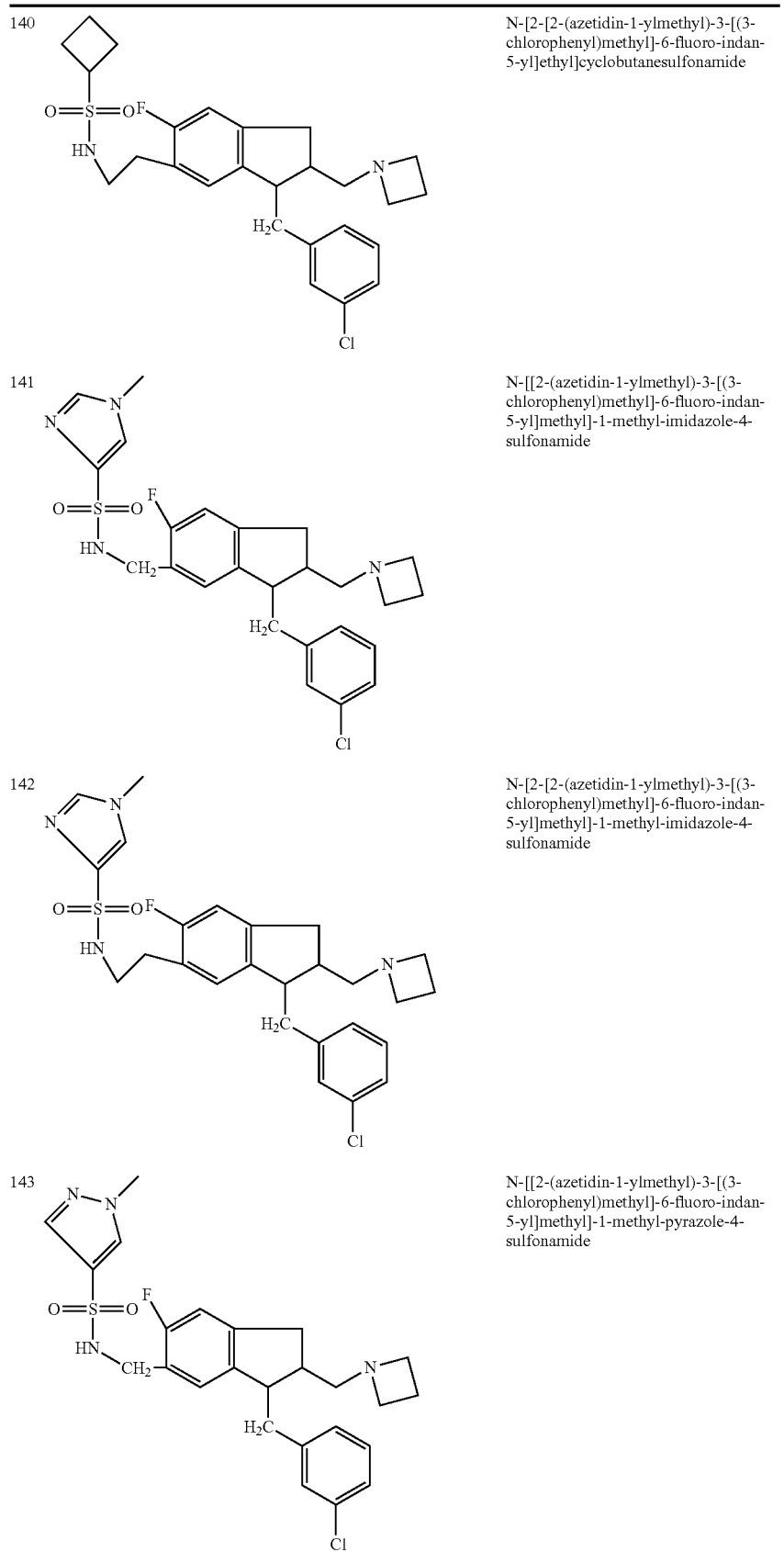

| 140 | N-[2-[2-(azetidin-1-ylmethyl)-3-[(3-chlorophenyl)methyl]-6-fluoro-indan-5-yl]ethyl]cyclobutanesulfonamide |
| 141 | N-[[2-(azetidin-1-ylmethyl)-3-[(3-chlorophenyl)methyl]-6-fluoro-indan-5-yl]methyl]-1-methyl-imidazole-4-sulfonamide |
| 142 | N-[2-[2-(azetidin-1-ylmethyl)-3-[(3-chlorophenyl)methyl]-6-fluoro-indan-5-yl]methyl]-1-methyl-imidazole-4-sulfonamide |
| 143 | N-[[2-(azetidin-1-ylmethyl)-3-[(3-chlorophenyl)methyl]-6-fluoro-indan-5-yl]methyl]-1-methyl-pyrazole-4-sulfonamide |

| 144 | 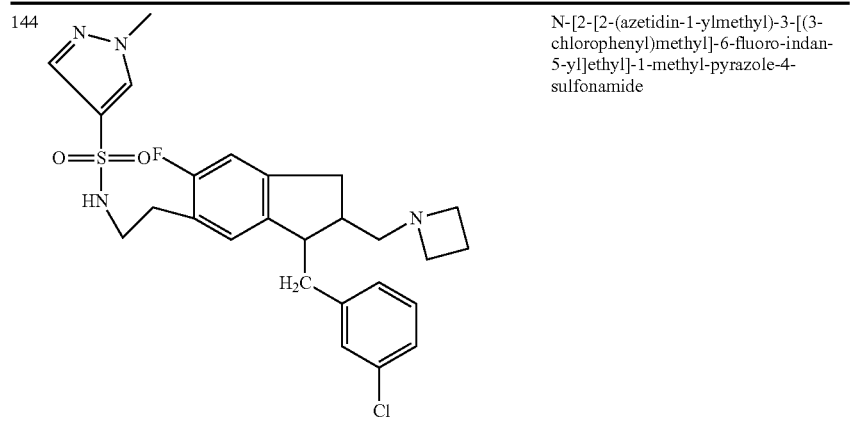 | N-[2-[2-(azetidin-1-ylmethyl)-3-[(3-chlorophenyl)methyl]-6-fluoro-indan-5-yl]ethyl]-1-methyl-pyrazole-4-sulfonamide |
|---|---|---|
| 145 | 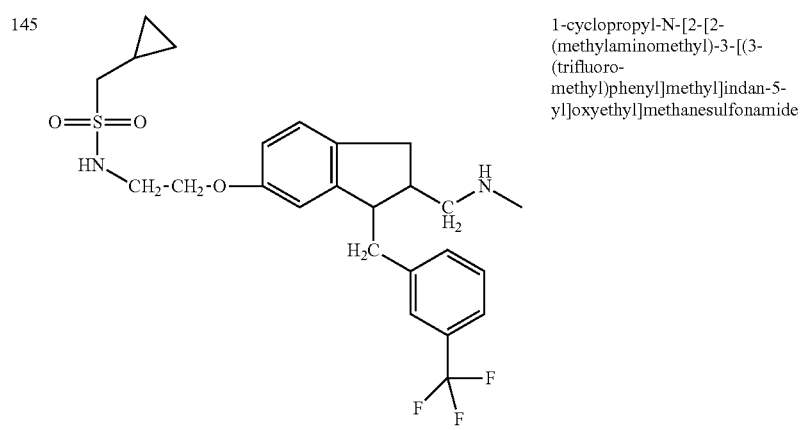 | 1-cyclopropyl-N-[2-[2-(methylaminomethyl)-3-[(3-(trifluoromethyl)phenyl]methyl]indan-5-yl]oxyethyl]methanesulfonamide |
| 146 | 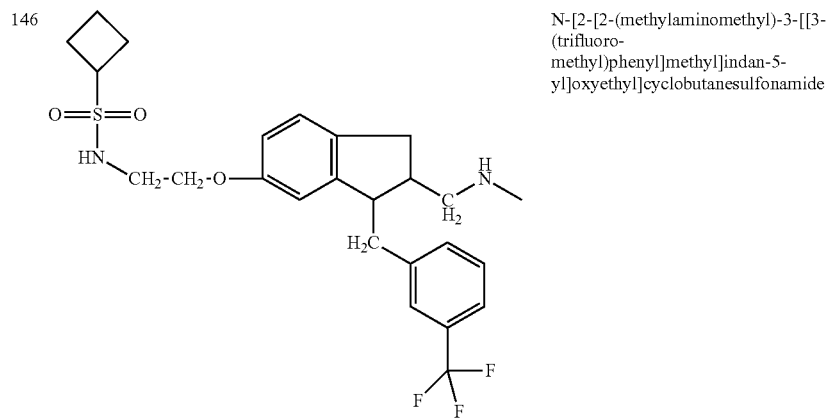 | N-[2-[2-(methylaminomethyl)-3-[[3-(trifluoromethyl)phenyl]methyl]indan-5-yl]oxyethyl]cyclobutanesulfonamide |

| | |
|---|---|
| 147 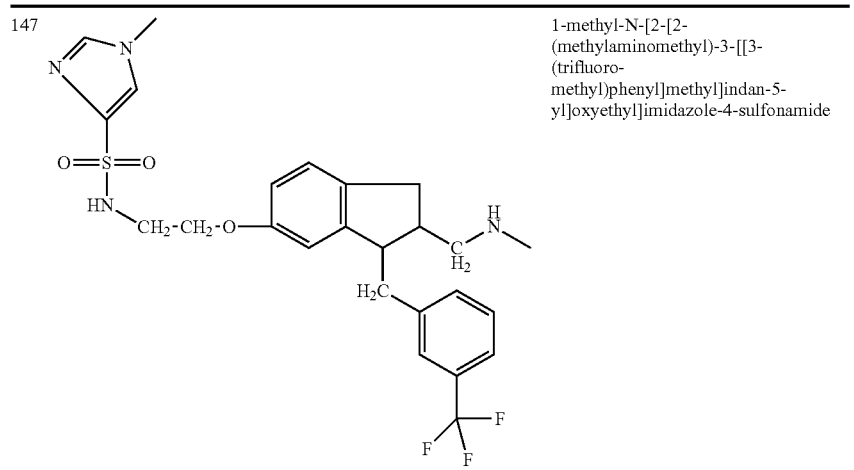 | 1-methyl-N-[2-[2-(methylaminomethyl)-3-[[3-(trifluoromethyl)phenyl]methyl]indan-5-yl]oxyethyl]imidazole-4-sulfonamide |
| 148 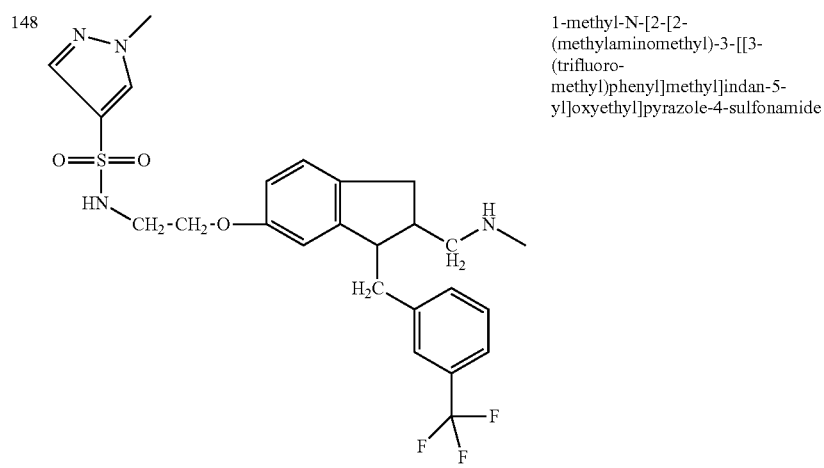 | 1-methyl-N-[2-[2-[2-(methylaminomethyl)-3-[[3-(trifluoromethyl)phenyl]methyl]indan-5-yl]oxyethyl]pyrazole-4-sulfonamide |
| 149 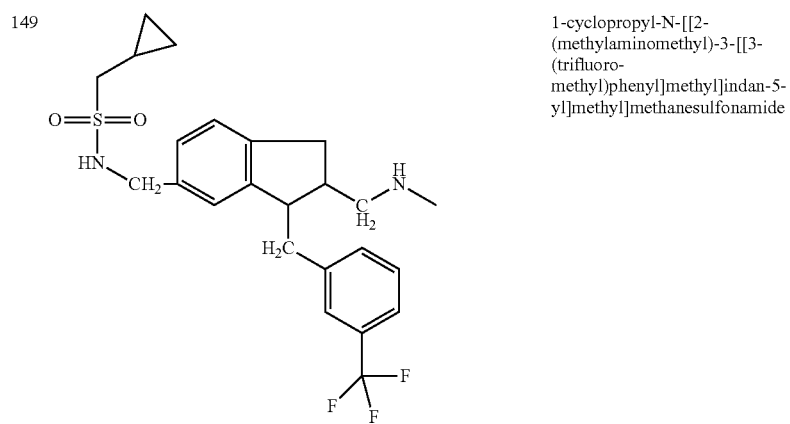 | 1-cyclopropyl-N-[[2-(methylaminomethyl)-3-[[3-(trifluoromethyl)phenyl]methyl]indan-5-yl]methyl]methanesulfonamide |

| | | |
|---|---|---|
| 150 | 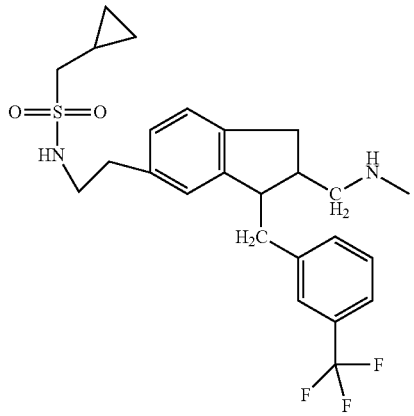 [SMILES: CNCC1Cc2ccc(CCNS(=O)(=O)CC3CC3)cc2C1Cc1cccc(C(F)(F)F)c1] | 1-cyclopropyl-N-[2-[2-(methylaminomethyl)-3-[[3-(trifluoromethyl)phenyl]methyl]indan-5-yl]ethyl]methanesulfonamide |
| 151 | 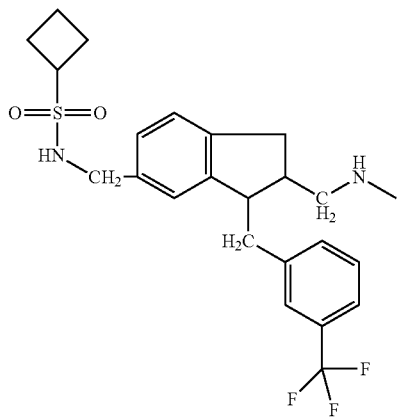 [SMILES: CNCC1Cc2ccc(CNS(=O)(=O)C3CCC3)cc2C1Cc1cccc(C(F)(F)F)c1] | N-[[2-(methylaminomethyl)-3-[[3-(trifluoromethyl)phenyl]methyl]indan-5-yl]methyl]cyclobutanesulfonamide |
| 152 | 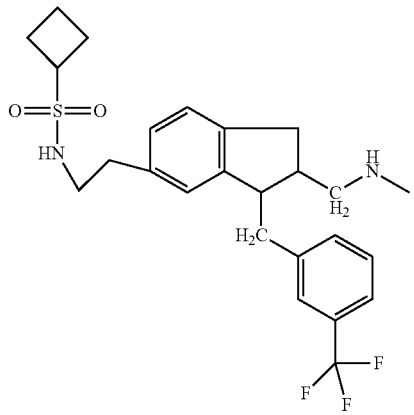 [SMILES: CNCC1Cc2ccc(CCNS(=O)(=O)C3CCC3)cc2C1Cc1cccc(C(F)(F)F)c1] | N-[2-[2-(methylaminomethyl)-3-[[3-(trifluoromethyl)phenyl]methyl]indan-5-yl]ethyl]cyclobutanesulfonamide |

| | | |
|---|---|---|
| 153 | 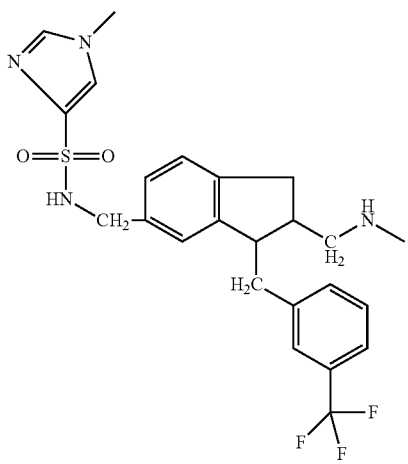 [SMILES: CNCC1Cc2ccc(CNS(=O)(=O)c3cn(C)cn3)cc2C1Cc1cccc(C(F)(F)F)c1] | 1-methyl-N-[[2-(methylaminomethyl)-3-[[3-(trifluoro-methyl)phenyl]methyl]indan-5-yl]methyl]imidazole-4-sulfonamide |
| 154 | 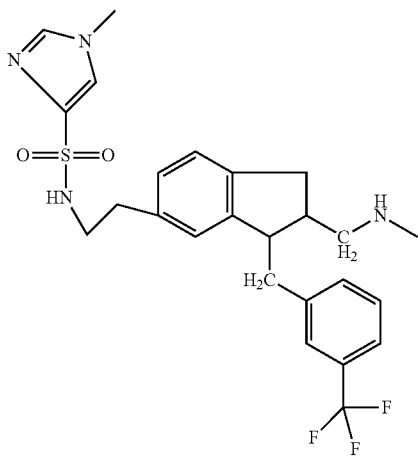 [SMILES: CNCC1Cc2ccc(CCNS(=O)(=O)c3cn(C)cn3)cc2C1Cc1cccc(C(F)(F)F)c1] | 1-methyl-N-[2-[2-(methylaminomethyl)-3-[[3-(trifluoro-methyl)phenyl]methyl]indan-5-yl]ethyl]imidazole-4-sulfonamide |
| 155 | 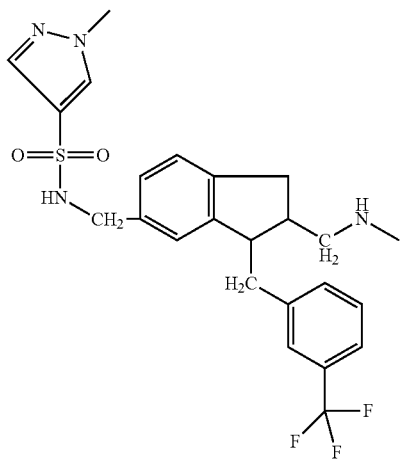 [SMILES: CNCC1Cc2ccc(CNS(=O)(=O)c3cnn(C)c3)cc2C1Cc1cccc(C(F)(F)F)c1] | 1- methyl-N-[[2-(methylaminomethyl)-3-[[3-(trifluoro-methyl)phenyl]methyl]indan-5-yl]methyl]pyrazole-4-sulfonamide |

| | | |
|---|---|---|
| 156 | 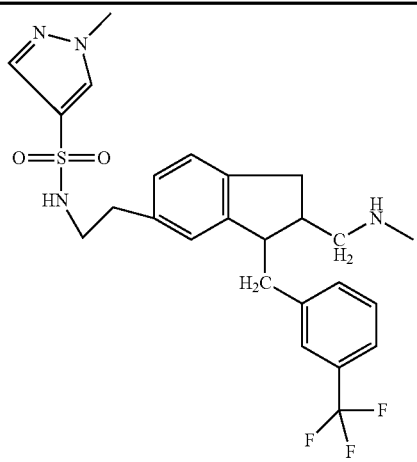 | 1-methyl-N-[2-[2-(methylaminomethyl)-3-[[3-(trifluoro-methyl)phenyl]methyl]indan-5-yl]ethyl]pyrazole-4-sulfonamide |
| 157 | 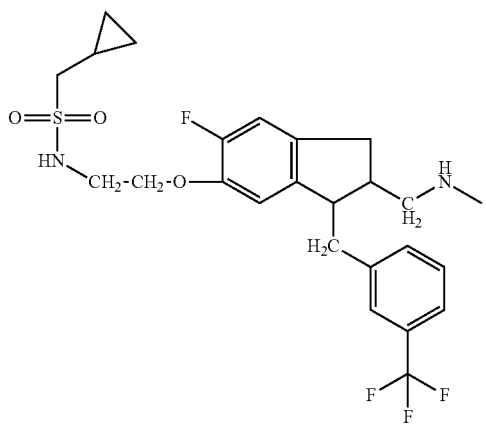 [SMILES: CNCC1Cc2cc(F)c(OCCNS(=O)(=O)CC3CC3)cc2C1Cc1cccc(C(F)(F)F)c1] | 1-cyclopropyl-N-[2-[6-fluoro-2-(methylaminomethyl)-3-[[3-(trifluoro-methyl)phenyl]methyl]indan-5-yl]oxyethyl]methanesulfonamide |
| 158 | 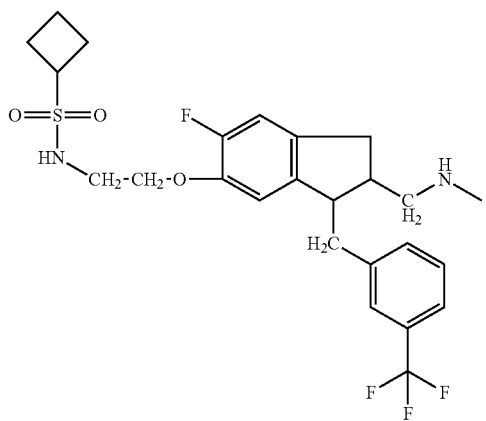 [SMILES: CNCC1Cc2cc(F)c(OCCNS(=O)(=O)C3CCC3)cc2C1Cc1cccc(C(F)(F)F)c1] | N-[2-[6-fluoro-2-(methylaminomethyl)-3-[[3-(trifluoro-methyl)phenyl]methyl]indan-5-yl]oxyethyl]cyclobutanesulfonamide |

| | | |
|---|---|---|
| 159 | 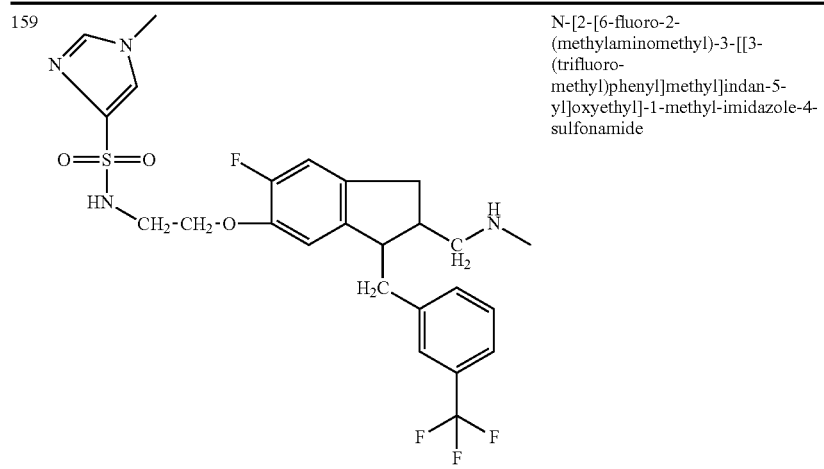 | N-[2-[6-fluoro-2-(methylaminomethyl)-3-[[3-(trifluoromethyl)phenyl]methyl]indan-5-yl]oxyethyl]-1-methyl-imidazole-4-sulfonamide |
| 160 | 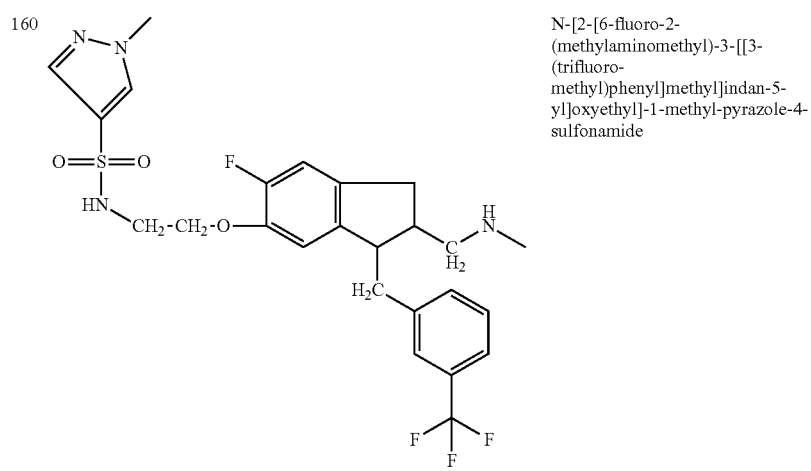 | N-[2-[6-fluoro-2-(methylaminomethyl)-3-[[3-(trifluoromethyl)phenyl]methyl]indan-5-yl]oxyethyl]-1-methyl-pyrazole-4-sulfonamide |
| 161 | 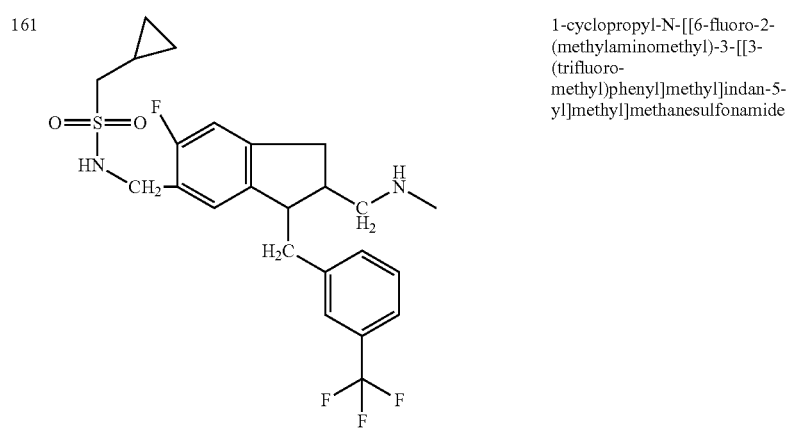 | 1-cyclopropyl-N-[[6-fluoro-2-(methylaminomethyl)-3-[[3-(trifluoromethyl)phenyl]methyl]indan-5-yl]methyl]methanesulfonamide |

| | | |
|---|---|---|
| 162 | 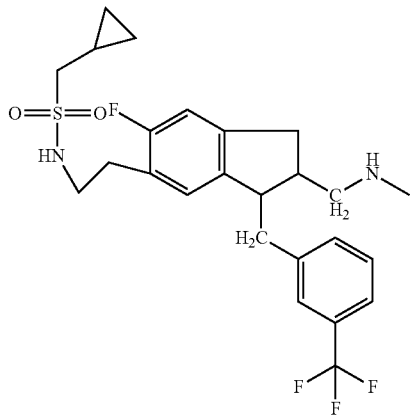 [SMILES: CNCC1Cc2cc(F)c(CCNS(=O)(=O)CC3CC3)cc2C1Cc1cccc(C(F)(F)F)c1] | 1-cyclopropyl-N-[2-[6-fluoro-2-(methylaminomethyl)-3-[[3-(trifluoromethyl)phenyl]methyl]indan-5-yl]ethyl]methanesulfonamide |
| 163 | 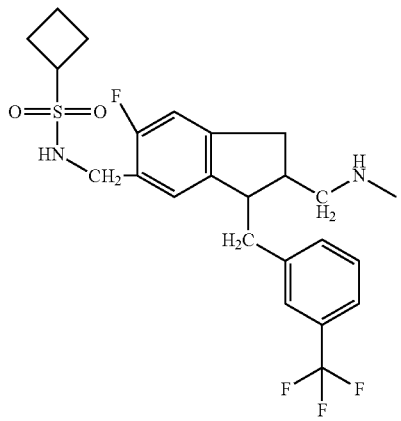 [SMILES: CNCC1Cc2cc(F)c(CNS(=O)(=O)C3CCC3)cc2C1Cc1cccc(C(F)(F)F)c1] | N-[[6-fluoro-2-(methylaminomethyl)-3-[[3-(trifluoromethyl)phenyl]methyl]indan-5-yl]methyl]cyclobutanesulfonamide |
| 164 | 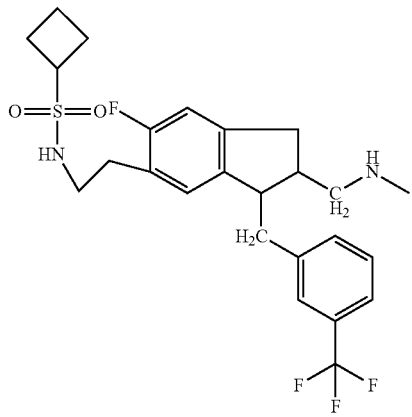 [SMILES: CNCC1Cc2cc(F)c(CCNS(=O)(=O)C3CCC3)cc2C1Cc1cccc(C(F)(F)F)c1] | N-[2-[6-fluoro-2-(methylaminomethyl)-3-[[3-(trifluoromethyl)phenyl]methyl]indan-5-yl]ethyl]cyclobutanesulfonamide |

| | | |
|---|---|---|
| 165 | 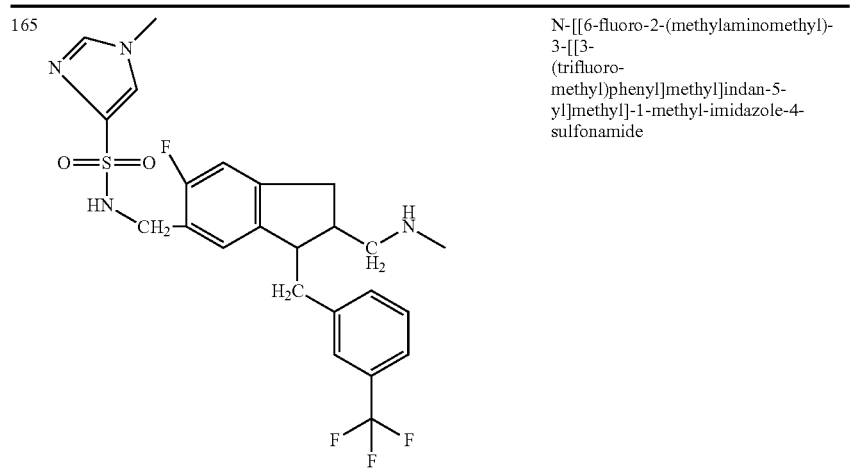 | N-[[6-fluoro-2-(methylaminomethyl)-3-[[3-(trifluoromethyl)phenyl]methyl]indan-5-yl]methyl]-1-methyl-imidazole-4-sulfonamide |
| 166 | 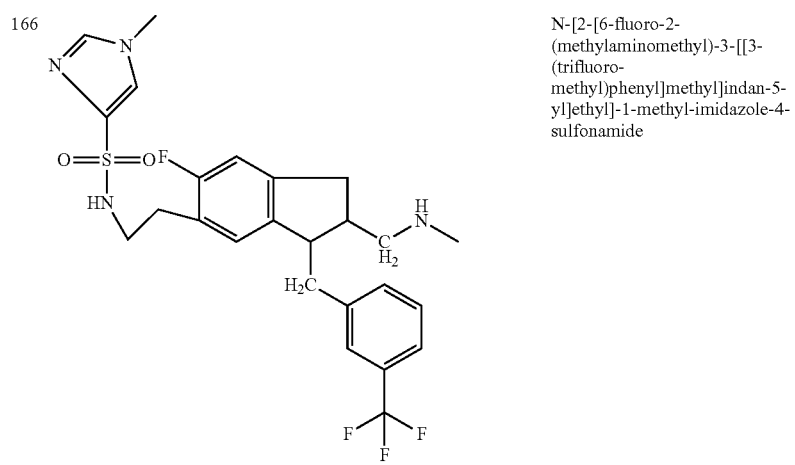 | N-[2-[6-fluoro-2-(methylaminomethyl)-3-[[3-(trifluoromethyl)phenyl]methyl]indan-5-yl]ethyl]-1-methyl-imidazole-4-sulfonamide |
| 167 | 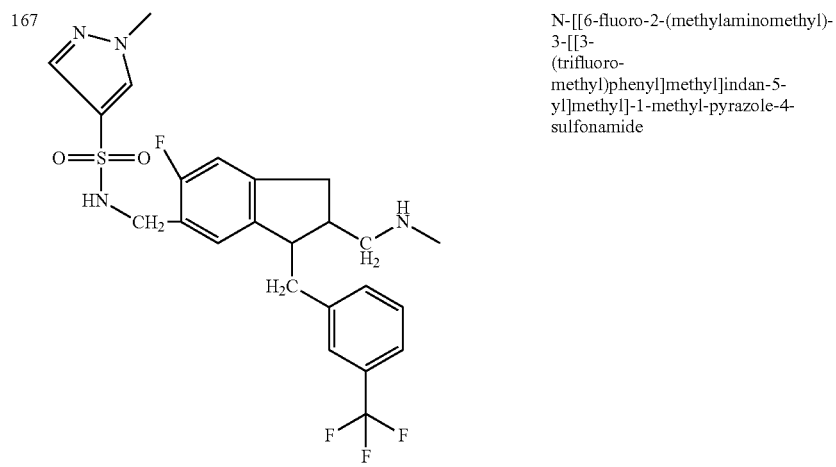 | N-[[6-fluoro-2-(methylaminomethyl)-3-[[3-(trifluoromethyl)phenyl]methyl]indan-5-yl]methyl]-1-methyl-pyrazole-4-sulfonamide |

| 168 | 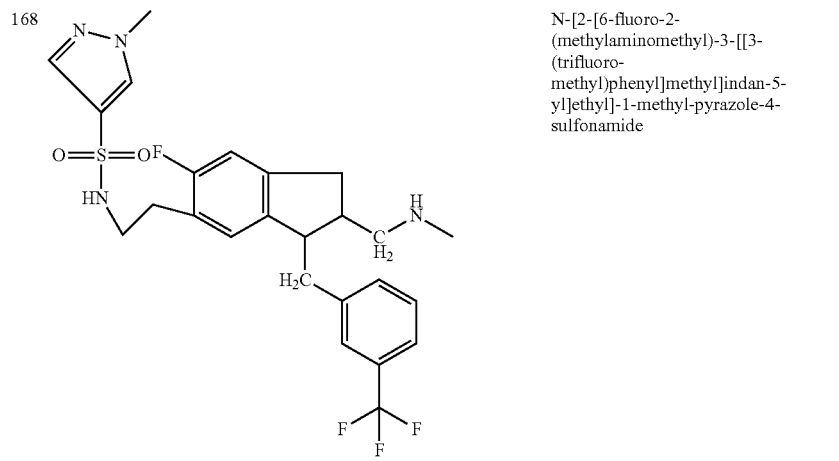 | N-[2-[6-fluoro-2-(methylaminomethyl)-3-[[3-(trifluoromethyl)phenyl]methyl]indan-5-yl]ethyl]-1-methyl-pyrazole-4-sulfonamide |
| 169 | 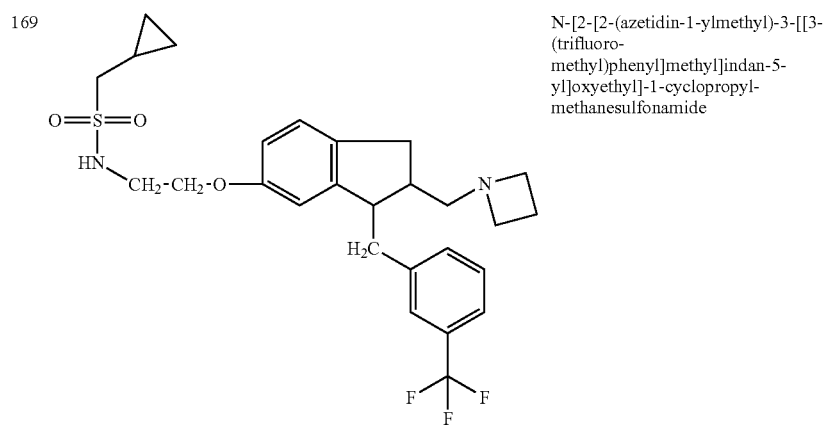 | N-[2-[2-(azetidin-1-ylmethyl)-3-[[3-(trifluoromethyl)phenyl]methyl]indan-5-yl]oxyethyl]-1-cyclopropyl-methanesulfonamide |
| 170 | 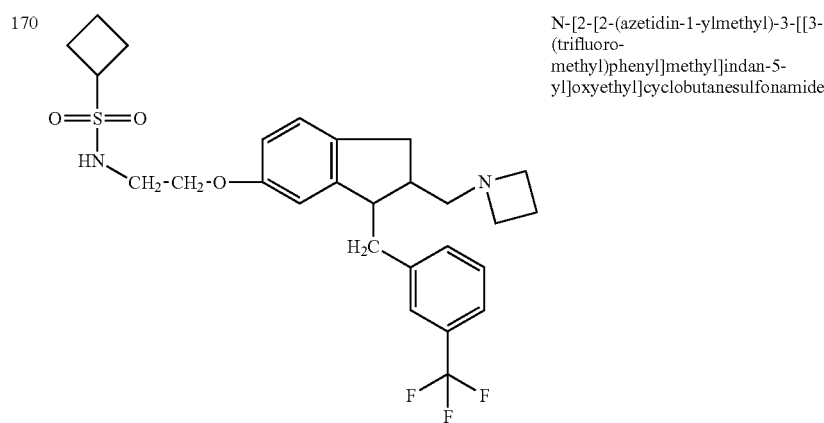 | N-[2-[2-(azetidin-1-ylmethyl)-3-[[3-(trifluoromethyl)phenyl]methyl]indan-5-yl]oxyethyl]cyclobutanesulfonamide |

| | | |
|---|---|---|
| 171 | 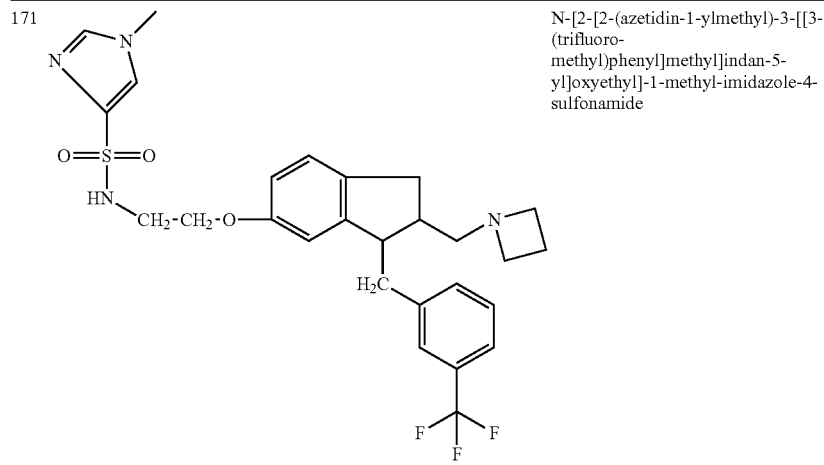 | N-[2-[2-(azetidin-1-ylmethyl)-3-[[3-(trifluoro-methyl)phenyl]methyl]indan-5-yl]oxyethyl]-1-methyl-imidazole-4-sulfonamide |
| 172 | 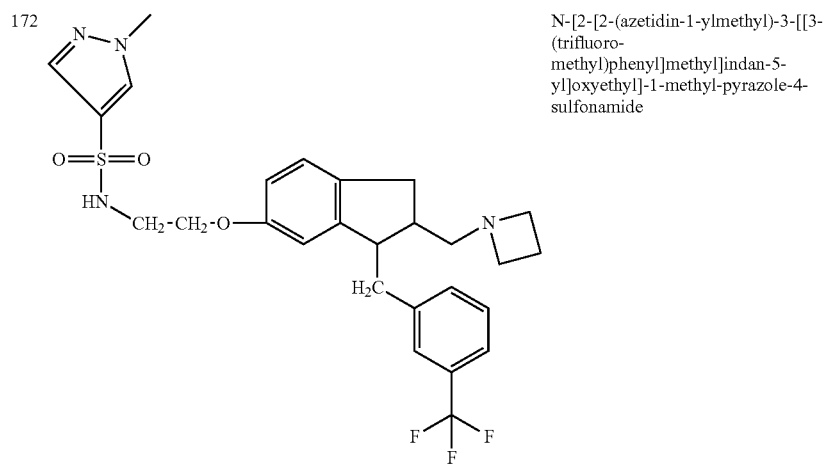 | N-[2-[2-(azetidin-1-ylmethyl)-3-[[3-(trifluoro-methyl)phenyl]methyl]indan-5-yl]oxyethyl]-1-methyl-pyrazole-4-sulfonamide |
| 173 | 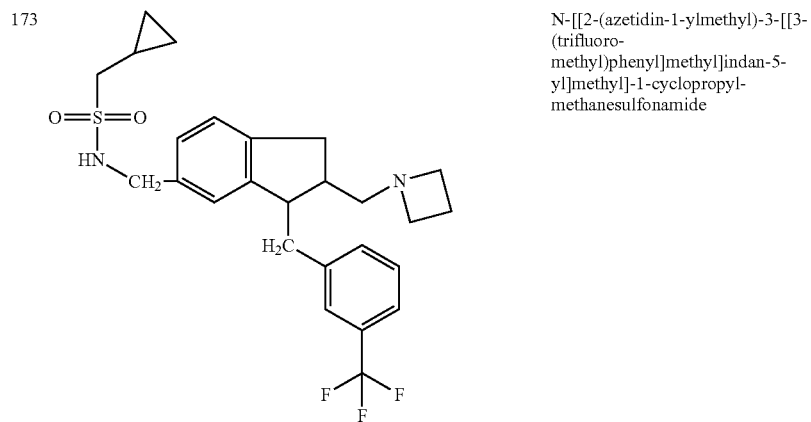 | N-[[2-(azetidin-1-ylmethyl)-3-[[3-(trifluoro-methyl)phenyl]methyl]indan-5-yl]methyl]-1-cyclopropyl-methanesulfonamide |

| | | |
|---|---|---|
| 174 | 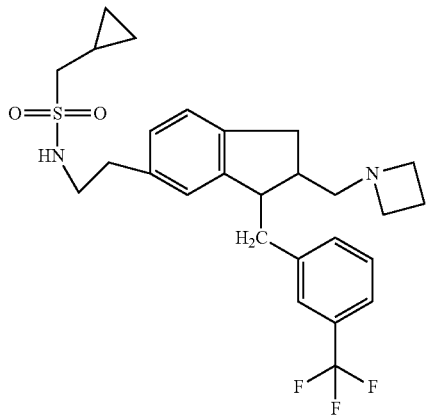 [SMILES: O=S(=O)(CC1CC1)NCCc1ccc2c(c1)C(Cc1cccc(C(F)(F)F)c1)C(CN1CCC1)C2] | N-[2-[2-(azetidin-1-ylmethyl)-3-[[3-(trifluoro-methyl)phenyl]methyl]indan-5-yl]ethyl]-1-cyclopropyl-methanesulfonamide |
| 175 | 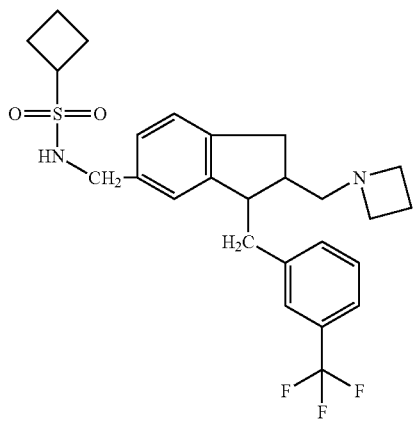 [SMILES: O=S(=O)(NCc1ccc2c(c1)C(Cc1cccc(C(F)(F)F)c1)C(CN1CCC1)C2)C1CCC1] | N-[[2-(azetidin-1-ylmethyl)-3-[[3-(trifluoro-methyl)phenyl]methyl]indan-5-yl]methyl]cyclobutanesulfonamide |
| 176 | 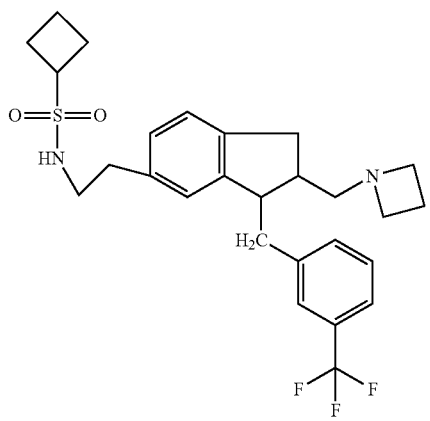 [SMILES: O=S(=O)(NCCc1ccc2c(c1)C(Cc1cccc(C(F)(F)F)c1)C(CN1CCC1)C2)C1CCC1] | N-[2-[2-(azetidin-1-ylmethyl)-3-[[3-(trifluoro-methyl)phenyl]methyl]indan-5-yl]ethyl]cyclobutanesulfonamide |

| | | |
|---|---|---|
| 177 | 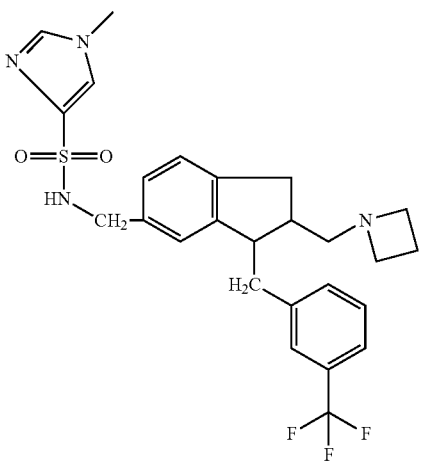 [SMILES: Cn1cnc(S(=O)(=O)NCc2ccc3c(c2)C(Cc2cccc(C(F)(F)F)c2)C(CN2CCC2)C3)c1] | N-[[2-(azetidin-1-ylmethyl)-3-[[3-(trifluoro-methyl)phenyl]methyl]indan-5-yl]methyl]-1-methyl-imidazole-4-sulfonamide |
| 178 | 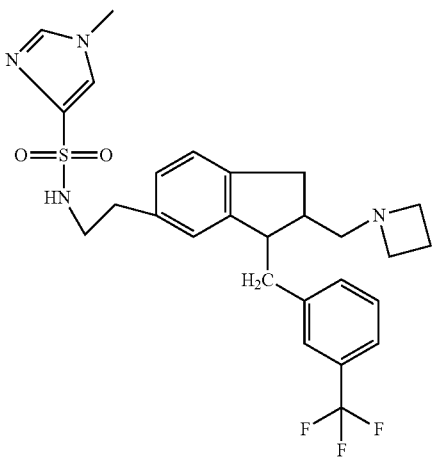 [SMILES: Cn1cnc(S(=O)(=O)NCCc2ccc3c(c2)C(Cc2cccc(C(F)(F)F)c2)C(CN2CCC2)C3)c1] | N-[2-[2-(azetidin-1-ylmethyl)-3-[[3-(trifluoro-methyl)phenyl]methyl]indan-5-yl]ethyl]-1-methyl-imidazole-4-sulfonamide |
| 179 | 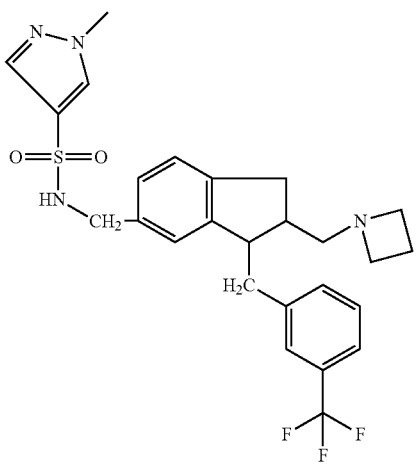 [SMILES: Cn1cc(S(=O)(=O)NCc2ccc3c(c2)C(Cc2cccc(C(F)(F)F)c2)C(CN2CCC2)C3)cn1] | N-[[2-(azetidin-1-ylmethyl)-3-[[3-(trifluoro-methyl)phenyl]methyl]indan-5-yl]ethyl]-1-methyl-pyrazole-4-sulfonamide |

| 180 | 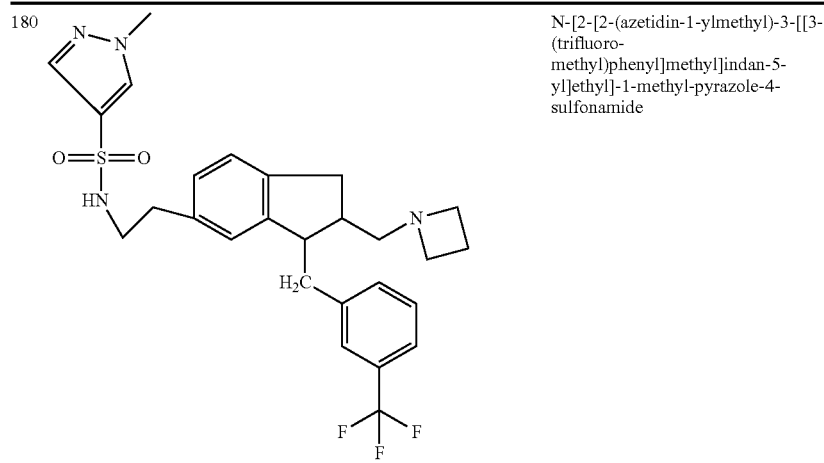 | N-[2-[2-(azetidin-1-ylmethyl)-3-[[3-(trifluoro-methyl)phenyl]methyl]indan-5-yl]ethyl]-1-methyl-pyrazole-4-sulfonamide |
|---|---|---|
| 181 | 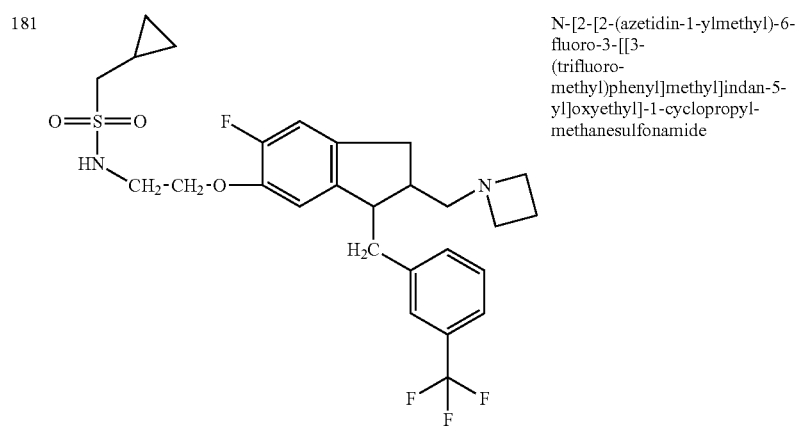 | N-[2-[2-(azetidin-1-ylmethyl)-6-fluoro-3-[[3-(trifluoro-methyl)phenyl]methyl]indan-5-yl]oxyethyl]-1-cyclopropyl-methanesulfonamide |
| 182 | 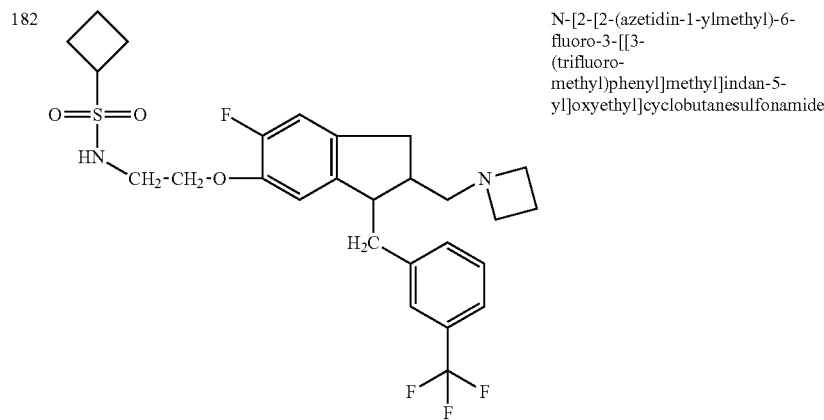 | N-[2-[2-(azetidin-1-ylmethyl)-6-fluoro-3-[[3-(trifluoro-methyl)phenyl]methyl]indan-5-yl]oxyethyl]cyclobutanesulfonamide |

| 183 | 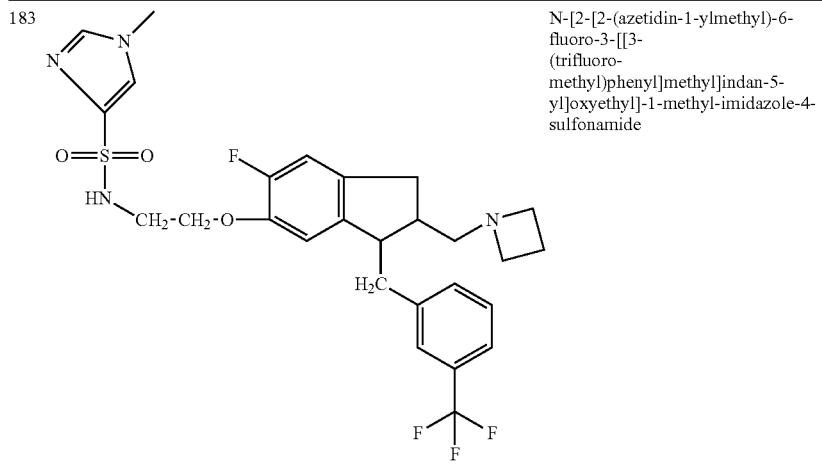 | N-[2-[2-(azetidin-1-ylmethyl)-6-fluoro-3-[[3-(trifluoromethyl)phenyl]methyl]indan-5-yl]oxyethyl]-1-methyl-imidazole-4-sulfonamide |
| --- | --- | --- |
| 184 | 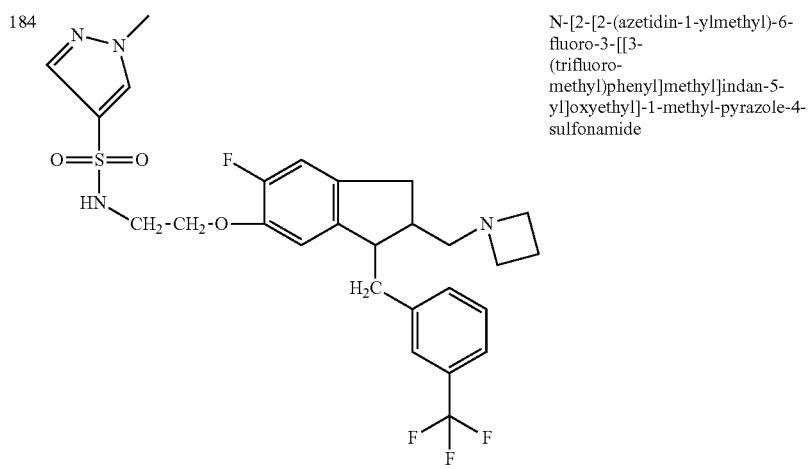 | N-[2-[2-(azetidin-1-ylmethyl)-6-fluoro-3-[[3-(trifluoromethyl)phenyl]methyl]indan-5-yl]oxyethyl]-1-methyl-pyrazole-4-sulfonamide |
| 185 | 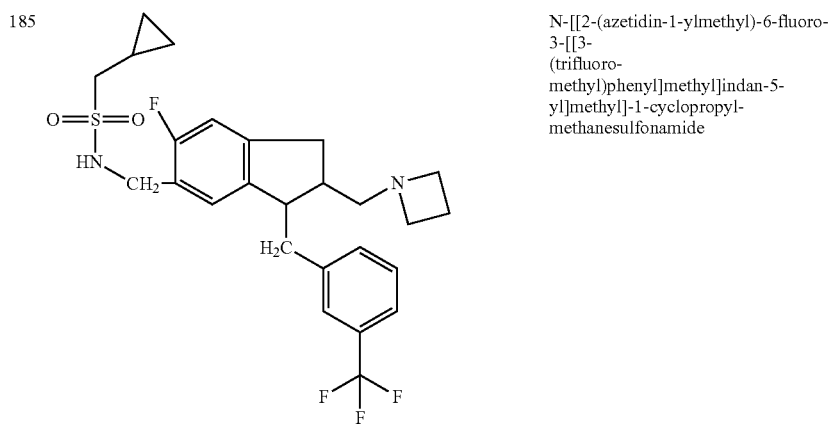 | N-[[2-(azetidin-1-ylmethyl)-6-fluoro-3-[[3-(trifluoromethyl)phenyl]methyl]indan-5-yl]methyl]-1-cyclopropyl-methanesulfonamide |

| | | |
|---|---|---|
| 186 | 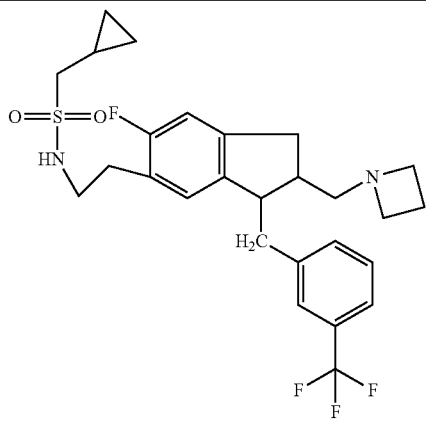 | N-[2-[2-(azetidin-1-ylmethyl)-6-fluoro-3-[[3-(trifluoromethyl)phenyl]methyl]indan-5-yl]ethyl]-1-cyclopropyl-methanesulfonamide |
| 187 | 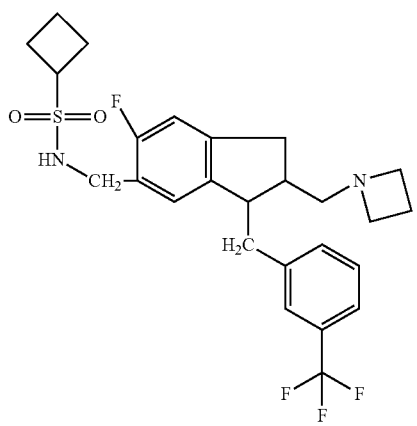 [SMILES: O=S(=O)(NCc1cc2c(cc1F)CC(CN1CCC1)C2Cc1cccc(C(F)(F)F)c1)C1CCC1] | N-[[2-(azetidin-1-ylmethyl)-6-fluoro-3-[[3-(trifluoromethyl)phenyl]methyl]indan-5-yl]methyl]cyclobutanesulfonamide |
| 188 | 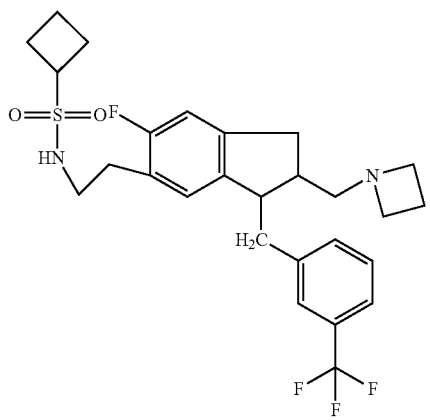 [SMILES: O=S(=O)(NCCc1cc2c(cc1F)CC(CN1CCC1)C2Cc1cccc(C(F)(F)F)c1)C1CCC1] | N-[2-[2-(azetidin-1-ylmethyl)-6-fluoro-3-[[3-(trifluoromethyl)phenyl]methyl]indan-5-yl]ethyl]cyclobutanesulfonamide |

| | | |
|---|---|---|
| 189 | 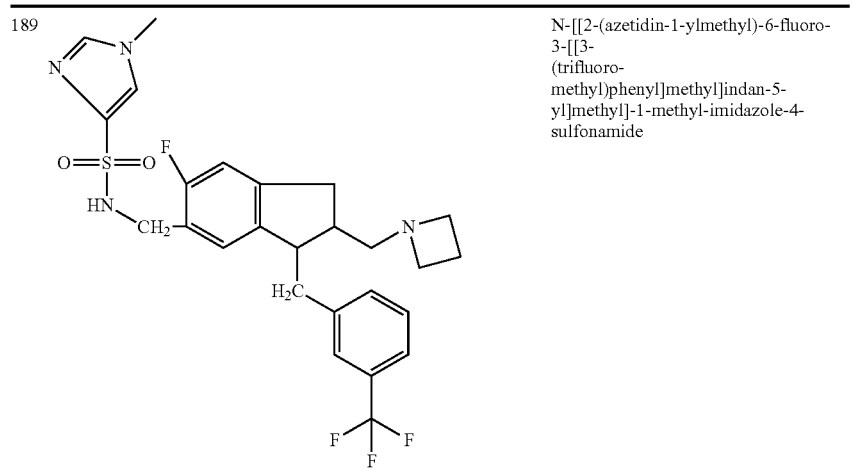 | N-[[2-(azetidin-1-ylmethyl)-6-fluoro-3-[[3-(trifluoromethyl)phenyl]methyl]indan-5-yl]methyl]-1-methyl-imidazole-4-sulfonamide |
| 190 | 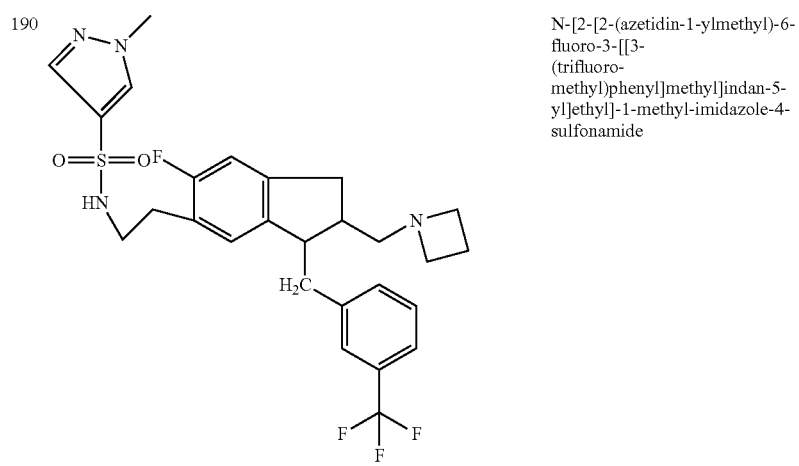 | N-[2-[2-(azetidin-1-ylmethyl)-6-fluoro-3-[[3-(trifluoromethyl)phenyl]methyl]indan-5-yl]ethyl]-1-methyl-imidazole-4-sulfonamide |
| 191 | 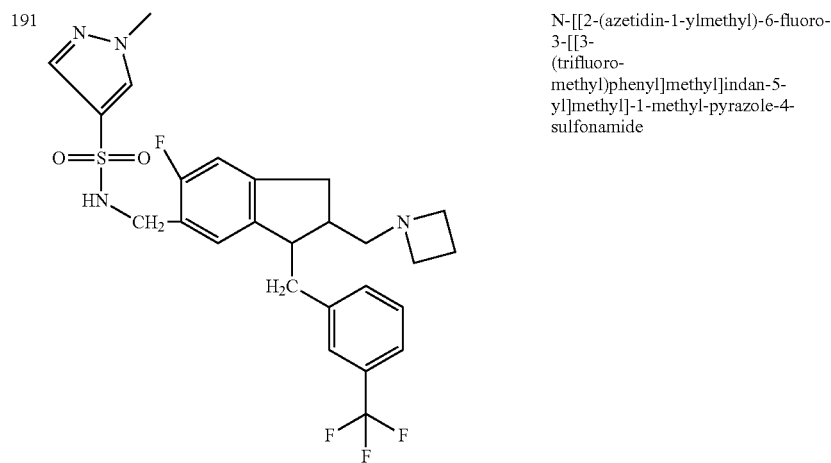 | N-[[2-(azetidin-1-ylmethyl)-6-fluoro-3-[[3-(trifluoromethyl)phenyl]methyl]indan-5-yl]methyl]-1-methyl-pyrazole-4-sulfonamide |

| | |
|---|---|
| 192 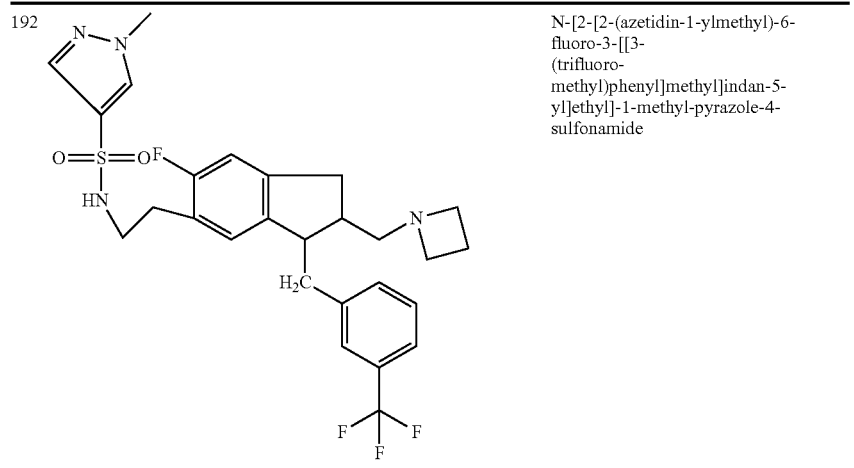 | N-[2-[2-(azetidin-1-ylmethyl)-6-fluoro-3-[[3-(trifluoromethyl)phenyl]methyl]indan-5-yl]ethyl]-1-methyl-pyrazole-4-sulfonamide |

Example 193

Propane-1-sulfonic acid (8-benzyl-7-cyclopropylamino-5,6,7,8-tetrahydro-naphthalen-2-ylmethyl)-amide hydrochloride N-((7-Amino-8-benzyl-5,6,7,8-tetrahydronaphthalen-2-yl)methyl)propane-1-sulfonamide (51 mg, 0.137 mmol), (1-ethoxycyclopropoxy)trimethylsilane (26 mg, 0.151 mmol), acetic acid (0.078 mL, 1.37 mmol), sodium cyanoborohydride (26 mg, 0.411 mmol) and molecular sieve (50 mg) in methanol (1.5 mL) were heated in the microwave at 100° C. for 25 min. The solvent was evaporated and the crude product purified by flash chromatography (silica gel, dichloromethane, methanol) and converted into the hydrochloride. Yield: 18 mg (0.04 mmol, 29%).

ESI-MS[M+H$^+$]=413 Calculated for $C_{24}H_{32}N_2O_2S$=412

Cis-ethyl[(1-benzyl-7-hydroxy-1,2,3,4-tetrahydronaphthalen-2-yl)methyl]carbamate (building block SM10) was synthesized as follows:

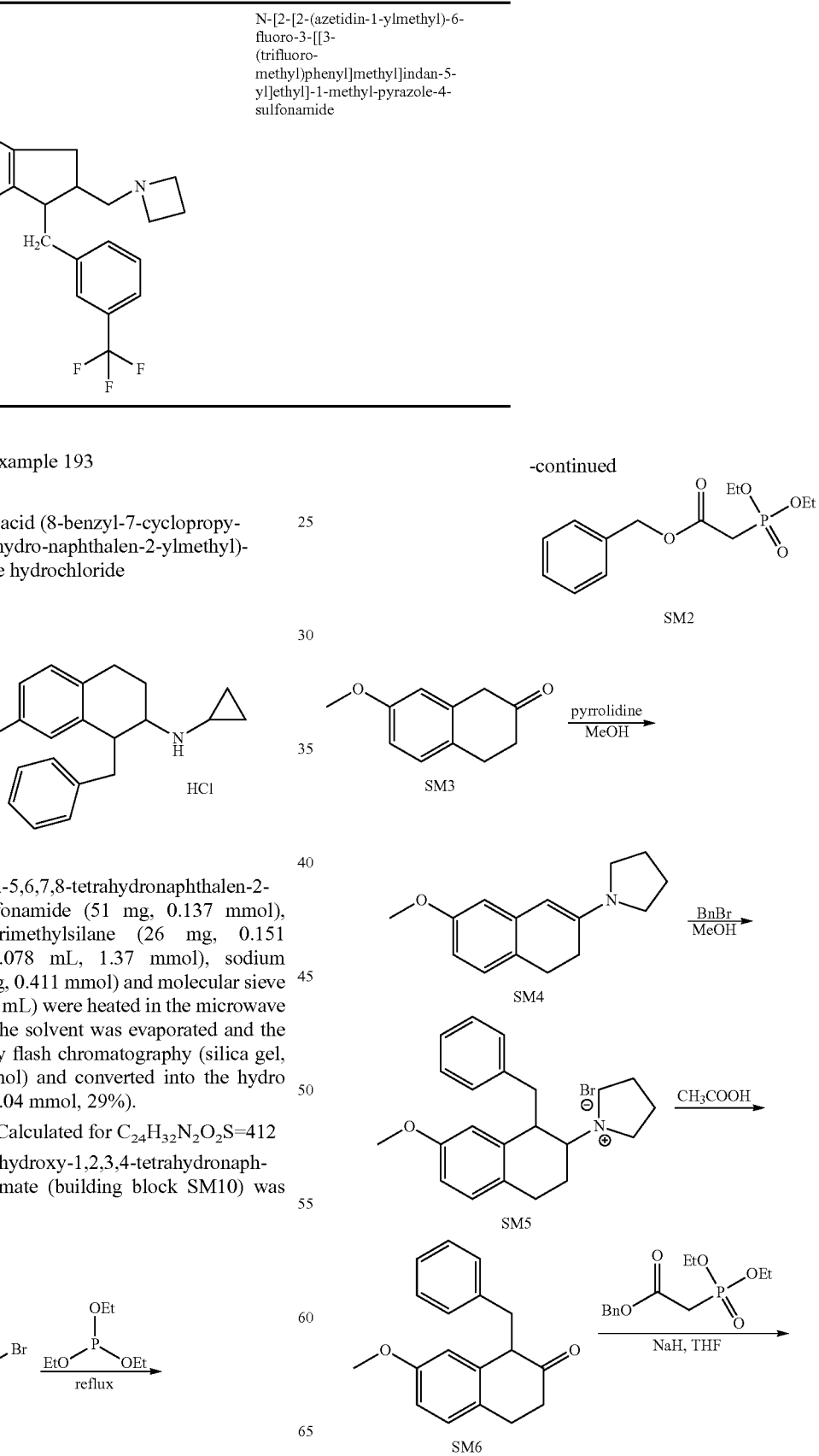

2. Synthesis of Compound SM4

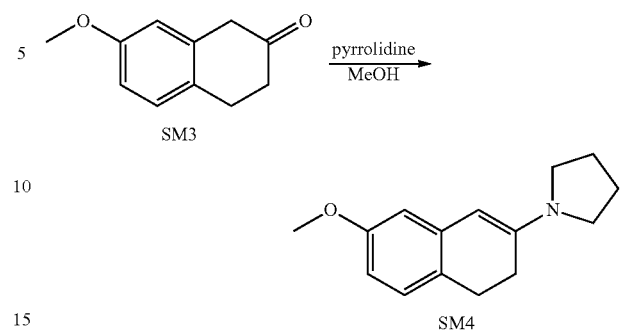

Under N₂ atmosphere, a solution of 7-hydroxy-3,4-dihydro-1H-naphthalen-2-one (85 g, 0.48 mol) and pyrrolidine (264 g, 1.5 mol) in MeOH (3000 mL) was stirred at room temperature for 2 hrs. The solvent was removed in vacuo to give crude 1-(7-methoxy-3,4-dihydro-naphthalen-2-yl)-pyrrolidine (320 g) which was directly used for next step.

3. Synthesis of Compound SM6

To a mixture of 1-(7-methoxy-3,4-dihydro-naphthalen-2-yl)-pyrrolidine (320 g, 1.4 mol) in MeCN (1000 mL) was added BnBr (263 g, 1.54 mol) dropwise at room temperature and stirred for 1 h. Then the solvent was evaporated in vacuo to give crude 1-(1-benzyl-7-methoxy-3,4-dihydro-1H-naphthalen-2-ylidene)-pyrrolidinium bromide which was directly used for next step.

A solution of 1-(1-benzyl-7-methoxy-3,4-dihydro-1H-naphthalen-2-ylidene)-pyrrolidinium bromide and AcOH (300 mL) in DCM (500 mL), H₂O (3000 mL) and MeOH (500 mL) was stirred at reflux for 10 hrs. The aqueous layer was washed with DCM (1000 mL), and the combined organic layers were washed with water, dried over Na₂SO₄ and concentrated to give crude product, purified by silica gel chromatography to give 1-benzyl-7-methoxy-3,4-dihydro-1H-naphthalen-2-one (195 g, yield 53%) as yellow solid.

4. Synthesis of Compound SM7

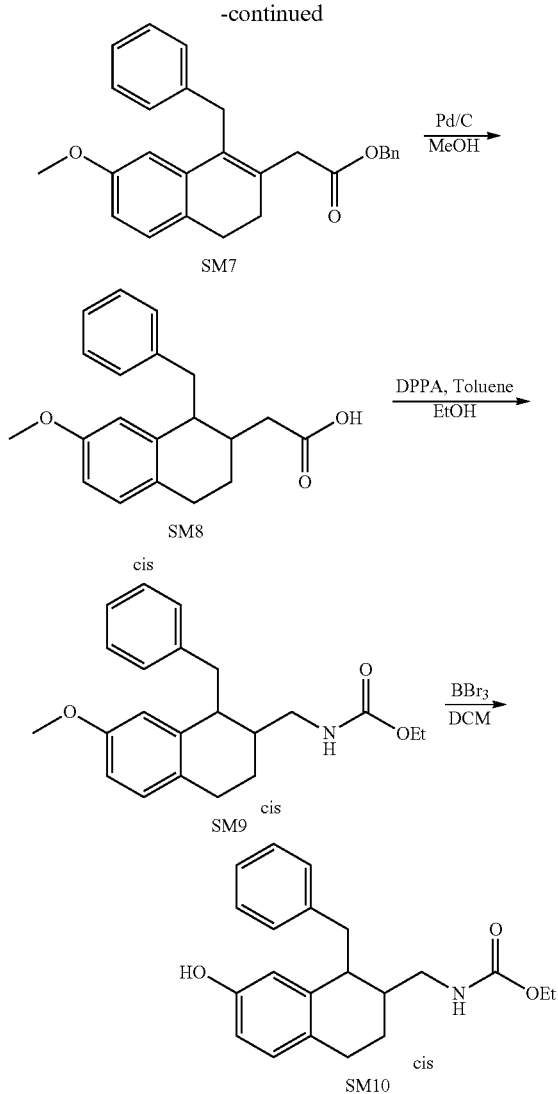

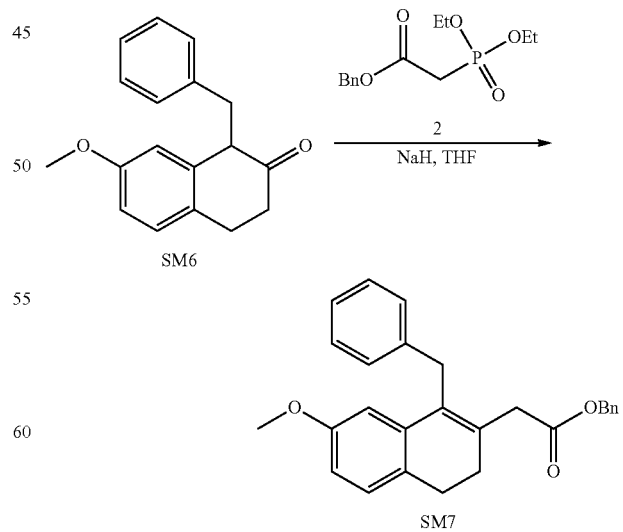

1. Synthesis of Compound SM2

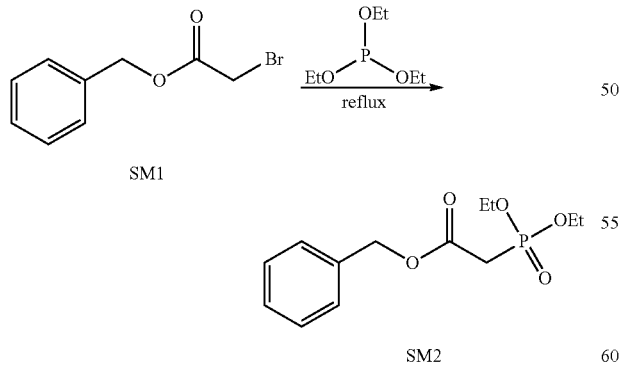

The mixture of bromo-acetic acid benzyl ester (229 g, 1.0 mol) and phosphorous acid triethyl ester (166 g, 1.0 mol) was stirred at reflux for 10 hrs and the solvent was evaporated in vacuo to give crude (diethoxy-phosphoryl)-acetic acid benzyl ester (230 g) which was directly used for next step.

To the mixture of NaH (19.44 g, 0.81 mol) in THF (2 L) was added (diethoxy-phosphoryl)-acetic acid benzyl ester (232 g, 0.81 mol) at 0° C. under $N_2$ atmosphere, then the mixture was stirred at room temperature for 1.5 hrs. 1-benzyl-7-methoxy-3,4-dihydro-1H-naphthalen-2-one (165 g, 0.62 mol) in THF (500 mL) was added dropwise at 15° C. for 1 h.

Then the mixture was stirred at room temperature for 18 hrs. AcOH (20 mL) was added at 0° C., poured into ice water and the mixture was extracted with EtOAc (500 mL×3), washed with brine, the organic phase was dried over $Na_2SO_4$ and concentrated to give crude product, purified by silica gel chromatography to give (1-benzyl-7-methoxy-3,4-dihydro-naphthalen-2-yl)-acetic acid benzyl ester (102 g, 41%) as white solid.

5. Synthesis of Compound SM8

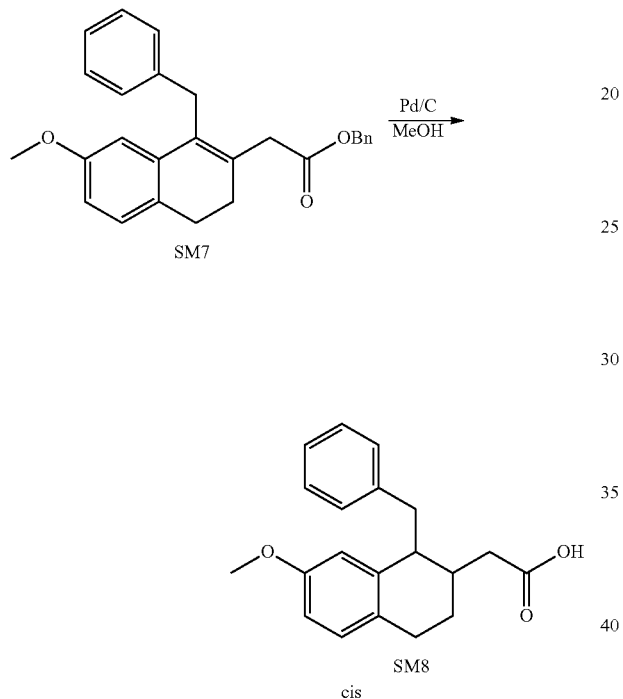

The mixture of (1-benzyl-7-methoxy-3,4-dihydro-naphthalen-2-yl)-acetic acid benzyl ester (102 g, 0.26 mol) and $Pd(OH)_2/C$ (30 g) in EtOH (5 L) was stirred under $H_2$ (30 psi) atmosphere overnight, then the solution was filtered to removed the solid and concentrated to give crude product, recrystallized from DCM to give (1-benzyl-7-methoxy-1,2,3,4-tetrahydro-naphthalen-2-yl)-acetic acid (60 g, yield 74%) as white solid.

8. Synthesis of Compound SM9

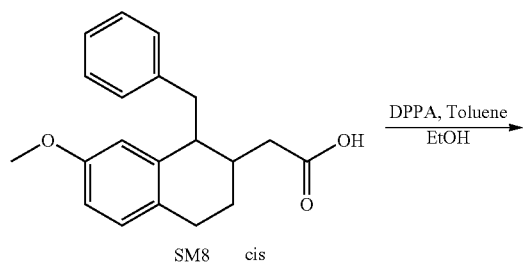

-continued

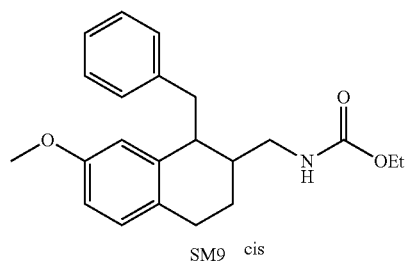

To a solution of (1-benzyl-7-methoxy-1,2,3,4-tetrahydro-naphthalen-2-yl)-acetic acid (60 g, 0.19 mol) in DPPA (53 g, 0.19 mol) and TEA (19.5 g, 0.19 mol) in toluene (1000 mL) was stirred at room temperature under $N_2$ atmosphere for 15 hrs. EtOH (35.4 g, 0.77 mol) was added, then the solution was stirred at reflux overnight. The mixture was concentrated and purified by silica gel chromatography to give (1-benzyl-7-methoxy-1,2,3,4-tetrahydro-naphthalen-2-ylmethyl)-carbamic acid ethyl ester (43 g, 63%) as white solid.

9. Synthesis of SM10

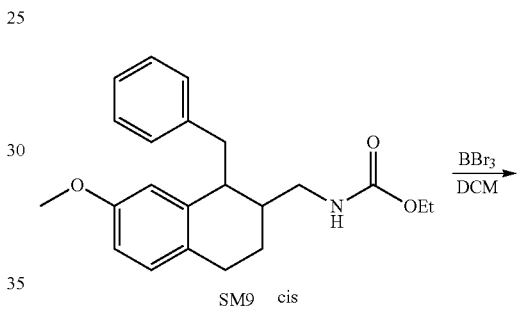

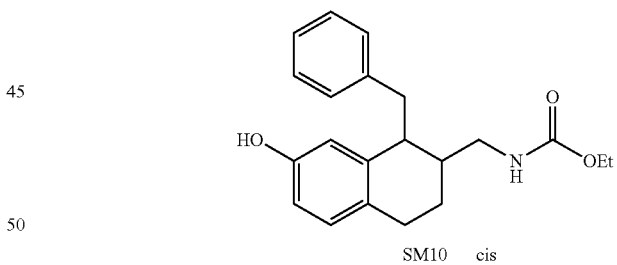

To a solution of (1-benzyl-7-methoxy-1,2,3,4-tetrahydro-naphthalen-2-ylmethyl)-carbamic acid ethyl ester (46.4 g, 131 mmol) in DCM (1000 mL), $BBr_3$ (50 mL) was added dropwise at −78° C. After addition, the solution was stirred for 13 hrs at room temperature. Then the solution was poured into aq.$NaHCO_3$ (500 mL), extracted with DCM (200 mL×3), washed with brine (200 mL×3), and the organic layer was dried over $Na_2SO_4$, then concentrated and purified by column chromatography on silica gel to give SM10 (17.2 g, yield 50%) as white solid.

Examples 194 to 203 were prepared starting from of cis-ethyl[(1-benzyl-7-hydroxy-1,2,3,4-tetrahydronaphthalen-2-yl)methyl]carbamate using well-known procedures such as those described in WO2010/092180 (which are incorporated herein in their entirety by reference).

Example 194

3-Methyl-3H-imidazole-4-sulfonic acid [2-(7-aminomethyl-8-benzyl-5,6,7,8-tetrahydro-naphthalen-2-yloxy)-ethyl]-amide

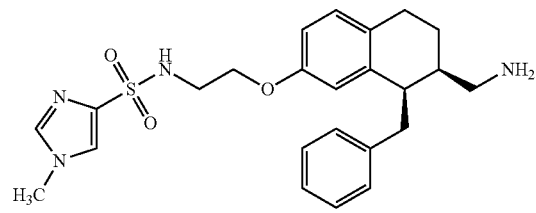

ESI-MS [M + H⁺] = .455.2    Calculated for $C_{24}H_{32}N_4O_3S$ = 454

Example 195

Ethanesulfonic acid [2-(7-aminomethyl-8-benzyl-5,6,7,8-tetrahydro-naphthalen-2-yloxy)-ethyl]-amide

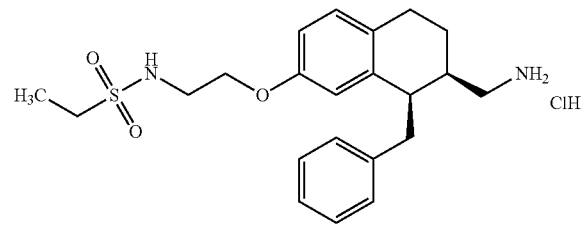

ESI—MS [M + H⁺] = 403.2
Calculated for $C_{22}H_{30}N_2O_3S$ = 402

Example 196

N-[2-(7-Aminomethyl-8-benzyl-5,6,7,8-tetrahydro-naphthalen-2-yloxy)-ethyl]-C-cyclopropyl-methanesulfonamide

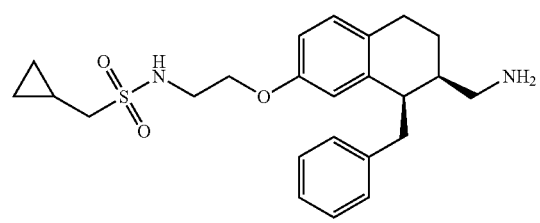

ESI-MS [M + H⁺] = 429    Calculated for $C_{24}H_{32}N_2O_3S$ = 428

Example 197

3-Methyl-3H-imidazole-4-sulfonic acid [2-(8-benzyl-7-methylaminomethyl-5,6,7,8-tetrahydro-naphthalen-2-yloxy)-ethyl]-amide

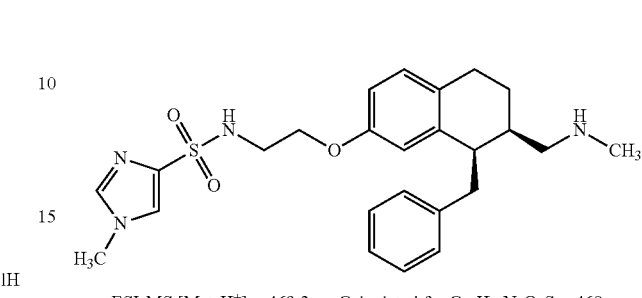

ESI-MS [M + H⁺] = 469.2    Calculated for $C_{25}H_{32}N_4O_3S$ = 468

Example 198

Ethanesulfonic acid [2-(8-benzyl-7-methylaminomethyl-5,6,7,8-tetrahydro-naphthalen-2-yloxy)-ethyl]-amide

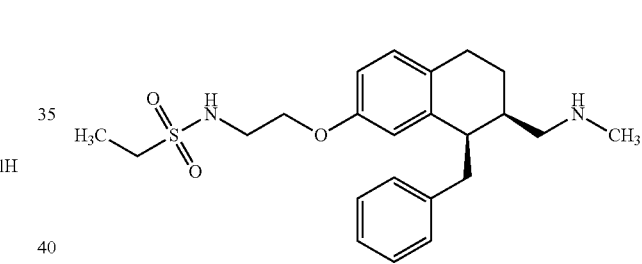

ESI-MS [M + H⁺] = 417    Calculated for $C_{23}H_{32}N_2O_3S$ = 416

Example 199

N-[2-(8-Benzyl-7-methylaminomethyl-5,6,7,8-tetrahydro-naphthalen-2-yloxy)-ethyl]-C-cyclopropyl-methanesulfonamide

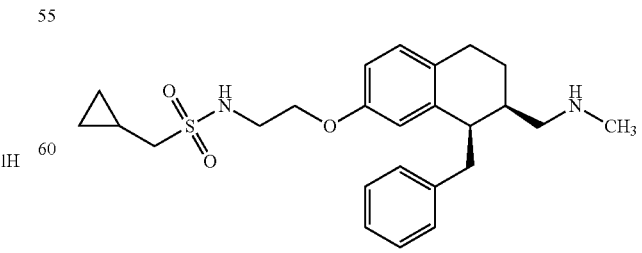

ESI-MS [M + H⁺] = 443    Calculated for $C_{25}H_{34}N_2O_3S$ = 442

Example 200

Ethanesulfonic acid [2-(7-azetidin-1-ylmethyl-8-benzyl-5,6,7,8-tetrahydro-naphthalen-2-yloxy)-ethyl]-amide

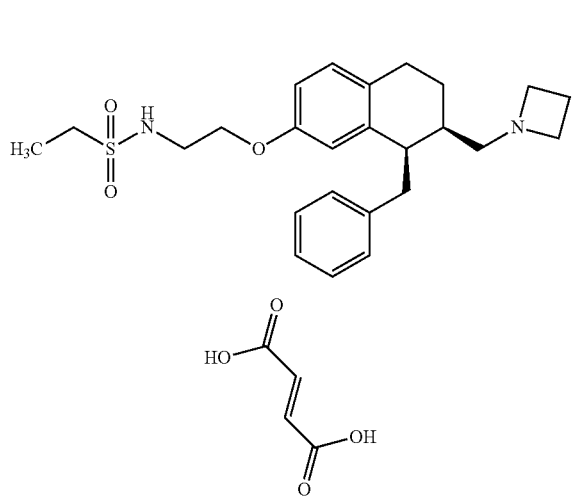

ESI-MS [M + H⁺] = 443    Calculated for $C_{25}H_{34}N_2O_3S$ = 442

Example 201

N-[2-(7-Azetidin-1-ylmethyl-8-benzyl-5,6,7,8-tetrahydro-naphthalen-2-yloxy)-ethyl]-C-cyclopropyl-methanesulfonamide

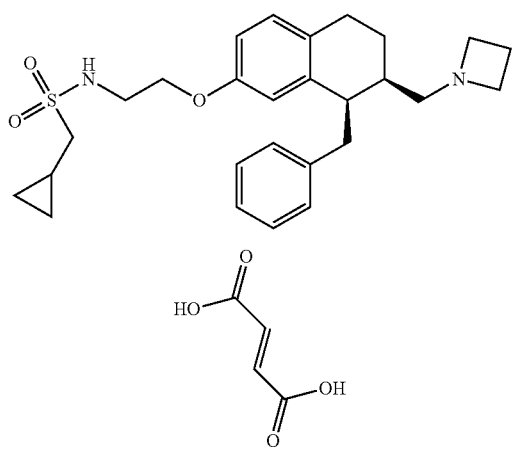

ESI-MS [M + H⁺] = 469    Calculated for $C_{27}H_{36}N_2O_3S$ = 468

Example 202

1-Methyl-1H-imidazole-4-sulfonic acid [2-(7-azetidin-1-ylmethyl-8-benzyl-5,6,7,8-tetrahydro-naphthalen-2-yloxy)-ethyl]-amide

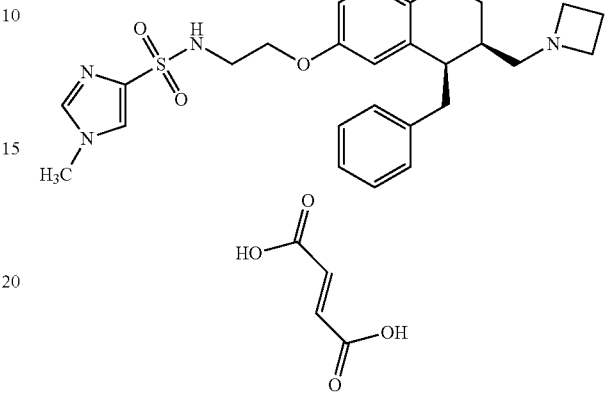

ESI-MS [M + H⁺] = 495    Calculated for $C_{27}H_{34}N_4O_3S$ = 494

Example 203

1-Methyl-1H-imidazole-4-sulfonic acid (7-azetidin-1-ylmethyl-8-benzyl-5,6,7,8-tetrahydro-naphthalen-2-ylmethyl)-amide

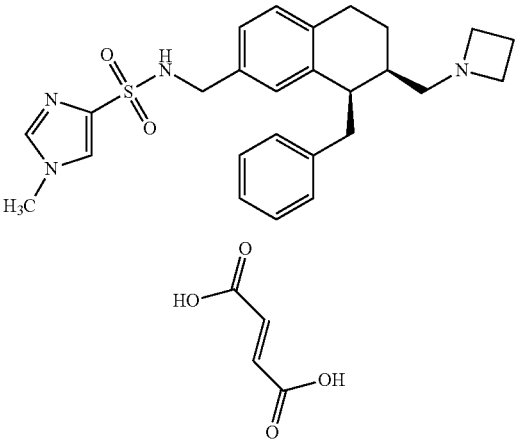

ESI-MS [M + H⁺] = 465    Calculated for $C_{26}H_{32}N_4O_2S$ = 464

Biological Testing

1. [³H]-Glycine uptake into recombinant CHO cells expressing human GlyT1: Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 µl HBSS (Gibco BRL, #14025-050) with 5 mM L-Alanine (Merck #1007). 80 µl HBSS buffer were added, followed by 10 µl inhibitor or vehicle (10% DMSO) and 10 µl [³H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 μM Org24598. $IC_{50}$ calculations were made by four-parametric logistic nonlinear regression analysis (GraphPad Prism) using determinations within the range of linear increase of [$^3$H]-glycine incorporation between 60 and 120 min.

2. Radioligand binding assays using recombinant CHO cell membranes expressing human GlyT1:

Radioligand binding to human GlyT1c transporter-expressing membranes was determined as described in Mezler et al., Molecular Pharmacology 74:1705-1715, 2008.

| Example | radioligand binding $K_{iapp}$ [nM] |
|---|---|
| 194 | ≤100 |
| 195 | ≤100 |
| 196 | ≤100 |
| 197 | ≤100 |
| 198 | ≤100 |
| 199 | ≤100 |
| 200 | ≤500 |
| 201 | ≤100 |
| 202 | ≤100 |
| 203 | ≤100 |

We claim:
1. A compound of formula (I)

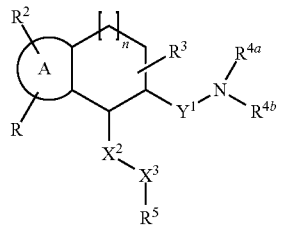

(I)

wherein
A is a 5- or 6-membered ring;
R is $R^1$—W—$A^1$-Q-Y-$A^2$-$X^1$—;
$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino, or optionally substituted $C_3$-$C_{12}$-heterocyclyl;
W is —$NR^8$— or a bond;
$A^1$ is optionally substituted $C_1$-$C_4$alkylene or a bond;
Q is —S(O)$_2$— or —C(O)—;
Y is —$NR^9$— or a bond;
$A^2$ is optionally substituted $C_1$-$C_4$-alkylene, $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_2$-$C_4$-alkenylene, optionally substituted $C_2$-$C_4$-alkynylene, optionally substituted $C_6$-$C_{12}$arylene, optionally substituted $C_6$-$C_{12}$-heteroarylene, or a bond;
$X^1$ is —O—, —$NR^{11}$—, —S—, optionally substituted $C_1$-$C_4$-alkylene, optionally substituted $C_2$-$C_4$-alkenylene, or optionally substituted $C_2$-$C_4$-alkynylene;
$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms of A to which they are bound form a 5- or 6 membered ring;
$R^3$ is hydrogen, halogen, $C_1$-$C_6$-alkyl, or $C_1$-$C_6$-alkoxy, or two radicals $R^3$ together with the carbon atom to which they are attached form a carbonyl group;
$Y^1$ is optionally substituted $C_1$-$C_4$-alkylene;
$R^{4a}$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, $C_6$-$C_{12}$-aryl-$C_1$-$C_4$-alkyl, $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO, or $C_3$-$C_{12}$-heterocyclyl; or
$R^{4a}$ is optionally substituted $C_1$-$C_4$-alkylene that is bound to a carbon atom in $Y^1$;
$R^{4b}$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO, or $C_3$-$C_{12}$-heterocyclyl; or $R^{4a}$, $R^{4b}$
    together are optionally substituted $C_1$-$C_6$-alkylene, wherein one —CH$_2$— of $C_1$-$C_4$-alkylene may be replaced by an oxygen atom or —NR$^{16}$;

$X^2$ is —O—, —NR$^6$—, —S—, >CR$^{12a}$R$^{12b}$, or a bond;
$X^3$ is —O—, —NR$^7$—, —S—, >CR$^{13a}$R$^{13b}$, or a bond;
$R^5$ is optionally substituted $C_6$-$C_{12}$-aryl, optionally substituted $C_3$-$C_{12}$-cycloalkyl, or optionally substituted $C_3$-$C_{12}$-heterocyclyl;
n is 0, 1, or 2;
$R^6$ is hydrogen or $C_1$-$C_6$-alkyl;
$R^7$ is hydrogen or $C_1$-$C_6$-alkyl;
$R^8$ is hydrogen or $C_1$-$C_6$-alkyl;
$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl, or $C_3$-$C_{12}$-heterocyclyl; or $R^9$, $R^1$
    together are $C_1$-$C_4$-alkylene; or $R^9$ is $C_1$-$C_4$-alkylene that is bound to a carbon atom in $A^2$ and $A^2$ is $C_1$-$C_4$-alkylene, or to a carbon atom in $X^1$ and $X^1$ is $C_1$-$C_4$-alkylene;
$R^{10}$ is hydrogen, $C_1$-$C_6$-alkyl, or $C_1$-$C_6$-alkylsulfonyl;
$R^{11}$ is hydrogen or $C_1$-$C_6$-alkyl; or $R^9$, $R^{11}$
    together are $C_1$-$C_4$-alkylene;

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl, or hydroxy;
$R^{12b}$ is hydrogen or $C_1$-$C_6$-alkyl; or $R^{12a}$, $R^{12b}$
    together are carbonyl or optionally substituted $C_1$-$C_4$-alkylene, wherein one —CH$_2$— of $C_1$-$C_4$-alkylene may be replaced by an oxygen atom or —NR$^{14}$—;

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl, or hydroxy;
$R^{13b}$ is hydrogen or $C_1$-$C_6$-alkyl; or $R^{13a}$, $R^{13b}$
    together are carbonyl or optionally substituted $C_1$-$C_4$-alkylene, wherein one —CH$_2$— of $C_1$-$C_4$-alkylene may be replaced by an oxygen atom or —NR$^{15}$—;

$R^{14}$ is hydrogen or $C_1$-$C_6$-alkyl;
$R^{15}$ is hydrogen or $C_1$-$C_6$-alkyl; and
$R^{16}$ is hydrogen or $C_1$-$C_6$-alkyl;
or a physiologically tolerated salt thereof.

2. A compound of claim 1, wherein A is a benzene ring or a ring selected from the group consisting of the following 5- or 6-membered heterocyclic rings:

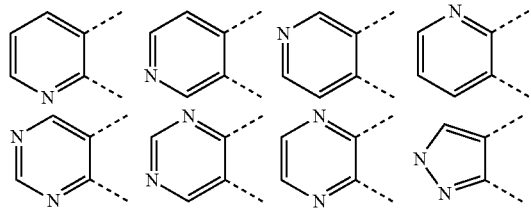

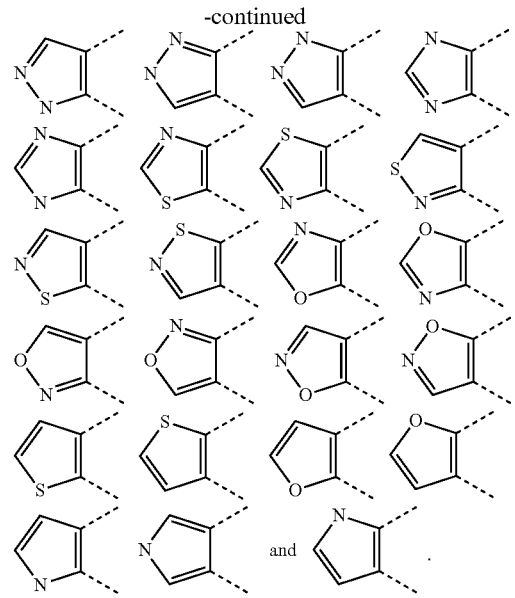

3. A compound of claim 1, wherein —Y-A$^2$-X$^1$— comprises at least 2, 3 or 4 atoms in the main chain.

4. A compound of claim 1, wherein $R^1$ is $C_1$-$C_6$-alkyl, $C_3$-$C_{12}$-cycloalkyl-$C_1$-$C_4$-alkyl, $C_3$-$C_{12}$-cycloalkyl, or optionally substituted $C_3$-$C_{12}$-heterocyclyl.

5. A compound of claim 1, wherein $A^1$ is a bond.

6. A compound of claim 1, wherein W is a bond and Y is a bond, or W is a bond and Y is —NR$^9$—.

7. A compound of claim 1, wherein $X^1$ is —O— and $A^2$ is $C_1$-$C_4$-alkylene, or $X^1$ is $C_1$-$C_4$-alkylene and $A^2$ is a bond.

8. A compound of claim 1, wherein $R^1$—W-$A^1$-Q-Y-$A^2$-$X^1$— is $R^1$—S(O)$_2$—NR$^9$-$A^2$-$X^1$— or $R^1$—S(O)$_2$—$X^1$—.

9. A compound of claim 1, having the formula

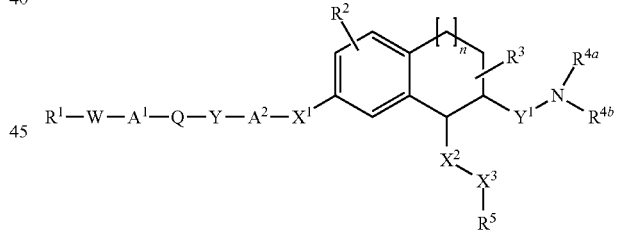

wherein $R^1$, W, $A^1$, Q, Y, $A^2$, $X^1$, $R^2$, $R^3$, $Y^1$, $R^{4a}$, $R^{4b}$, $X^2$, $X^3$, $R^5$, n are as defined in claim 1.

10. A compound of claim 1, wherein $Y^1$ is methylene or 1,2-ethylene.

11. A compound of claim 1, wherein $R^{4a}$ is $C_1$-$C_6$-alkyl, $C_3$-$C_{12}$-cycloalkyl, or $C_3$-$C_{12}$-heterocyclyl, or $R^{4a}$ is $C_1$-$C_4$-alkylene that is bound to a carbon atom in $Y^1$.

12. A compound of claim 1, wherein $R^{4b}$ is hydrogen or $C_1$-$C_6$-alkyl.

13. A compound of claim 1, wherein $R^{4a}$, $R^{4b}$ together are optionally substituted $C_1$-$C_6$-alkylene, wherein one —CH$_2$— of $C_1$-$C_4$-alkylene may be replaced by an oxygen atom.

14. A compound of claim 1, wherein $X^2$ is CR$^{12a}$R$^{12b}$ and $X^3$ is a bond.

15. A compound of claim 1, wherein $R^{12a}$ is hydrogen or $C_1$-$C_6$-alkyl, and $R^{12b}$ is hydrogen or $C_1$-$C_6$-alkyl, or $R^{12a}$, $R^{12b}$ together are optionally substituted $C_1$-$C_4$-alkylene.

16. A compound of claim 1, having the formula

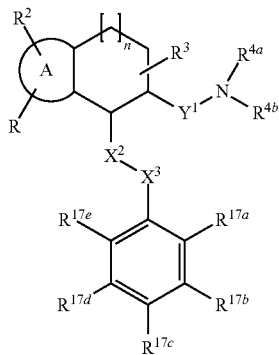

wherein A, R, $R^2$, $R^3$, $Y^1$, $R^{4a}$, $R^{4b}$, $X^2$, $X^3$, n are as defined in claims 1; and
$R^{17a}$, $R^{17b}$, $R^{17c}$, $R^{17d}$, $R^{17e}$ independently are hydrogen, halogen, or halogenated $C_1$-$C_6$-alkyl.

17. A compound of claim 1, wherein
A is a benzene ring;
R is $R^1$—W-$A^1$-Q-Y-$A^2$-$X^1$—;
$R^1$ is $C_1$-$C_6$-alkyl, $C_3$-$C_{12}$-cycloalkyl-$C_1$-$C_4$-alkyl, $C_3$-$C_{12}$-cycloalkyl, or optionally substituted $C_3$-$C_{12}$-heterocyclyl;
W is a bond;
$A^1$ is a bond;
Q is —S(O)$_2$—;
Y is —$NR^9$— or a bond;
$A^2$ is $C_1$-$C_4$-alkylene or a bond;
$X^1$ is —O— or $C_1$-$C_4$-alkylene;
$R^2$ is hydrogen or halogen;
$R^3$ is hydrogen;
$Y^1$ is optionally substituted $C_1$-$C_4$-alkylene;
$R^{4a}$ is hydrogen, $C_1$-$C_6$-alkyl, $C_3$-$C_{12}$-cycloalkyl, or $C_3$-$C_{12}$-heterocyclyl; or
$R^{4a}$ is optionally substituted $C_1$-$C_4$-alkylene that is bound to a carbon atom in $Y^1$;
$R^{4b}$ is hydrogen; or
$R^{4a}$, $R^{4b}$ together are $C_1$-$C_6$-alkylene, wherein one —CH$_2$— of $C_1$-$C_4$-alkylene may be replaced by an oxygen atom;
$X^2$ is $CR^{12a}R^{12b}$;
$X^3$ is a bond;
$R^5$ is optionally substituted phenyl;
n is 0 or 1;
$R^9$ is hydrogen; or
$R^9$ is $C_1$-$C_4$-alkylene that is bound to a carbon atom in $X^1$ and $X^1$ is $C_1$-$C_4$-alkylene;
$R^{12a}$ is hydrogen; and
$R^{12b}$ is hydrogen; or
$R^{12a}$, $R^{12b}$ together are $C_1$-$C_4$-alkylene.

18. A compound of claim 1, which is selected from the group consisting of:
N-[2-[3-benzyl-2-(methylaminomethyl)indan-5-yl]oxyethyl]-1-cyclopropyl-methanesulfonamide;
N-[2-[3-benzyl-2-(methylaminomethyl)indan-5-yl]oxyethyl]cyclobutanesulfonamide;
N-[2-[3-benzyl-2-(methylaminomethyl)indan-5-yl]oxyethyl]-1-methyl-imidazole-4-sulfonamide;
N-[2-[3-benzyl-2-(methylaminomethyl)indan-5-yl]oxyethyl]-1-methyl-pyrazole-4-sulfonamide;
N-[[3-benzyl-2-(methylaminomethyl)indan-5-yl]-methyl]-1-cyclopropyl-methanesulfonamide;
N-[2-[3-benzyl-2-(methylaminomethyl)indan-5-yl]ethyl]-1-cyclopropyl-methanesulfonamide;
N-[[3-benzyl-2-(methylaminomethyl)indan-5-yl]methyl]cyclobutanesulfonamide;
N-[2-[3-benzyl-2-(methylaminomethyl)indan-5-yl]ethyl]cyclobutanesulfonamide;
N-[[3-benzyl-2-(methylaminomethyl)indan-5yl]methyl]-1-methyl-imidazole-4-sulfonamide;
N-[2-[3-benzyl-2-(methylaminomethyl)indan-5-yl]ethyl]-1-methyl-imidazole-4-sulfonamide;
N-[[3-benzyl-2-(methylaminomethyl)indan-5yl]methyl]-1-methyl-pyrazole-4-sulfonamide;
N-[2-[3-benzyl-2-(methylaminomethyl)indan-5yl]ethyl]-1-methyl-pyrazole-4-sulfonamide;
N-[2-[3-benzyl-6-fluoro-2-(methylaminomethyl)indan-5-yl]oxyethyl]-1-cyclopropyl-methanesulfonamide;
N-[2-[3-benzyl-6-fluoro-2-(methylaminomethyl)indan-5-yl]oxyethyl]-cyclobutanesulfonamide;
N-[2-[3-benzyl-6-fluoro-2-(methylaminomethyl)indan-5-yl]oxyethyl]-1-methyl-imidazole-4-sulfonamide;
N-[2-[3-benzyl-6-fluoro-2-(methylaminomethyl)indan-5-yl]oxyethyl]-1-methyl-pyrazole-4-sulfonamide;
N-[[3-benzyl-6-fluoro-2-(methylaminomethyl)indan-5-yl]methyl]-1-cyclopropyl-methanesulfonamide;
N-[2-[3-benzyl-6-fluoro-2-(methylaminomethyl)indan-5-yl]ethyl]-1-cyclopropyl-methanesulfonamide;
N-[[3-benzyl-6-fluoro-2-(methylaminomethyl)indan-5-yl]methyl]-cyclobutanesulfonamide;
N-[2-[3-benzyl-6-fluoro-2-(methylaminomethyl)indan-5-yl]ethyl]-cyclobutanesulfonamide;
N-[[3-benzyl-6-fluoro-2-(methylaminomethyl)indan-5-yl]methyl]-1-methyl-imidazole-4-sulfonamide;
N-[2-[3-benzyl-6-fluoro-2-(methylaminomethyl)indan-5-yl]ethyl]-1-methyl-imidazole-4-sulfonamide;
N-[[3-benzyl-6-fluoro-2-(methylaminomethyl)indan-5-yl]methyl]-1-methyl-pyrazole-4-sulfonamide;
N-[2-[3-benzyl-6-fluoro-2-(methylaminomethyl)indan-5-yl]ethyl]-1-methyl-pyrazole-4-sulfonamide;
N-[2-[2-(azetidin-1-ylmethyl)-3-benzyl-indan-5-yl]oxyethyl]-1-cyclopropyl-methanesulfonamide;
N-[2-[2-(azetidin-1-ylmethyl)-3-benzyl-indan-5-yl]oxyethyl]cyclobutanesulfonamide;
N-[2-[2-(azetidin-1-ylmethyl)-3-benzyl-indan-5-yl]oxyethyl]-1-methyl-imidazole-4-sulfonamide;
N-[2-[2-(azetidin-1-ylmethyl)-3-benzyl-indan-5-yl]oxyethyl]-1-methyl-pyrazole-4-sulfonamide;
N-[[2-(azetidin-1-ylmethyl)-3-benzyl-indan-5-yl]methyl]-1-cyclopropyl-methanesulfonamide;
N-[2-[2-(azetidin-1-ylmethyl)-3-benzyl-indan-5-yl]ethyl]-1-cyclopropyl-methanesulfonamide;
N-[[2-(azetidin-1-ylmethyl)-3-benzyl-indan-5-yl]methyl]cyclobutanesulfonamide;
N-[2-[2-(azetidin-1-ylmethyl)-3-benzyl-indan-5-yl]ethyl]cyclobutanesulfonamide;
N-[[2-(azetidin-1-ylmethyl)-3-benzyl-indan-5-yl]methyl]-1-methyl-imidazole-4-sulfonamide;
N-[2-[2-(azetidin-1-ylmethyl)-3-benzyl-indan-5-yl]ethyl]-1-methyl-imidazole-4-sulfonamide;
N-[[2-(azetidin-1-ylmethyl)-3-benzyl-indan-5-yl]methyl]-1-methyl-pyrazole-4-sulfonamide;
N-[2-[2-(azetidin-1-ylmethyl)-3-benzyl-indan-5-yl]ethyl]-1-methyl-pyrazole-4-sulfonamide;
N-[2-[2-(azetidin-1-ylmethyl)-3-benzyl-6-fluoro-indan-5-yl]oxyethyl]-1-cyclopropyl-methanesulfonamide;

N-[2-[2-(azetidin-1-ylmethyl)-3-benzyl-6-fluoro-indan-5-yl]oxyethyl]-cyclobutanesulfonamide;
N-[2-[2-(azetidin-1-ylmethyl)-3-benzyl-6-fluoro-indan-5-yl]oxyethyl]-1-methyl-imidazole-4-sulfonamide;
N-[2-[2-(azetidin-1-ylmethyl)-3-benzyl-6-fluoro-indan-5-yl]oxyethyl]-1-methyl-pyrazole-4-sulfonamide;
N-[[2-(azetidin-1-ylmethyl)-3-benzyl-6-fluoro-indan-5-yl]methyl]-1-cyclopropyl-methanesulfonamide;
N-[2-[2-(azetidin-1-ylmethyl)-3-benzyl-6-fluoro-indan-5-yl]ethyl]-1-cyclopropyl-methanesulfonamide;
N-[[2-(azetidin-1-ylmethyl)-3-benzyl-6-fluoro-indan-5-yl]methyl]cyclobutanesulfonamide;
N-[2-[2-(azetidin-1-ylmethyl)-3-benzyl-6-fluoro-indan-5-yl]ethyl]cyclobutanesulfonamide;
N-[[2-(azetidin-1-ylmethyl)-3-benzyl-6-fluoro-indan-5-yl]methyl]-1-methyl-imidazole-4-sulfonamide;
N-[2-[2-(azetidin-1-ylmethyl)-3-benzyl-6-fluoro-indan-5-yl]ethyl]-1-methyl-imidazole-4-sulfonamide;
N-[[2-(azetidin-1-ylmethyl)-3-benzyl-6-fluoro-indan-5-yl]methyl]-1-methyl-pyrazole-4-sulfonamide;
N-[2-[2-(azetidin-1-ylmethyl)-3-benzyl-6-fluoro-indan-5-yl]ethyl]-1-methyl-pyrazole-4-sulfonamide;
1-cyclopropyl-N-[2-[3-[(3-fluorophenyl)methyl]-2-(methylaminomethyl)indan-5-yl]oxyethyl]methanesulfonamide;
N-[2-[3-[(3-fluorophenyl)methyl]-2-(methylaminomethyl)indan-5-yl]oxyethyl]-cyclobutanesulfonamide;
N-[2-[3-[(3-fluorophenyl)methyl]-2-(methylaminomethyl)indan-5-yl]oxyethyl]-1-methyl-imidazole-4-sulfonamide;
N-[2-[3-[(3-fluorophenyl)methyl]-2-(methylaminomethyl)indan-5-yl]oxyethyl]-1-methyl-pyrazole-4-sulfonamide;
1-cyclopropyl-N-[[3-[(3-fluorophenyl)methyl]-2-(methylaminomethyl)indan-5-yl]methyl]methanesulfonamide;
1-cyclopropyl-N-[2-[3-[(3-fluorophenyl)methyl]-2-(methylaminomethyl)indan-5-yl]ethyl]methanesulfonamide;
N-[[3-[(3-fluorophenyl)methyl]-2-(methylaminomethyl)indan-5-yl]methyl]-cyclobutanesulfonamide;
N-[2-[3-[(3-fluorophenyl)methyl]-2-(methylaminomethyl)indan-5-yl]ethyl]cyclobutanesulfonamide;
N-[[3-[(3-fluorophenyl)methyl]-2-(methylaminomethyl)indan-5-yl]methyl]-1-methyl-imidazole-4-sulfonamide;
N-[2-[3-[(3-fluorophenyl)methyl]-2-(methylaminomethyl)indan-5-yl]ethyl]-1-methyl-imidazole-4-sulfonamide;
N-[[3-[(3-fluorophenyl)methyl]-2-(methylaminomethyl)indan-5-yl]methyl]-1-methyl-pyrazole-4-sulfonamide;
N-[2-[3-[(3-fluorophenyl)methyl]-2-(methylaminomethyl)indan-5-yl]ethyl]-1-methyl-pyrazole-4-sulfonamide;
1-cyclopropyl-N-[2-[6-fluoro-3-[(3-fluorophenyl)methyl]-2-(methylaminomethyl)indan-5-yl]oxyethyl]methanesulfonamide;
N-[2-[6-fluoro-3-[(3-fluorophenyl)methyl]-2-(methylaminomethyl)indan-5-yl]oxyethyl]cyclobutanesulfonamide;
N-[2-[6-fluoro-3-[(3-fluorophenyl)methyl]-2-(methylaminomethyl)indan-5-yl]oxyethyl]-1-methyl-imidazole-4-sulfonamide;
N-[2-[6-fluoro-3-[(3-fluorophenyl)methyl]-2-(methylaminomethyl)indan-5-yl]oxyethyl]-1-methyl-pyrazole-4-sulfonamide;
1-cyclopropyl-N-[[6-fluoro-3-[(3-fluorophenyl)methyl]-2-(methylaminomethyl)indan-5-yl]methyl]methanesulfonamide;
1-cyclopropyl-N-[2-[6-fluoro-3-[(3-fluorophenyl)methyl]-2-(methylaminomethyl)indan-5-yl]ethyl]methanesulfonamide;
N-[[6-fluoro-3-[(3-fluorophenyl)methyl]-2-(methylaminomethyl)indan-5-yl]methyl]cyclobutanesulfonamide;
N-[2-[6-fluoro-3-[(3-fluorophenyl)methyl]-2-(methylaminomethyl)indan-5-yl]ethyl]cyclobutanesulfonamide;
N-[[6-fluoro-3-[(3-fluorophenyl)methyl]-2-(methylaminomethyl)indan-5-yl]methyl]-1-methyl-imidazole-4-sulfonamide;
N-[2-[6-fluoro-3-[(3-fluorophenyl)methyl]-2-(methylaminomethyl)indan-5-yl]ethyl]-1-methyl-imidazole-4-sulfonamide;
N-[[6-fluoro-3-[(3-fluorophenyl)methyl]-2-(methylaminomethyl)indan-5-yl]methyl]-1-methyl-pyrazole-4-sulfonamide;
N-[2-[6-fluoro-3-[(3-fluorophenyl)methyl]-2-(methylaminomethyl)indan-5-yl]ethyl]-1-methyl-pyrazole-4-sulfonamide;
N-[2-[2-(azetidin-1-ylmethyl)-3-[(3-fluorophenyl)methyl]indan-5-yl]oxyethyl]-1-cyclopropyl-methanesulfonamide;
N-[2-[2-(azetidin-1-ylmethyl)-3-[(3-fluorophenyl)methyl]indan-5-yl]oxyethyl]cyclobutanesulfonamide;
N-[2-[2-(azetidin-1-ylmethyl)-3-[(3-fluorophenyl)methyl]indan-5-yl]oxyethyl]-1-methyl-imidazole-4-sulfonamide;
N-[2-[2-(azetidin-1-ylmethyl)-3-[(3-fluorophenyl)methyl]indan-5-yl]oxyethyl]-1-methyl-pyrazole-4-sulfonamide;
N-[[2-(azetidin-1-ylmethyl)-3-[(3-fluorophenyl)methyl]indan-5-yl]methyl]-1-cyclopropyl-methanesulfonamide;
N-[2-[2-(azetidin-1-ylmethyl)-3-[(3-fluorophenyl)methyl]indan-5-yl]ethyl]-1-cyclopropyl-methanesulfonamide;
N-[[2-(azetidin-1-ylmethyl)-3-[(3-fluorophenyl)methyl]indan-5-yl]methyl]cyclobutanesulfonamide;
N-[2-[2-(azetidin-1-ylmethyl)-3-[(3-fluorophenyl)methyl]indan-5-yl]ethyl]cyclobutanesulfonamide;
N-[[2-(azetidin-1-ylmethyl)-3-[(3-fluorophenyl)methyl]indan-5-yl]methyl]-1-methyl-imidazole-4-sulfonamide;
N-[2-[2-(azetidin-1-ylmethyl)-3-[(3-fluorophenyl)methyl]indan-5-yl]ethyl]-1-methyl-imidazole-4-sulfonamide;
N-[[2-(azetidin-1-ylmethyl)-3-[(3-fluorophenyl)methyl]indan-5-yl]methyl]-1-methyl-pyrazole-4-sulfonamide;
N-[2-[2-(azetidin-1-ylmethyl)-3-[(3-fluorophenyl)methyl]indan-5-yl]ethyl]-1-methyl-pyrazole-4-sulfonamide;
N-[2-[2-(azetidin-1-ylmethyl)-6-fluoro-3-[(3-fluorophenyl)methyl]indan-5-yl]oxyethyl]-1-cyclopropyl-methanesulfonamide;
N-[2-[2-(azetidin-1-ylmethyl)-6-fluoro-3-[(3-fluorophenyl)methyl]indan-5-yl]oxyethyl]cyclobutanesulfonamide;
N-[2-[2-(azetidin-1-ylmethyl)-6-fluoro-3-[(3-fluorophenyl)methyl]indan-5-yl]oxyethyl]-1-methyl-imidazole-4-sulfonamide;
N-[2-[2-(azetidin-1-ylmethyl)-6-fluoro-3-[(3-fluorophenyl)methyl]indan-5-yl]oxyethyl]-1-methyl-pyrazole-4-sulfonamide;

N-[[2-(azetidin-1-ylmethyl)-6-fluoro-3-[(3-fluorophenyl)methyl]indan-5-yl]methyl]-1-cyclopropyl-methanesulfonamide;
N-[2-[2-(azetidin-1-ylmethyl)-6-fluoro-3-[(3-fluorophenyl)methyl]indan-5-yl]ethyl]-1-cyclopropyl-methanesulfonamide;
N-[[2-(azetidin-1-ylmethyl)-6-fluoro-3-[(3-fluorophenyl)methyl]indan-5-yl]methyl]cyclobutanesulfonamide;
N-[2-[2-(azetidin-1-ylmethyl)-6-fluoro-3-[(3-fluorophenyl)methyl]indan-5-yl]ethyl]cyclobutanesulfonamide;
N-[[2-(azetidin-1-ylmethyl)-6-fluoro-3-[(3-fluorophenyl)methyl]indan-5-yl]methyl]-1-methyl-imidazole-4-sulfonamide;
N-[2-[2-(azetidin-1-ylmethyl)-6-fluoro-3-[(3-fluorophenyl)methyl]indan-5-yl]ethyl]-1-methyl-imidazole-4-sulfonamide;
N-[[2-(azetidin-1-ylmethyl)-6-fluoro-3-[(3-fluorophenyl)methyl]indan-5-yl]methyl]-1-methyl-pyrazole-4-sulfonamide;
N-[2-[2-(azetidin-1-ylmethyl)-6-fluoro-3-[(3-fluorophenyl)methyl]indan-5-yl]ethyl]-1-methyl-pyrazole-4-sulfonamide;
N-[2-[3-[(3-chlorophenyl)methyl]-2-(methylaminomethyl)indan-5-yl]oxyethyl]-1-cyclopropyl-methanesulfonamide;
N-[2-[3-[(3-chlorophenyl)methyl]-2-(methylaminomethyl)indan-5-yl]oxyethyl]cyclobutanesulfonamide;
N-[2-[3-[(3-chlorophenyl)methyl]-2-(methylaminomethyl)indan-5-yl]oxyethyl]-1-methyl-imidazole-4-sulfonamide;
N-[2-[3-[(3-chlorophenyl)methyl]-2-(methylaminomethyl)indan-5-yl]oxyethyl]-1-methyl-pyrazole-4-sulfonamide;
N-[2-[3-[(3-chlorophenyl)methyl]-2-(methylaminomethyl)indan-5-yl]oxyethyl]-1-methyl-pyrazole-4-sulfonamide;
N-[2-[3-[(3-chlorophenyl)methyl]-2-(methylaminomethyl)indan-5-yl]ethyl]-1-cyclopropyl-methanesulfonamide;
N-[[3-[(3-chlorophenyl)methyl]-2-(methylaminomethyl)indan-5-yl]methyl]cyclobutanesulfonamide;
N-[2-[3-[(3-chlorophenyl)methyl]-2-(methylaminomethyl)indan-5-yl]ethyl]cyclobutanesulfonamide;
N-[[3-[(3-chlorophenyl)methyl]-2-(methylaminomethyl)indan-5-yl]methyl]-1-methyl-imidazole-4-sulfonamide;
N-[2-[3-[(3-chlorophenyl)methyl]-2-(methylaminomethyl)indan-5-yl]ethyl]-1-methyl-imidazole-4-sulfonamide;
N-[[3-[(3-chlorophenyl)methyl]-2-(methylaminomethyl)indan-5-yl]methyl]-1-methyl-pyrazole-4-sulfonamide;
N-[2-[3-[(3-chlorophenyl)methyl]-2-(methylaminomethyl)indan-5-yl]ethyl]-1-methyl-pyrazole-4-sulfonamide;
N-[2-[3-[(3-chlorophenyl)methyl]-6-fluoro-2-(methylaminomethyl)indan-5-yl]oxyethyl]-1-cyclopropyl-methanesulfonamide;
N-[2-[3-[(3-chlorophenyl)methyl]-6-fluoro-2-(methylaminomethyl)indan-5-yl]oxyethyl]cyclobutanesulfonamide;
N-[2-[3-[(3-chlorophenyl)methyl]-6-fluoro-2-(methylaminomethyl)indan-5-yl]oxyethyl]-1-methyl-imidazole-4-sulfonamide;
N-[2-[3-[(3-chlorophenyl)methyl]-6-fluoro-2-(methylaminomethyl)indan-5-yl]oxyethyl]-1-methyl-pyrazole-4-sulfonamide;
N-[[3-[(3-chlorophenyl)methyl]-6-fluoro-2-(methylaminomethyl)indan-5-yl]methyl]-1-cyclopropyl-methanesulfonamide;
N-[2-[3-[(3-chlorophenyl)methyl]-6-fluoro-2-(methylaminomethyl)indan-5-yl]ethyl]-1-cyclopropyl-methanesulfonamide;
N-[[3-[(3-chlorophenyl)methyl]-6-fluoro-2-(methylaminomethyl)indan-5-yl]methyl]cyclobutanesulfonamide;
N-[2-[3-[(3-chlorophenyl)methyl]-6-fluoro-2-(methylaminomethyl)indan-5-yl]ethyl]cyclobutanesulfonamide;
N-[[3-[(3-chlorophenyl)methyl]-6-fluoro-2-(methylaminomethyl)indan-5-yl]methyl]-1-methyl-imidazole-4-sulfonamide;
N-[2-[3-[(3-chlorophenyl)methyl]-6-fluoro-2-(methylaminomethyl)indan-5-yl]ethyl]-1-methyl-imidazole-4-sulfonamide;
N-[[3-[(3-chlorophenyl)methyl]-6-fluoro-2-(methylaminomethyl)indan-5-yl]methyl]-1-methyl-pyrazole-4-sulfonamide;
N-[2-[3-[(3-chlorophenyl)methyl]-6-fluoro-2-(methylaminomethyl)indan-5-yl]ethyl]-1-methyl-pyrazole-4-sulfonamide;
N-[2-[2-(azetidin-1-ylmethyl)-3-[(3-chlorophenyl)methyl]indan-5-yl]oxyethyl]-1-cyclopropyl-methanesulfonamide;
N-[2-[2-(azetidin-1-ylmethyl)-3-[(3-chlorophenyl)methyl]indan-5-yl]oxyethyl]cyclobutanesulfonamide;
N-[2-[2-(azetidin-1-ylmethyl)-3-[(3-chlorophenyl)methyl]indan-5-yl]oxyethyl]-1-methyl-imidazole-4-sulfonamide;
N-[2-[2-(azetidin-1-ylmethyl)-3-[(3-chlorophenyl)methyl]indan-5-yl]oxyethyl]-1-methyl-pyrazole-4-sulfonamide;
N-[[2-(azetidin-1-ylmethyl)-3-[(3-chlorophenyl)methyl]indan-5-yl]methyl]-1-cyclopropyl-methanesulfonamide;
N-[2-[2-(azetidin-1-ylmethyl)-3-[(3-chlorophenyl)methyl]indan-5-yl]ethyl]-1-cyclopropyl-methanesulfonamide;
N-[[2-(azetidin-1-ylmethyl)-3-[(3-chlorophenyl)methyl]indan-5-yl]methyl]cyclobutanesulfonamide;
N-[2-[2-(azetidin-1-ylmethyl)-3-[(3-chlorophenyl)methyl]indan-5-yl]ethyl]cyclobutanesulfonamide;
N-[[2-(azetidin-1-ylmethyl)-3-[(3-chlorophenyl)methyl]indan-5-yl]methyl]-1-methyl-imidazole-4-sulfonamide;
N-[2-[2-(azetidin-1-ylmethyl)-3-[(3-chlorophenyl)methyl]indan-5-yl]ethyl]-1-methyl-imidazole-4-sulfonamide;
N-[[2-(azetidin-1-ylmethyl)-3-[(3-chlorophenyl)methyl]indan-5-yl]methyl]-1-methyl-pyrazole-4-sulfonamide;
N-[2-[2-(azetidin-1-ylmethyl)-3-[(3-chlorophenyl)methyl]indan-5-yl]ethyl]-1-methyl-pyrazole-4-sulfonamide;
N-[2-[2-(azetidin-1-ylmethyl)-3-[(3-chlorophenyl)methyl]-6-fluoro-indan-5-yl]oxyethyl]-1-cyclopropyl-methanesulfonamide;
N-[2-[2-(azetidin-1-ylmethyl)-3-[(3-chlorophenyl)methyl]-6-fluoro-indan-5-yl]oxyethyl]cyclobutanesulfonamide;
N-[2-[2-(azetidin-1-ylmethyl)-3-[(3-chlorophenyl)methyl]-6-fluoro-indan-5-yl]oxyethyl]-1-methyl-imidazole-4-sulfonamide;
N-[2-[2-(azetidin-1-ylmethyl)-3-[(3-chlorophenyl)methyl]-6-fluoro-indan-5-yl]oxyethyl]-1-methyl-pyrazole-4-sulfonamide;

N-[[2-(azetidin-1-ylmethyl)-3-[(3-chlorophenyl)methyl]-6-fluoro-indan-5-yl]methyl]-1-cyclopropyl-methanesulfonamide;
N-[2-[2-(azetidin-1-ylmethyl)-3-[(3-chlorophenyl)methyl]-6-fluoro-indan-5-yl]ethyl]-1-cyclopropyl-methanesulfonamide;
N-[[2-(azetidin-1-ylmethyl)-3-[(3-chlorophenyl)methyl]-6-fluoro-indan-5-yl]methyl]cyclobutanesulfonamide;
N-[2-[2-(azetidin-1-ylmethyl)-3-[(3-chlorophenyl)methyl]-6-fluoro-indan-5-yl]ethyl]cyclobutanesulfonamide;
N-[[2-(azetidin-1-ylmethyl)-3-[(3-chlorophenyl)methyl]-6-fluoro-indan-5-yl]methyl]-1-methyl-imidazole-4-sulfonamide;
N-[2-[2-(azetidin-1-ylmethyl)-3-[(3-chlorophenyl)methyl]-6-fluoro-indan-5-yl]ethyl]-1-methyl-imidazole-4-sulfonamide;
N-[[2-(azetidin-1-ylmethyl)-3-[(3-chlorophenyl)methyl]-6-fluoro-indan-5-yl]methyl]-1-methyl-pyrazole-4-sulfonamide;
N-[2-[2-(azetidin-1-ylmethyl)-3-[(3-chlorophenyl)methyl]-6-fluoro-indan-5-yl]ethyl]-1-methyl-pyrazole-4-sulfonamide;
1-cyclopropyl-N-[2-[2-(methylaminomethyl)-3-[[3-(trifluoromethyl)phenyl]methyl]indan-5-yl]oxyethyl]methanesulfonamide;
N-[2-[2-(methylaminomethyl)-3-[[3-(trifluoromethyl)phenyl]methyl]indan-5-yl]oxyethyl]cyclobutanesulfonamide;
1-methyl-N-[2-[2-(methylaminomethyl)-3-[[3-(trifluoromethyl)phenyl]methyl]indan-5-yl]oxyethyl]imidazole-4-sulfonamide;
1-methyl-N-[2-[2-(methylaminomethyl)-3-[[3-(trifluoromethyl)phenyl]methyl]indan-5-yl]oxyethyl]pyrazole-4-sulfonamide;
1-cyclopropyl-N-[[2-(methylaminomethyl)-3-[[3-(trifluoromethyl)phenyl]methyl]indan-5-yl]methyl]methanesulfonamide;
1-cyclopropyl-N-[2-[2-(methylaminomethyl)-3-[[3-(trifluoromethyl)phenyl]methyl]indan-5-yl]ethyl]methanesulfonamide;
N-[[2-(methylaminomethyl)-3-[[3-(trifluoromethyl)phenyl]methyl]indan-5-yl]methyl]cyclobutanesulfonamide;
N-[2-[2-(methylaminomethyl)-3-[[3-(trifluoromethyl)phenyl]methyl]indan-5-yl]ethyl]cyclobutanesulfonamide;
1-methyl-N-[[2-(methylaminomethyl)-3-[[3-(trifluoromethyl)phenyl]methyl]indan-5-yl]methyl]imidazole-4-sulfonamide;
1-methyl-N-[2-[2-(methylaminomethyl)-3-[[3-(trifluoromethyl)phenyl]methyl]indan-5-yl]ethyl]imidazole-4-sulfonamide;
1-methyl-N-[[2-(methylaminomethyl)-3-[[3-(trifluoromethyl)phenyl]methyl]indan-5-yl]methyl]pyrazole-4-sulfonamide;
1-methyl-N-[2-[2-(methylaminomethyl)-3-[[3-(trifluoromethyl)phenyl]methyl]indan-5-yl]ethyl]pyrazole-4-sulfonamide;
1-cyclopropyl-N-[2-[6-fluoro-2-(methylaminomethyl)-3-[[3-(trifluoromethyl)phenyl]methyl]indan-5-yl]oxyethyl]methanesulfonamide;
N-[2-[6-fluoro-2-(methylaminomethyl)-3-[[3-(trifluoromethyl)phenyl]methyl]indan-5-yl]oxyethyl]cyclobutanesulfonamide;
N-[2-[6-fluoro-2-(methylaminomethyl)-3-[[3-(trifluoromethyl)phenyl]methyl]indan-5-yl]oxyethyl]-1-methyl-imidazole-4-sulfonamide;
N-[2-[6-fluoro-2-(methylaminomethyl)-3-[[3-(trifluoromethyl)phenyl]methyl]indan-5-yl]oxyethyl]-1-methyl-pyrazole-4-sulfonamide;
1-cyclopropyl-N-[[6-fluoro-2-(methylaminomethyl)-3-[[3-(trifluoromethyl)phenyl]methyl]indan-5-yl]methyl]methanesulfonamide;
1-cyclopropyl-N-[2-[6-fluoro-2-(methylaminomethyl)-3-[[3-(trifluoromethyl)phenyl]methyl]indan-5-yl]ethyl]methanesulfonamide;
N-[[6-fluoro-2-(methylaminomethyl)-3-[[3-(trifluoromethyl)phenyl]methyl]indan-5-yl]methyl]cyclobutanesulfonamide;
N-[2-[6-fluoro-2-(methylaminomethyl)-3-[[3-(trifluoromethyl)phenyl]methyl]indan-5-yl]ethyl]cyclobutanesulfonamide;
N-[[6-fluoro-2-(methylaminomethyl)-3-[[3-(trifluoromethyl)phenyl]methyl]indan-5-yl]methyl]-1-methyl-imidazole-4-sulfonamide;
N-[2-[6-fluoro-2-(methylaminomethyl)-3-[[3-(trifluoromethyl)phenyl]methyl]indan-5-yl]ethyl]-1-methyl-imidazole-4-sulfonamide;
N-[[6-fluoro-2-(methylaminomethyl)-3-[[3-(trifluoromethyl)phenyl]methyl]indan-5-yl]methyl]-1-methyl-pyrazole-4-sulfonamide;
N-[2-[6-fluoro-2-(methylaminomethyl)-3-[[3-(trifluoromethyl)phenyl]methyl]indan-5-yl]ethyl]-1-methyl-pyrazole-4-sulfonamide;
N-[2-[2-(azetidin-1-ylmethyl)-3-[[3-(trifluoromethyl)phenyl]methyl]indan-5-yl]oxyethyl]-1-cyclopropyl-methanesulfonamide;
N-[2-[2-(azetidin-1-ylmethyl)-3-[[3-(trifluoromethyl)phenyl]methyl]indan-5-yl]oxyethyl]cyclobutanesulfonamide;
N-[2-[2-(azetidin-1-ylmethyl)-3-[[3-(trifluoromethyl)phenyl]methyl]indan-5-yl]oxyethyl]-1-methyl-imidazole-4-sulfonamide;
N-[2-[2-(azetidin-1-ylmethyl)-3-[[3-(trifluoromethyl)phenyl]methyl]indan-5-yl]oxyethyl]-1-methyl-pyrazole-4-sulfonamide;
N-[[2-(azetidin-1-ylmethyl)-3-[[3-(trifluoromethyl)phenyl]methyl]indan-5-yl]methyl]-1-cyclopropyl-methanesulfonamide;
N-[2-[2-(azetidin-1-ylmethyl)-3-[[3-(trifluoromethyl)phenyl]methyl]indan-5-yl]ethyl]-1-cyclopropyl-methanesulfonamide;
N-[[2-(azetidin-1-ylmethyl)-3-[[3-(trifluoromethyl)phenyl]methyl]indan-5-yl]methyl]cyclobutanesulfonamide;
N-[2-[2-(azetidin-1-ylmethyl)-3-[[3-(trifluoromethyl)phenyl]methyl]indan-5-yl]ethyl]cyclobutanesulfonamide;
N-[[2-(azetidin-1-ylmethyl)-3-[[3-(trifluoromethyl)phenyl]methyl]indan-5-yl]methyl]-1-methyl-imidazole-4-sulfonamide;
N-[2-[2-(azetidin-1-ylmethyl)-3-[[3-(trifluoromethyl)phenyl]methyl]indan-5-yl]ethyl]-1-methyl-imidazole-4-sulfonamide;
N-[[2-(azetidin-1-ylmethyl)-3-[[3-(trifluoromethyl)phenyl]methyl]indan-5-yl]methyl]-1-methyl-pyrazole-4-sulfonamide;
N-[2-[2-(azetidin-1-ylmethyl)-3-[[3-(trifluoromethyl)phenyl]methyl]indan-5-yl]ethyl]-1-methyl-pyrazole-4-sulfonamide;

N-[2-[2-(azetidin-1-ylmethyl)-6-fluoro-3-[[3-(trifluoromethyl)phenyl]methyl]indan-5-yl]oxyethyl]-1-cyclopropyl-methanesulfonamide;

N-[2-[2-(azetidin-1-ylmethyl)-6-fluoro-3-[[3-(trifluoromethyl)phenyl]methyl]indan-5-yl]oxyethyl]cyclobutanesulfonamide;

N-[2-[2-(azetidin-1-ylmethyl)-6-fluoro-3-[[3-(trifluoromethyl)phenyl]methyl]indan-5-yl]oxyethyl]-1-methyl-imidazole-4-sulfonamide;

N-[2-[2-(azetidin-1-ylmethyl)-6-fluoro-3-[[3-(trifluoromethyl)phenyl]methyl]indan-5-yl]oxyethyl]-1-methyl-pyrazole-4-sulfonamide;

N-[[2-(azetidin-1-ylmethyl)-6-fluoro-3-[[3-(trifluoromethyl)phenyl]methyl]indan-5-yl]methyl]-1-cyclopropyl-methanesulfonamide;

N-[2-[2-(azetidin-1-ylmethyl)-6-fluoro-3-[[3-(trifluoromethyl)phenyl]methyl]indan-5-yl]ethyl]-1-cyclopropyl-methanesulfonamide;

N-[[2-(azetidin-1-ylmethyl)-6-fluoro-3-[[3-(trifluoromethyl)phenyl]methyl]indan-5-yl]methyl]cyclobutanesulfonamide;

N-[2-[2-(azetidin-1-ylmethyl)-6-fluoro-3-[[3-(trifluoromethyl)phenyl]methyl]indan-5-yl]ethyl]cyclobutanesulfonamide;

N-[[2-(azetidin-1-ylmethyl)-6-fluoro-3-[[3-(trifluoromethyl)phenyl]methyl]indan-5-yl]methyl]-1-methyl-imidazole-4-sulfonamide;

N-[2-[2-(azetidin-1-ylmethyl)-6-fluoro-3-[[3-(trifluoromethyl)phenyl]methyl]indan-5-yl]ethyl]-1-methyl-imidazole-4-sulfonamide;

N-[[2-(azetidin-1-ylmethyl)-6-fluoro-3-[[3-(trifluoromethyl)phenyl]methyl]indan-5-yl]methyl]-1-methyl-pyrazole-4-sulfonamide;

N-[2-[2-(azetidin-1-ylmethyl)-6-fluoro-3-[[3-(trifluoromethyl)phenyl]methyl]indan-5-yl]ethyl]-1-methyl-pyrazole-4-sulfonamide;

3-Methyl-3H-imidazole-4-sulfonic acid [2-(7-aminomethyl-8-benzyl-5,6,7,8-tetrahydro-naphthalen-2-yloxy)-ethyl]-amide;

Ethanesulfonic acid [2-(7-aminomethyl-8-benzyl-5,6,7,8-tetrahydro-naphthalen-2-yloxy)-ethyl]-amide;

N-[2-(7-Aminomethyl-8-benzyl-5,6,7,8-tetrahydro-naphthalen-2-yloxy)-ethyl]-C-cyclopropyl-methanesulfonamide;

3-Methyl-3H-imidazole-4-sulfonic acid [2-(8-benzyl-7-methylaminomethyl-5,6,7,8-tetrahydro-naphthalen-2-yloxy)-ethyl]-amide;

Ethanesulfonic acid [2-(8-benzyl-7-methylaminomethyl-5,6,7,8-tetrahydro-naphthalen-2-yloxy)-ethyl]-amide;

N-[2-(8-Benzyl-7-methylaminomethyl-5,6,7,8-tetrahydro-naphthalen-2-yloxy)-ethyl]-C-cyclopropyl-methanesulfonamide;

Ethanesulfonic acid [2-(7-azetidin-1-ylmethyl-8-benzyl-5,6,7,8-tetrahydro-naphthalen-2-yloxy)-ethyl]-amide;

N-[2-(7-Azetidin-1-ylmethyl-8-benzyl-5,6,7,8-tetrahydro-naphthalen-2-yloxy)-ethyl]-C-cyclopropyl-methanesulfonamide;

1-Methyl-1H-imidazole-4-sulfonic acid [2-(7-azetidin-1-ylmethyl-8-benzyl-5,6,7,8-tetrahydro-naphthalen-2-yloxy)-ethyl]-amide; and 1-Methyl-1H-imidazole-4-sulfonic acid (7-azetidin-1-ylmethyl-8-benzyl-5,6,7,8-tetrahydro-naphthalen-2-ylmethyl)-amide;

or a physiologically tolerated salt thereof.

19. A pharmaceutical composition which comprises a carrier and a compound of claim 1.

20. A method for treating a neurologic or psychiatric disorder or pain in a mammalian patient in need thereof which comprises administering to the patient a therapeutically effective amount of a compound of claim 1, wherein the neurologic disorder is selected from the group consisting of dementia, cognitive impairment, and attention deficit disorder, and wherein the psychiatric disorder is selected from the group consisting of anxiety disorder, depression, bipolar disorder, schizophrenia, and psychosis.

* * * * *